United States Patent
Kiebish et al.

(10) Patent No.: US 12,320,812 B2
(45) Date of Patent: Jun. 3, 2025

(54) MARKERS FOR THE DIAGNOSIS OF BIOCHEMICAL RECURRENCE IN PROSTATE CANCER

(71) Applicants: BPGbio, Inc., Framingham, MA (US); The Henry M. Jackson Foundation for the Advancement of Military Medicine, Inc., Bethesda, MD (US)

(72) Inventors: Michael Andrew Kiebish, Millis, MA (US); Niven Rajin Narain, Cambridge, MA (US); Rangaprasad Sarangarajan, Boylston, MA (US); Viatcheslav R. Akmaev, Sudbury, MA (US); Leonardo Rodrigues, Ashland, MA (US); Lixia Zhang, Natick, MA (US); Eric Milliman, Natick, MA (US); Shiv Srivastava, Potomac, MD (US); Albert Dobi, Rockville, MD (US); Jennifer Cullen, Gaithersburg, MD (US)

(73) Assignees: BPGbio, Inc., Framingham, MA (US); Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 572 days.

(21) Appl. No.: 16/783,238

(22) Filed: Feb. 6, 2020

(65) Prior Publication Data
US 2020/0292548 A1    Sep. 17, 2020

Related U.S. Application Data

(60) Provisional application No. 62/801,963, filed on Feb. 6, 2019.

(51) Int. Cl.
G01N 33/574    (2006.01)
A61P 35/00    (2006.01)

(52) U.S. Cl.
CPC ........ *G01N 33/57434* (2013.01); *A61P 35/00* (2018.01); *G01N 2333/775* (2013.01); *G01N 2405/04* (2013.01); *G01N 2800/54* (2013.01); *G01N 2800/60* (2013.01)

(58) Field of Classification Search
CPC ....... G01N 33/57434; G01N 2333/775; G01N 2800/54; G01N 2800/60; G01N 2405/04
See application file for complete search history.

(56) References Cited

U.S. PATENT DOCUMENTS

| | | | | |
|---|---|---|---|---|
| 6,821,784 B1 * | 11/2004 | Bezabeh | ............ | G01R 33/465 436/63 |
| 7,229,770 B1 * | 6/2007 | Price | ............ | A61P 19/02 435/7.1 |
| 8,440,409 B2 * | 5/2013 | Zhang | ............ | A61P 13/08 435/7.1 |
| 2014/0051601 A1 | 2/2014 | Chinnaiyan et al. | | |
| 2014/0220613 A1 | 8/2014 | Swinnen et al. | | |
| 2014/0322354 A1 * | 10/2014 | Goel | ............ | A61B 1/31 435/6.12 |
| 2017/0010269 A1 | 1/2017 | Pennington et al. | | |
| 2017/0299594 A1 | 10/2017 | Depinho et al. | | |

FOREIGN PATENT DOCUMENTS

JP    2012178990 A  *  9/2012  ......... C12Q 1/6886

OTHER PUBLICATIONS

Morrissey et al., Proteomics Clin. Appl, 2013, 7: 316-326.*
Stephenson et al., J Clin. Oncol. 2007, 25(15): 2035-2041.*
Takeda et al., Surgery, 2007, 141(1): 124-125.*
Ni et al., BBRC, 2017, 486: 607-612.*
English translation of JP-2012178990-A , pub. date 2012.*
Sakane t al., Advances in Biological Regulation, 2018, 67:101-108, available online Sep. 9, 2017. (Year: 2017).*
Oloomi et al., Heliyon, 6(4): e03728: pp. 1-7. (Year: 2020).*
Ayala et al., Loss of caveolin-1 in prostate cancer stroma correlates with reduced relapse-free survival and is functionally relevant to tumour progression. J Pathol. Sep. 2013;231(1):77-87.
International Search Report and Written Opinion for Application No. PCT/US2020/016989, dated Jun. 23, 2020, 19 pages.

* cited by examiner

*Primary Examiner* — Hong Sang
(74) *Attorney, Agent, or Firm* — McCarter & English, LLP; Jill Mello

(57) ABSTRACT

Methods for diagnosing the presence of BCR in prostate cancer in a subject are provided, such methods including the detection of levels of a variety of biomarkers diagnostic of BCR. Compositions in the form of kits and panels of reagents for detecting the biomarkers of the invention are also provided.

7 Claims, 20 Drawing Sheets

Specification includes a Sequence Listing.

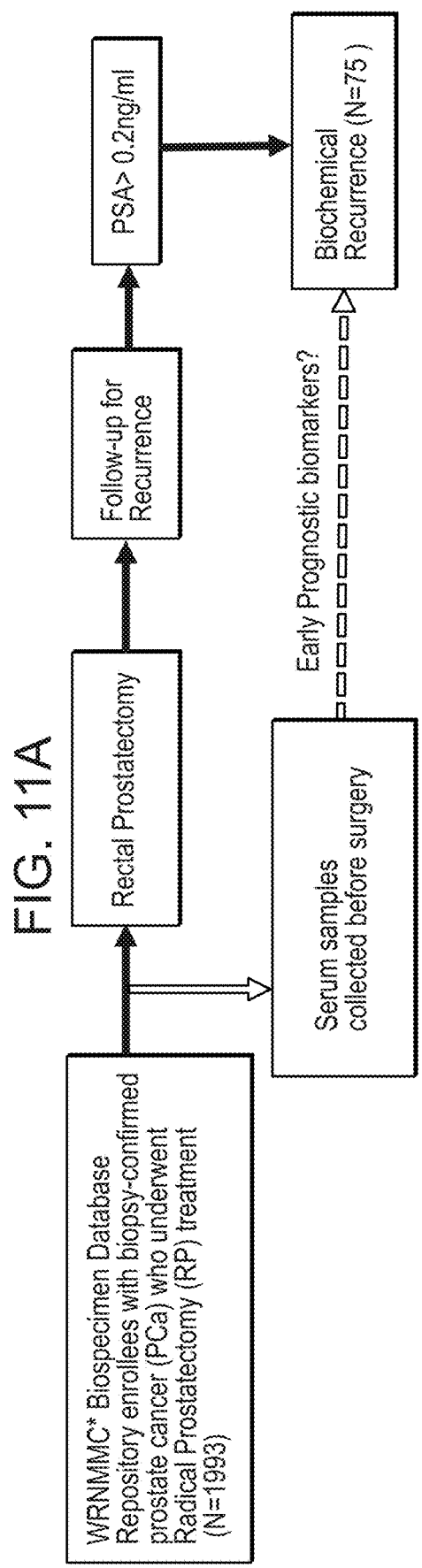

MARKERS FOR THE DIAGNOSIS OF BIOCHEMICAL RECURRENCE IN PROSTATE CANCER

REFERENCE TO RELATED APPLICATIONS

This application claims the benefit of priority to U.S. provisional application Ser. No. 62/801,963, filed on Feb. 6, 2019. The entire contents of the foregoing application are incorporated herein by reference.

GOVERNMENT SUPPORT

This invention was made with government support under HU0001-10-2-0002 awarded by the Uniformed Services University of the Health Sciences. The Government has certain rights in the invention.

SEQUENCE LISTING

The instant application contains a Sequence Listing which has been submitted electronically in ASCII format and is hereby incorporated by reference in its entirety. Said ASCII copy, created on Feb. 3, 2020, is named 119992-19203_SL.txt and is 107,684 bytes in size.

BACKGROUND

A. Field of the Invention

The invention relates generally to novel biomarkers and combinations thereof which can be used to diagnose, prognose, monitor, and treat prostate cancer and biochemical recurrence (BCR) of prostate cancer. The invention also generally relates to methods for diagnosing, prognosing, monitoring, and treating BCR of prostate cancer involving the detection of biomarkers of the invention.

B. Background of the Invention

Prostate cancer is a leading cause of male cancer-related deaths—second only to lung cancer—and afflicts one out of nine men over the age of 65. According to the American Cancer Society, 241,000 new cases of prostate cancer were reported with about 30,000 prostate cancer-related deaths that same year. Although the disease is typically diagnosed in men over the age of 65, its impact is still significant in that the average life span of a man who dies from prostate cancer is reduced by nearly a decade on average. However, if prostate cancer is discovered early, 90% of the cases may be cured with surgery. Once the tumor spreads outside the area of the prostate gland and forms distant metastases, the disease is more difficult to treat. Therefore, early detection is of critical importance to the success of interventional therapies, and for reducing the mortality rate associated with prostate cancer.

Prostate cancer typically develops in the various tissues of the prostate, a gland in the male reproductive system. Most prostate cancers are slow growing. However, there are also a significant number of cases per year of aggressive prostate cancers, in which the cancer cells may metastasize from the prostate to other parts of the body, particularly to the bones and lymph nodes. Prostate cancer may cause pain, difficulty in urinating, problems during sexual intercourse, or erectile dysfunction. Other symptoms can potentially develop during later stages of the disease.

Among men treated with prostatectomy or radiation therapy for localized prostate cancer, the state of an increasing prostate-specific antigen (PSA) level is known as biochemical recurrence (BCR). BCR can be predictive of the development of subsequent distant metastases and ultimately death, but BCR often predates other signs of clinical progression by several years (Paller, et al. (2013) Clin Adv Hematol Oncol. January; 11(1): 14-23). In clinical care, BCR often triggers secondary therapy for prostate cancer, including salvage treatment or androgen deprivation (Uchio et al. (2010) Arch Internal Med. 170(15):1390-1395). Accordingly, there is also an unmet need for improved prostate cancer screening tools that improve the accuracy of BCR detection.

SUMMARY OF THE INVENTION

The present invention is based, at least in part, on the discovery that the markers in Tables 1-5 are differentially regulated in subjects with biochemical recurrence (BCR) in prostate cancer. In particular, the invention is based on the surprising discovery that the markers in Tables 1-5 are either elevated or depressed in the serum of patients with BCR in prostate cancer. In addition, the invention is based on the discovery that tenascin C, apolipoprotein A-IV, 1-methyladenosine, phosphatidic acid (PA)-18:0/22:0 or any combination thereof is particularly useful for diagnosing the presence of BCR in prostate cancer and, thus, differentiating patients with BCR from those with disease-free survival. The invention is also based on the discovery that any one or more of these markers in further combination with one or more pathological or clinical features, e.g., tumor stage and/or Gleason score, is particularly useful for diagnosing BCR in prostate cancer and differentiating patients with BCR from those with disease-free survival.

Accordingly, in one aspect, the present invention provides methods for diagnosing the presence of BCR in prostate cancer in a subject. The methods comprise (a) detecting the level of a BCR marker in a biological sample from the subject, wherein the BCR marker comprises one or more markers selected from Tables 1-5; and (b) comparing the level of the BCR marker in the biological sample with a predetermined threshold value; wherein the level of the BCR marker above or below the predetermined threshold value indicates a diagnosis that BCR is present in the subject. In some embodiments, the BCR marker comprises one or more of tenascin C, phosphatidic acid (PA)-18:0/22:0, 1-methyladenosine, and apolipoprotein A-IV.

In some embodiments, one or more pathological or clinical features, e.g., tumor stage and/or Gleason score, or both tumor stage and Gleason score, of the subject, are determined.

In some embodiments, tumor stage T3/T4 is associated with BCR. In some embodiments, as used in the methods of the invention, the tumor stage, e.g., T stage T3/T4, alone or in combination with one or more additional clinical features or parameters (such as Gleason score), is used as a prognostic marker in combination with one or more molecular markers described herein, for example, tenascin C, apolipoprotein A-IV, 1-methyladenosine, PA-18:0/22:0, or any combination thereof, to determine the likelihood of BCR in a subject.

In some embodiments, Gleason score is associated with BCR. In some embodiments, patients having a Gleason score of 8-10 have a higher risk for BCR. In some embodiments, patients having a Gleason score of 7 have a moderate risk for BCR. In some embodiments, patients having a Gleason score of 6 or less have a minimal risk for BCR. In some embodiments, the Gleason score, alone or in combination with one or more additional clinical features or parameters (such as tumor stage), is used as a prognostic marker in combination with one or more molecular markers described herein, for example, tenascin C, apolipoprotein A-IV, 1-methyladenosine, PA-18:0/22:0, or any combination thereof, to determine the likelihood of BCR in a subject.

In some embodiments, one or more of (i) a tumor stage of T3/T4 or (ii) a Gleason score of greater than or equal to Gleason score 7, indicates a diagnosis that BCR is present in the subject.

In some embodiments, one or more of (i) a tumor stage of T3/T4 or (ii) a Gleason score of greater than or equal to Gleason score 8, indicates a diagnosis that BCR is present in the subject.

In some embodiments, one or more of (i) a tumor stage of T3/T4 or (ii) a Gleason score of greater than or equal to Gleason score 9, indicates a diagnosis that BCR is present in the subject.

In some embodiments of the foregoing aspects, the biological sample is selected from the group consisting of blood, serum, plasma, urine, organ tissue, biopsy tissue, and seminal fluid.

In some embodiments of the foregoing aspects, the organ tissue or biopsy tissue is prostate tissue.

In some embodiments of the foregoing aspects, the BCR marker comprises at least two or more markers, wherein each of the two of more markers are selected from the proteins set forth in Table 1, the metabolites set forth in Table 2, the signaling lipids set forth in Table 3 and the structural lipids set forth in Table 4. In some embodiments of the foregoing aspects, the BCR marker comprises at least two or more markers, wherein each of the two of more markers are selected from the combination of markers (proteins, metabolites, signaling lipids, and/or structural lipids) set forth in Table 5. In some embodiments, the BCR marker comprises one or more of tenascin C, phosphatidic acid (PA)-18:0/22:0, 1-methyladenosine, and apolipoprotein A-IV.

In some embodiments of the foregoing aspects, the BCR marker is a protein selected from Table 1.

In some embodiments of the foregoing aspects, the BCR marker is a metabolite selected from Table 2.

In some embodiments of the foregoing aspects, the BCR marker is a signaling lipid selected from Table 3.

In some embodiments of the foregoing aspects, the BCR marker is a structural lipid selected from Table 4.

In some embodiments of the foregoing aspects, the BCR marker is selected from Table 5. In some embodiments, the BCR marker comprises one or more of tenascin C, phosphatidic acid (PA)-18:0/22:0, 1-methyladenosine, and apolipoprotein A-IV.

In some embodiments, the marker, e.g., a BCR marker, comprises one or more of the protein markers listed in Table 1 having a Rank A and/or Rank B. For example, in one embodiment, the markers comprise one or more of tenascin C, apolipoprotein A-IV, Poliovirus receptor and Coagulation factor XIII A chain. In one embodiment, tenascin C, apolipoprotein A-IV, Poliovirus receptor and Coagulation factor XIII A chain have a combined predictive diagnostic value (AUC) of 0.731 for BCR patients. In another embodiment, one or more of the markers are Poliovirus receptor and Coagulation factor XIII A chain. In one embodiment, Poliovirus receptor and Coagulation factor XIII A chain have a combined predictive diagnostic value (AUC) of 0.621 for BCR patients. In another embodiment, one or more of the markers are tenascin C and apolipoprotein A-IV. In one embodiment, tenascin C and apolipoprotein A-IV have a combined predictive diagnostic value (AUC) of 0.686 for BCR patients.

In some embodiments, the marker, e.g., a BCR marker, comprises one or more of the metabolite markers listed in Table 2 having a Rank A and/or Rank B. For example, in one embodiment, the markers comprise one or more of 1-methyladenosine, dimethylglycine, 2-aminooctanoic acid, allantoate, 1,5-anhydrohexitol, thymidine, and glycerol. In one embodiment, 1-methyladenosine, dimethylglycine, 2-aminooctanoic acid, allantoate, 1,5-anhydrohexitol, thymidine, and glycerol have a combined predictive diagnostic value (AUC) of 0.67 for BCR patients. In another embodiment, one of more of the markers are 2-aminooctanoic acid, allantoate, 1,5-anhydrohexitol, thymidine, and glycerol. In one embodiment, 2-aminooctanoic acid, allantoate, 1,5-anhydrohexitol, thymidine, and glycerol have a combined predictive diagnostic value (AUC) of 0.667 for BCR patients. In another embodiment, one or more of the markers are 1-methyladenosine and dimethylglycine. In one embodiment, 1-methyladeno sine and dimethylglycine have a combined predictive diagnostic value (AUC) of 0.617 for BCR patients.

In some embodiments, the marker, e.g., a BCR marker, comprises one or more of the signaling lipid markers listed in Table 3 having a Rank A and/or Rank B. For example, in one embodiment, the markers comprise one or more of 5-HETrE, 9-HETE, 14-HDHA, and TxB3. In one embodiment, 5-HETrE, 9-HETE, 14-HDHA, and TxB3 have a combined predictive diagnostic value (AUC) of 0.655 for BCR patients. In another embodiment, one or more of the markers are 9-HETE, 14-HDHA, and TxB3. In one embodiment, 9-HETE, 14-HDHA, and TxB3 have a combined predictive diagnostic value (AUC) of 0.415 for BCR patients. In another embodiment, the marker is 5-HETrE and has a predictive diagnostic value (AUC) of 0.538 for BCR patients.

In some embodiments, the marker, e.g., a BCR marker, comprises one or more of the structural lipid markers listed in Table 4 having a Rank A and/or Rank B. For example, in one embodiment, the markers comprise one or more of PA-18:0/22:0, AC-18:2-OH, and PS-18:0/22:3. In one embodiment, PA-18:0/22:0, AC-18:2-OH, and PS-18:0/22:3 have a combined predictive diagnostic value (AUC) of 0.651 for BCR patients. In another embodiment, one or more of the markers are AC-18:2-OH and PS-18:0/22:3. In one embodiment, AC-18:2-OH and PS-18:0/22:3 have a combined predictive diagnostic value (AUC) of 0.634 for BCR patients. In another embodiment, the marker is PA-18:0/22:0 and has a predictive diagnostic value (AUC) of 0.617 for BCR patients.

In some embodiments, the marker, e.g., a BCR marker, comprises one or more of the protein markers listed in Table 5 having a Rank A and/or Rank B. For example, in one embodiment, the markers comprise one or more of tenascin C, phosphatidic acid (PA)-18:0/22:0, 1-methyladenosine, and apolipoprotein A-IV. In one embodiment, tenascin C, PA-18:0/22:0, 1-methyladeno sine, and apolipoprotein A-IV have a combined predictive diagnostic value (AUC) of 0.784 for BCR patients. In another embodiment, one or more of the markers are 1-methyladenosine and apolipoprotein A-IV. In one embodiment, 1-methyladenosine and apolipoprotein A-IV have a combined predictive diagnostic value (AUC) of 0.647 for BCR patients. In another embodiment, one or more of the markers are tenascin C and PA-18:0/22:0.

In one embodiment, tenascin C and PA-18:0/22:0 have a combined predictive diagnostic value (AUC) of 0.712 for BCR patients.

In some embodiments of the foregoing aspects, the level of the BCR marker is increased when compared to the predetermined threshold value in the subject.

In some embodiments of the foregoing aspects, the level of the BCR marker is decreased when compared to the predetermined threshold value in the subject.

In some embodiments of the foregoing aspects, the BCR marker comprises one or more markers with an increased level when compared to the predetermined threshold value in the subject, and/or one or more markers with a decreased level when compared to the predetermined threshold value in the subject.

In some embodiments of the foregoing aspects, the BCR marker is selected from the group consisting of tenascin C, apolipoprotein A-IV, poliovirus receptor, thrombospondin-4, mimecan, hypoxia up-regulated protein 1, interleukin-18-binding protein, coagulation factor VII, SH3 domain-binding glutamic acid-rich-like protein 3, follistatin-related protein 1, CD109 antigen, insulin-like growth factor-binding protein 7, complement component C7, 1-methyladeno sine, dimethylglycine, 2-aminooctanoic acid, allantoate, 1,5-anhydrohexitol, glycerol, guanidinebutyric acid, threonine, hydroxyproline, glutamic acid, oxo-octadecanoic acid, proline, uric acid, ribosylimidazoleacetic acid, 2-hydroxyglutarate, acetyllysine, 5-HETrE, TxB3, 20-HETE, LTB4, AC-18:2-OH, AC-16:1-OH, PG-18:3/20:1, PC-34:4, PE-40:4, GLYCOLIPID-D18:0/22:4-DIHEX, GLYCOLIPID-D18:2/22:0-TRIHEX, GLYCOLIPID-D18:1/24:0-TRIHEX, LPC-16:1, PG-22:0/22:6, FFA-18:3.

In some embodiments of the foregoing aspects, the BCR marker is selected from the group consisting of apolipoprotein F, coagulation factor XIII A chain, metalloproteinase inhibitor 2, fibrinogen beta chain, creatine kinase M-type, histone H3.3C, 78 kDa glucose-regulated protein, thymidine, glucose, tartaric acid, guanine, 9-HETE, 14-HDHA, 12-HEPE, 11-HEPE, PA-18:0/22:0, PS-18:0/22:3, TAG-58:7+NH4, PA-18:0/22:2, CE-22:6+NH4, DAG-42:6+NH4, PI-18:2/20:0, SM-D18:2/20:0, and PG-16:1/20:0.

In some embodiments, the BCR markers further comprise one or more pathological or clinical features, e.g., tumor stage and/or Gleason score, or both tumor stage and Gleason score.

In some embodiments, tumor stage T3/T4 is associated with BCR. In some embodiments, as used in the methods of the invention, the tumor stage, e.g., T stage T3/T4, alone or in combination with one or more additional clinical features or parameters (such as Gleason score), is used as a prognostic marker in combination with one or more molecular markers described herein, for example, tenascin C, apolipoprotein A-IV, 1-methyladenosine, PA-18:0/22:0, or any combination thereof, to determine the likelihood of BCR in a subject.

In some embodiments, Gleason score is associated with BCR. In some embodiments, patients having a Gleason score of 8-10 have a higher risk for BCR. In some embodiments, patients having a Gleason score of 7 have a moderate risk for BCR. In some embodiments, patients having a Gleason score of 6 or less have a minimal risk for BCR. In some embodiments, the Gleason score, alone or in combination with one or more additional clinical features or parameters (such as tumor stage), is used as a prognostic marker in combination with one or more molecular markers described herein, for example, tenascin C, apolipoprotein A-IV, 1-methyladenosine, PA-18:0/22:0, or any combination thereof, to determine the likelihood of BCR in a subject.

In some embodiments of the foregoing aspects, the level of the BCR marker is detected by HPLC/UV-Vis spectroscopy, enzymatic analysis, mass spectrometry, NMR, immunoassay, ELISA, or any combination thereof.

In some embodiments of the foregoing aspects, the level of the BCR marker is detected by determining the level of its corresponding mRNA in the biological sample.

In some embodiments of the foregoing aspects, the method further comprises detecting the level of one or more additional markers of BCR.

In some embodiments of the foregoing aspects, the one or more additional markers of BCR is prostate specific antigen (PSA).

In some embodiments of the foregoing aspects, the method further comprises administering a therapeutic anti-cancer treatment where the diagnosis indicates the presence of BCR in the subject.

In some embodiments of the foregoing aspects, the anti-cancer treatment is selected from the group consisting of (a) radiation therapy, (b) chemotherapy, (c) surgery, (d) hormone therapy, (e) antibody therapy, (f) immunotherapy, (g) cytokine therapy, (h) growth factor therapy, and (i) any combination of (a)-(h).

In some embodiments of the foregoing aspects, the methods further comprise selecting a subject suspected of having or being at risk of having BCR.

In some embodiments of the foregoing aspects, the methods further comprise obtaining a biological sample from a subject suspected of having or being at risk of having BCR In another aspect, the present invention provides methods for identifying a subject as being at an increased risk for developing BCR, comprising: (a) detecting the level of a BCR marker in a biological sample from the subject, wherein the BCR marker comprises one or more markers selected from Tables 1-5; and (b) comparing the level of the BCR marker in the biological sample with a predetermined threshold value; wherein the level of the BCR marker above or below the predetermined threshold value indicates that the subject is being at an increased risk for developing BCR.

In some embodiments of the foregoing aspects, the biological sample is selected from the group consisting of blood, serum, plasma, urine, organ tissue, biopsy tissue, and seminal fluid. In some embodiments of the foregoing aspects, the organ tissue or biopsy tissue is prostate tissue.

In some embodiments of the foregoing aspects, the BCR marker comprises at least two or more markers, wherein each of the two of more markers are selected from the proteins set forth in Table 1, the metabolites set forth in Table 2, the signaling lipids set forth in Table 3, the structural lipids set forth in Table 4, or the markers (proteins, metabolites, signaling lipids, and/or structural lipids) set forth in Table 5.

In some embodiments of the foregoing aspects, the BCR marker is a protein selected from Table 1.

In some embodiments of the foregoing aspects, the BCR marker is a metabolite selected from Table 2.

In some embodiments of the foregoing aspects, the BCR marker is a signaling lipid selected from Table 3.

In some embodiments of the foregoing aspects, the BCR marker is a structural lipid selected from Table 4.

In some embodiments of the foregoing aspects, the BCR marker is a marker selected from Table 5. In some embodiments, the BCR marker comprises one or more of tenascin C, phosphatidic acid (PA)-18:0/22:0, 1-methyladenosine, and apolipoprotein A-IV.

In some embodiments of the foregoing aspects, the level of the BCR marker is increased when compared to the predetermined threshold value in the subject.

In some embodiments of the foregoing aspects, the level of the BCR marker is decreased when compared to the predetermined threshold value in the subject.

In some embodiments of the foregoing aspects, the BCR marker comprises one or more markers with an increased level when compared to the predetermined threshold value in the subject, and/or one or more markers with a decreased level when compared to the predetermined threshold value in the subject.

In some embodiments of the foregoing aspects, the BCR marker is selected from the group consisting of tenascin C, apolipoprotein A-IV, poliovirus receptor, thrombospondin-4, mimecan, hypoxia up-regulated protein 1, interleukin-18-binding protein, coagulation factor VII, SH3 domain-binding glutamic acid-rich-like protein 3, follistatin-related protein 1, CD109 antigen, insulin-like growth factor-binding protein 7, complement component C7, 1-methyladenosine, dimethylglycine, 2-aminooctanoic acid, allantoate, 1,5-anhydrohexitol, glycerol, guanidinebutyric acid, threonine, hydroxyproline, glutamic acid, oxo-octadecanoic acid, proline, uric acid, ribosylimidazoleacetic acid, 2-hydroxyglutarate, acetyllysine, 5-HETrE, TxB3, 20-HETE, LTB4, AC-18:2-OH, AC-16:1-OH, PG-18:3/20:1, PC-34:4, PE-40:4, GLYCOLIPID-D18:0/22:4-DIHEX, GLYCOLIPID-D18:2/22:0-TRIHEX, GLYCOLIPID-D18:1/24:0-TRIHEX, LPC-16:1, PG-22:0/22:6, FFA-18:3

In some embodiments of the foregoing aspects, the BCR marker is selected from the group consisting of apolipoprotein F, coagulation factor XIII A chain, metalloproteinase inhibitor 2, fibrinogen beta chain, creatine kinase M-type, histone H3.3C, 78 kDa glucose-regulated protein, thymidine, glucose, tartaric acid, guanine, 9-HETE, 14-HDHA, 12-HEPE, 11-HEPE, PA-18:0/22:0, PS-18:0/22:3, TAG-58:7+NH4, PA-18:0/22:2, CE-22:6+NH4, DAG-42:6+NH4, PI-18:2/20:0, SM-D18:2/20:0, and PG-16:1/20:0.

In some embodiments, the BCR markers further comprise one or more pathological or clinical features, e.g., tumor stage and/or Gleason score, or both tumor stage and Gleason score.

In some embodiments of the foregoing aspects, the level of the BCR marker is detected by HPLC/UV-Vis spectroscopy, enzymatic analysis, mass spectrometry, NMR, immunoassay, ELISA, or any combination thereof.

In some embodiments of the foregoing aspects, the level of the BCR marker is detected by determining the level of its corresponding mRNA in the biological sample.

In some embodiments of the foregoing aspects, the method further comprises detecting the level of one or more additional markers of BCR.

In some embodiments of the foregoing aspects, the one or more additional markers of BCR is prostate specific antigen (PSA).

In some embodiments, the one or more additional markers of BCR is one or more pathological or clinical features, e.g., tumor stage and/or Gleason score, or both tumor stage and Gleason score.

In some embodiments of the foregoing aspects, the method further comprises administering a therapeutic anti-cancer treatment to the subject based on the prognosis.

In some embodiments of the foregoing aspects, the anti-cancer treatment is selected from the group consisting of (a) radiation therapy, (b) chemotherapy, (c) surgery, (d) hormone therapy, (e) antibody therapy, (f) immunotherapy, (g) cytokine therapy, (h) growth factor therapy, and (i) any combination of (a)-(h).

In yet another aspect, the invention provides a method for monitoring BCR in a subject, the method comprises (1) detecting the level of a BCR marker in a first biological sample obtained at a first time from the subject having BCR, wherein the BCR marker comprises one or more markers selected from Tables 1-5; (2) detecting the level of the BCR marker in a second biological sample obtained from the subject at a second time, wherein the second time is later than the first time; and (3) comparing the level of the BCR marker in the second sample with the level of the BCR marker in the first sample; wherein a change in the level of the BCR marker is indicative of a change in BCR status in the subject.

In some embodiments of the foregoing aspects, the biological sample is selected from the group consisting of blood, serum, plasma, urine, organ tissue, biopsy tissue, and seminal fluid.

In some embodiments of the foregoing aspects, steps (1) and (2) further comprise determining the amount of one or more additional markers of BCR.

In some embodiments of the foregoing aspects, the subject is actively treated for prostate cancer or BCR prior to obtaining the second sample.

In some embodiments of the foregoing aspects, an increased or decreased level of the BCR marker in the second biological sample as compared to the first biological sample is indicative of progression of the BCR in the subject.

In some embodiments of the foregoing aspects, an increased, decreased, or equivalent level of the BCR marker in the second biological sample as compared to the first biological sample is indicative of non-progression of the BCR in the subject.

In some embodiments of the foregoing aspects, an increased level of the BCR marker selected from the group consisting of tenascin C, apolipoprotein A-IV, poliovirus receptor, thrombospondin-4, mimecan, hypoxia up-regulated protein 1, interleukin-18-binding protein, coagulation factor VII, SH3 domain-binding glutamic acid-rich-like protein 3, follistatin-related protein 1, CD109 antigen, insulin-like growth factor-binding protein 7, complement component C7, 1-methyladenosine, dimethylglycine, 2-aminooctanoic acid, allantoate, 1,5-anhydrohexitol, glycerol, guanidinebutyric acid, threonine, hydroxyproline, glutamic acid, oxo-octadecanoic acid, proline, uric acid, ribosylimidazoleacetic acid, 2-hydroxyglutarate, acetyllysine, 5-HETrE, TxB3, 20-HETE, LTB4, AC-18:2-OH, AC-16:1-OH, PG-18:3/20:1, PC-34:4, PE-40:4, GLYCOLIPID-D18:0/22:4-DIHEX, GLYCOLIPID-D18:2/22:0-TRIHEX, GLYCOLIPID-D18:1/24:0-TRIHEX, LPC-16:1, PG-22:0/22:6, FFA-18:3 in the second biological sample as compared to the first biological sample is indicative of progression of the BCR in the subject.

In some embodiments of the foregoing aspects, a decreased level of the BCR marker selected from the group consisting ofapolipoprotein F, coagulation factor XIII A chain, metalloproteinase inhibitor 2, fibrinogen beta chain, creatine kinase M-type, histone H3.3C, 78 kDa glucose-regulated protein, thymidine, glucose, tartaric acid, guanine, 9-HETE, 14-HDHA, 12-HEPE, 11-HEPE, PA-18:0/22:0, PS-18:0/22:3, TAG-58:7+NH4, PA-18:0/22:2, CE-22:6+NH4, DAG-42:6+NH4, PI-18:2/20:0, SM-D18:2/20:0, and PG-16:1/20:0 in the second biological sample as compared to the first biological sample is indicative of progression of the BCR in the subject.

In yet another aspect, the present invention provides methods for identifying an agent that modulates BCR progression, comprising: (a) contacting a cell with a test compound, and (b) determining the expression and/or activity of a BCR marker, wherein the BCR marker comprises one or more markers selected from Tables 1-5.

In some embodiments of the foregoing aspects, the cell is a prostate cell.

In some embodiments of the foregoing aspects, the cell is engineered to produce the BCR marker selected from Tables 1-5.

In some embodiments of the foregoing aspects, the at least one test compound is selected from the group consisting of small molecules, antibodies, and nucleic acid inhibitors.

In another aspect, the present invention also provides methods of treating BCR in a subject, comprising administering to the subject a modulator of a BCR marker, wherein the BCR marker comprises one or more markers selected from Tables 1-5.

In some embodiments of the foregoing aspects, the modulator increases the level or activity of the BCR marker.

In some embodiments of the foregoing aspects, the BCR marker comprises one or more markers selected from the group consisting of tenascin C, apolipoprotein A-IV, poliovirus receptor, thrombospondin-4, mimecan, hypoxia up-regulated protein 1, interleukin-18-binding protein, coagulation factor VII, SH3 domain-binding glutamic acid-rich-like protein 3, follistatin-related protein 1, CD109 antigen, insulin-like growth factor-binding protein 7, complement component C7, 1-methyladenosine, dimethylglycine, 2-aminooctanoic acid, allantoate, 1,5-anhydrohexitol, glycerol, guanidinebutyric acid, threonine, hydroxyproline, glutamic acid, oxo-octadecanoic acid, proline, uric acid, ribosylimidazoleacetic acid, 2-hydroxyglutarate, acetyllysine, 5-HETrE, TxB3, 20-HETE, LTB4, AC-18:2-OH, AC-16:1-OH, PG-18:3/20:1, PC-34:4, PE-40:4, GLYCOLIPID-D18:0/22:4-DIHEX, GLYCOLIPID-D18:2/22:0-TRIHEX, GLYCOLIPID-D18:1/24:0-TRIHEX, LPC-16:1, PG-22:0/22:6, FFA-18:3.

In some embodiments of the foregoing aspects, the modulator decreases the level or activity of the BCR marker.

In some embodiments of the foregoing aspects, the BCR marker is selected from the group consisting of apolipoprotein F, coagulation factor XIII A chain, metalloproteinase inhibitor 2, fibrinogen beta chain, creatine kinase M-type, histone H3.3C, 78 kDa glucose-regulated protein, thymidine, glucose, tartaric acid, guanine, 9-HETE, 14-HDHA, 12-HEPE, 11-HEPE, PA-18:0/22:0, PS-18:0/22:3, TAG-58:7+NH4, PA-18:0/22:2, CE-22:6+NH4, DAG-42:6+NH4, PI-18:2/20:0, SM-D18:2/20:0, and PG-16:1/20:0.

In another aspect, the present invention also provides kits for detecting a BCR marker in a biological sample from a subject having, suspected of having, or at risk for having BCR, comprising one or more reagents for measuring the level of the BCR marker in the biological sample from the subject, wherein the BCR marker comprises one or more markers selected from Tables 1-5 and a set of instructions for measuring the level of the BCR marker. In some embodiments, the BCR marker comprises one or more of tenascin C, phosphatidic acid (PA)-18:0/22:0, 1-methyladenosine, and apolipoprotein A-IV.

In some embodiments of the foregoing aspects, the reagent is an antibody.

In some embodiments of the foregoing aspects, the kit further comprises a means to detect the antibody.

In some embodiments of the foregoing aspects, the reagent is an oligonucleotide that is complementary to the corresponding mRNA of the BCR marker.

In some embodiments of the foregoing aspects, the instructions set forth an immunoassay, ELISA, or mass spectrometry assay for detecting the level of the BCR marker in the biological sample.

In some embodiments of the foregoing aspects, the instructions set forth an amplification reaction for assaying the level of the mRNA in the biological sample corresponding to the BCR marker.

In some embodiments of the foregoing aspects, the instructions set forth a hybridization assay for detecting the level of the mRNA in the biological sample corresponding to the BCR marker.

In some embodiments of the foregoing aspects, the instructions further set forth comparing the level of the BCR marker in the biological sample from the subject to a predetermined threshold value of the BCR marker.

In some embodiments of the foregoing aspects, the instructions further set forth making a diagnosis of BCR based on the level of the BCR marker in the biological sample from the subject as compared to a predetermined threshold value of the BCR marker.

In another aspect, the present invention also provides panels for use in a method of monitoring the treatment of BCR, the panel comprising one or more detection reagents, wherein each detection reagent is specific for the detection of a BCR marker, wherein the BCR marker comprises one or more markers selected from Tables 1-5. In some embodiments, the BCR marker comprises one or more of tenascin C, phosphatidic acid (PA)-18:0/22:0, 1-methyladeno sine, and apolipoprotein A-IV.

In some embodiments of the foregoing aspects, the BCR marker comprises at least two or more markers, wherein each of the two of more markers are selected from the proteins set forth in Table 1, the metabolites set forth in Table 2, the signaling lipids set forth in Table 3, the structural lipids set forth in Table 4, or the combination of one or more protein, metabolite, signaling lipid, and/or structural lipid markers set forth in Table 5. In some embodiments, the BCR marker comprises one or more of tenascin C, phosphatidic acid (PA)-18:0/22:0, 1-methyladeno sine, and apolipoprotein A-IV.

In some embodiments of the foregoing aspects, the invention provides a kit comprising the foregoing panel and a set of instructions for obtaining diagnostic information based on a level of the BCR marker.

In some embodiments of the foregoing aspects, the level of the BCR marker is increased when compared to a predetermined threshold value.

In some embodiments of the foregoing aspects, the level of the BCR marker is decreased when compared to a predetermined threshold value.

In some embodiments of the foregoing aspects, the BCR marker comprises one or more markers with an increased level when compared to a predetermined threshold value, and/or one or more markers with a decreased level when compared to a predetermined threshold value.

In some embodiments of the foregoing aspects, the BCR marker is selected from the group consisting of tenascin C, apolipoprotein A-IV, poliovirus receptor, thrombospondin-4, mimecan, hypoxia up-regulated protein 1, interleukin-18-binding protein, coagulation factor VII, SH3 domain-binding glutamic acid-rich-like protein 3, follistatin-related protein 1, CD109 antigen, insulin-like growth factor-binding protein 7, complement component C7, 1-methyladenosine, dimethylglycine, 2-aminooctanoic acid, allantoate, 1,5-anhydrohexitol, glycerol, guanidinebutyric acid, threonine, hydroxyproline, glutamic acid, oxo-octadecanoic acid, proline, uric acid, ribosylimidazoleacetic acid, 2-hydroxyglutarate, acetyllysine, 5-HETrE, TxB3, 20-HETE, LTB4, AC-18:2-OH, AC-16:1-OH, PG-18:3/20:1, PC-34:4, PE-40: 4, GLYCOLIPID-D18:0/22:4-DIHEX, GLYCOLIPID-D18: 2/22:0-TRIHEX, GLYCOLIPID-D18:1/24:0-TRIHEX, LPC-16:1, PG-22:0/22:6, FFA-18:3.

In some embodiments of the foregoing aspects, the BCR marker is selected from the group consisting of apolipoprotein F, coagulation factor XIII A chain, metalloproteinase inhibitor 2, fibrinogen beta chain, creatine kinase M-type, histone H3.3C, 78 kDa glucose-regulated protein, thymidine, glucose, tartaric acid, guanine, 9-HETE, 14-HDHA, 12-HEPE, 11-HEPE, PA-18:0/22:0, PS-18:0/22:3, TAG-58: 7+NH4, PA-18:0/22:2, CE-22:6+NH4, DAG-42:6+NH4, PI-18:2/20:0, SM-D18:2/20:0, and PG-16:1/20:0.

In some embodiments of the foregoing aspects, the BCR marker comprises one or more of tenascin C, phosphatidic acid (PA)-18:0/22:0, 1-methyladenosine, and apolipoprotein A-IV.

BRIEF DESCRIPTION OF THE DRAWINGS

FIGS. 11A-11B illustrate the prostate cancer cohort design and biomarker strategy described herein (11A) and the OMIC platform approach for integrating multiomics using statistical and artificial intelligence strategies for biomarker discovery (11B).

FIGS. 14A-4B are graphical representations of the results of two ROC analyses demonstrating the cumulative sensitivity and specificity of four markers (tenascin C, apolipoprotein A-IV, 1-methyladenosine, and PA-18:0/22:0) with an AUC=0.78, OR (CI)=6.56 (2.98, 14.40) (14A) selected as biomarkers for a diagnostic/prognostic test; and the combined sensitivity and specificity of four markers along with the pathological/clinical features increasing the AUC=0.89 and OR (CI)=12.47 (4.85, 32.05) (14B) representing an enhanced diagnostic/prognostic test.

DETAILED DESCRIPTION OF THE INVENTION

A. Overview

Figure 1:
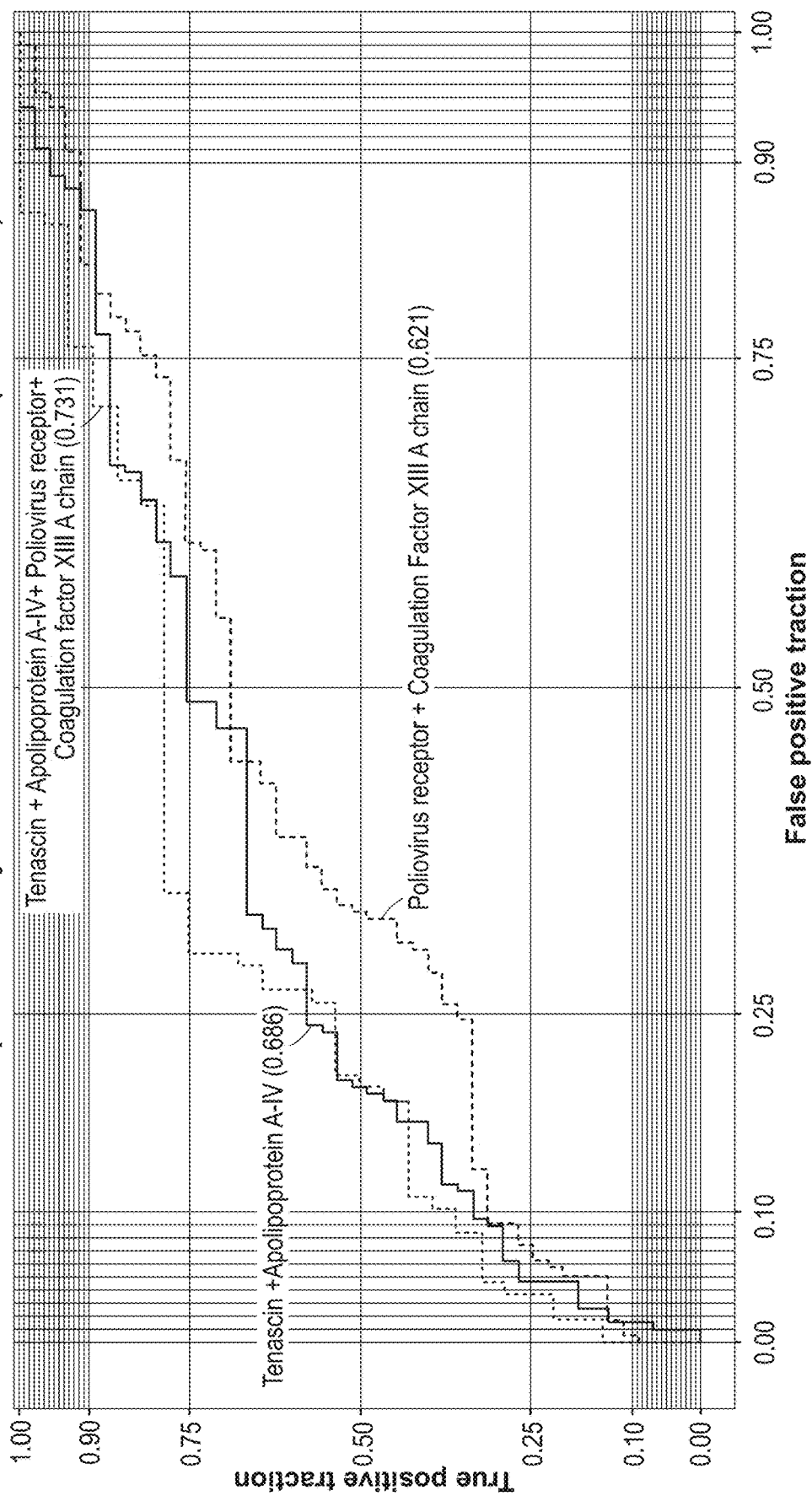
FIG. 1 depicts three ROC curves for three sets of proteomics markers (Rank A, Rank B, and Rank A+B), identified in Table 1.

Among men treated with prostatectomy or radiation therapy for localized prostate cancer, the state of an increasing prostate-specific antigen (PSA) level is known as biochemical recurrence (BCR). BCR can be predictive of the development of subsequent distant metastases and ultimately death, but often predates other signs of clinical progression by several years (Paller, et al. (2013) Clin Adv Hematol Oncol. January; 11(1): 14-23). BCR is widely used as an early end point to assess treatment success and frequently prompts the initiation of secondary therapy. Accordingly, there is a need for efficient, accurate, and rapid molecular prognosis and diagnosis means for the prediction and early detection of BCR in prostate cancer. The present invention addresses this need by providing the use of biomarkers, i.e., one or more markers selected from Tables 1-5, for example, tenascin C, apolipoprotein A-IV, 1-methyladenosine, PA-18:0/22:0, or any combination of two, three, four or more thereof, for the accurate and reliable detection of BCR in prostate cancer. In addition, the invention provides for the use of at least one of these markers, e.g., at least one, two, three, or four or more markers, in combination with pathological or clinical features such as tumor stage and/or Gleason score, for the accurate and reliable detection of BCR in prostate cancer.

As presently described herein, the invention at hand is based, at least in part, on the discovery that the one or more markers selected from Tables 1-5, for example, tenascin C, apolipoprotein A-IV, 1-methyladenosine, PA-18:0/22:0, or any combination thereof, alone or in combination with one or more pathological or clinical features, e.g., tumor stage and/or Gleason score, are differentially regulated in subjects having BCR, and serve as useful biomarkers of BCR in prostate cancer. In particular, the invention is based on the surprising discovery that the markers in Tables 1-5, for example, tenascin C, apolipoprotein A-IV, 1-methyladenosine, PA-18:0/22:0, or any combination thereof, alone or in combination with one or more pathological or clinical features, e.g., tumor stage and/or Gleason score, are differentially expressed, e.g., either increased or decreased as compared to a control, in the serum of patients with BCR in prostate cancer, and are thus useful in the diagnosis and/or prognosis of BCR in prostate cancer.

Accordingly, the invention provides methods for diagnosing and/or monitoring (e.g., monitoring of disease progression or treatment) and/or prognosing an oncological disease state, e.g., BCR in prostate cancer, in a subject.

In one embodiment, these one or more markers selected from Tables 1-5, for example, tenascin C, apolipoprotein A-IV, 1-methyladenosine, PA-18:0/22:0, or any combination thereof, alone or in combination with one or more pathological or clinical features, e.g., tumor stage and/or Gleason score, can serve as useful diagnostic biomarkers to predict and/or detect the presence of BCR in prostate cancer in a subject. In another embodiment, these one or more markers, e.g., tenascin C, apolipoprotein A-IV, 1-methyladenosine, PA-18:0/22:0, or any combination thereof, alone or in combination with one or more pathological or clinical features, e.g., tumor stage and/or Gleason score, can serve as useful prognostic biomarkers, serving to inform on the likely development or progression of BCR in prostate cancer in a subject with or without treatment. In still another embodiment, these one or more markers, e.g., tenascin C, apolipoprotein A-IV, 1-methyladenosine, PA-18:0/22:0, or any combination thereof, alone or in combination with one or more pathological or clinical features, e.g., tumor stage and/or Gleason score, can serve as useful predictive biomarkers for helping to assess the likely response of BCR in prostate cancer to a particular treatment.

Accordingly, the invention provides methods that use the one or more markers selected from Tables 1-5, for example, tenascin C, apolipoprotein A-IV, 1-methyladenosine, PA-18:0/22:0, or any combination thereof, alone or in combination with one or more pathological or clinical features, e.g., tumor stage and/or Gleason score, in the diagnosis of BCR in prostate cancer (e.g., prediction of the presence of prostate cancer in a subject), in the prognosis of BCR in prostate cancer (e.g., prediction of the development of BCR in prostate cancer, or the course or outcome of BCR in prostate cancer with or without treatment), and in the assessment of therapies intended to treat BCR in prostate cancer (e.g., the one or more markers selected from Tables 1-5, for example, tenascin C, apolipoprotein A-IV, 1-methyladenosine, PA-18:0/22:0, or any combination thereof, alone or in combination with one or more pathological or clinical features, e.g., tumor stage and/or Gleason score, as a theragnostic or predictive marker).

The following is a detailed description of the invention provided to aid those skilled in the art in practicing the present invention. Those of ordinary skill in the art may make modifications and variations in the embodiments described herein without departing from the spirit or scope of the present invention. Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, figures and other references mentioned herein are expressly incorporated by reference in their entirety.

Although any methods and materials similar or equivalent to those described herein can also be used in the practice or testing of the present invention, the preferred methods and materials are now described. All publications mentioned herein are incorporated herein by reference to disclose and described the methods and/or materials in connection with which the publications are cited.

B. Definitions

Unless defined otherwise, all technical and scientific terms used herein have the meaning commonly understood by a person skilled in the art to which this invention belongs. The following references, the entire disclosures of which are incorporated herein by reference, provide one of skill with a general definition of many of the terms (unless defined otherwise herein) used in this invention: Singleton et al., Dictionary of Microbiology and Molecular Biology ($2^{nd}$ ed. 1994); The Cambridge Dictionary of Science and Technology (Walker ed., 1988); The Glossary of Genetics, $5^{th}$ Ed., R. Rieger et al. (eds.), Springer Verlag (1991); and Hale & Marham, the Harper Collins Dictionary of Biology (1991). Generally, the procedures of molecular biology methods described or inherent herein and the like are common methods used in the art. Such standard techniques can be found in reference manuals such as for example Sambrook et al., (2000, Molecular Cloning—A Laboratory Manual, Third Edition, Cold Spring Harbor Laboratories); and Ausubel et al., (1994, Current Protocols in Molecular Biology, John Wiley & Sons, New-York).

The following terms may have meanings ascribed to them below, unless specified otherwise. However, it should be understood that other meanings that are known or understood by those having ordinary skill in the art are also possible, and within the scope of the present invention. All publications, patent applications, patents, and other references mentioned herein are incorporated by reference in their entirety. In the case of conflict, the present specification, including definitions, will control. In addition, the materials, methods, and examples are illustrative only and not intended to be limiting.

As used herein, the singular forms "a", "and", and "the" include plural references unless the context clearly dictates otherwise. All technical and scientific terms used herein have the same meaning.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

As used herein, the term "amplification" refers to any known in vitro procedure for obtaining multiple copies ("amplicons") of a target nucleic acid sequence or its complement or fragments thereof. In vitro amplification refers to production of an amplified nucleic acid that may contain less than the complete target region sequence or its complement. Known in vitro amplification methods include, e.g., transcription-mediated amplification, replicase-mediated amplification, polymerase chain reaction (PCR) amplification, ligase chain reaction (LCR) amplification and strand-displacement amplification (SDA including multiple strand-displacement amplification method (MSDA)). Replicase-mediated amplification uses self-replicating RNA molecules, and a replicase such as Q-β-replicase (e.g., Kramer et al., U.S. Pat. No. 4,786,600). PCR amplification is well known and uses DNA polymerase, primers and thermal cycling to synthesize multiple copies of the two complementary strands of DNA or cDNA (e.g., Mullis et al., U.S. Pat. Nos. 4,683,195, 4,683,202, and 4,800,159). LCR amplification uses at least four separate oligonucleotides to amplify a target and its complementary strand by using multiple cycles of hybridization, ligation, and denaturation (e.g., EP Pat. App. Pub. No. 0 320 308). SDA is a method in which a primer contains a recognition site for a restriction endonuclease that permits the endonuclease to nick one strand of a hemimodified DNA duplex that includes the target sequence, followed by amplification in a series of primer extension and strand displacement steps (e.g., Walker et al., U.S. Pat. No. 5,422,252). Two other known strand-displacement amplification methods do not require endonuclease nicking (Dattagupta et al., U.S. Pat. Nos. 6,087,133 and 6,124,120 (MSDA)). Those skilled in the art will understand that the oligonucleotide primer sequences of the present invention may be readily used in any in vitro amplification method based on primer extension by a polymerase. (see generally Kwoh et al., 1990, Am. Biotechnol. Lab. 8:14-25 and (Kwoh et al., 1989, Proc. Natl. Acad. Sci. USA 86, 1173-1177; Lizardi et al., 1988, BioTechnology 6:1197-1202; Malek et al., 1994, Methods Mol. Biol., 28:253-260; and Sambrook et al., 2000, Molecular Cloning—A Laboratory Manual, Third Edition, CSH Laboratories). As commonly known in the art, the oligos are designed to bind to a complementary sequence under selected conditions.

As used herein, the term "antigen" refers to a molecule, e.g., a peptide, polypeptide, protein, fragment, or other biological moiety, which elicits an antibody response in a subject, or is recognized and bound by an antibody.

As used herein, the term "BCR" or "biochemical recurrence" or "BCR in prostate cancer" refers to early disease recurrence in subjects who have received treatment for localized prostate cancer, e.g., surgery (e.g., prostatectomy) or radiation therapy. BCR generally is identified before there are signs or symptoms of either locoregional recurrence or distant metastases, but other signs and symptoms of prostate cancer may be exhibited. Depending on the type of initial local therapy, treatment options for local recurrence can include, in one embodiment, salvage radiation therapy or salvage prostatectomy (surgery). If systemic recurrence is suspected, other options include, for example, androgen deprivation therapy (ADT) via gonadotropin releasing hormone agonists or antagonists, radiation, chemotherapy, or other known prostate cancer therapies.

Detection of increasing levels of prostate specific antigen (PSA) in the subject has been used to identify BCR in a subject. (See Paller, et al. (2013) Clin Adv Hematol Oncol. January; 11(1): 14-23, the contents of which are hereby incorporated herein by reference). Gleason score has also been identified as predictive of BCR (see, for example, Buchner et al. Radiother Oncol. 2015 July; 116(1):119-24, the contents of which are hereby incorporated herein by reference). In one embodiment, BCR is indicated by a post-radical prostatectomy (RP) PSA level of ≥0.2 ng/mL followed by a successive, confirmatory PSA level ≥0.2, or the initiation of salvage radiation or hormonal therapy after a rising PSA level of ≥0.1. As described herein, BCR markers have been identified which can diagnose or predict BCR in a subject, alone or in combination with PSA or clinical BCR markers, including, but not limited to, tumor stage or Gleason score.

As used herein, the term "marker" is, in one embodiment, a biological molecule, or a panel of biological molecules, for example, tenascin C, apolipoprotein A-IV, 1-methyladenosine, PA-18:0/22:0, or any combination thereof, whose altered level in a tissue or cell as compared to its level in normal or healthy tissue or cell is associated with a disease state, such as BCR, e.g., prior to the detection of one or more symptoms associated with BCR. Examples of biomarkers include, for example, polypeptides, peptides, polypeptide fragments, proteins, antibodies, hormones, polynucleotides, RNA or RNA fragments, microRNA (miRNAs), lipids, metabolites, or polysaccharides. In a preferred embodiment, the marker is detected in a blood sample, e.g., serum or plasma. In one embodiment, the marker is detected in serum. In one embodiment, the marker is detected in plasma. In certain embodiments, the serum or plasma can be further processed to remove abundant blood proteins (e.g., albumin) or proteins that are not marker proteins prior to analysis.

The term "marker" as used herein, also includes any one or more pathological or clinical feature or parameter. For example, as described herein, a marker includes clinical parameters such as, e.g., tumor stage, Gleason score or grade, e.g., Gleason grade 1, grade 2, grade 3, grade 4, grade 5, grade 6, grade 7, grade 8, grade 9, or grade 10 prostate cancer, tumor size, age, performance status, imaging-based measures, or any clinical and/or patient-related health data, for example, data obtained from an Electronic Medical Record (e.g., collection of electronic health information about individual patients or populations relating to various types of data, such as, demographics, medical history, laboratory test results, radiology images, vital signs, personal statistics like weight, and billing information.

As used herein, the term "BCR marker" or "BCR in prostate cancer marker" is a "marker" as set forth above, which is associated with BCR in prostate cancer. As used herein, in one embodiment, a BCR marker includes one or more of the markers set forth in Tables 1-5, for example, tenascin C, apolipoprotein A-IV, 1-methyladenosine, PA-18: 0/22:0, or any combination thereof, alone or in combination with one or more pathological or clinical features, e.g., tumor stage and/or Gleason score.

Preferably, a marker of the present invention is modulated (e.g., increased or decreased level) in a biological sample from a subject or a group of subjects having a first phenotype (e.g., having a disease, e.g., BCR) as compared to a biological sample from a subject or group of subjects having a second phenotype (e.g., not having the disease, e.g., a control). A biomarker may be differentially present at any level, but is generally present at a level that is increased relative to normal or control levels by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100%, by at least 110%, by at least 120%, by at least 130%, by at least 140%, by at least 150%, or more; or is generally present at a level that is decreased relative to normal or control levels by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100% (i.e., absent). A biomarker is preferably differentially present at a level that is statistically significant (e.g., a p-value less than 0.05 and/or a q-value of less than 0.10 as determined using either Welch's T-test or Wilcoxon's rank-sum Test). As such, the difference between the level of a biomarker of the present invention and a corresponding control or reference value can be a statistically significant positive or negative value.

As used herein, the term "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "control sample" or "control," as used herein, refers to any clinically relevant comparative sample, including, for example, a sample from a healthy subject not afflicted with BCR, or a sample from a subject from an earlier time point, e.g., prior to treatment, an earlier tumor assessment time point, at an earlier stage of treatment, or prior to onset of prostate cancer. A control sample can be a purified sample, protein, and/or nucleic acid provided with a kit. Such control samples can be diluted, for example, in a dilution series to allow for quantitative measurement of levels of analytes, e.g., markers, in test samples. A control sample may include a sample derived from one or more subjects. A control sample may also be a sample made at an earlier time point from the subject to be assessed. For example, the control sample could be a sample taken from the subject to be assessed before the onset of BCR, or at an earlier stage of disease. The control sample may also be a sample from an animal model, or from a tissue or cell line derived from the animal model of BCR in prostate cancer. The level of activity or expression of one or more markers (e.g., 1, 2, 3, 4, 5, 6, 7, 8, 9, 10, 11, 12, 13, 14, 15 or more markers) in a control sample consists of a group of measurements that may be determined, e.g., based on any appropriate statistical measurement, such as, for example, measures of central tendency including average, median, or modal values. In one embodiment, "different from a control" is preferably statistically significantly different from a control.

As used herein, "changed, altered, increased or decreased as compared to a control" sample or subject is understood as having a level of the analyte or diagnostic or therapeutic indicator (e.g., marker) to be detected at a level that is statistically different, e.g., increased or decreased, as compared to a sample from a normal, untreated, or abnormal state control sample. In other words, the difference between the level of the marker in the subject and that in a corresponding control or reference is statistically significant. Change as compared to control can also include a difference in the rate of change of the level of one or more markers obtained in a series of at least two subject samples obtained over time. Determination of statistical significance is within the ability of those skilled in the art and can include any acceptable means for determining and/or measuring statistical significance, such as, for example, the number of standard deviations from the mean that constitute a positive or negative result, an increase in the detected level of a biomarker in a sample (e.g., a sample from a subject having BCR) versus a control or healthy sample, wherein the increase is above some threshold value, or a decrease in the detected level of a biomarker in a sample (e.g., a sample from a subject having BCR) versus a control or healthy sample, wherein the decrease is below some threshold value. The threshold value can be determine by any suitable means by measuring the biomarker levels in a plurality of tissues or samples known to have a disease, e.g., BCR in prostate cancer, and comparing those levels to a normal sample and calculating a statistically significant threshold value.

The term "control level" refers to an accepted or predetermined level of a marker in a subject sample. A control level can be a range of values. Marker levels can be compared to a single control value, to a range of control values, to the upper level of normal, or to the lower level of normal as appropriate for the assay.

In one embodiment, the control is a standardized control, such as, for example, a control which is predetermined using an average of the levels of expression of one or more markers from a population of subjects having no BCR. In certain embodiments, the control can be from a subject, or a population of subject, having an abnormal prostate state. For example, the control can be from a subject suffering from benign prostate hyperplasia (BPH), androgen sensitive prostate cancer, androgen insensitive or resistant prostate cancer, aggressive prostate cancer, non-aggressive prostate cancer, metastatic prostate cancer, or non-metastatic prostate cancer. It is understood that not all markers will have different levels for each of the abnormal prostate states listed. It is understood that a combination of marker levels may be most useful to distinguish between abnormal prostate states, possibly in combination with other diagnostic methods. Further, marker levels in biological samples can be compared to more than one control sample (e.g., normal, abnormal, from the same subject, from a population control). Marker levels can be used in combination with other signs or symptoms of an abnormal prostate state to provide a diagnosis for the subject.

A control can also be a sample from a subject at an earlier time point, e.g., a baseline level prior to suspected presence of disease, before the diagnosis of a disease, at an earlier assessment time point during watchful waiting, before the treatment with a specific agent (e.g., chemotherapy, hormone therapy) or intervention (e.g., radiation, surgery). In certain embodiments, a change in the level of the marker in a subject can be more significant than the absolute level of a marker, e.g., as compared to control.

As used herein, "detecting", "detection", "determining", and the like are understood to refer to an assay performed for identification of one or more markers selected from Tables 1-5. The amount of marker expression or activity detected in the sample can be none or below the level of detection of the assay or method.

As used herein, the term "DNA" or "RNA" molecule or sequence (as well as sometimes the term "oligonucleotide") refers to a molecule comprised generally of the deoxyribonucleotides or ribonucleotides, respectively, that have the following bases: adenine (A), guanine (G), cytosine (C), and thymine (T) in DNA or uracil (U) in RNA, i.e., T is replaced by uracil (U).

The terms "disorders", "diseases", and "abnormal state" are used inclusively and refer to any deviation from the normal structure or function of any part, organ, or system of the body (or any combination thereof). A specific disease is manifested by characteristic symptoms and signs, including biological, chemical, and physical changes, and is often associated with a variety of other factors including, but not limited to, demographic, environmental, employment, genetic, and medically historical factors. An early stage disease state includes a state wherein one or more physical symptoms are not yet detectable. Certain characteristic signs, symptoms, and related factors can be quantitated through a variety of methods to yield important diagnostic information. As used herein the disorder, disease, or abnormal state is an abnormal prostate state, including BCR.

As used herein, a sample obtained at an "earlier time point" is a sample that was obtained at a sufficient time in the past such that clinically relevant information could be obtained in the sample from the earlier time point as compared to the later time point. In certain embodiments, an earlier time point is at least four weeks earlier. In certain embodiments, an earlier time point is at least six weeks earlier. In certain embodiments, an earlier time point is at least two months earlier. In certain embodiments, an earlier time point is at least three months earlier. In certain embodiments, an earlier time point is at least six months earlier. In certain embodiments, an earlier time point is at least nine months earlier. In certain embodiments, an earlier time point is at least one year earlier. Multiple subject samples (e.g., 3, 4, 5, 6, 7, or more) can be obtained at regular or irregular intervals over time and analyzed for trends in changes in marker levels. Appropriate intervals for testing for a particular subject can be determined by one of skill in the art based on ordinary considerations.

The term "expression" is used herein to mean the process by which a polypeptide is produced from DNA. The process involves the transcription of the gene into mRNA and the translation of this mRNA into a polypeptide. Depending on the context in which used, "expression" may refer to the production of RNA, or protein, or both.

As used herein, "fold change ratio" or "FC ratio" refers to a change, e.g., increase or decrease, of the expression or level of a marker, e.g., one or more marker selected from Tables 1-5. In some embodiments, the FC ratio is greater than 1, which indicates an up-regulation or increase in the expression or level of the marker. In other embodiments, the FC ratio is less than 1, indicating a down-regulation or decrease in the expression or level of the marker. FC ratio can also be calculated and expressed as a Log unit. When the FC ratio is expressed as a Log FC value, a Log FC value greater than 0 is equivalent to an FC ratio greater than 1, indicating an up-regulation or increase in the expression or level of the marker. Alternatively, a Log FC value less than 0 is equivalent to an FC ratio less than 1, indicating a down-regulation or decrease in the expression or level of the marker.

As used herein, "greater predictive value" is understood as an assay that has significantly greater sensitivity and/or specificity, preferably greater sensitivity and specificity, than the test to which it is compared. The predictive value of a test can be determined using an ROC analysis. In an ROC analysis, a test that provides perfect discrimination or accuracy between normal and disease states would have an area under the curve (AUC)=1, whereas a very poor test that provides no better discrimination than random chance would have AUC=0.5. As used herein, a test with a greater predictive value will have a statistically improved AUC as compared to another assay. The assays are performed in an appropriate subject population.

A "higher level of expression", "higher level", "increased level," and the like of a marker refers to an expression level in a test sample that is greater than the standard error of the assay employed to assess expression, and is preferably at least 25% more, at least 50% more, at least 75% more, at least two, at least three, at least four, at least five, at least six, at least seven, at least eight, at least nine, or at least ten times the expression level of the marker in a control sample (e.g., sample from a healthy subject not having the marker associated disease, i.e., BCR) and preferably, the average expression level of the marker or markers in several control samples.

As used herein, the term "hybridization," as in "nucleic acid hybridization," refers generally to the hybridization of two single-stranded nucleic acid molecules having complementary base sequences, which under appropriate conditions will form a thermodynamically favored double-stranded structure. Examples of hybridization conditions can be found in the two laboratory manuals referred above (Sambrook et al., 2000, supra and Ausubel et al., 1994, supra, or further in Higgins and Hames (Eds.) "Nucleic acid hybridization, a practical approach" IRL Press Oxford, Washington D.C., (1985)) and are commonly known in the art. In the case of a hybridization to a nitrocellulose filter (or other such support like nylon), as for example in the well-known Southern blotting procedure, a nitrocellulose filter can be incubated overnight at a temperature representative of the desired stringency condition (60-65° C. for high stringency, 50-60° C. for moderate stringency and 40-45° C. for low stringency conditions) with a labeled probe in a solution containing high salt (6×SSC or 5×SSPE), 5×Denhardt's solution, 0.5% SDS, and 100 µg/ml denatured carrier DNA (e.g., salmon sperm DNA). The non-specifically binding probe can then be washed off the filter by several washes in 0.2×SSC/0.1% SDS at a temperature which is selected in view of the desired stringency: room temperature (low stringency), 42° C. (moderate stringency) or 65° C. (high stringency). The salt and SDS concentration of the washing solutions may also be adjusted to accommodate for the desired stringency. The selected temperature and salt concentration is based on the melting temperature (Tm) of the DNA hybrid. Of course, RNA-DNA hybrids can also be formed and detected. In such cases, the conditions of hybridization and washing can be adapted according to well-known methods by the person of ordinary skill. Stringent conditions will be preferably used (Sambrook et al., 2000, supra). Other protocols or commercially available hybridization kits (e.g., ExpressHyb® from BD Biosciences Clonetech) using different annealing and washing solutions can also be used as well known in the art. As is well known, the length of the probe and the composition of the nucleic acid to be determined constitute further parameters of the hybridization conditions. Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility. Hybridizing nucleic acid molecules also comprise fragments of the above described molecules. Furthermore, nucleic acid molecules which hybridize with any of the aforementioned nucleic acid molecules also include complementary fragments, derivatives and allelic variants of these molecules. Additionally, a hybridization complex refers to a complex between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., Cot or Rot analysis) or between one nucleic acid sequence present in solution and another nucleic acid sequence immobilized on a solid support (e.g., membranes, filters, chips, pins or glass slides to which, e.g., cells have been fixed).

As used herein, the term "identical" or "percent identity" in the context of two or more nucleic acid or amino acid sequences, refers to two or more sequences or subsequences that are the same, or that have a specified percentage of amino acid residues or nucleotides that are the same (e.g., 60% or 65% identity, preferably, 70-95% identity, more preferably at least 95% identity), when compared and aligned for maximum correspondence over a window of comparison, or over a designated region as measured using a sequence comparison algorithm as known in the art, or by manual alignment and visual inspection. Sequences having, for example, 60% to 95% or greater sequence identity are considered to be substantially identical. Such a definition also applies to the complement of a test sequence. Preferably the described identity exists over a region that is at least about 15 to 25 amino acids or nucleotides in length, more preferably, over a region that is about 50 to 100 amino acids or nucleotides in length. Those having skill in the art will know how to determine percent identity between/among sequences using, for example, algorithms such as those based on CLUSTALW computer program (Thompson Nucl. Acids Res. 2 (1994), 4673-4680) or FASTDB (Brutlag Comp. App. Biosci. 6 (1990), 237-245), as known in the art. Although the FASTDB algorithm typically does not consider internal non-matching deletions or additions in sequences, i.e., gaps, in its calculation, this can be corrected manually to avoid an overestimation of the % identity. CLUSTALW, however, does take sequence gaps into account in its identity calculations. Also available to those having skill in this art are the BLAST and BLAST 2.0 algorithms (Altschul Nucl. Acids Res. 25 (1977), 3389-3402). The BLASTN program for nucleic acid sequences uses as defaults a word length (W) of 11, an expectation (E) of 10, M=5, N=4, and a comparison of both strands. For amino acid sequences, the BLASTP program uses as defaults a wordlength (W) of 3, and an expectation (E) of 10. The BLOSUM62 scoring matrix (Henikoff Proc. Natl. Acad. Sci., USA, 89, (1989), 10915) uses alignments (B) of 50, expectation (E) of 10, M=5, N=4, and a comparison of both strands. Moreover, the present invention also relates to nucleic acid molecules the sequence of which is degenerate in comparison with the sequence of an above-described hybridizing molecule. When used in accordance with the present invention the term "being degenerate as a result of the genetic code" means that due to the redundancy of the genetic code different nucleotide sequences code for the same amino acid. The present invention also relates to nucleic acid molecules which comprise one or more mutations or deletions, and to nucleic acid molecules which hybridize to one of the herein described nucleic acid molecules, which show (a) mutation(s) or (a) deletion(s).

The term "including" is used herein to mean, and is used interchangeably with, the phrase "including but not limited to."

A subject at "increased risk for developing BCR" may or may not develop BCR. Identification of a subject at increased risk for developing BCR should be monitored for additional signs or symptoms of BCR or prostate cancer. The methods provided herein for identifying a subject with increased risk for developing BCR can be used in combination with assessment of other known risk factors or signs of BCR.

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment. As used herein, a "label" refers to a molecular moiety or compound that can be detected or can lead to a detectable signal. A label is joined, directly or indirectly, to a molecule, such as an antibody, a nucleic acid probe or the protein/antigen or nucleic acid to be detected (e.g., an amplified sequence). Direct labeling can occur through bonds or interactions that link the label to the nucleic acid (e.g., covalent bonds or non-covalent interactions), whereas indirect labeling can occur through the use of a "linker" or bridging moiety, such as oligonucleotide(s) or small molecule carbon chains, which is either directly or indirectly labeled. Bridging moieties may amplify a detectable signal. Labels can include any detectable moiety (e.g., a radionuclide, ligand such as biotin or avidin, enzyme or enzyme substrate, reactive group, chromophore such as a dye or colored particle, luminescent compound including a bioluminescent, phosphorescent or chemiluminescent compound, and fluorescent compound). Preferably, the label on a labeled probe is detectable in a homogeneous assay system, i.e., in a mixture, the bound label exhibits a detectable change compared to an unbound label.

The terms "level of expression of a gene", "gene expression level", "level of a marker", and the like refer to the level of mRNA, as well as pre-mRNA nascent transcript(s), transcript processing intermediates, mature mRNA(s) and degradation products, or the level of protein, encoded by the gene in the cell. The "level" of one of more biomarkers means the absolute or relative amount or concentration of the biomarker in the sample.

A "lower level of expression" or "lower level" or "decreased level" of a marker refers to an expression level in a test sample that is less than 90%, 85%, 80%, 75%, 70%, 65%, 60%, 55%, 50%, 45%, 40%, 35%, 30%, 25%, 20%, 15%, or 10% of the expression level of the marker in a control sample (e.g., sample from a healthy subjects not having the marker associated disease, i.e., BCR) and preferably, the average expression level of the marker in several control samples.

The term "modulation" refers to upregulation (i.e., activation or stimulation), down-regulation (i.e., inhibition or suppression) of a response (e.g., level of a marker), or the two in combination or apart. A "modulator" is a compound or molecule that modulates, and may be, e.g., an agonist, antagonist, activator, stimulator, suppressor, or inhibitor.

As used herein, "nucleic acid molecule" or "polynucleotides", refers to a polymer of nucleotides. Non-limiting examples thereof include DNA (e.g., genomic DNA, cDNA), RNA molecules (e.g., mRNA) and chimeras thereof. The nucleic acid molecule can be obtained by cloning techniques or synthesized. DNA can be double-stranded or single-stranded (coding strand or non-coding strand [antisense]). Conventional ribonucleic acid (RNA) and deoxyribonucleic acid (DNA) are included in the term "nucleic acid" and polynucleotides as are analogs thereof. A nucleic acid backbone may comprise a variety of linkages known in the art, including one or more of sugar-phosphodiester linkages, peptide-nucleic acid bonds (referred to as "peptide nucleic acids" (PNA); Hydig-Hielsen et al., PCT Intl Pub. No. WO 95/32305), phosphorothioate linkages, methylphosphonate linkages or combinations thereof. Sugar moieties of the nucleic acid may be ribose or deoxyribose, or similar compounds having known substitutions, e.g., 2' methoxy substitutions (containing a 2'-O-methylribofuranosyl moiety; see PCT No. WO 98/02582) and/or 2' halide substitutions. Nitrogenous bases may be conventional bases (A, G, C, T, U), known analogs thereof (e.g., inosine or others; see The Biochemistry of the Nucleic Acids 5-36, Adams et al., ed., 11th ed., 1992), or known derivatives of purine or pyrimidine bases (see, Cook, PCT Int'l Pub. No. WO 93/13121) or "abasic" residues in which the backbone includes no nitrogenous base for one or more residues (Arnold et al., U.S. Pat. No. 5,585,481). A nucleic acid may comprise only conventional sugars, bases and linkages, as found in RNA and DNA, or may include both conventional components and substitutions (e.g., conventional bases linked via a methoxy backbone, or a nucleic acid including conventional bases and one or more base analogs). An "isolated nucleic acid molecule", as is generally understood and used herein, refers to a polymer of nucleotides, and includes, but should not limited to DNA and RNA. The "isolated" nucleic acid molecule is purified from its natural in vivo state, obtained by cloning or chemically synthesized.

As used herein, the term "obtaining" is understood herein as manufacturing, purchasing, or otherwise coming into possession of.

As used herein, "oligonucleotides" or "oligos" define a molecule having two or more nucleotides (ribo or deoxyribonucleotides). The size of the oligo will be dictated by the particular situation and ultimately on the particular use thereof and adapted accordingly by the person of ordinary skill. An oligonucleotide can be synthesized chemically or derived by cloning according to well-known methods. While they are usually in a single-stranded form, they can be in a double-stranded form and even contain a "regulatory region". They can contain natural rare or synthetic nucleotides. They can be designed to enhance a chosen criteria like stability for example. Chimeras of deoxyribonucleotides and ribonucleotides may also be within the scope of the present invention.

As used herein, the term "one or more" or "at least one of" is understood as each value 1, 2, 3, 4, 5, 6, 7, 8, 9, 10, 11, 12, 13, 14, 15, 16, 17, 18, 19, and 20 and any value greater than 20.

The term "or" is used inclusively herein to mean, and is used interchangeably with, the term "and/or," unless context clearly indicates otherwise.

As used herein, "patient" or "subject" can mean either a human or non-human animal, preferably a mammal. By "subject" is meant any animal, including horses, dogs, cats, pigs, goats, rabbits, hamsters, monkeys, guinea pigs, rats, mice, lizards, snakes, sheep, cattle, fish, and birds. A human subject may be referred to as a patient. It should be noted that clinical observations described herein were made with human subjects and, in at least some embodiments, the subjects are human.

As used herein, "preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease). Prevention does not require that the disease or condition never occurs in the subject. Prevention includes delaying the onset or severity of the disease or condition.

As used herein, a "predetermined threshold value" or "threshold value" of a biomarker refers to the level of the biomarker (e.g., the expression level or quantity (e.g., ng/ml) in a biological sample) in a corresponding control/normal sample or group of control/normal samples obtained from normal or healthy subjects, e.g., those males that do not have BCR. The predetermined threshold value may be determined prior to or concurrently with measurement of marker levels in a biological sample. The control sample may be from the same subject at a previous time or from different subjects.

As used herein, a "probe" is meant to include a nucleic acid oligomer or oligonucleotide that hybridizes specifically to a target sequence in a nucleic acid or its complement, under conditions that promote hybridization, thereby allowing detection of the target sequence or its amplified nucleic acid. Detection may either be direct (i.e., resulting from a probe hybridizing directly to the target or amplified sequence) or indirect (i.e., resulting from a probe hybridizing to an intermediate molecular structure that links the probe to the target or amplified sequence). A probe's "target" generally refers to a sequence within an amplified nucleic acid sequence (i.e., a subset of the amplified sequence) that hybridizes specifically to at least a portion of the probe sequence by standard hydrogen bonding or "base pairing." Sequences that are "sufficiently complementary" allow stable hybridization of a probe sequence to a target sequence, even if the two sequences are not completely complementary. A probe may be labeled or unlabeled. A probe can be produced by molecular cloning of a specific DNA sequence or it can also be synthesized. Numerous primers and probes which can be designed and used in the context of the present invention can be readily determined by a person of ordinary skill in the art to which the present invention pertains.

As used herein, the terminology "prognosis", "staging" and "determination of aggressiveness" are defined herein as the prediction of the degree of severity of the BCR and of its evolution as well as the prospect of recovery as anticipated from usual course of the disease. According to the present invention, once the aggressiveness of the BCR has been determined appropriate methods of treatments can be chosen.

As used herein, "prophylactic" or "therapeutic" treatment refers to administration to the subject of one or more agents or interventions to provide the desired clinical effect. If it is administered prior to clinical manifestation of the unwanted condition (e.g., disease or other unwanted state of the host animal) then the treatment is prophylactic, i.e., it protects the host against developing at least one sign or symptom of the unwanted condition, whereas if administered after manifestation of the unwanted condition, the treatment is therapeutic (i.e., it is intended to diminish, ameliorate, or maintain at least one sign or symptom of the existing unwanted condition or side effects therefrom).

As used herein, "prostate cancer," refers to any malignant or pre-malignant form of cancer of the prostate. The term includes prostate in situ carcinomas, invasive carcinomas, metastatic carcinomas and pre-malignant conditions. The term also encompasses any stage or grade of cancer in the prostate. Where the prostate cancer is "metastatic," the cancer has spread or metastasized beyond the prostate gland to a distant site, such as a lymph node or to the bone.

As used herein, a "reference level" of a biomarker means a level of the biomarker that is indicative of a particular disease state, phenotype, or lack thereof, as well as combinations of disease states, phenotypes, or lack thereof. A "positive" reference level of a biomarker means a level that is indicative of a particular disease state or phenotype. A "negative" reference level of a biomarker means a level that is indicative of a lack of a particular disease state or phenotype. For example, a "BCR-positive reference level" of a biomarker means a level of a biomarker that is indicative of a positive diagnosis of BCR in a subject, and a "BCR-negative reference level" of a biomarker means a level of a biomarker that is indicative of a negative diagnosis of BCR in a subject. A "reference level" of a biomarker may be an absolute or relative amount or concentration of the biomarker, a presence or absence of the biomarker, a range of amount or concentration of the biomarker, a minimum and/or maximum amount or concentration of the biomarker, a mean amount or concentration of the biomarker, and/or a median amount or concentration of the biomarker; and, in addition, "reference levels" of combinations of biomarkers may also be ratios of absolute or relative amounts or concentrations of two or more biomarkers with respect to each other. Appropriate positive and negative reference levels of biomarkers for a particular disease state, phenotype, or lack thereof may be determined by measuring levels of desired biomarkers in one or more appropriate subjects, and such reference levels may be tailored to specific populations of subjects (e.g., a reference level may be age-matched so that comparisons may be made between biomarker levels in samples from subjects of a certain age and reference levels for a particular disease state, phenotype, or lack thereof in a certain age group). Such reference levels may also be tailored to specific techniques that are used to measure levels of biomarkers in biological samples (e.g., LC-MS, GC-MS, etc.), where the levels of biomarkers may differ based on the specific technique that is used.

As used herein, "sample" or "biological sample" includes a specimen or culture obtained from any source. Biological samples can be obtained from blood (including any blood product, such as whole blood, plasma, serum, or specific types of cells of the blood), urine, saliva, seminal fluid, and the like. Biological samples also include tissue samples, such as biopsy tissues or pathological tissues that have previously been fixed (e.g., formaline snap frozen, cytological processing, etc.). In an embodiment, the biological sample is from blood. In another embodiment, the biological sample is a biopsy tissue from the prostate gland.

As use herein, the phrase "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabeled A) in a reaction containing labeled "A" and the antibody will reduce the amount of labeled A bound to the antibody.

The phrase "specific identification" is understood as detection of a marker of interest with sufficiently low background of the assay and cross-reactivity of the reagents used such that the detection method is diagnostically useful. In certain embodiments, reagents for specific identification of a marker bind to only one isoform of the marker. In certain embodiments, reagents for specific identification of a marker bind to more than one isoform of the marker. In certain embodiments, reagents for specific identification of a marker bind to all known isoforms of the marker.

As used herein, the phrase "subject suspected of having BCR" refers to a subject who has received treatment for localized prostate cancer, e.g., surgery (e.g., prostatectomy) or radiation therapy and/or has an increased level of prostate specific antigen (PSA).

The term "such as" is used herein to mean, and is used interchangeably, with the phrase "such as but not limited to."

As used herein, the term "stage of cancer" or "tumor stage" or "T stage" refers to a qualitative or quantitative assessment of the level of advancement of a cancer or tumor. Criteria used to determine the stage of a cancer or tumor include, but are not limited to, the size of the tumor, whether the tumor has spread to other parts of the body and where the cancer has spread (e.g., within the same organ or region of the body or to another organ). The most widely used staging system for prostate cancer is the AJCC (American Joint Committee on Cancer) TNM system, which was most recently updated in January 2018 (see, e.g., the website cancer.net/cancer-types/appendix-cancer/stages-and-grades). The TNM System describes the extent of the primary tumor (T stage), the absence or presence of spread to nearby lymph nodes (N stage) and the absence or presence of distant spread, or metastasis (M stage). Each category of the TNM classification is divided into subcategories representative of its particular state. For example, primary tumors (T stage) may be classified into:

T1: The tumor cannot be felt during a digital rectal exam, or seen by imaging studies, but cancer cells are found in a biopsy specimen;

T2: The tumor can be felt during a DRE and the cancer is confined within the prostate gland;

T3: The tumor has extended through the prostatic capsule (a layer of fibrous tissue surrounding the prostate gland) and/or to the seminal vesicles (two small sacs next to the prostate that store semen), but no other organs are affected;

T4: The tumor has spread or attached to tissues next to the prostate (other than the seminal vesicles).

Lymph node involvement is divided into the following 4 categories:

N0: Cancer has not spread to any lymph nodes;

N1: Cancer has spread to a single regional lymph node (inside the pelvis) and is not larger than 2 centimeters;

N2: Cancer has spread to one or more regional lymph nodes and is larger than 2 centimeters, but not larger than 5 centimeters; and N3: Cancer has spread to a lymph node and is larger than 5 centimeters (2 inches). Metastasis is generally divided into the following two categories:

M0: The cancer has not metastasized (spread) beyond the regional lymph nodes; and M1: The cancer has metastasized to distant lymph nodes (outside of the pelvis), bones, or other distant organs such as lungs, liver, or brain.

In some embodiments, tumor stage, as used herein, is categorized as T1, T2, T3, or T4, with some stages separated further into subcategories, such as, for example, T2a, T2b, or T2c. The characteristics of each of these subcategories are well known in the art and can be found in a number of textbooks.

In some embodiments, as used in the methods described herein, tumor stage is separated into groups of T2 and T3/T4 tumor staging groups. In some embodiments, as used in the methods of the invention, the tumor stage, alone or in combination with one or more additional clinical features or parameters, is used as a diagnostic or prognostic marker, in combination with one or more molecular markers described herein, to determine the likelihood of BCR in a subject. In some embodiments, tumor stage T3/T4 is associated with BCR.

As used herein, the term "staging" refers to commonly used systems for grading/stating cancer, e.g., prostate cancer.

In one aspect, staging can take the form of the "Gleason Score", as well known in the art, is the most commonly used system for the grading/staging and prognosis of adenocarcinoma. The system describes a score between 2 and 10, with 2 being the least aggressive and 10 being the most aggressive. The score is the sum of the two most common patterns (grade 1-5) of tumor growth found. To be counted a pattern (grade) needs to occupy more than 5% of the biopsy specimen. The scoring system requires biopsy material (core biopsy or operative specimens) in order to be accurate; cytological preparations cannot be used. The "Gleason Grade" is the most commonly used prostate cancer grading system. It involves assigning numbers to cancerous prostate tissue, ranging from 1 through 5, based on how much the arrangement of the cancer cells mimics the way normal prostate cells form glands. Two grades are assigned to the most common patterns of cells that appear; these two grades (they can be the same or different) are then added together to determine the Gleason score (a number from 1 to 10). The Gleason system is based exclusively on the architectural pattern of the glands of the prostate tumor. It evaluates how effectively the cells of any particular cancer are able to structure themselves into glands resembling those of the normal prostate. The ability of a tumor to mimic normal gland architecture is called its differentiation, and experience has shown that a tumor whose structure is nearly normal (well differentiated) will probably have a biological behavior relatively close to normal, i.e., that is not very aggressively malignant.

A Gleason grading from very well differentiated (grade 1) to very poorly differentiated (grade 5) is usually done for the most part by viewing the low magnification microscopic image of the cancer. There are important additional details which require higher magnification, and an ability to accurately grade any tumor is achieved only through much training and experience in pathology. Gleason grades 1 and 2: These two grades closely resemble normal prostate. They are the least important grades because they seldom occur in the general population and because they confer a prognostic benefit which is only slightly better than grade 3. Both of these grades are composed by mass; in grade 2 they are more loosely aggregated, and some glands wander (invade) into the surrounding muscle (stroma). Gleason grade 3 is the most common grade and is also considered well differentiated (like grades 1 and 2). This is because all three grades have a normal "gland unit" like that of a normal prostate; that is, every cell is part of a circular row which forms the lining of a central space (the lumen). The lumen contains prostatic secretion like normal prostate, and each gland unit is surrounded by prostate muscle which keeps the gland units apart. In contrast to grade 2, wandering of glands (invading) into the stroma (muscle) is very prominent and is the main defining feature. The cells are dark rather than pale and the glands often have more variable shapes.

Gleason Grade 4 is probably the most important grade because it is fairly common and because of the fact that if a lot of it is present, patient prognosis is usually (but not always) worsened by a considerable degree. Grade 4 also shows a considerable loss of architecture. For the first time, disruption and loss of the normal gland unit is observed. In fact, grade 4 is identified almost entirely by loss of the ability to form individual, separate gland units, each with its separate lumen (secretory space). This important distinction is simple in concept but complex in practice. The reason is that there are a variety of different-appearing ways in which the cancer's effort to form gland units can be distorted. Each cancer has its own partial set of tools with which it builds part of the normal structure. Grade 4 is like the branches of a large tree, reaching in a number of directions from the (well differentiated) trunk of grades 1, 2, and 3. Much experience is required for this diagnosis, and not all patterns are easily distinguished from grade 3. This is the main class of poorly differentiated prostate cancer, and its distinction from grade 3 is the most commonly important grading decision.

Gleason grade 5 is an important grade because it usually predicts another significant step towards poor prognosis. Its overall importance for the general population is reduced by the fact that it is less common than grade 4, and it is seldom seen in men whose prostate cancer is diagnosed early in its development. This grade too shows a variety of patterns, all of which demonstrate no evidence of any attempt to form gland units. This grade is often called undifferentiated, because its features are not significantly distinguishing to make it look any different from undifferentiated cancers which occur in other organs. When a pathologist looks at prostate cancer specimens under the microscope and gives them a Gleason grade, an attempt to identify two architectural patterns and assign a Gleason grade to each one is made. There may be a primary or most common pattern and then a secondary or second most common pattern which the pathologist will seek to describe for each specimen; alternatively, there may often be only a single pure grade. In developing his system, Dr. Gleason discovered that by giving a combination of the grades of the two most common patterns he could see in any particular patient's specimens, that he was better able to predict the likelihood that a particular patient would do well or badly. Therefore, although it may seem confusing, the Gleason score which a physician usually gives to a patient, is actually a combination or sum of two numbers which is accurate enough to be very widely used. These combined Gleason sums or scores may be determined as follows:

The lowest possible Gleason score is 2 (1+1), where both the primary and secondary patterns have a Gleason grade of 1 and therefore when added together their combined sum is 2.

Very typical Gleason scores might be 5 (2+3), where the primary pattern has a Gleason grade of 2 and the secondary pattern has a grade of 3, or 6 (3+3), a pure pattern.

Another typical Gleason score might be 7 (4+3), where the primary pattern has a Gleason grade of 4 and the secondary pattern has a grade of 3.

Finally, the highest possible Gleason score is 10 (5+5), when the primary and secondary patterns both have the most disordered Gleason grades of 5.

As used herein, the higher the Gleason score, the greater association with BCR. In some embodiments, the risk for BCR is based on the distribution of patients measured in synergy with the one or more molecular markers described herein. In some embodiments, as used in the methods of the invention, the Gleason score, alone or in combination with one or more additional clinical features or parameters, is used as a diagnostic or prognostic marker, combination with one or more molecular marker described herein, to determine the likelihood of BCR in a subject. In some embodiments, patients having a Gleason score of 8, 9, or 10 have a higher risk for BCR. In some embodiments, patients having a Gleason score of 7 have a moderate risk for BCR. In some embodiments, patients having a Gleason score of 6 or less have a minimal risk for BCR. In some embodiments, a Gleason score of 6 or higher is associated with BCR. In some embodiments, a Gleason score of 7 or higher is associated with BCR. In some embodiments, a Gleason score of 8 or higher is associated with BCR. In some embodiments, a Gleason score of 9 or higher is associated with BCR. In some embodiments, a Gleason score of 10 is associated with BCR.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present invention. In some embodiments of the present invention, test compounds include antisense compounds.

The term "therapeutic effect" refers to a local or systemic effect in animals, particularly mammals, and more particularly humans caused by a pharmacologically active substance. The term thus means any substance intended for use in the diagnosis, cure, mitigation, treatment, or prevention of disease, or in the enhancement of desirable physical or mental development and conditions in an animal or human. A therapeutic effect can be understood as a decrease in tumor growth, decrease in tumor growth rate, stabilization or decrease in tumor burden, stabilization or reduction in tumor size, stabilization or decrease in tumor malignancy, increase in tumor apoptosis, and/or a decrease in tumor angiogenesis.

As used herein, "therapeutically effective amount" means the amount of a compound that, when administered to a patient for treating a disease, is sufficient to effect such treatment for the disease, e.g., the amount of such a substance that produces some desired local or systemic effect at a reasonable benefit/risk ratio applicable to any treatment, e.g., is sufficient to ameliorate at least one sign or symptom of the disease, e.g., to prevent progression of the disease or condition, e.g., prevent tumor growth, decrease tumor size, induce tumor cell apoptosis, reduce tumor angiogenesis, prevent metastasis. When administered for preventing a disease, the amount is sufficient to avoid or delay onset of the disease. The "therapeutically effective amount" will vary depending on the compound, its therapeutic index, solubility, the disease and its severity and the age, weight, etc., of the patient to be treated, and the like. For example, certain compounds discovered by the methods of the present invention may be administered in a sufficient amount to produce a reasonable benefit/risk ratio applicable to such treatment. Administration of a therapeutically effective amount of a compound may require the administration of more than one dose of the compound.

A "transcribed polynucleotide" or "nucleotide transcript" is a polynucleotide (e.g. an mRNA, hnRNA, a cDNA, or an analog of such RNA or cDNA) which is complementary to or having a high percentage of identity (e.g., at least 80% identity) with all or a portion of a mature mRNA made by transcription of a marker of the invention and normal post-transcriptional processing (e.g. splicing), if any, of the RNA transcript, and reverse transcription of the RNA transcript.

As used herein, "treatment," particularly "active treatment," refers to performing an intervention to treat BCR of prostate cancer in a subject. Patients with BCR typically exhibit no signs of prostate cancer. BCR can be due to local recurrence or systemic disease. Depending on the type of initial local therapy, treatment options for local recurrence include, but are not limited to, salvage radiation therapy or salvage prostatectomy. For systemic recurrence, treatment may include, for example, androgen deprivation therapy (ADT), via, for example, gonadotropin releasing hormone agonists or antagonists, or other treatments known in the art. (See e.g., Kolodziej, *J. Manage Care*, 2014, 20:S273-S281). Other prostate cancer and BCR treatments include therapy to, e.g., reduce at least one of the growth rate, reduction of tumor burden, reduce or maintain the tumor size, or the malignancy (e.g., likelihood of metastasis) of the tumor; or to increase apoptosis in the tumor by one or more of administration of a therapeutic agent, e.g., chemotherapy or hormone therapy; administration of radiation therapy (e.g., pellet implantation, brachytherapy), or surgical resection of the tumor, or any combination thereof appropriate for treatment of the subject based on grade and stage of the tumor and other routine considerations. Active treatment is distinguished from "watchful waiting" (i.e., not active treatment) in which the subject is monitored, but no interventions are performed. Watchful waiting can include administration of agents that alter effects caused by the recurrence that are not administered to alter the growth or pathology of the recurrence itself.

The recitation of a listing of chemical group(s) in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Reference will now be made in detail to exemplary embodiments of the invention. While the invention will be described in conjunction with the exemplary embodiments, it will be understood that it is not intended to limit the Exemplary compositions and methods of the present invention are described in more detail in the following sections: (C) Biomarkers of the invention; (D) Prostate tissue samples; (E) Detection and/or measurement of the biomarkers of the invention; (F) Isolated biomarkers; (G) Applications of biomarkers of the invention; (H) Therapeutics; (I) Drug screening; and (J) Kits/panels.

C. Biomarkers of the Invention

The present invention is based, at least in part, on the discovery that the markers (hereinafter "biomarkers", "markers" or "markers of the invention") in Tables 1-5, for example, tenascin C, apolipoprotein A-IV, 1-methyladenosine, PA-18:0/22:0, or any combination thereof, are differentially regulated in subjects having BCR in prostate cancer versus normal subjects. In particular, the invention is based on the surprising discovery that the markers in Tables 1-5, for example, tenascin C, apolipoprotein A-IV, 1-methyladenosine, PA-18:0/22:0, or any combination thereof, are either elevated (e.g., tenascin C, apolipoprotein A-IV, 1-methyladenosine) or depressed (e.g., PA-18:0/22:0) in the serum of patients with BCR. In addition, the invention is also based on the discovery that any one or more of these markers in further combination with one or more pathological or clinical features, e.g., tumor stage and/or Gleason score, is particularly useful for diagnosing BCR in prostate cancer.

In some embodiments, tumor stage T3/T4 is associated with BCR. In some embodiments, as used in the methods of the invention, the tumor stage, e.g., T stage T3/T4, alone or in combination with one or more additional clinical features or parameters (such as Gleason score), is used as a prognostic marker in combination with one or more molecular markers described herein, for example, tenascin C, apolipoprotein A-IV, 1-methyladenosine, PA-18:0/22:0, or any combination thereof, to determine the likelihood of BCR in a subject.

In some embodiments, Gleason score is associated with BCR. In some embodiments, patients having a Gleason score of 8-10 have a higher risk for BCR. In some embodiments, patients having a Gleason score of 7 have a moderate risk for BCR. In some embodiments, patients having a Gleason score of 6 or less have a minimal risk for BCR. In some embodiments, the Gleason score, alone or in combination with one or more additional clinical features or parameters (such as tumor stage), is used as a prognostic marker in combination with one or more molecular markers described herein, for example, tenascin C, apolipoprotein A-IV, 1-methyladenosine, PA-18:0/22:0, or any combination thereof, to determine the likelihood of BCR in a subject.

Accordingly, the invention provides methods for prognosing, diagnosing and/or monitoring (e.g., monitoring of disease progression or treatment) and/or prognosing BCR in prostate cancer, in a subject.

The invention also provides methods for treating or for adjusting treatment regimens based on diagnostic information relating to the levels of one or more of the markers in Tables 1-5, for example, tenascin C, apolipoprotein A-IV, 1-methyladenosine, PA-18:0/22:0, or any combination thereof, alone or in combination with one or more pathological or clinical features, e.g., tumor stage and/or Gleason score, in the serum of a subject with an oncological disease state, e.g., BCR in prostate cancer. The invention further provides panels and kits for practicing the methods of the invention.

The present invention provides new markers and combinations of markers for use in diagnosing and/or prognosing an oncological disorder, and in particular, markers for use in diagnosing and/or prognosing BCR in prostate cancer. These markers are particularly useful in screening for the presence of an oncologic disorder, e.g., BCR in prostate cancer, in assessing aggressiveness and metastatic potential of BCR in prostate cancer, assessing whether a subject is afflicted with BCR, identifying a composition for treating BCR or prostate cancer, assessing the efficacy of a compound for treating BCR, monitoring the progression of BCR, prognosing the aggressiveness of BCR, prognosing the survival of a subject with BCR, prognosing the recurrence of BCR, and prognosing whether a subject is predisposed to developing BCR.

The markers of the invention include, but are not limited to, one or more BCR markers selected from Tables 1-5, for example, tenascin C, apolipoprotein A-IV, 1-methyladenosine, PA-18:0/22:0, or any combination thereof, alone or in combination with one or more pathological or clinical features, e.g., tumor stage and/or Gleason score.

In some embodiments of the present invention, other biomarkers can be used in connection with the methods of the present invention. As used herein, the term "one or more biomarkers" or "at least one of" is intended to mean that one or more (e.g., 1, 2, 3, 4, 5, 6, 7, 8, 9, 10, 11, 12, 13, 14, 15, 16, 17, 18, 19, 20, or more) markers selected from Tables 1-5, for example, tenascin C, apolipoprotein A-IV, 1-methyladenosine, PA-18:0/22:0, or any combination thereof, alone or in combination with one or more pathological or clinical features, e.g., tumor stage and/or Gleason score, are assayed, optionally in combination with PSA, or another prostate cancer marker, and, in various embodiments, more than one other biomarker may be assayed, such as one or more biomarkers from Tables 1-5, for example, any combination of tenascin C, apolipoprotein A-IV, 1-methyladenosine, PA-18:0/22:0, may be assayed.

Methods, kits, and panels provided herein include any combination of e.g., 1, 2, 3, 4, 5, 6, 7, 8, 9, 10, 11, 12, 13, 14, 15, 16, 17, 18, 19, 20, or more markers selected from Tables 1-5, for example, tenascin C, apolipoprotein A-IV, 1-methyladenosine, PA-18:0/22:0, or any combination thereof, alone or in combination with one or more pathological or clinical features, e.g., tumor stage and/or Gleason score. Any one marker or any combination of more than one marker selected from Tables 1-5, for example, tenascin C, apolipoprotein A-IV, 1-methyladenosine, PA-18:0/22:0, or any combination thereof, alone or in combination with one or more pathological or clinical features, e.g., tumor stage and/or Gleason score, can be used in combination with PSA or another prostate cancer marker.

In one embodiment, one or more markers ranked A or B in any one or more of Tables 1-5, alone or in combination, are used.

The markers of the invention are meant to encompass any measurable characteristic that reflects in a quantitative or qualitative manner the physiological state of an organism, e.g., whether the organism has BCR in prostate cancer. The physiological state of an organism is inclusive of any disease or non-disease state, e.g., a subject having BCR in prostate cancer or a subject who is otherwise healthy. Said another way, the markers of the invention include characteristics that can be objectively measured and evaluated as indicators of normal processes, pathogenic processes, or pharmacologic responses to a therapeutic intervention, including, in particular, BCR in prostate cancer. Examples of markers include, for example, polypeptides, peptides, polypeptide fragments, proteins, antibodies, hormones, polynucleotides, RNA or RNA fragments, microRNA (miRNAs), lipids (e.g. structural lipids or signaling lipids), polysaccharides, and other bodily metabolites that are diagnostic and/or indicative and/or predictive of an oncological disease, e.g., BCR in prostate cancer, including one or more of the markers of Tables 1-5.

The markers of the invention, e.g., one or more markers selected from Tables 1-5, for example, tenascin C, apolipoprotein A-IV, 1-methyladenosine, PA-18:0/22:0, or any combination thereof, alone or in combination with one or more pathological or clinical features, e.g., tumor stage and/or Gleason score, are diagnostic and/or indicative and/or predicative of BCR in prostate cancer in a subject. In one aspect, the present invention relates to using, measuring, detecting, and the like of one or more of the markers in Tables 1-5, for example, tenascin C, apolipoprotein A-IV, 1-methyladenosine, PA-18:0/22:0, or any combination thereof, alone or in combination with one or more pathological or clinical features, e.g., tumor stage and/or Gleason score, for diagnosis of the presence of BCR in prostate cancer in a subject.

In another aspect, the present invention relates to using, measuring, detecting, and the like of one or more of the markers in Tables 1-5 alone, or together with one or more additional markers of BCR in prostate cancer. Other markers that may be used in combination with the one or more markers in Tables 1-5 include any measurable characteristic described herein that reflects in a quantitative or qualitative manner the physiological state of an organism, e.g., whether the organism has BCR in prostate cancer. The physiological state of an organism is inclusive of any disease or non-disease state, e.g., a subject having BCR in prostate cancer or a subject who is otherwise healthy. The markers of the invention that may be used in combination with the markers in Tables 1-5 include characteristics that can be objectively measured and evaluated as indicators of normal processes, pathogenic processes, or pharmacologic responses to a therapeutic intervention, including, in particular, BCR in prostate cancer. Such combination markers can be clinical features or parameters (e.g., tumor stage, Gleason score, age, performance status), laboratory measures (e.g., molecular markers, such as prostate specific antigen), imaging-based measures, or genetic or other molecular determinants. Examples of markers for use in combination with the markers in Tables 1-5 include, for example, polypeptides, peptides, polypeptide fragments, proteins, antibodies, hormones, polynucleotides, RNA or RNA fragments, microRNA (miRNAs), lipids, polysaccharides, and other bodily metabolites that are diagnostic and/or indicative and/or predictive of BCR in prostate cancer.

In some embodiments, tumor stage T3/T4 is associated with BCR. In some embodiments, as used in the methods of the invention, the tumor stage, e.g., T stage T3/T4, alone or in combination with one or more additional clinical features or parameters (such as Gleason score), is used as a prognostic marker in combination with one or more molecular markers described herein, for example, tenascin C, apolipoprotein A-IV, 1-methyladenosine, PA-18:0/22:0, or any combination thereof, to determine the likelihood of BCR in a subject.

In some embodiments, Gleason score is associated with BCR. In some embodiments, patients having a Gleason score of 8-10 have a higher risk for BCR. In some embodiments, patients having a Gleason score of 7 have a moderate risk for BCR. In some embodiments, patients having a Gleason score of 6 or less have a minimal risk for BCR. In some embodiments, the Gleason score, alone or in combination with one or more additional clinical features or parameters (such as tumor stage), is used as a prognostic marker in combination with one or more molecular markers described herein, for example, tenascin C, apolipoprotein A-IV, 1-methyladenosine, PA-18:0/22:0, or any combination thereof, to determine the likelihood of BCR in a subject.

In other embodiments, the present invention also involves the analysis and consideration of any clinical and/or patient-related health data, for example, data obtained from an Electronic Medical Record (e.g., collection of electronic health information about individual patients or populations relating to various types of data, such as, demographics, medical history, medication and allergies, immunization status, laboratory test results, radiology images, vital signs, personal statistics like age and weight, and billing information).

The present invention also contemplates the use of particular combinations of the markers of Tables 1-5, for example, tenascin C, apolipoprotein A-IV, 1-methyladenosine, PA-18:0/22:0, or any combination thereof, alone or in combination with one or more pathological or clinical features, e.g., tumor stage and/or Gleason score. In one embodiment, the invention contemplates marker sets with at least two (2) members, which may include any two of the markers in Tables 1-5, for example, any two of tenascin C, apolipoprotein A-IV, 1-methyladenosine, and PA-18:0/22:0, alone or in combination with one or more pathological or clinical features, e.g., tumor stage and/or Gleason score. In another embodiment, the invention contemplates marker sets with at least three (3) members, which may include any three of the markers in Tables 1-5, for example, any three of tenascin C, apolipoprotein A-IV, 1-methyladenosine, and PA-18:0/22:0, alone or in combination with one or more pathological or clinical features, e.g., tumor stage and/or Gleason score. In another embodiment, the invention contemplates marker sets with at least four (4) members, which may include any four of the markers in Tables 1-5, for example, tenascin C, apolipoprotein A-IV, 1-methyladenosine, and PA-18:0/22:0, alone or in combination with one or more pathological or clinical features, e.g., tumor stage and/or Gleason score.

In another embodiment, the invention contemplates marker sets with at least five (5) members, which may include any five of the markers in Tables 1-5. In another embodiment, the invention contemplates marker sets with at least six (6) members, which may include any six of the markers in Tables 1-5. In another embodiment, the invention contemplates marker sets with at least seven (7) members, which may include any seven of the markers in Tables 1-5. In another embodiment, the invention contemplates marker sets with at least eight (8) members, which may include any eight of the markers in Tables 1-5. In another embodiment, the invention contemplates marker sets with at least nine (9) members, which may include any nine of the markers in Tables 1-5. In another embodiment, the invention contemplates marker sets with at least ten (10) members, which may include any ten of the markers in Tables 1-5. In other embodiments, the invention contemplates a marker set comprising at least 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 or more of the markers listed in Tables 1-5. In one embodiment, one or more markers are ranked A or B in any one or more of Tables 1-5, alone or in combination. In one embodiment, the markers are used alone or in combination with one or more pathological or clinical features, e.g., tumor stage and/or Gleason score.

In certain embodiments, the markers in Tables 1-5, for example, tenascin C, apolipoprotein A-IV, 1-methyladenosine, PA-18:0/22:0, or any combination thereof, alone or in combination with one or more pathological or clinical features, e.g., tumor stage and/or Gleason score, may be used in combination with at least one other marker, or more preferably, with at least two other markers, or still more preferably, with at least three other markers, or even more preferably with at least four other markers. Still further, the markers in Tables 1-5 in certain embodiments, may be used in combination with at least five other markers, or at least six other markers, or at least seven other markers, or at least eight other markers, or at least nine other markers, or at least ten other markers, or at least eleven other markers, or at least twelve other markers, or at least thirteen other markers, or at least fourteen other markers, or at least fifteen other markers, or at least sixteen other markers, or at least seventeen other markers, or at least eighteen other markers, or at least nineteen other markers, or at least twenty other markers. Further, the markers in Tables 1-5 may be used in combination with a multitude of other markers, including, for example, with between about 20-50 other markers, or between 50-100, or between 100-500, or between 500-1000, or between 1000-10,000 or markers or more.

In certain embodiments, the at least one other marker is any BCR or prostate cancer marker previously known in the art. In certain other embodiments, the at least one other marker can include genes that have been described in the literature as being specifically expressed in the prostate. These genes can include, for example, prostate-specific membrane antigen (PSM) (Fair et al., 1997, Prostate-specific membrane antigen. Prostate 32:140-148), prostate stem cell antigen (PSCA) (Reiter et al., 1998, Prostate stem cell antigen: a cell surface marker overexpressed in prostate cancer. Proc. Natl. Acad. Sci. USA 95:1735-1740), TMPRSS2 (Lin et al., 1999. Prostate-localized and androgen-regulated expression of the membrane-bound serine protease TMPRSS2. Cancer Res. 59:4180-4184), PDEF (Oettgen et al., 2000, PDEF, a novel prostate epithelium-specific ETS transcription factor, interacts with the androgen receptor and activates prostate-specific antigen gene expression. J. Biol. Chem. 275:1216-1225), prostate-specific gene-1 (Herness, 2003. A novel human prostate-specific gene-1 (HPG-1): molecular cloning, sequencing, and its potential involvement in prostate carcinogenesis. Cancer Res. 63:329-336), and even various non-coding RNA's (ncRNA's), like PCA3 (Bussemakers et al., 1999. DD3: a new prostate-specific gene, highly overexpressed in prostate cancer, Cancer Res. 59:5975-5979), PCGEM1 (Srikantan et al., 2000. PCGEM1, a prostate-specific gene, is overexpressed in prostate cancer. Proc. Natl. Acad. Sci. USA 97:12216-12221) and the gene cluster P704P, P712P, and P775P (Stolk et al., 2004. P704P, P712P, and P775P: A genomic cluster of prostate-specific genes. Prostate 60:214-226). Only a fraction of these markers have been associated with prostate cancer prognosis, progression and/or metastatic capacity and as such, their potential as valuable biomarkers and/or therapeutic targets is largely unknown.

In certain other embodiments, the at least one other marker is prostate-specific antigen (PSA), also known as kallikrein-3, seminin, P-30 antigen, semenogelase, gamma-seminoprotein, APS, hK3, and KLK2A1. Kallikreins are a subgroup of serine proteases having diverse physiological functions. Growing evidence suggests that many kallikreins are implicated in carcinogenesis and some have potential as novel cancer and other disease biomarkers. This gene is one of the fifteen kallikrein subfamily members located in a cluster on chromosome 19. Its protein product is a protease present in seminal plasma. It is thought to function normally in the liquefaction of seminal coagulum, presumably by hydrolysis of the high molecular mass seminal vesicle protein. Serum level of this protein, called PSA in the clinical setting, is useful in the diagnosis and monitoring of prostatic carcinoma. Alternate splicing of this gene generates several transcript variants encoding different isoforms.

As used herein, PSA refers to both the gene and the protein, in both processed and unprocessed forms, unless clearly indicated otherwise by context. The NCBI gene ID for PSA is 354 and detailed information can be found at the NCBI website (incorporated herein by reference in the version available on the filing date of the application to which this application claims priority).

Homo sapiens PSA is located on chromosome 19 at 19q13.41Sequence: NC_000019.9 (51358171..51364020). Four splice variants of human PSA are known. Prostate-specific antigen isoform 3 preproprotein, NM_001030047.1, is provided as SEQ ID NO: 21. Prostate-specific antigen isoform 4 preproprotein, NM_001030048.1, is provided as SEQ ID NO: 22. Prostate-specific antigen isoform 1 preproprotein, NM_001648.2, is provided in SEQ ID NO: 23. (Each GenBank number is incorporated herein by reference in the version available on the filing date of the application to which this application claims priority).

It is understood that the invention includes the use of any combination of one or more of the PSA sequences provided in the sequence listing or any fragments thereof as long as the fragment can allow for the specific identification of PSA. Methods of the invention and reagents can be used to detect single isoforms of PSA, combinations of PSA isoforms, or all of the PSA isoforms simultaneously. Unless specified, PSA can be considered to refer to one or more isoforms of PSA, including total PSA. Moreover, it is understood that there are naturally occurring variants of PSA, which may or may not be associated with a specific disease state, the use of which are also included in the instant application.

In addition, it is understood that the invention includes the use of any fragments of PSA polypeptide as long as the fragment allow for the specific identification of PSA by a detection method of the invention. For example, an ELISA antibody must be able to bind to the PSA fragment so that detection is possible. Moreover, it is understood that there are naturally occurring variants of PSA which may or may not be associated with a specific disease state, the use of which are also included in this application. Accordingly, the present inventions also contemplate fragments and variants of PSA which may be associated with a disease state, e.g., BCR in prostate cancer. It is also understood that the invention encompasses the use of nucleic acid molecules encoding PSA, including for example, PSA-encoding DNA, PSA mRNA, and fragments and/or variants thereof. Reference to "PSA" may refer to PSA polypeptide or to the PSA gene, unless otherwise indicated.

The specific marker identified herein as prostate-specific membrane antigen (PSM) is further described in Sokoll et al., 1997, Prostate-specific antigen—Its discovery and biochemical characteristics, Urol. Clin. North Am., 24:253-259, which is incorporated herein by reference.

The specific marker identified herein as prostate stem cell antigen (PSCA) is further described in Fair et al., 1997, Prostate-specific membrane antigen, Prostate, 32:140-148, which is incorporated herein by reference.

The specific marker identified herein as TMPRSS2 is further described in Lin et al., 1999, Prostate-localized and androgen-regulated expression of the membrane-bound serine protease TMPRSS2, Cancer Res., 59:4180-4184, which is incorporated herein by reference.

The specific marker identified herein as PDEF is further described in Oettgen et al., PDEF, a novel prostate epithelium-specific ETS transcription factor interacts with the androgen receptor and activates prostate-specific antigen gene expression, J. Biol. Chem., 275: 1216-1225, which is incorporated herein by reference.

The specific marker identified herein as prostate-specific gene-1 (HPG-1) is further described in Herness, A novel human prostate-specific gene-1 (HPG-1): molecular cloning, sequencing, and its potential involvement in prostate carcinogenesis, 2003, Cancer Res. 63:329-336, which is incorporated herein by reference.

The non-coding RNA's (ncRNA's) identified as PCA3 is further described in Bussemakers et al., 1999, DD3: a new prostate-specific gene, highly overexpressed in prostate cancer, Cancer Res. 59:5975-5979, which is incorporated herein by reference.

The non-coding RNA identified as PCGEM1 is further described in Srikantan et al., 2000. PCGEM1, a prostate-specific gene, is overexpressed in prostate cancer. Proc. Natl. Acad. Sci. USA 97:12216-12221, which is incorporated herein by reference.

The gene cluster P704P, P712P, and P775P is further described in Stolk et al., 2004. P704P, P712P, and P775P: A genomic cluster of prostate-specific genes. Prostate 60:214-226), which is incorporated herein by reference.

In certain embodiments, the marker, e.g., a BCR marker, is a protein, for example, a protein listed in Table 1. In some embodiments, the invention also relates to a marker comprising one or more of the protein listed in Table 1. Exemplary Genbank Accession numbers and SEQ ID NOs for the protein markers listed in Table 1 are set forth in Table 8, as follows:

TABLE 8

| Protein Marker | GenBank Accession No. | SEQ ID NO |
| --- | --- | --- |
| tenascin C | NP_002151.2 | 1 |
| apolipoprotein A-IV | NP_000473.2 | 2 |
| Poliovirus receptor | CAA45479.1 | 3 |
| Coagulation factor XIII A chain | NP_000120.2 | 4 |
| apolipoprotein F | NP_001629.1 | 5 |
| Thrombospondin-4 | NP_001293141.1 | 6 |
| Metalloproteinase inhibitor 2 | NP_003246.1 | 7 |
| Mimecan | NP_054776.1 | 8 |
| Hypoxia up-regulated protein 1 | NP_001124463.1 | 9 |
| Interleukin-18-binding protein | NP_001034748.1 | 10 |
| Coagulation factor VII | NP_000122.1 | 11 |
| Fibrinogen beta chain | NP_001171670.1 | 12 |
| SH3 domain-binding glutamic acid-rich-like protein 3 | NP_112576.1 | 13 |
| Creatine kinase M-type | NP_001815.2 | 14 |
| Follistatin-related protein 1 | NP_009016.1 | 15 |
| CD109 antigen | NP_001153059.1 | 16 |
| Insulin-like growth factor-binding protein 7 | NP_001240764.1 | 17 |
| Histone H3.3C | NP_001013721.2 | 18 |
| Complement component C7 | NP_000578.2 | 19 |
| 78 kDa glucose-regulated protein | NP_005338.1 | 20 |

Each GenBank number is incorporated herein by reference in the version available on the filing date of the application to which this application claims priority. The protein markers are not limited to the protein sequences set forth in the GenBank Accession Numbers or sequence listing.

In certain embodiments, the marker, e.g., a BCR marker, is a metabolite, for example, a metabolite listed in Table 2. In some embodiments, the invention also relates to a marker set comprising one or more of the metabolites listed in Table 2.

In certain embodiments, the marker, e.g., a BCR marker, is a signaling lipid, for example, a signaling lipid listed in Table 3. In some embodiments, the invention also relates to a marker comprising one or more of the signaling lipids listed in Table 3.

In certain embodiments, the marker, e.g., a BCR marker, is a structural lipid, for example, a structural lipid listed in Table 4. In some embodiments, the invention also relates to a marker set comprising one or more of the structural lipids listed in Table 4.

In certain embodiments, the marker, e.g., a BCR marker, is a protein, metabolite, signaling lipid, and/or structural lipid listed in Table 5. In some embodiments, the invention also relates to a marker set comprising one or more of the markers listed in Table 5.

In some embodiments, the marker, e.g., a BCR marker, comprises at least two or more markers, wherein each of the two of more markers are selected from the proteins set forth in Table 1, the metabolites set forth in Table 2, the signaling lipids set forth in Table 3, the structural lipids set forth in Table 4, and/or the protein, metabolite, signaling lipid, and/or structural lipid markers listed in Table 5.

In some embodiments, the marker, e.g., a BCR marker, comprises one or more of the protein markers listed in Table 1 having a Rank A and/or Rank B. For example, in one embodiment, the markers comprise one or more of tenascin C, apolipoprotein A-IV, Poliovirus receptor and Coagulation factor XIII A chain. In one embodiment, tenascin C, apolipoprotein A-IV, Poliovirus receptor and Coagulation factor XIII A chain have a combined predictive diagnostic value (AUC) of 0.731 for BCR patients. In another embodiment, one or more of the markers are Poliovirus receptor and Coagulation factor XIII A chain. In one embodiment, Poliovirus receptor and Coagulation factor XIII A chain have a combined predictive diagnostic value (AUC) of 0.621 for BCR patients. In another embodiment, one or more of the markers are tenascin C and apolipoprotein A-IV. In one embodiment, tenascin C and apolipoprotein A-IV have a combined predictive diagnostic value (AUC) of 0.686 for BCR patients.

In some embodiments, the marker, e.g., a BCR marker, comprises one or more of the metabolite markers listed in Table 2 having a Rank A and/or Rank B. For example, in one embodiment, the markers comprise one or more of 1-methyladenosine, dimethylglycine, 2-aminooctanoic acid, allantoate, 1,5-anhydrohexitol, thymidine, and glycerol. In one embodiment, 1-methyladenosine, dimethylglycine, 2-aminooctanoic acid, allantoate, 1,5-anhydrohexitol, thymidine, and glycerol have a combined predictive diagnostic value (AUC) of 0.67 for BCR patients. In another embodiment, one of more of the markers are 2-aminooctanoic acid, allantoate, 1,5-anhydrohexitol, thymidine, and glycerol. In one embodiment, 2-aminooctanoic acid, allantoate, 1,5-anhydrohexitol, thymidine, and glycerol have a combined predictive diagnostic value (AUC) of 0.667 for BCR patients. In another embodiment, one or more of the markers are 1-methyladenosine and dimethylglycine. In one embodiment, 1-methyladeno sine and dimethylglycine have a combined predictive diagnostic value (AUC) of 0.617 for BCR patients.

In some embodiments, the marker, e.g., a BCR marker, comprises one or more of the signaling lipid markers listed in Table 3 having a Rank A and/or Rank B. For example, in one embodiment, the markers comprise one or more of 5-HETrE, 9-HETE, 14-HDHA, and TxB3. In one embodiment, 5-HETrE, 9-HETE, 14-HDHA, and TxB3 have a combined predictive diagnostic value (AUC) of 0.655 for BCR patients. In another embodiment, one or more of the markers are 9-HETE, 14-HDHA, and TxB3. In one embodiment, 9-HETE, 14-HDHA, and TxB3 have a combined predictive diagnostic value (AUC) of 0.415 for BCR patients. In another embodiment, the marker is 5-HETrE and has a predictive diagnostic value (AUC) of 0.538 for BCR patients.

In some embodiments, the marker, e.g., a BCR marker, comprises one or more of the structural lipid markers listed in Table 4 having a Rank A and/or Rank B. For example, in one embodiment, the markers comprise one or more of PA-18:0/22:0, AC-18:2-OH, and PS-18:0/22:3. In one embodiment, PA-18:0/22:0, AC-18:2-OH, and PS-18:0/22:3 have a combined predictive diagnostic value (AUC) of 0.651 for BCR patients. In another embodiment, one or more of the markers are AC-18:2-OH and PS-18:0/22:3. In one embodiment, AC-18:2-OH and PS-18:0/22:3 have a combined predictive diagnostic value (AUC) of 0.634 for BCR patients. In another embodiment, the marker is PA-18:0/22:0 and has a predictive diagnostic value (AUC) of 0.617 for BCR patients.

In some embodiments, the marker, e.g., a BCR marker, comprises one or more of the protein markers listed in Table 5 having a Rank A and/or Rank B. For example, in one embodiment, the markers comprise one or more of tenascin C, PA-18:0/22:0, 1-methyladenosine, and apolipoprotein A-IV. In one embodiment, tenascin C, PA-18:0/22:0, 1-methyladeno sine, and apolipoprotein A-IV have a combined predictive diagnostic value (AUC) of 0.784 in differentiating patients with progression free survival (PFS) from those who have BCR. In another embodiment, one or more of the markers are 1-methyladenosine and apolipoprotein A-IV. In one embodiment, 1-methyladenosine and apolipoprotein A-IV have a combined predictive diagnostic value (AUC) of 0.647 for BCR patients. In another embodiment, one or more of the markers are tenascin C and PA-18:0/22:0. In one embodiment, tenascin C and PA-18:0/22:0 have a combined predictive diagnostic value (AUC) of 0.712 for BCR patients.

In another embodiment, tenascin C, apolipoprotein A-IV, 1-methyladenosine, and PA-18:0/22:0, in combination with the two clinical variables tumor stage and Gleason score, have a combined predictive diagnostic value (AUC) of 0.89, positive predictive value (PPV) of 0.3, negative predictive value (NPV) of 0.96, and an odds ratio (OR) of 12.47 (p=1.003 e-09) (see Example 6).

In certain embodiments, the level of the marker, e.g., a BCR marker, is increased when compared to the predetermined threshold value in the subject. In other embodiments, the level of the marker, e.g., a BCR marker, is decreased when compared to the predetermined threshold value in the subject.

In another aspect, the present invention provides for the identification of a "diagnostic signature" or "disease profile" based on the levels of the markers of the invention in a biological sample, including in a diseased tissue or directly from the serum or blood, that correlates with the presence and/or risk and/or prognosis of BCR. The "levels of the markers" can refer to the level of a marker lipid, protein, or metabolite in a biological sample, e.g., plasma or serum. The "levels of the markers" can also refer to the expression level of the genes corresponding to the proteins, e.g., by measuring the expression levels of the corresponding marker mRNAs. The collection or totality of levels of markers provide a diagnostic signature that correlates with the presence and/or diagnosis and/or progression of BCR. The methods for obtaining a diagnostic signature or disease profile of the invention are meant to encompass any measurable characteristic that reflects in a quantitative or qualitative manner the physiological state of an organism, e.g., whether the organism has BCR. The physiological state of an organism is inclusive of any disease or non-disease state, e.g., a subject having BCR or a subject who is otherwise healthy. Said another way, the methods used for identifying a diagnostic signature or disease profile of the invention include determining characteristics that can be objectively measured and evaluated as indicators of normal processes, pathogenic processes, or pharmacologic responses to a therapeutic intervention, including, in particular, BCR. These characteristics can be clinical parameters (e.g., age, performance status), laboratory measures (e.g., molecular markers, such as proteins, lipids, or metabolites), imaging-based measures, or genetic or other molecular determinants. Examples of markers include, for example, polypeptides, peptides, polypeptide fragments, proteins, antibodies, hormones, polynucleotides, RNA or RNA fragments, microRNA (miRNAs), lipids, polysaccharides, and other metabolites that are diagnostic and/or indicative and/or predictive of BCR.

In a particular embodiment, a BCR profile or diagnostic signature is determined on the basis of the combination of the markers in Tables 1-5 together with one or more additional markers of BCR. Other markers that may be used in combination with the markers in Tables 1-5 include any measurable characteristic that reflects in a quantitative or qualitative manner the physiological state of an organism, e.g., whether the organism has BCR. The physiological state of an organism is inclusive of any disease or non-disease state, e.g., a subject having BCR or a subject who is otherwise healthy. Said another way, the markers of the invention that may be used in combination with the markers in Tables 1-5 include characteristics that can be objectively measured and evaluated as indicators of normal processes, pathogenic processes, or pharmacologic responses to a therapeutic intervention, including, in particular, BCR. Such combination markers can be clinical parameters (e.g., tumor stage, Gleason score, age, performance status), laboratory measures (e.g., molecular markers), imaging-based measures, or genetic or other molecular determinants. Example of markers for use in combination with the markers in Tables 1-5 include, for example, polypeptides, peptides, polypeptide fragments, proteins, antibodies, hormones, polynucleotides, RNA or RNA fragments, microRNA (miRNAs), lipids, polysaccharides, and other metabolites that are diagnostic and/or indicative and/or predictive of BCR. In certain embodiments, markers for use in combination with the markers in Tables 1-5 include polypeptides, peptides, polypeptide fragments, proteins, antibodies, hormones, polynucleotides, RNA or RNA fragments, microRNA (miRNAs), lipids, polysaccharides, and other bodily metabolites which are diagnostic and/or indicative and/or predictive of BCR, or any stage or clinical phase thereof. In other embodiments, the present invention also involves the analysis and consideration of any clinical and/or patient-related health data, for example, data obtained from an Electronic Medical Record (e.g., collection of electronic health information about individual patients or populations relating to various types of data, such as, demographics, medical history, medication and allergies, immunization status, laboratory test results, radiology images, vital signs, personal statistics like age and weight, and billing information).

In certain embodiments, the diagnostic signature is obtained by (1) detecting the level of at least one of the markers in Tables 1-5 in a biological sample, (2) comparing the level of the at least one marker in Tables 1-5 to the levels of the same marker from a control sample, and (3) determining if the at least one marker in Tables 1-5 is above or below a certain threshold level. If the at least one marker in Tables 1-5 is above or below the threshold level, then the diagnostic signature is indicative of BCR in the biological sample. In certain embodiments, the diagnostic signature can be determined based on an algorithm or computer program that predicts whether the biological sample is from a subject with BCR based on the level of the at least one marker in Tables 1-5.

In certain other embodiments, the diagnostic signature is obtained by (1) detecting the level of at least two markers in Tables 1-5, for example, at least two of tenascin C, apolipoprotein A-IV, 1-methyladenosine, and PA-18:0/22:0 in a biological sample, (2) comparing the levels of the at least two markers in Tables 1-5 to the levels of the same markers from a control sample, and (3) determining if the at least two markers in Tables 1-5 detected in the biological sample are above or below a certain threshold level. If the at least two markers in Tables 1-5 are above or below the threshold level, then the diagnostic signature is indicative of BCR in the biological sample. In certain embodiments, the diagnostic signature can be determined based on an algorithm or computer program that predicts whether the biological sample is from a subject with BCR based on the levels of the at least two markers in Tables 1-5.

In certain other embodiments, the diagnostic signature is obtained by (1) detecting the level of at least three markers in Tables 1-5, for example, at least three of tenascin C, apolipoprotein A-IV, 1-methyladenosine, and PA-18:0/22:0 in a biological sample, (2) comparing the levels of the at least three markers in Tables 1-5 to the levels of the same markers from a control sample, and (3) determining if the at least three markers in Tables 1-5 detected in the biological sample are above or below a certain threshold level. If the at least three markers in Tables 1-5 are above the threshold level, then the diagnostic signature is indicative of BCR in the biological sample. In certain embodiments, the diagnostic signature can be determined based on an algorithm or computer program that predicts whether the biological sample is from a subject with BCR based on the levels of the at least three markers in Tables 1-5.

In certain other embodiments, the diagnostic signature is obtained by (1) detecting the level of at least four markers in Tables 1-5, for example, at least tenascin C, apolipoprotein A-IV, 1-methyladenosine, and PA-18:0/22:0 in a biological sample, (2) comparing the levels of the at least four markers in Tables 1-5 to the levels of the same markers from a control sample, and (3) determining if the at least four markers in Tables 1-5 detected in the biological sample are above or below a certain threshold level. If the at least four markers in Tables 1-5 are above the threshold level, then the diagnostic signature is indicative of BCR in the biological sample. In certain embodiments, the diagnostic signature can be determined based on an algorithm or computer program that predicts whether the biological sample is from a subject with BCR based on the levels of the at least four markers in Tables 1-5.

In certain other embodiments, the diagnostic signature is obtained by (1) detecting the level of at least five markers in Tables 1-5 in a biological sample, (2) comparing the levels of the at least five markers in Tables 1-5 to the levels of the same markers from a control sample, and (3) determining if the at least five markers in Tables 1-5 detected in the biological sample are above or below a certain threshold level. If the at least five markers in Tables 1-5 are above the threshold level, then the diagnostic signature is indicative of BCR in the biological sample. In certain embodiments, the diagnostic signature can be determined based on an algorithm or computer program that predicts whether the biological sample is from a subject with BCR based on the levels of the at least five markers in Tables 1-5.

In certain other embodiments, the diagnostic signature is obtained by (1) detecting the level of at least six markers in Tables 1-5 in a biological sample, (2) comparing the levels of the at least six markers in Tables 1-5 to the levels of the same markers from a control sample, and (3) determining if the at least six markers in Tables 1-5 detected in the biological sample are above or below a certain threshold level. If the at least six markers in Tables 1-5 are above the threshold level, then the diagnostic signature is indicative of BCR in the biological sample. In certain embodiments, the diagnostic signature can be determined based on an algorithm or computer program that predicts whether the biological sample is from a subject with BCR based on the levels of the at least six markers in Tables 1-5.

In certain other embodiments, the diagnostic signature is obtained by (1) detecting the level of at least seven markers in Tables 1-5 in a biological sample, (2) comparing the levels of the at least seven markers in Tables 1-5 to the levels of the same markers from a control sample, and (3) determining if the at least seven markers in Tables 1-5 detected in the biological sample are above or below a certain threshold level. If the at least seven markers in Tables 1-5 are above the threshold level, then the diagnostic signature is indicative of BCR in the biological sample. In certain embodiments, the diagnostic signature can be determined based on an algorithm or computer program that predicts whether the biological sample is from a subject with BCR based on the levels of the at least seven markers in Tables 1-5.

In certain other embodiments, the diagnostic signature is obtained by (1) detecting the level of at least eight markers in Tables 1-5 in a biological sample, (2) comparing the levels of the at least eight markers in Tables 1-5 to the levels of the same markers from a control sample, and (3) determining if the at least eight markers in Tables 1-5 detected in the biological sample are above or below a certain threshold level. If the at least eight markers in Tables 1-5 are above the threshold level, then the diagnostic signature is indicative of BCR in the biological sample. In certain embodiments, the diagnostic signature can be determined based on an algorithm or computer program that predicts whether the biological sample is from a subject with BCR based on the levels of the at least eight markers in Tables 1-5.

In certain other embodiments, the diagnostic signature is obtained by (1) detecting the level of at least nine markers in Tables 1-5 in a biological sample, (2) comparing the levels of the at least nine markers in Tables 1-5 to the levels of the same markers from a control sample, and (3) determining if the at least nine markers in Tables 1-5 detected in the biological sample are above or below a certain threshold level. If the at least nine markers in Tables 1-5 are above the threshold level, then the diagnostic signature is indicative of BCR in the biological sample. In certain embodiments, the diagnostic signature can be determined based on an algorithm or computer program that predicts whether the biological sample is from a subject with BCR based on the levels of the at least nine markers in Tables 1-5.

In certain other embodiments, the diagnostic signature is obtained by (1) detecting the level of at least ten markers in Tables 1-5 in a biological sample, (2) comparing the levels of the at least ten markers in Tables 1-5 to the levels of the same markers from a control sample, and (3) determining if the at least ten markers in Tables 1-5 detected in the biological sample are above or below a certain threshold level. If the at least ten markers in Tables 1-5 are above the threshold level, then the diagnostic signature is indicative of BCR in the biological sample. In certain embodiments, the diagnostic signature can be determined based on an algorithm or computer program that predicts whether the biological sample is from a subject with BCR based on the levels of the at least ten markers in Tables 1-5.

In certain embodiments, the marker, e.g., a BCR marker, is a protein, for example, a protein listed in Table 1. In some embodiments, the invention also relates to a marker comprising one or more of the proteins listed in Table 1.

In certain embodiments, the marker, e.g., a BCR marker, is a metabolite, for example, a metabolite listed in Table 2. In some embodiments, the invention also relates to a marker set comprising one or more of the metabolites listed in Table 2.

In certain embodiments, the marker, e.g., a BCR marker, is a signaling lipid, for example, a signaling lipid listed in Table 3. In some embodiments, the invention also relates to a marker comprising one or more of the signaling lipids listed in Table 3.

In certain embodiments, the marker, e.g., a BCR marker, is a structural lipid, for example, a structural lipid listed in Table 4. In some embodiments, the invention also relates to a marker set comprising one or more of the structural lipids listed in Table 4.

In certain embodiments, the marker, e.g., a BCR marker, is a protein, metabolite, signaling lipid, and/or structural lipid listed in Table 5. In some embodiments, the invention also relates to a marker set comprising one or more of the structural lipids listed in Table 5.

In some embodiments, the marker, e.g., a BCR marker, comprises at least two or more markers, wherein each of the two of more markers are selected from the proteins set forth in Table 1, the metabolites set forth in Table 2, the signaling lipids set forth in Table 3, the structural lipids set forth in Table 4, protein, metabolite, signaling lipid, and/or structural lipid markers set forth in Table 5.

In certain embodiments, the level of the marker, e.g., a BCR marker, is increased when compared to the predetermined threshold value in the subject. In other embodiments, the level of the marker, e.g., a BCR marker, is decreased when compared to the predetermined threshold value in the subject.

In accordance with various embodiments, algorithms may be employed to predict whether or not a biological sample is likely to be diseased, e.g., have BCR. The skilled artisan will appreciate that an algorithm can be any computation, formula, statistical survey, nomogram, look-up Tables, decision tree method, or computer program which processes a set of input variables (e.g., number of markers (n) which have been detected at a level exceeding some threshold level, or number of markers (n) which have been detected at a level below some threshold level) through a number of well-defined successive steps to eventually produce a score or "output," e.g., a diagnosis of prostate cancer. Any suitable algorithm—whether computer-based or manual-based (e.g., look-up Tables)—is contemplated herein.

In certain embodiments, an algorithm of the invention is used to predict whether a biological sample is from a subject that has BCR in prostate cancer by producing a score on the basis of the detected level of at least 1, 2, 3, 4, 5, 6, 7, 8, 9, 10, 11, 12, 13, 14, 15, 20, 30, 40, 50, 60, or more of the markers in Tables 1-5 in the sample, wherein if the score is above or below a certain threshold score, then the biological sample is from a subject that has BCR.

Moreover, a BCR profile or signature may be obtained by detecting at least one of the markers in Tables 1-5 in combination with at least one other marker, or more preferably, with at least two other markers, or still more preferably, with at least three other markers, or even more preferably with at least four other markers. Still further, the markers in Tables 1-5 in certain embodiments, may be used in combination with at least five other markers, or at least six other markers, or at least seven other markers, or at least eight other markers, or at least nine other markers, or at least ten other markers, or at least eleven other markers, or at least twelve other markers, or at least thirteen other markers, or at least fourteen other markers, or at least fifteen other markers, or at least sixteen other markers, or at least seventeen other markers, or at least eighteen other markers, or at least nineteen other markers, or at least twenty other markers. Further still, the markers in Tables 1-5 may be used in combination with a multitude of other markers, including, for example, with between about 20-50 other markers, or between 50-100, or between 100-500, or between 500-1000, or between 1000-10,000 or markers or more.

In certain embodiments, the markers of the invention can include variant sequences. More particularly, certain binding agents/reagents used for detecting certain of the markers of the invention can bind and/or identify variants of these certain markers of the invention. As used herein, the term "variant" encompasses nucleotide or amino acid sequences different from the specifically identified sequences, wherein one or more nucleotides or amino acid residues is deleted, substituted, or added. Variants may be naturally occurring allelic variants, or non-naturally occurring variants. Variant sequences (polynucleotide or polypeptide) preferably exhibit at least 80%, 85%, 90%, 95%, 96%, 97%, 98% or 99% identity to a sequence disclosed herein. The percentage identity is determined by aligning the two sequences to be compared as described below, determining the number of identical residues in the aligned portion, dividing that number by the total number of residues in the inventive (queried) sequence, and multiplying the result by 100.

In addition to exhibiting the recited level of sequence identity, variants of the disclosed protein markers are preferably themselves expressed in subjects with BCR at levels that are higher or lower than the levels of expression in normal, healthy individuals.

Variant sequences generally differ from the specifically identified sequence only by conservative substitutions, deletions or modifications. As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. Variants may also, or alternatively, contain other modifications, including the deletion or addition of amino acids that have minimal influence on the antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Polypeptide and polynucleotide sequences may be aligned, and percentages of identical amino acids or nucleotides in a specified region may be determined against another polypeptide or polynucleotide sequence, using computer algorithms that are publicly available. The percentage identity of a polynucleotide or polypeptide sequence is determined by aligning polynucleotide and polypeptide sequences using appropriate algorithms, such as BLASTN or BLASTP, respectively, set to default parameters; identifying the number of identical nucleic or amino acids over the aligned portions; dividing the number of identical nucleic or amino acids by the total number of nucleic or amino acids of the polynucleotide or polypeptide of the present invention; and then multiplying by 100 to determine the percentage identity.

Two exemplary algorithms for aligning and identifying the identity of polynucleotide sequences are the BLASTN and FASTA algorithms. The alignment and identity of polypeptide sequences may be examined using the BLASTP algorithm. BLASTX and FASTX algorithms compare nucleotide query sequences translated in all reading frames against polypeptide sequences. The FASTA and FASTX algorithms are described in Pearson and Lipman, Proc. Natl. Acad. Sci. USA 85:2444-2448, 1988; and in Pearson, Methods in Enzymol. 183:63-98, 1990. The FASTA software package is available from the University of Virginia, Charlottesville, Va. 22906-9025. The FASTA algorithm, set to the default parameters described in the documentation and distributed with the algorithm, may be used in the determination of polynucleotide variants. The readme files for FASTA and FASTX Version 2.0x that are distributed with the algorithms describe the use of the algorithms and describe the default parameters.

The BLASTN software is available on the NCBI anonymous FTP server and is available from the National Center for Biotechnology Information (NCBI), National Library of Medicine, Building 38A, Room 8N805, Bethesda, Md. 20894. The BLASTN algorithm Version 2.0.6 [Sep. 10, 1998] and Version 2.0.11 [Jan. 20, 2000] set to the default parameters described in the documentation and distributed with the algorithm, is preferred for use in the determination of variants according to the present invention. The use of the BLAST family of algorithms, including BLASTN, is described at NCBI's website and in the publication of Altschul, et al., "Gapped BLAST and PSI-BLAST: a new generation of protein database search programs," Nucleic Acids Res. 25:3389-3402, 1997.

In an alternative embodiment, variant polypeptides are encoded by polynucleotide sequences that hybridize to a disclosed polynucleotide under stringent conditions. Stringent hybridization conditions for determining complementarity include salt conditions of less than about 1 M, more usually less than about 500 mM, and preferably less than about 200 mM. Hybridization temperatures can be as low as 5° C., but are generally greater than about 22° C., more preferably greater than about 30° C., and most preferably greater than about 37° C. Longer DNA fragments may require higher hybridization temperatures for specific hybridization. Since the stringency of hybridization may be affected by other factors such as probe composition, presence of organic solvents and extent of base mismatching, the combination of parameters is more important than the absolute measure of any one alone. An example of "stringent conditions" is prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

The invention provides for the use of various combinations and sub-combinations of markers. It is understood that any single marker or combination of the markers provided herein can be used in the invention unless clearly indicated otherwise. Further, any single marker or combination of the markers of the invention can be used in conjunction with PSA.

D. Tissue Samples

The present invention may be practiced with any suitable biological sample that potentially contains, expresses, includes, a detectable disease biomarker, e.g., a lipid biomarker, a polypeptide biomarker, a nucleic acid biomarker, a mRNA biomarker, a microRNA biomarker. For example, the biological sample may be obtained from sources that include whole blood, serum, urine, diseased and/or healthy organ tissue, for example, biopsy of prostate, and seminal fluid. In certain embodiments, the biological sample urine collected after a digital rectal exam, i.e., post-DRE urine. Preferably, the biological sample is serum or urine.

The methods of the invention may be applied to the study of any prostate tissue sample, i.e., a sample of prostate tissue or fluid, as well as cells (or their progeny) isolated from such tissue or fluid. In another embodiment, the present invention may be practiced with any suitable prostate tissue samples which are freshly isolated or which have been frozen or stored after having been collected from a subject, or archival tissue samples, for example, with known diagnosis, treatment, and/or outcome history. Prostate tissue may be collected by any non-invasive means, such as, for example, fine needle aspiration and needle biopsy, or alternatively, by an invasive method, including, for example, surgical biopsy.

The inventive methods may be performed at the single cell level (e.g., isolation and testing of cancerous cells from the prostate tissue sample). However, the inventive methods may also be performed using a sample comprising many cells, where the assay is "averaging" expression over the entire collection of cells and tissue present in the sample. Preferably, there is enough of the prostate tissue sample to accurately and reliably determine the expression levels of interest. In certain embodiments, multiple samples may be taken from the same prostate tissue in order to obtain a representative sampling of the tissue. In addition, sufficient biological material can be obtained in order to perform duplicate, triplicate or further rounds of testing.

Any commercial device or system for isolating and/or obtaining prostate tissue and/or blood or other biological products, and/or for processing said materials prior to conducting a detection reaction is contemplated.

In certain embodiments, the present invention relates to detecting biomarker nucleic acid molecules (e.g., mRNA encoding the protein markers of Tables 1-5). In such embodiments, RNA can be extracted from a biological sample, e.g., a prostate tissue sample, before analysis. Methods of RNA extraction are well known in the art (see, for example, J. Sambrook et al., "Molecular Cloning: A Laboratory Manual", 1989, 2$^{nd}$ Ed., Cold Spring Harbour Laboratory Press: New York). Most methods of RNA isolation from bodily fluids or tissues are based on the disruption of the tissue in the presence of protein denaturants to quickly and effectively inactivate RNases. Generally, RNA isolation reagents comprise, among other components, guanidinium thiocyanate and/or beta-mercaptoethanol, which are known to act as RNase inhibitors. Isolated total RNA is then further purified from the protein contaminants and concentrated by selective ethanol precipitations, phenol/chloroform extractions followed by isopropanol precipitation (see, for example, P. Chomczynski and N. Sacchi, Anal. Biochem., 1987, 162: 156-159) or cesium chloride, lithium chloride or cesium trifluoroacetate gradient centrifugations.

Numerous different and versatile kits can be used to extract RNA (i.e., total RNA or mRNA) from bodily fluids or tissues (e.g., prostate tissue samples) and are commercially available from, for example, Ambion, Inc. (Austin, Tex.), Amersham Biosciences (Piscataway, N.J.), BD Biosciences Clontech (Palo Alto, Calif.), BioRad Laboratories (Hercules, Calif.), GIBCO BRL (Gaithersburg, Md.), and Giagen, Inc. (Valencia, Calif.). User Guides that describe in great detail the protocol to be followed are usually included in all these kits. Sensitivity, processing time and cost may be different from one kit to another. One of ordinary skill in the art can easily select the kit(s) most appropriate for a particular situation.

In certain embodiments, after extraction, mRNA is amplified, and transcribed into cDNA, which can then serve as template for multiple rounds of transcription by the appropriate RNA polymerase. Amplification methods are well known in the art (see, for example, A. R. Kimmel and S. L. Berger, Methods Enzymol. 1987, 152: 307-316; J. Sambrook et al., "Molecular Cloning: A Laboratory Manual", 1989, 2nd Ed., Cold Spring Harbour Laboratory Press: New York; "Short Protocols in Molecular Biology", F. M. Ausubel (Ed.), 2002, 5.sup.th Ed., John Wiley & Sons; U.S. Pat. Nos. 4,683,195; 4,683,202 and 4,800,159). Reverse transcription reactions may be carried out using non-specific primers, such as an anchored oligo-dT primer, or random sequence primers, or using a target-specific primer complementary to the RNA for each genetic probe being monitored, or using thermostable DNA polymerases (such as avian myeloblastosis virus reverse transcriptase or Moloney murine leukemia virus reverse transcriptase).

In certain embodiments, the RNA isolated from the prostate tissue sample (for example, after amplification and/or conversion to cDNA or cRNA) is labeled with a detectable agent before being analyzed. The role of a detectable agent is to facilitate detection of RNA or to allow visualization of hybridized nucleic acid fragments (e.g., nucleic acid fragments hybridized to genetic probes in an array-based assay). Preferably, the detectable agent is selected such that it generates a signal which can be measured and whose intensity is related to the amount of labeled nucleic acids present in the sample being analyzed. In array-based analysis methods, the detectable agent is also preferably selected such that it generates a localized signal, thereby allowing spatial resolution of the signal from each spot on the array.

Methods for labeling nucleic acid molecules are well-known in the art. For a review of labeling protocols, label detection techniques and recent developments in the field, see, for example, L. J. Kricka, Ann. Clin. Biochem. 2002, 39: 114-129; R. P. van Gijlswijk et al., Expert Rev. Mol. Diagn. 2001, 1: 81-91; and S. Joos et al., J. Biotechnol. 1994, 35: 135-153. Standard nucleic acid labeling methods include: incorporation of radioactive agents, direct attachment of fluorescent dyes (see, for example, L. M. Smith et al., Nucl. Acids Res. 1985, 13: 2399-2412) or of enzymes (see, for example, B. A. Connoly and P. Rider, Nucl. Acids. Res. 1985, 13: 4485-4502); chemical modifications of nucleic acid fragments making them detectable immunochemically or by other affinity reactions (see, for example, T. R. Broker et al., Nucl. Acids Res. 1978, 5: 363-384; E. A. Bayer et al., Methods of Biochem. Analysis, 1980, 26: 1-45; R. Langer et al., Proc. Natl. Acad. Sci. USA, 1981, 78: 6633-6637; R. W. Richardson et al., Nucl. Acids Res. 1983, 11: 6167-6184; D. J. Brigati et al., Virol. 1983, 126: 32-50; P. Tchen et al., Proc. Natl Acad. Sci. USA, 1984, 81: 3466-3470; J. E. Landegent et al., Exp. Cell Res. 1984, 15: 61-72; and A. H. Hopman et al., Exp. Cell Res. 1987, 169: 357-368); and enzyme-mediated labeling methods, such as random priming, nick translation, PCR and tailing with terminal transferase (for a review on enzymatic labeling, see, for example, J. Temsamani and S. Agrawal, Mol. Biotechnol. 1996, 5: 223-232).

Any of a wide variety of detectable agents can be used in the practice of the present invention. Suitable detectable agents include, but are not limited to: various ligands, radionuclides, fluorescent dyes, chemiluminescent agents, microparticles (such as, for example, quantum dots, nanocrystals, phosphors and the like), enzymes (such as, for example, those used in an ELISA, i.e., horseradish peroxidase, beta-galactosidase, luciferase, alkaline phosphatase), colorimetric labels, magnetic labels, and biotin, dioxigenin or other haptens and proteins for which antisera or monoclonal antibodies are available.

However, in some embodiments, the expression levels are determined by detecting the expression of a gene product (e.g., protein) thereby eliminating the need to obtain a genetic sample (e.g., RNA) from the prostate tissue sample.

In still other embodiments, the present invention relates to preparing a prediction model for BCR and/or the likelihood of BCR by preparing a model for BCR based on measuring the biomarkers of the invention in known control samples. More particularly, the present invention relates in some embodiments to preparing a predictive model by evaluating the biomarkers of the invention, i.e., the markers of Tables 1-5.

The skilled person will appreciate that patient tissue samples containing prostate cells or prostate cancer cells may be used in the methods of the present invention including, but not limited to those aimed at predicting relapse probability. In these embodiments, the level of expression of the signature gene can be assessed by assessing the amount, e.g. absolute amount or concentration, of a signature gene product, e.g., protein and RNA transcript encoded by the signature gene and fragments of the protein and RNA transcript) in a sample, e.g., stool and/or blood obtained from a patient. The sample can, of course, be subjected to a variety of well-known post-collection preparative and storage techniques (e.g. fixation, storage, freezing, lysis, homogenization, DNA or RNA extraction, ultrafiltration, concentration, evaporation, centrifugation, etc.) prior to assessing the amount of the signature gene product in the sample.

The invention further relates to the preparation of a model for BCR by evaluating the biomarkers of the invention in known samples of BCR in prostate cancer. More particularly, the present invention relates to a model for diagnosing and/or monitoring and/or prognosing BCR using the biomarkers of the invention, i.e., the markers of Tables 1-5.

In the methods of the invention aimed at preparing a model for prostate cancer relapse prediction, it is understood that the particular clinical outcome associated with each sample contributing to the model preferably should be known. Consequently, the model can be established using archived tissue samples. In the methods of the invention aimed at preparing a model for BCR prediction, total RNA can be generally extracted from the source material of interest, generally an archived tissue such as a formalin-fixed, paraffin-embedded tissue, and subsequently purified. Methods for obtaining robust and reproducible gene expression patterns from archived tissues, including formalin-fixed, paraffin-embedded (FFPE) tissues are taught in U.S. Publ. No. 2004/0259105, which is incorporated herein by reference in its entirety. Commercial kits and protocols for RNA extraction from FFPE tissues are available including, for example, ROCHE High Pure RNA Paraffin Kit (Roche) MasterPure™ Complete DNA and RNA Purification Kit (EPICENTRE®Madison, Wis.); Paraffin Block RNA Isolation Kit (Ambion, Inc.) and RNeasy™ Mini kit (Qiagen, Chatsworth, Calif.).

The use of FFPE tissues as a source of RNA for RT-PCR has been described previously (Stanta et al., Biotechniques 11:304-308 (1991); Stanta et al., Methods Mol. Biol. 86:23-26 (1998); Jackson et al., Lancet 1:1391 (1989); Jackson et al., J. Clin. Pathol. 43:499-504 (1999); Finke et al., Biotechniques 14:448-453 (1993); Goldsworthy et al., Mol. Carcinog. 25:86-91 (1999); Stanta and Bonin, Biotechniques 24:271-276 (1998); Godfrey et al., J. Mol. Diagnostics 2:84 (2000); Specht et al., J. Mol. Med. 78:B27 (2000); Specht et al., Am. J. Pathol. 158:419-429 (2001)). For quick analysis of the RNA quality, RT-PCR can be performed utilizing a pair of primers targeting a short fragment in a highly expressed gene, for example, actin, ubiquitin, gapdh or other well-described commonly used housekeeping gene. If the cDNA synthesized from the RNA sample can be amplified using this pair of primers, then the sample is suitable for the a quantitative measurements of RNA target sequences by any method preferred, for example, the DASL assay, which requires only a short cDNA fragment for the annealing of query oligonucleotides.

There are numerous tissue banks and collections including exhaustive samples from all stages of a wide variety of disease states, most notably cancer and in particular, prostate cancer. The ability to perform genotyping and/or gene expression analysis, including both qualitative and quantitative analysis on these samples enables the application of this methodology to the methods of the invention. In particular, the ability to establish a correlation of gene expression and a known predictor of disease extent and/or outcome by probing the genetic state of tissue samples for which clinical outcome is already known, allows for the establishment of a correlation between a particular molecular signature and the known predictor, such as a Gleason score, to derive a score that allows for a more sensitive prognosis than that based on the known predictor alone. The skilled person will appreciate that by building databases of molecular signatures from tissue samples of known outcomes, many such correlations can be established, thus allowing both diagnosis and prognosis of any condition. Thus, such approaches may be used to correlate the expression levels of the biomarkers of the invention, i.e., the markers of Tables 1-5.

Tissue samples useful for preparing a model for BCR in prostate cancer prediction include, for example, paraffin and polymer embedded samples, ethanol embedded samples and/or formalin and formaldehyde embedded tissues, although any suitable sample may be used. In general, nucleic acids isolated from archived samples can be highly degraded and the quality of nucleic preparation can depend on several factors, including the sample shelf life, fixation technique and isolation method. However, using the methodologies taught in U.S. Publ. No. 2004/0259105, which have the significant advantage that short or degraded targets can be used for analysis as long as the sequence is long enough to hybridize with the oligonucleotide probes, highly reproducible results can be obtained that closely mimic results found in fresh samples.

Archived tissue samples, which can be used for all methods of the invention, typically have been obtained from a source and preserved. Preferred methods of preservation include, but are not limited to paraffin embedding, ethanol fixation and formalin, including formaldehyde and other derivatives, fixation as are known in the art. A tissue sample may be temporally "old", e.g. months or years old, or recently fixed. For example, post-surgical procedures generally include a fixation step on excised tissue for histological analysis. In a preferred embodiment, the tissue sample is a diseased tissue sample, particularly a prostate cancer tissue, including primary and secondary tumor tissues as well as lymph node tissue and metastatic tissue.

Thus, an archived sample can be heterogeneous and encompass more than one cell or tissue type, for example, tumor and non-tumor tissue. Similarly, depending on the condition, suitable tissue samples include, but are not limited to, bodily fluids (including, but not limited to, blood, urine, serum, lymph, saliva, anal and vaginal secretions, perspiration and semen, of virtually any organism, with mammalian samples being preferred and human samples being particularly preferred). In embodiments directed to methods of establishing a model for BCR prediction, the tissue sample is one for which patient history and outcome is known. Generally, the invention methods can be practiced with the signature gene sequence contained in an archived sample or can be practiced with signature gene sequences that have been physically separated from the sample prior to performing a method of the invention.

E. Detection and/or Measurement of Biomarkers

The present invention contemplates any suitable means, techniques, and/or procedures for detecting and/or measuring the biomarkers of the invention. The skilled artisan will appreciate that the methodologies employed to measure the biomarkers of the invention will depend at least on the type of biomarker being detected or measured (e.g., lipid or polypeptide biomarker) and the source of the biological sample (e.g., whole blood versus prostate biopsy tissue). Certain biological samples may also require certain specialized treatments prior to measuring the biomarkers of the invention, e.g., the extraction of lipids from a serum in the case of lipid markers being measured.

1. Detection of Lipid Markers

The present invention contemplates any suitable method for detecting lipid biomarkers of the invention, i.e., the lipids of Tables 3 or 4. In certain embodiments, a lipid sample may be extracted from a biological sample using any method known in the art such as chloroform-methanol based methods, isopropanol-hexane methods, the Bligh & Dyer lipid extraction method or a modified version thereof, or any combination thereof. Suitable modifications to the Bligh & Dyer method include treatment of crude lipid extracts with lithium methoxide followed by subsequent liquid-liquid extraction to remove generated free fatty acids, fatty acid methyl esters, cholesterol, and water-soluble components that may hinder the shotgun analysis of sphingolipidomes. Since sphingolipids are inert to the described base-treatment, the global analysis and accurate quantitation to assess low and even very low abundant sphingolipids is possible by using a modified Bligh & Dyer method. Following lipid extraction, it may be beneficial to separate the lipids prior to mass spectrometric analysis. Methods for separating lipids are known in the art. Suitable methods include, but are not limited to, chromatography methods such as solid-phase extraction, high performance liquid chromatography (HPLC), normal-phase HPLC, or reverse-phase HPLC. The resultant lipid extracts are then analyzed by mass spectrometric techniques commonly known in the art.

2. Detection of Protein Markers

The present invention contemplates any suitable method for detecting polypeptide biomarkers of the invention, i.e., the proteins of Table 1 or Table 5. In certain embodiments, the detection method is an immunodetection method involving an antibody that specifically binds to one or more of the proteins of Table 1 or Table 5. The steps of various useful immunodetection methods have been described in the scientific literature, such as, e.g., Nakamura et al. (1987), which is incorporated herein by reference.

In general, the immunobinding methods include obtaining a sample suspected of containing a biomarker protein, peptide or antibody, and contacting the sample with an antibody or protein or peptide in accordance with the present invention, as the case may be, under conditions effective to allow the formation of immunocomplexes.

The immunobinding methods include methods for detecting or quantifying the amount of a reactive component in a sample, which methods require the detection or quantitation of any immune complexes formed during the binding process. Here, one would obtain a sample suspected of containing a prostate specific protein, peptide or a corresponding antibody, and contact the sample with an antibody or encoded protein or peptide, as the case may be, and then detect or quantify the amount of immune complexes formed under the specific conditions.

In terms of biomarker detection, the biological sample analyzed may be any sample that is suspected of containing one more proteins of Table 1 or Table 5. The biological sample may be, for example, a prostate or lymph node tissue section or specimen, a homogenized tissue extract, an isolated cell, a cell membrane preparation, separated or purified forms of any of the above protein-containing compositions, or even any biological fluid that comes into contact with prostate tissues, including blood or lymphatic fluid.

Contacting the chosen biological sample with the protein under conditions effective and for a period of time sufficient to allow the formation of immune complexes (primary immune complexes). Generally, complex formation is a matter of simply adding the composition to the biological sample and incubating the mixture for a period of time long enough for the antibodies to form immune complexes with, i.e., to bind to, any antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any radioactive, fluorescent, biological or enzymatic tags or labels of standard use in the art. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

The protein employed in the detection may itself be linked to a detectable label, wherein one would then simply detect this label, thereby allowing the amount of the primary immune complexes in the composition to be determined.

Alternatively, the first added component that becomes bound within the primary immune complexes may be detected by means of a second binding ligand that has binding affinity for the encoded protein, peptide or corresponding antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the encoded protein, peptide or corresponding antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

The immunodetection methods of the present invention have evident utility in the diagnosis of conditions such as BCR. Here, a biological or clinical sample suspected of containing either the encoded protein or peptide or corresponding antibody is used. However, these embodiments also have applications to non-clinical samples, such as in the tittering of antigen or antibody samples, in the selection of hybridomas, and the like.

The present invention, in particular, contemplates the use of ELISAs as a type of immunodetection assay. It is contemplated that the biomarker proteins or peptides of the invention will find utility as immunogens in ELISA assays in diagnosis and prognostic monitoring of BCR in prostate cancer. Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and Western blotting, dot blotting, FACS analyses, and the like also may be used.

In one exemplary ELISA, antibodies binding to the biomarkers of the invention are immobilized onto a selected surface exhibiting protein affinity, such as a well in a polystyrene microtiter plate. Then, a test composition suspected of containing the marker antigen, such as a clinical sample, is added to the wells. After binding and washing to remove non-specifically bound immunecomplexes, the bound antigen may be detected. Detection is generally achieved by the addition of a second antibody specific for the target protein, that is linked to a detectable label. This type of ELISA is a simple "sandwich ELISA." Detection also may be achieved by the addition of a second antibody, followed by the addition of a third antibody that has binding affinity for the second antibody, with the third antibody being linked to a detectable label.

In another exemplary ELISA, the samples suspected of containing the BCR marker antigen are immobilized onto the well surface and then contacted with the anti-biomarker antibodies of the invention. After binding and washing to remove non-specifically bound immunecomplexes, the bound antigen is detected. Where the initial antibodies are linked to a detectable label, the immunecomplexes may be detected directly. Again, the immunecomplexes may be detected using a second antibody that has binding affinity for the first antibody, with the second antibody being linked to a detectable label.

Irrespective of the format employed, ELISAs have certain features in common, such as coating, incubating or binding, washing to remove non-specifically bound species, and detecting the bound immunecomplexes. These are described as follows.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the control human prostate, cancer and/or clinical or biological sample to be tested under conditions effective to allow immunecomplex (antigen/antibody) formation. Detection of the immunecomplex then requires a labeled secondary binding ligand or antibody, or a secondary binding ligand or antibody in conjunction with a labeled tertiary antibody or third binding ligand.

The phrase "under conditions effective to allow immunecomplex (antigen/antibody) formation" means that the conditions preferably include diluting the antigens and antibodies with solutions such as BSA, bovine gamma globulin (BGG) and phosphate buffered saline (PBS)/Tween. These added agents also tend to assist in the reduction of nonspecific background. The "suitable" conditions also mean that the incubation is at a temperature and for a period of time sufficient to allow effective binding. Incubation steps are typically from about 1 to 2 to 4 h, at temperatures preferably on the order of 25 to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immunecomplexes between the test sample and the originally bound material, and subsequent washing, the occurrence of even minute amounts of immunecomplexes may be determined.

To provide a detecting means, the second or third antibody will have an associated label to allow detection. Preferably, this will be an enzyme that will generate color development upon incubating with an appropriate chromogenic substrate. Thus, for example, one will desire to contact and incubate the first or second immunecomplex with a urease, glucose oxidase, alkaline phosphatase or hydrogen peroxidase-conjugated antibody for a period of time and under conditions that favor the development of further immunecomplex formation (e.g., incubation for 2 h at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple. Quantitation is then achieved by measuring the degree of color generation, e.g., using a visible spectra spectrophotometer.

The protein biomarkers of the invention can also be measured, quantitated, detected, and otherwise analyzed using protein mass spectrometry methods and instrumentation. Protein mass spectrometry refers to the application of mass spectrometry to the study of proteins. Although not intending to be limiting, two approaches are typically used for characterizing proteins using mass spectrometry. In the first, intact proteins are ionized and then introduced to a mass analyzer. This approach is referred to as "top-down" strategy of protein analysis. The two primary methods for ionization of whole proteins are electrospray ionization (ESI) and matrix-assisted laser desorption/ionization (MALDI). In the second approach, proteins are enzymatically digested into smaller peptides using a protease such as trypsin. Subsequently these peptides are introduced into the mass spectrometer and identified by peptide mass fingerprinting or tandem mass spectrometry. Hence, this latter approach (also called "bottom-up" proteomics) uses identification at the peptide level to infer the existence of proteins.

Whole protein mass analysis of the biomarkers of the invention can be conducted using time-of-flight (TOF) MS, or Fourier transform ion cyclotron resonance (FT-ICR). These two types of instruments are useful because of their wide mass range, and in the case of FT-ICR, its high mass accuracy. The most widely used instruments for peptide mass analysis are the MALDI time-of-flight instruments as they permit the acquisition of peptide mass fingerprints (PMFs) at high pace (1 PMF can be analyzed in approx. 10 sec). Multiple stage quadrupole-time-of-flight and the quadrupole ion trap also find use in this application.

The protein biomarkers of the invention can also be measured in complex mixtures of proteins and molecules that co-exist in a biological medium or sample, however, fractionation of the sample may be required and is contemplated herein. It will be appreciated that ionization of complex mixtures of proteins can result in situation where the more abundant proteins have a tendency to "drown" or suppress signals from less abundant proteins in the same sample. In addition, the mass spectrum from a complex mixture can be difficult to interpret because of the overwhelming number of mixture components. Fractionation can be used to first separate any complex mixture of proteins prior to mass spectrometry analysis. Two methods are widely used to fractionate proteins, or their peptide products from an enzymatic digestion. The first method fractionates whole proteins and is called two-dimensional gel electrophoresis. The second method, high performance liquid chromatography (LC or HPLC) is used to fractionate peptides after enzymatic digestion. In some situations, it may be desirable to combine both of these techniques. Any other suitable methods known in the art for fractionating protein mixtures are also contemplated herein.

Gel spots identified on a 2D Gel are usually attributable to one protein. If the identity of the protein is desired, usually the method of in-gel digestion is applied, where the protein spot of interest is excised, and digested proteolytically. The peptide masses resulting from the digestion can be determined by mass spectrometry using peptide mass fingerprinting. If this information does not allow unequivocal identification of the protein, its peptides can be subject to tandem mass spectrometry for de novo sequencing.

Characterization of protein mixtures using HPLC/MS may also be referred to in the art as "shotgun proteomics" and MuDPIT (Multi-Dimensional Protein Identification Technology). A peptide mixture that results from digestion of a protein mixture is fractionated by one or two steps of liquid chromatography (LC). The eluent from the chromatography stage can be either directly introduced to the mass spectrometer through electrospray ionization, or laid down on a series of small spots for later mass analysis using MALDI.

The protein biomarkers of the present invention can be identified using MS using a variety of techniques, all of which are contemplated herein. Peptide mass fingerprinting uses the masses of proteolytic peptides as input to a search of a database of predicted masses that would arise from digestion of a list of known proteins. If a protein sequence in the reference list gives rise to a significant number of predicted masses that match the experimental values, there is some evidence that this protein was present in the original sample. It will be further appreciated that the development of methods and instrumentation for automated, data-dependent electrospray ionization (ESI) tandem mass spectrometry (MS/MS) in conjunction with microcapillary liquid chromatography (LC) and database searching has significantly increased the sensitivity and speed of the identification of gel-separated proteins. Microcapillary LC-MS/MS has been used successfully for the large-scale identification of individual proteins directly from mixtures without gel electrophoretic separation (Link et al., 1999; Opitek et al., 1997).

Several recent methods allow for the quantitation of proteins by mass spectrometry. For example, stable (e.g., non-radioactive) heavier isotopes of carbon ($^{13}C$) or nitrogen ($^{15}N$) can be incorporated into one sample while the other one can be labeled with corresponding light isotopes (e.g. $^{12}C$ and $^{14}N$). The two samples are mixed before the analysis. Peptides derived from the different samples can be distinguished due to their mass difference. The ratio of their peak intensities corresponds to the relative abundance ratio of the peptides (and proteins). The most popular methods for isotope labeling are SILAC (stable isotope labeling by amino acids in cell culture), trypsin-catalyzed $^{18}O$ labeling, ICAT (isotope coded affinity tagging), iTRAQ (isobaric tags for relative and absolute quantitation). "Semi-quantitative" mass spectrometry can be performed without labeling of samples. Typically, this is done with MALDI analysis (in linear mode). The peak intensity, or the peak area, from individual molecules (typically proteins) is here correlated to the amount of protein in the sample. However, the individual signal depends on the primary structure of the protein, on the complexity of the sample, and on the settings of the instrument. Other types of "label-free" quantitative mass spectrometry, uses the spectral counts (or peptide counts) of digested proteins as a means for determining relative protein amounts.

In one embodiment, any one or more of the protein markers of the invention can be identified and quantified from a complex biological sample using mass spectroscopy in accordance with the following exemplary method, which is not intended to limit the invention or the use of other mass spectrometry-based methods.

In the first step of this embodiment, (A) a biological sample, e.g., a biological sample suspected of having BCR in prostate cancer, which comprises a complex mixture of protein (including at least one biomarker of interest) is fragmented and labeled with a stable isotope X. (B) Next, a known amount of an internal standard is added to the biological sample, wherein the internal standard is prepared by fragmenting a standard protein that is identical to the at least one target biomarker of interest, and labeled with a stable isotope Y. (C) This sample obtained is then introduced in an LC-MS/MS device, and multiple reaction monitoring (MRM) analysis is performed using MRM transitions selected for the internal standard to obtain an MRM chromatogram. (D) The MRM chromatogram is then viewed to identify a target peptide biomarker derived from the biological sample that shows the same retention time as a peptide derived from the internal standard (an internal standard peptide), and quantifying the target protein biomarker in the test sample by comparing the peak area of the internal standard peptide with the peak area of the target peptide biomarker.

Any suitable biological sample may be used as a starting point for LC-MS/MS/MRM analysis, including biological samples derived blood, urine, saliva, hair, cells, cell tissues, biopsy materials, and treated products thereof; and protein-containing samples prepared by gene recombination techniques.

Each of the above steps (A) to (D) is described further below. Step (A) (Fragmentation and Labeling). In step (A), the target protein biomarker is fragmented to a collection of peptides, which is subsequently labeled with a stable isotope X. To fragment the target protein, for example, methods of digesting the target protein with a proteolytic enzyme (protease) such as trypsin, and chemical cleavage methods, such as a method using cyanogen bromide, can be used. Digestion by protease is preferable. It is known that a given mole quantity of protein produces the same mole quantity for each tryptic peptide cleavage product if the proteolytic digest is allowed to proceed to completion. Thus, determining the mole quantity of tryptic peptide to a given protein allows determination of the mole quantity of the original protein in the sample. Absolute quantification of the target protein can be accomplished by determining the absolute amount of the target protein-derived peptides contained in the protease digestion (collection of peptides). Accordingly, in order to allow the proteolytic digest to proceed to completion, reduction and alkylation treatments are preferably performed before protease digestion with trypsin to reduce and alkylate the disulfide bonds contained in the target protein.

Subsequently, the obtained digest (collection of peptides, comprising peptides of the target biomarker in the biological sample) is subjected to labeling with a stable isotope X. Examples of stable isotopes X include $^1H$ and $^2H$ for hydrogen atoms, $^{12}$C and $^{13}$C for carbon atoms, and $^{14}$N and $^{15}$N for nitrogen atoms. Any isotope can be suitably selected therefrom. Labeling by a stable isotope X can be performed by reacting the digest (collection of peptides) with a reagent containing the stable isotope. Preferable examples of such reagents that are commercially available include mTRAQ (registered trademark) (produced by Applied Biosystems), which is an amine-specific stable isotope reagent kit. mTRAQ is composed of 2 or 3 types of reagents (mTRAQ-light and mTRAQ-heavy; or mTRAQ-D0, mTRAQ-D4, and mTRAQ-D8) that have a constant mass difference therebetween as a result of isotope-labeling, and that are bound to the N-terminus of a peptide or the primary amine of a lysine residue.

Step (B) (Addition of the Internal Standard). In step (B), a known amount of an internal standard is added to the sample obtained in step (A). The internal standard used herein is a digest (collection of peptides) obtained by fragmenting a protein (standard protein) consisting of the same amino acid sequence as the target protein (target biomarker) to be measured, and labeling the obtained digest (collection of peptides) with a stable isotope Y. The fragmentation treatment can be performed in the same manner as above for the target protein. Labeling with a stable isotope Y can also be performed in the same manner as above for the target protein. However, the stable isotope Y used herein must be an isotope that has a mass different from that of the stable isotope X used for labeling the target protein digest. For example, in the case of using the aforementioned mTRAQ (registered trademark) (produced by Applied Biosystems), when mTRAQ-light is used to label a target protein digest, mTRAQ-heavy should be used to label a standard protein digest.

Step (C) (LC-MS/MS and MRM Analysis). In step (C), the sample obtained in step (B) is first placed in an LC-MS/MS device, and then multiple reaction monitoring (MRM) analysis is performed using MRM transitions selected for the internal standard. By LC (liquid chromatography) using the LC-MS/MS device, the sample (collection of peptides labeled with a stable isotope) obtained in step (B) is separated first by one-dimensional or multi-dimensional high-performance liquid chromatography. Specific examples of such liquid chromatography include cation exchange chromatography, in which separation is conducted by utilizing electric charge difference between peptides; and reversed-phase chromatography, in which separation is conducted by utilizing hydrophobicity difference between peptides. Both of these methods may be used in combination.

Subsequently, each of the separated peptides is subjected to tandem mass spectrometry by using a tandem mass spectrometer (MS/MS spectrometer) comprising two mass spectrometers connected in series. The use of such a mass spectrometer enables the detection of several fmol levels of a target protein. Furthermore, MS/MS analysis enables the analysis of internal sequence information on peptides, thus enabling identification without false positives. Other types of MS analyzers may also be used, including magnetic sector mass spectrometers (Sector MS), quadrupole mass spectrometers (QMS), time-of-flight mass spectrometers (TOFMS), and Fourier transform ion cyclotron resonance mass spectrometers (FT-ICRMS), and combinations of these analyzers.

Subsequently, the obtained data are put through a search engine to perform a spectral assignment and to list the peptides experimentally detected for each protein. The detected peptides are preferably grouped for each protein, and preferably at least three fragments having an m/z value larger than that of the precursor ion and at least three fragments with an m/z value of, preferably, 500 or more are selected from each MS/MS spectrum in descending order of signal strength on the spectrum. From these, two or more fragments are selected in descending order of strength, and the average of the strength is defined as the expected sensitivity of the MRR transitions. When a plurality of peptides is detected from one protein, at least two peptides with the highest sensitivity are selected as standard peptides using the expected sensitivity as an index.

Step (D) (Quantification of the Target Protein in the Test Sample). Step (D) comprises identifying, in the MRM chromatogram detected in step (C), a peptide derived from the target protein (a target biomarker of interest) that shows the same retention time as a peptide derived from the internal standard (an internal standard peptide), and quantifying the target protein in the test sample by comparing the peak area of the internal standard peptide with the peak area of the target peptide. The target protein can be quantified by utilizing a calibration curve of the standard protein prepared beforehand.

The calibration curve can be prepared by the following method. First, a recombinant protein consisting of an amino acid sequence that is identical to that of the target biomarker protein is digested with a protease such as trypsin, as described above. Subsequently, precursor-fragment transition selection standards (PFTS) of a known concentration are individually labeled with two different types of stable isotopes (i.e., one is labeled with a stable isomer used to label an internal standard peptide (labeled with IS), whereas the other is labeled with a stable isomer used to label a target peptide (labeled with T). A plurality of samples are produced by blending a certain amount of the IS-labeled PTFS with various concentrations of the T-labeled PTFS. These samples are placed in the aforementioned LC-MS/MS device to perform MRM analysis. The area ratio of the T-labeled PTFS to the IS-labeled PTFS (T-labeled PTFS/IS-labeled PTFS) on the obtained MRM chromatogram is plotted against the amount of the T-labeled PTFS to prepare a calibration curve. The absolute amount of the target protein contained in the test sample can be calculated by reference to the calibration curve.

3. Detection of Nucleic Acids Corresponding to Protein Markers

In certain embodiments, the invention involves the detection of nucleic acid biomarkers, e.g., the corresponding genes or mRNA of the protein markers of the invention.

In various embodiments, the diagnostic/prognostic methods of the present invention generally involve the determination of expression levels of a set of genes in a biological sample. Determination of gene expression levels in the practice of the inventive methods may be performed by any suitable method. For example, determination of gene expression levels may be performed by detecting the expression of mRNA expressed from the genes of interest and/or by detecting the expression of a polypeptide encoded by the genes.

For detecting nucleic acids encoding biomarkers of the invention, any suitable method can be used, including, but not limited to, Southern blot analysis, Northern blot analysis, polymerase chain reaction (PCR) (see, for example, U.S. Pat. Nos. 4,683,195; 4,683,202, and 6,040,166; "PCR Protocols: A Guide to Methods and Applications", Innis et al. (Eds), 1990, Academic Press: New York), reverse transcriptase PCR (RT-PCT), anchored PCR, competitive PCR (see, for example, U.S. Pat. No. 5,747,251), rapid amplification of cDNA ends (RACE) (see, for example, "Gene Cloning and Analysis: Current Innovations, 1997, pp. 99-115); ligase chain reaction (LCR) (see, for example, EP 01 320 308), one-sided PCR (Ohara et al., Proc. Natl. Acad. Sci., 1989, 86: 5673-5677), in situ hybridization, Taqman-based assays (Holland et al., Proc. Natl. Acad. Sci., 1991, 88: 7276-7280), differential display (see, for example, Liang et al., Nucl. Acid. Res., 1993, 21: 3269-3275) and other RNA fingerprinting techniques, nucleic acid sequence based amplification (NASBA) and other transcription based amplification systems (see, for example, U.S. Pat. Nos. 5,409,818 and 5,554,527), Qbeta Replicase, Strand Displacement Amplification (SDA), Repair Chain Reaction (RCR), nuclease protection assays, subtraction-based methods, Rapid-Scan®, etc.

In other embodiments, gene expression levels of biomarkers of interest may be determined by amplifying complementary DNA (cDNA) or complementary RNA (cRNA) produced from mRNA and analyzing it using a microarray. A number of different array configurations and methods of their production are known to those skilled in the art (see, for example, U.S. Pat. Nos. 5,445,934; 5,532,128; 5,556,752; 5,242,974; 5,384,261; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,599,695; 5,624,711; 5,658,734; and 5,700,637). Microarray technology allows for the measurement of the steady-state mRNA level of a large number of genes simultaneously. Microarrays currently in wide use include cDNA arrays and oligonucleotide arrays. Analyses using microarrays are generally based on measurements of the intensity of the signal received from a labeled probe used to detect a cDNA sequence from the sample that hybridizes to a nucleic acid probe immobilized at a known location on the microarray (see, for example, U.S. Pat. Nos. 6,004,755; 6,218,114; 6,218,122; and 6,271,002). Array-based gene expression methods are known in the art and have been described in numerous scientific publications as well as in patents (see, for example, M. Schena et al., Science, 1995, 270: 467-470; M. Schena et al., Proc. Natl. Acad. Sci. USA 1996, 93: 10614-10619; J. J. Chen et al., Genomics, 1998, 51: 313-324; U.S. Pat. Nos. 5,143,854; 5,445,934; 5,807,522; 5,837,832; 6,040,138; 6,045,996; 6,284,460; and 6,607,885).

Nucleic acid used as a template for amplification can be isolated from cells contained in the biological sample, according to standard methodologies. (Sambrook et al., 1989) The nucleic acid may be genomic DNA or fractionated or whole cell RNA. Where RNA is used, it may be desired to convert the RNA to a complementary cDNA. In one embodiment, the RNA is whole cell RNA and is used directly as the template for amplification.

Pairs of primers that selectively hybridize to nucleic acids corresponding to any of the BCR biomarker nucleotide sequences identified herein are contacted with the isolated nucleic acid under conditions that permit selective hybridization. Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced. Next, the amplification product is detected. In certain applications, the detection may be performed by visual means. Alternatively, the detection may involve indirect identification of the product via chemiluminescence, radioactive scintigraphy of incorporated radiolabel or fluorescent label or even via a system using electrical or thermal impulse signals (Affymax technology; Bellus, 1994). Following detection, one may compare the results seen in a given patient with a statistically significant reference group of normal patients and cancer patients. In this way, it is possible to correlate the amount of nucleic acid detected with various clinical states.

The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences may be employed. Primers may be provided in double-stranded or single-stranded form, although the single-stranded form is preferred.

A number of template dependent processes are available to amplify the nucleic acid sequences present in a given template sample. One of the best known amplification methods is the polymerase chain reaction (referred to as PCR) which is described in detail in U.S. Pat. Nos. 4,683,195, 4,683,202 and 4,800,159, and in Innis et al., 1990, each of which is incorporated herein by reference in its entirety.

In PCR, two primer sequences are prepared which are complementary to regions on opposite complementary strands of the target nucleic acid sequence. An excess of deoxynucleoside triphosphates are added to a reaction mixture along with a DNA polymerase, e.g., Taq polymerase. If the target nucleic acid sequence is present in a sample, the primers will bind to the target nucleic acid and the polymerase will cause the primers to be extended along the target nucleic acid sequence by adding on nucleotides. By raising and lowering the temperature of the reaction mixture, the extended primers will dissociate from the target nucleic acid to form reaction products, excess primers will bind to the target nucleic acid and to the reaction products and the process is repeated.

A reverse transcriptase PCR amplification procedure may be performed in order to quantify the amount of mRNA amplified. Methods of reverse transcribing RNA into cDNA are well known and described in Sambrook et al., 1989. Alternative methods for reverse transcription utilize thermostable DNA polymerases. These methods are described in WO 90/07641 filed Dec. 21, 1990. Polymerase chain reaction methodologies are well known in the art.

Another method for amplification is the ligase chain reaction ("LCR"), disclosed in European Application No. 320 308, incorporated herein by reference in its entirely. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, also may be used as still another amplification method in the present invention. In this method, a replicative sequence of RNA which has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[α-thio]-triphosphates in one strand of a restriction site also may be useful in the amplification of nucleic acids in the present invention. Walker et al. (1992), incorporated herein by reference in its entirety.

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases may be added as biotinylated derivatives for easy detection. A similar approach is used in SDA. Target specific sequences also may be detected using a cyclic probe reaction (CPR). In CPR, a probe having 3' and 5' sequences of non-specific DNA and a middle sequence of specific RNA is hybridized to DNA which is present in a sample. Upon hybridization, the reaction is treated with RNase H, and the products of the probe identified as distinctive products which are released after digestion. The original template is annealed to another cycling probe and the reaction is repeated.

Still other amplification methods described in GB Application No. 2 202 328, and in PCT Application No. PCT/US89/01025, each of which is incorporated herein by reference in its entirety, may be used in accordance with the present invention. In the former application, "modified" primers are used in a PCR like, template and enzyme dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other contemplated nucleic acid amplification procedures include transcription-based amplification systems (TAS), including nucleic acid sequence based amplification (NASBA) and 3SR. Kwoh et al. (1989); Gingeras et al., PCT Application WO 88/10315, incorporated herein by reference in their entirety. In NASBA, the nucleic acids may be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by a polymerase such as T7 or SP6. In an isothermal cyclic reaction, the RNA's are reverse transcribed into double stranded DNA, and transcribed once against with a polymerase such as T7 or SP6. The resulting products, whether truncated or complete, indicate target specific sequences.

Davey et al., European Application No. 329 822 (incorporated herein by reference in its entirely) disclose a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from the resulting DNA:RNA duplex by the action of ribonuclease H(RNase H, an RNase specific for RNA in duplex with either DNA or RNA). The resultant ssDNA is a second template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase 1), resulting in a double-stranded DNA ("dsDNA") molecule, having a sequence identical to that of the original RNA between the primers and having additionally, at one end, a promoter sequence. This promoter sequence may be used by the appropriate RNA polymerase to make many RNA copies of the DNA. These copies may then re-enter the cycle leading to very swift amplification. With proper choice of enzymes, this amplification may be done isothermally without addition of enzymes at each cycle. Because of the cyclical nature of this process, the starting sequence may be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR." Frohman (1990) and Ohara et al. (1989), each herein incorporated by reference in their entirety.

Methods based on ligation of two (or more) oligonucleotides in the presence of nucleic acid having the sequence of the resulting "di-oligonucleotide", thereby amplifying the di-oligonucleotide, also may be used in the amplification step of the present invention. Wu et al. (1989), incorporated herein by reference in its entirety.

Oligonucleotide probes or primers of the present invention may be of any suitable length, depending on the particular assay format and the particular needs and targeted sequences employed. In a preferred embodiment, the oligonucleotide probes or primers are at least 10 nucleotides in length (preferably, 10, 11, 12, 13, 14, 15, 16, 17, 18, 19, 20, 21, 22, 23, 24, 25, 26, 27, 28, 29, 30, 31, 32 . . . ) and they may be adapted to be especially suited for a chosen nucleic acid amplification system and/or hybridization system used. Longer probes and primers are also within the scope of the present invention as well known in the art. Primers having more than 30, more than 40, more than 50 nucleotides and probes having more than 100, more than 200, more than 300, more than 500 more than 800 and more than 1000 nucleotides in length are also covered by the present invention. Of course, longer primers have the disadvantage of being more expensive and thus, primers having between 12 and 30 nucleotides in length are usually designed and used in the art. As well known in the art, probes ranging from 10 to more than 2000 nucleotides in length can be used in the methods of the present invention. As for the % of identity described above, non-specifically described sizes of probes and primers (e.g., 16, 17, 31, 24, 39, 350, 450, 550, 900, 1240 nucleotides, . . . ) are also within the scope of the present invention. In one embodiment, the oligonucleotide probes or primers of the present invention specifically hybridize with a marker RNA (or its complementary sequence) or a marker mRNA. More preferably, the marker primers and probes will be chosen to detect a marker RNA which is associated with BCR.

In other embodiments, the detection means can utilize a hybridization technique, e.g., where a specific primer or probe is selected to anneal to a target biomarker of interest and thereafter detection of selective hybridization is made.

As commonly known in the art, the oligonucleotide probes and primers can be designed by taking into consideration the melting point of hybridization thereof with its targeted sequence (see below and in Sambrook et al., 1989, Molecular Cloning—A Laboratory Manual, 2nd Edition, CSH Laboratories; Ausubel et al., 1994, in Current Protocols in Molecular Biology, John Wiley & Sons Inc., N.Y.).

To enable hybridization to occur under the assay conditions of the present invention, oligonucleotide primers and probes should comprise an oligonucleotide sequence that has at least 70% (at least 71%, 72%, 73%, 74%), preferably at least 75% (75%, 76%, 77%, 78%, 79%, 80%, 81%, 82%, 83%, 84%, 85%, 86%, 87%, 88%, 89%) and more preferably at least 90% (90%, 91%, 92%, 93%, 94%, 95%, 96%, 97%, 98%, 99%, 100%) identity to a portion of a filamin A or polynucleotide of another biomarker of the invention. Probes and primers of the present invention are those that hybridize under stringent hybridization conditions and those that hybridize to biomarker homologs of the invention under at least moderately stringent conditions. In certain embodiments probes and primers of the present invention have complete sequence identity to the biomarkers of the invention (filamin A, gene sequences (e.g., cDNA or mRNA). It should be understood that other probes and primers could be easily designed and used in the present invention based on the biomarkers of the invention disclosed herein by using methods of computer alignment and sequence analysis known in the art (cf. Molecular Cloning: A Laboratory Manual, Third Edition, edited by Cold Spring Harbor Laboratory, 2000).

4. Antibodies and Labels

In some embodiments, the invention provides methods and compositions that include labels for the highly sensitive detection and quantitation of the markers of the invention. One skilled in the art will recognize that many strategies can be used for labeling target molecules to enable their detection or discrimination in a mixture of particles. The labels may be attached by any known means, including methods that utilize non-specific or specific interactions of label and target. Labels may provide a detectable signal or affect the mobility of the particle in an electric field. In addition, labeling can be accomplished directly or through binding partners.

In some embodiments, the label comprises a binding partner that binds to the biomarker of interest, where the binding partner is attached to a fluorescent moiety. The compositions and methods of the invention may utilize highly fluorescent moieties, e.g., a moiety capable of emitting at least about 200 photons when simulated by a laser emitting light at the excitation wavelength of the moiety, wherein the laser is focused on a spot not less than about 5 microns in diameter that contains the moiety, and wherein the total energy directed at the spot by the laser is no more than about 3 microJoules. Moieties suitable for the compositions and methods of the invention are described in more detail below.

In some embodiments, the invention provides a label for detecting a biological molecule comprising a binding partner for the biological molecule that is attached to a fluorescent moiety, wherein the fluorescent moiety is capable of emitting at least about 200 photons when simulated by a laser emitting light at the excitation wavelength of the moiety, wherein the laser is focused on a spot not less than about 5 microns in diameter that contains the moiety, and wherein the total energy directed at the spot by the laser is no more than about 3 microJoules. In some embodiments, the moiety comprises a plurality of fluorescent entities, e.g., about 2 to 4, 2 to 5, 2 to 6, 2 to 7, 2 to 8, 2 to 9, 2 to 10, or about 3 to 5, 3 to 6, 3 to 7, 3 to 8, 3 to 9, or 3 to 10 fluorescent entities. In some embodiments, the moiety comprises about 2 to 4 fluorescent entities. In some embodiments, the biological molecule is a protein or a small molecule. In some embodiments, the biological molecule is a protein. The fluorescent entities can be fluorescent dye molecules. In some embodiments, the fluorescent dye molecules comprise at least one substituted indolium ring system in which the substituent on the 3-carbon of the indolium ring contains a chemically reactive group or a conjugated substance. In some embodiments, the dye molecules are Alexa Fluor molecules selected from the group consisting of Alexa Fluor 488, Alexa Fluor 532, Alexa Fluor 647, Alexa Fluor 680 or Alexa Fluor 700. In some embodiments, the dye molecules are Alexa Fluor molecules selected from the group consisting of Alexa Fluor 488, Alexa Fluor 532, Alexa Fluor 680 or Alexa Fluor 700. In some embodiments, the dye molecules are Alexa Fluor 647 dye molecules. In some embodiments, the dye molecules comprise a first type and a second type of dye molecules, e.g., two different Alexa Fluor molecules, e.g., where the first type and second type of dye molecules have different emission spectra. The ratio of the number of first type to second type of dye molecule can be, e.g., 4 to 1, 3 to 1, 2 to 1, 1 to 1, 1 to 2, 1 to 3 or 1 to 4. The binding partner can be, e.g., an antibody.

In some embodiments, the invention provides a label for the detection of a biological marker of the invention, wherein the label comprises a binding partner for the marker and a fluorescent moiety, wherein the fluorescent moiety is capable of emitting at least about 200 photons when simulated by a laser emitting light at the excitation wavelength of the moiety, wherein the laser is focused on a spot not less than about 5 microns in diameter that contains the moiety, and wherein the total energy directed at the spot by the laser is no more than about 3 microJoules. In some embodiments, the fluorescent moiety comprises a fluorescent molecule. In some embodiments, the fluorescent moiety comprises a plurality of fluorescent molecules, e.g., about 2 to 10, 2 to 8, 2 to 6, 2 to 4, 3 to 10, 3 to 8, or 3 to 6 fluorescent molecules. In some embodiments, the label comprises about 2 to 4 fluorescent molecules. In some embodiments, the fluorescent dye molecules comprise at least one substituted indolium ring system in which the substituent on the 3-carbon of the indolium ring contains a chemically reactive group or a conjugated substance. In some embodiments, the fluorescent molecules are selected from the group consisting of Alexa Fluor 488, Alexa Fluor 532, Alexa Fluor 647, Alexa Fluor 680 or Alexa Fluor 700. In some embodiments, the fluorescent molecules are selected from the group consisting of Alexa Fluor 488, Alexa Fluor 532, Alexa Fluor 680 or Alexa Fluor 700. In some embodiments, the fluorescent molecules are Alexa Fluor 647 molecules. In some embodiments, the binding partner comprises an antibody. In some embodiments, the antibody is a monoclonal antibody. In other embodiments, the antibody is a polyclonal antibody.

The term "antibody," as used herein, is a broad term and is used in its ordinary sense, including, without limitation, to refer to naturally occurring antibodies as well as non-naturally occurring antibodies, including, for example, single chain antibodies, chimeric, bifunctional and humanized antibodies, as well as antigen-binding fragments thereof. An "antigen-binding fragment" of an antibody refers to the part of the antibody that participates in antigen binding. The antigen binding site is formed by amino acid residues of the N-terminal variable ("V") regions of the heavy ("H") and light ("L") chains. It will be appreciated that the choice of epitope or region of the molecule to which the antibody is raised will determine its specificity, e.g., for various forms of the molecule, if present, or for total (e.g., all, or substantially all of the molecule).

Methods for producing antibodies are well-established. One skilled in the art will recognize that many procedures are available for the production of antibodies, for example, as described in Antibodies, A Laboratory Manual, Ed Harlow and David Lane, Cold Spring Harbor Laboratory (1988), Cold Spring Harbor, N.Y. One skilled in the art will also appreciate that binding fragments or Fab fragments which mimic antibodies can also be prepared from genetic information by various procedures (Antibody Engineering: A Practical Approach (Borrebaeck, C., ed.), 1995, Oxford University Press, Oxford; J. Immunol. 149, 3914-3920 (1992)). Monoclonal and polyclonal antibodies to molecules, e.g., proteins, and markers also commercially available (R and D Systems, Minneapolis, Minn.; HyTest, HyTest Ltd., Turku Finland; Abcam Inc., Cambridge, Mass., USA, Life Diagnostics, Inc., West Chester, Pa., USA; Fitzgerald Industries International, Inc., Concord, Mass. 01742-3049 USA; BiosPacific, Emeryville, Calif.).

In some embodiments, the antibody is a polyclonal antibody. In other embodiments, the antibody is a monoclonal antibody.

Antibodies may be prepared by any of a variety of techniques known to those of ordinary skill in the art (see, for example, Harlow and Lane, Antibodies: A Laboratory Manual, Cold Spring Harbor Laboratory, 1988). In general, antibodies can be produced by cell culture techniques, including the generation of monoclonal antibodies as described herein, or via transfection of antibody genes into suitable bacterial or mammalian cell hosts, in order to allow for the production of recombinant antibodies.

Monoclonal antibodies may be prepared using hybridoma methods, such as the technique of Kohler and Milstein (Eur. J. Immunol. 6:511-519, 1976), and improvements thereto. These methods involve the preparation of immortal cell lines capable of producing antibodies having the desired specificity. Monoclonal antibodies may also be made by recombinant DNA methods, such as those described in U.S. Pat. No. 4,816,567. DNA encoding antibodies employed in the disclosed methods may be isolated and sequenced using conventional procedures. Recombinant antibodies, antibody fragments, and/or fusions thereof, can be expressed in vitro or in prokaryotic cells (e.g. bacteria) or eukaryotic cells (e.g. yeast, insect or mammalian cells) and further purified as necessary using well known methods.

More particularly, monoclonal antibodies (MAbs) may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified expressed protein, polypeptide or peptide. The immunizing composition is administered in a manner effective to stimulate antibody producing cells. The methods for generating monoclonal antibodies (MAbs) generally begin along the same lines as those for preparing polyclonal antibodies. Rodents such as mice and rats are preferred animals, however, the use of rabbit, sheep or frog cells is also possible. The use of rats may provide certain advantages (Goding, 1986, pp. 60-61), but mice are preferred, with the BALB/c mouse being most preferred as this is most routinely used and generally gives a higher percentage of stable fusions.

The animals are injected with antigen as described above. The antigen may be coupled to carrier molecules such as keyhole limpet hemocyanin if necessary. The antigen would typically be mixed with adjuvant, such as Freund's complete or incomplete adjuvant. Booster injections with the same antigen would occur at approximately two-week intervals. Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of the animal with the highest antibody titer will be removed and the spleen lymphocytes obtained by homogenizing the spleen with a syringe.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

The selected hybridomas would then be serially diluted and cloned into individual antibody-producing cell lines, which clones may then be propagated indefinitely to provide MAbs. The cell lines may be exploited for MAb production in two basic ways. A sample of the hybridoma may be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, may then be tapped to provide MAbs in high concentration. The individual cell lines also may be cultured in vitro, where the MAbs are naturally secreted into the culture medium from which they may be readily obtained in high concentrations. MAbs produced by either means may be further purified, if desired, using filtration, centrifugation and various chromatographic methods such as HPLC or affinity chromatography.

Large amounts of the monoclonal antibodies of the present invention also may be obtained by multiplying hybridoma cells in vivo. Cell clones are injected into mammals which are histocompatible with the parent cells, e.g., syngeneic mice, to cause growth of antibody-producing tumors. Optionally, the animals are primed with a hydrocarbon, especially oils such as pristane (tetramethylpentadecane) prior to injection.

In accordance with the present invention, fragments of the monoclonal antibody of the invention may be obtained from the monoclonal antibody produced as described above, by methods which include digestion with enzymes such as pepsin or papain and/or cleavage of disulfide bonds by chemical reduction. Alternatively, monoclonal antibody fragments encompassed by the present invention may be synthesized using an automated peptide synthesizer.

Antibodies may also be derived from a recombinant antibody library that is based on amino acid sequences that have been designed in silico and encoded by polynucleotides that are synthetically generated. Methods for designing and obtaining in silico-created sequences are known in the art (Knappik et al., J. Mol. Biol. 296:254:57-86, 2000; Krebs et al., J. Immunol. Methods 254:67-84, 2001; U.S. Pat. No. 6,300,064).

Digestion of antibodies to produce antigen-binding fragments thereof can be performed using techniques well known in the art. For example, the proteolytic enzyme papain preferentially cleaves IgG molecules to yield several fragments, two of which (the "F(ab)" fragments) each comprise a covalent heterodimer that includes an intact antigen-binding site. The enzyme pepsin is able to cleave IgG molecules to provide several fragments, including the "F(ab')2" fragment, which comprises both antigen-binding sites. "Fv" fragments can be produced by preferential proteolytic cleavage of an IgM, IgG or IgA immunoglobulin molecule, but are more commonly derived using recombinant techniques known in the art. The Fv fragment includes a non-covalent VH::VL heterodimer including an antigen-binding site which retains much of the antigen recognition and binding capabilities of the native antibody molecule (Inbar et al., Proc. Natl. Acad. Sci. USA 69:2659-2662 (1972); Hochman et al., Biochem. 15:2706-2710 (1976); and Ehrlich et al., Biochem. 19:4091-4096 (1980)).

Antibody fragments that specifically bind to the protein biomarkers disclosed herein can also be isolated from a library of scFvs using known techniques, such as those described in U.S. Pat. No. 5,885,793.

A wide variety of expression systems are available in the art for the production of antibody fragments, including Fab fragments, scFv, VL and VHs. For example, expression systems of both prokaryotic and eukaryotic origin may be used for the large-scale production of antibody fragments. Particularly advantageous are expression systems that permit the secretion of large amounts of antibody fragments into the culture medium. Eukaryotic expression systems for large-scale production of antibody fragments and antibody fusion proteins have been described that are based on mammalian cells, insect cells, plants, transgenic animals, and lower eukaryotes. For example, the cost-effective, large-scale production of antibody fragments can be achieved in yeast fermentation systems. Large-scale fermentation of these organisms is well known in the art and is currently used for bulk production of several recombinant proteins.

Antibodies that bind to the protein biomarkers employed in the present methods are, in some cases, available commercially or can be obtained without undue experimentation.

In still other embodiments, particularly where oligonucleotides are used as binding partners to detect and hybridize to mRNA biomarkers or other nucleic acid based biomarkers, the binding partners (e.g., oligonucleotides) can comprise a label, e.g., a fluorescent moiety or dye. In addition, any binding partner of the invention, e.g., an antibody, can also be labeled with a fluorescent moiety. The fluorescence of the moiety will be sufficient to allow detection in a single molecule detector, such as the single molecule detectors described herein. A "fluorescent moiety," as that term is used herein, includes one or more fluorescent entities whose total fluorescence is such that the moiety may be detected in the single molecule detectors described herein. Thus, a fluorescent moiety may comprise a single entity (e.g., a Quantum Dot or fluorescent molecule) or a plurality of entities (e.g., a plurality of fluorescent molecules). It will be appreciated that when "moiety," as that term is used herein, refers to a group of fluorescent entities, e.g., a plurality of fluorescent dye molecules, each individual entity may be attached to the binding partner separately or the entities may be attached together, as long as the entities as a group provide sufficient fluorescence to be detected.

Typically, the fluorescence of the moiety involves a combination of quantum efficiency and lack of photobleaching sufficient that the moiety is detectable above background levels in a single molecule detector, with the consistency necessary for the desired limit of detection, accuracy, and precision of the assay. For example, in some embodiments, the fluorescence of the fluorescent moiety is such that it allows detection and/or quantitation of a molecule, e.g., a marker, at a limit of detection of less than about 10, 5, 4, 3, 2, 1, 0.1, 0.01, 0.001, 0.00001, or 0.000001 pg/ml and with a coefficient of variation of less than about 20, 15, 14, 13, 12, 11, 10, 9, 8, 7, 6, 5, 4, 3, 2, 1% or less, e.g., about 10% or less, in the instruments described herein. In some embodiments, the fluorescence of the fluorescent moiety is such that it allows detection and/or quantitation of a molecule, e.g., a marker, at a limit of detection of less than about 5, 1, 0.5, 0.1, 0.05, 0.01, 0.005, 0.001 pg/ml and with a coefficient of variation of less than about 10%, in the instruments described herein. "Limit of detection," or LoD, as those terms are used herein, includes the lowest concentration at which one can identify a sample as containing a molecule of the substance of interest, e.g., the first non-zero value. It can be defined by the variability of zeros and the slope of the standard curve. For example, the limit of detection of an assay may be determined by running a standard curve, determining the standard curve zero value, and adding 2 standard deviations to that value. A concentration of the substance of interest that produces a signal equal to this value is the "lower limit of detection" concentration.

Furthermore, the moiety has properties that are consistent with its use in the assay of choice. In some embodiments, the assay is an immunoassay, where the fluorescent moiety is attached to an antibody; the moiety must have properties such that it does not aggregate with other antibodies or proteins, or experiences no more aggregation than is consistent with the required accuracy and precision of the assay. In some embodiments, fluorescent moieties that are preferred are fluorescent moieties, e.g., dye molecules that have a combination of 1) high absorption coefficient; 2) high quantum yield; 3) high photostability (low photobleaching); and 4) compatibility with labeling the molecule of interest (e.g., protein) so that it may be analyzed using the analyzers and systems of the invention (e.g., does not cause precipitation of the protein of interest, or precipitation of a protein to which the moiety has been attached).

Any suitable fluorescent moiety may be used. Examples include, but are not limited to, Alexa Fluor dyes (Molecular Probes, Eugene, Oreg.). The Alexa Fluor dyes are disclosed in U.S. Pat. Nos. 6,977,305; 6,974,874; 6,130,101; and 6,974,305 which are herein incorporated by reference in their entirety. Some embodiments of the invention utilize a dye chosen from the group consisting of Alexa Fluor 647, Alexa Fluor 488, Alexa Fluor 532, Alexa Fluor 555, Alexa Fluor 610, Alexa Fluor 680, Alexa Fluor 700, and Alexa Fluor 750. Some embodiments of the invention utilize a dye chosen from the group consisting of Alexa Fluor 488, Alexa Fluor 532, Alexa Fluor 647, Alexa Fluor 700 and Alexa Fluor 750. Some embodiments of the invention utilize a dye chosen from the group consisting of Alexa Fluor 488, Alexa Fluor 532, Alexa Fluor 555, Alexa Fluor 610, Alexa Fluor 680, Alexa Fluor 700, and Alexa Fluor 750. Some embodiments of the invention utilize the Alexa Fluor 647 molecule, which has an absorption maximum between about 650 and 660 nm and an emission maximum between about 660 and 670 nm. The Alexa Fluor 647 dye is used alone or in combination with other Alexa Fluor dyes.

In some embodiments, the fluorescent label moiety that is used to detect a biomarker in a sample using the analyzer systems of the invention is a quantum dot. Quantum dots (QDs), also known as semiconductor nanocrystals or artificial atoms, are semiconductor crystals that contain anywhere between 100 to 1,000 electrons and range from 2-10 nm. Some QDs can be between 10-20 nm in diameter. QDs have high quantum yields, which makes them particularly useful for optical applications. QDs are fluorophores that fluoresce by forming excitons, which are similar to the excited state of traditional fluorophores, but have much longer lifetimes of up to 200 nanoseconds. This property provides QDs with low photobleaching. The energy level of QDs can be controlled by changing the size and shape of the QD, and the depth of the QDs' potential. One optical feature of small excitonic QDs is coloration, which is determined by the size of the dot. The larger the dot, the redder, or more towards the red end of the spectrum the fluorescence. The smaller the dot, the bluer or more towards the blue end it is. The bandgap energy that determines the energy and hence the color of the fluoresced light is inversely proportional to the square of the size of the QD. Larger QDs have more energy levels which are more closely spaced, thus allowing the QD to absorb photons containing less energy, i.e., those closer to the red end of the spectrum. Because the emission frequency of a dot is dependent on the bandgap, it is possible to control the output wavelength of a dot with extreme precision. In some embodiments the protein that is detected with the single molecule analyzer system is labeled with a QD. In some embodiments, the single molecule analyzer is used to detect a protein labeled with one QD and using a filter to allow for the detection of different proteins at different wavelengths.

F. Isolated Biomarkers

1. Isolated Polypeptide Biomarkers

One aspect of the invention pertains to isolated marker proteins and biologically active portions thereof, as well as polypeptide fragments suitable for use as immunogens to raise antibodies directed against a marker protein or a fragment thereof. In one embodiment, the native marker protein can be isolated by an appropriate purification scheme using standard protein purification techniques. In another embodiment, a protein or peptide comprising the whole or a segment of the marker protein is produced by recombinant DNA techniques. Alternative to recombinant expression, such protein or peptide can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a marker protein include polypeptides comprising amino acid sequences sufficiently identical to or derived from the amino acid sequence of the marker protein, which include fewer amino acids than the full length protein, and exhibit at least one activity of the corresponding full-length protein. Typically, biologically active portions comprise a domain or motif with at least one activity of the corresponding full-length protein. A biologically active portion of a marker protein of the invention can be a polypeptide which is, for example, 10, 25, 50, 100 or more amino acids in length. Moreover, other biologically active portions, in which other regions of the marker protein are deleted, can be prepared by recombinant techniques and evaluated for one or more of the functional activities of the native form of the marker protein.

Preferred marker proteins are encoded by nucleotide sequences provided in the sequence listing. Other useful proteins are substantially identical (e.g., at least about 40%, preferably 50%, 60%, 70%, 80%, 90%, 91%, 92%, 93%, 94%, 95%, 96%, 97%, 98% or 99%) to one of these sequences and retain the functional activity of the corresponding naturally-occurring marker protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. Preferably, the percent identity between the two sequences is calculated using a global alignment. Alternatively, the percent identity between the two sequences is calculated using a local alignment. The percent identity between the two sequences is a function of the number of identical positions shared by the sequences (i.e., % identity=# of identical positions/total # of positions (e.g., overlapping positions)×100). In one embodiment the two sequences are the same length. In another embodiment, the two sequences are not the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the BLASTN and BLASTX programs of Altschul, et al. (1990) *J. Mol. Biol.* 215:403-410. BLAST nucleotide searches can be performed with the BLASTN program, score=100, wordlength=12 to obtain nucleotide sequences homologous to a nucleic acid molecules of the invention. BLAST protein searches can be performed with the BLASTP program, score=50, wordlength=3 to obtain amino acid sequences homologous to a protein molecules of the invention. To obtain gapped alignments for comparison purposes, a newer version of the BLAST algorithm called Gapped BLAST can be utilized as described in Altschul et al. (1997) *Nucleic Acids Res.* 25:3389-3402, which is able to perform gapped local alignments for the programs BLASTN, BLASTP and BLASTX. Alternatively, PSI-Blast can be used to perform an iterated search which detects distant relationships between molecules. When utilizing BLAST, Gapped BLAST, and PSI-Blast programs, the default parameters of the respective programs (e.g., BLASTX and BLASTN) can be used. See the NCBI website. Another preferred, non-limiting example of a mathematical algorithm utilized for the comparison of sequences is the algorithm of Myers and Miller, (1988) *CABIOS* 4:11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

Another aspect of the invention pertains to antibodies directed against a protein of the invention. In preferred embodiments, the antibodies specifically bind a marker protein or a fragment thereof. The terms "antibody" and "antibodies" as used interchangeably herein refer to immunoglobulin molecules as well as fragments and derivatives thereof that comprise an immunologically active portion of an immunoglobulin molecule, (i.e., such a portion contains an antigen binding site which specifically binds an antigen, such as a marker protein, e.g., an epitope of a marker protein). An antibody which specifically binds to a protein of the invention is an antibody which binds the protein, but does not substantially bind other molecules in a sample, e.g., a biological sample, which naturally contains the protein. Examples of an immunologically active portion of an immunoglobulin molecule include, but are not limited to, single-chain antibodies (scAb), F(ab) and F(ab')$_2$ fragments.

An isolated protein of the invention or a fragment thereof can be used as an immunogen to generate antibodies. The full-length protein can be used or, alternatively, the invention provides antigenic peptide fragments for use as immunogens. The antigenic peptide of a protein of the invention comprises at least 8 (preferably 10, 15, 20, or 30 or more) amino acid residues of the amino acid sequence of one of the proteins of the invention, and encompasses at least one epitope of the protein such that an antibody raised against the peptide forms a specific immune complex with the protein. Preferred epitopes encompassed by the antigenic peptide are regions that are located on the surface of the protein, e.g., hydrophilic regions. Hydrophobicity sequence analysis, hydrophilicity sequence analysis, or similar analyses can be used to identify hydrophilic regions. In preferred embodiments, an isolated marker protein or fragment thereof is used as an immunogen.

The invention provides polyclonal and monoclonal antibodies. The term "monoclonal antibody" or "monoclonal antibody composition", as used herein, refers to a population of antibody molecules that contain only one species of an antigen binding site capable of immunoreacting with a particular epitope. Preferred polyclonal and monoclonal antibody compositions are ones that have been selected for antibodies directed against a protein of the invention. Particularly preferred polyclonal and monoclonal antibody preparations are ones that contain only antibodies directed against a marker protein or fragment thereof. Methods of making polyclonal, monoclonal, and recombinant antibody and antibody fragments are well known in the art.

2. Isolated Nucleic Acid Biomarkers

One aspect of the invention pertains to isolated nucleic acid molecules which encode a marker protein or a portion thereof. Isolated nucleic acids of the invention also include nucleic acid molecules sufficient for use as hybridization probes to identify marker nucleic acid molecules, and fragments of marker nucleic acid molecules, e.g., those suitable for use as PCR primers for the amplification of a specific product or mutation of marker nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. In one embodiment, an "isolated" nucleic acid molecule (preferably a protein-encoding sequences) is free of sequences which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. In another embodiment, an "isolated" nucleic acid molecule, such as a cDNA molecule, can be substantially free of other cellular material, or culture medium when produced by recombinant techniques, or substantially free of chemical precursors or other chemicals when chemically synthesized. A nucleic acid molecule that is substantially free of cellular material includes preparations having less than about 30%, 20%, 10%, or 5% of heterologous nucleic acid (also referred to herein as a "contaminating nucleic acid").

A nucleic acid molecule of the present invention can be isolated using standard molecular biology techniques and the sequence information in the database records described herein. Using all or a portion of such nucleic acid sequences, nucleic acid molecules of the invention can be isolated using standard hybridization and cloning techniques (e.g., as described in Sambrook et al., ed., *Molecular Cloning: A Laboratory Manual,* 2nd ed., Cold Spring Harbor Laboratory Press, Cold Spring Harbor, N.Y., 1989).

A nucleic acid molecule of the invention can be amplified using cDNA, mRNA, or genomic DNA as a template and appropriate oligonucleotide primers according to standard PCR amplification techniques. The nucleic acid so amplified can be cloned into an appropriate vector and characterized by DNA sequence analysis. Furthermore, nucleotides corresponding to all or a portion of a nucleic acid molecule of the invention can be prepared by standard synthetic techniques, e.g., using an automated DNA synthesizer.

In another preferred embodiment, an isolated nucleic acid molecule of the invention comprises a nucleic acid molecule which has a nucleotide sequence complementary to the nucleotide sequence of a marker nucleic acid or to the nucleotide sequence of a nucleic acid encoding a marker protein. A nucleic acid molecule which is complementary to a given nucleotide sequence is one which is sufficiently complementary to the given nucleotide sequence that it can hybridize to the given nucleotide sequence thereby forming a stable duplex.

Moreover, a nucleic acid molecule of the invention can comprise only a portion of a nucleic acid sequence, wherein the full length nucleic acid sequence comprises a marker nucleic acid or which encodes a marker protein. Such nucleic acids can be used, for example, as a probe or primer. The probe/primer typically is used as one or more substantially purified oligonucleotides. The oligonucleotide typically comprises a region of nucleotide sequence that hybridizes under stringent conditions to at least about 15, more preferably at least about 25, 50, 75, 100, 125, 150, 175, 200, 250, 300, 350, or 400 or more consecutive nucleotides of a nucleic acid of the invention.

Probes based on the sequence of a nucleic acid molecule of the invention can be used to detect transcripts or genomic sequences corresponding to one or more markers of the invention. In certain embodiments, the probes hybridize to nucleic acid sequences that traverse splice junctions. The probe comprises a label group attached thereto, e.g., a radioisotope, a fluorescent compound, an enzyme, or an enzyme co-factor. Such probes can be used as part of a diagnostic test kit or panel for identifying cells or tissues which express or mis-express the protein, such as by measuring levels of a nucleic acid molecule encoding the protein in a sample of cells from a subject, e.g., detecting mRNA levels or determining whether a gene encoding the protein or its translational control sequences have been mutated or deleted.

The invention further encompasses nucleic acid molecules that differ, due to degeneracy of the genetic code, from the nucleotide sequence of nucleic acids encoding a marker protein (e.g., protein having the sequence provided in the sequence listing), and thus encode the same protein.

It will be appreciated by those skilled in the art that DNA sequence polymorphisms that lead to changes in the amino acid sequence can exist within a population (e.g., the human population). Such genetic polymorphisms can exist among individuals within a population due to natural allelic variation and changes known to occur in cancer. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

As used herein, the phrase "allelic variant" refers to a nucleotide sequence which occurs at a given locus or to a polypeptide encoded by the nucleotide sequence.

As used herein, the terms "gene" and "recombinant gene" refer to nucleic acid molecules comprising an open reading frame encoding a polypeptide corresponding to a marker of the invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

In another embodiment, an isolated nucleic acid molecule of the invention is at least 15, 20, 25, 30, 40, 60, 80, 100, 150, 200, 250, 300, 350, 400, 450, 550, 650, 700, 800, 900, 1000, 1200, 1400, 1600, 1800, 2000, 2200, 2400, 2600, 2800, 3000, 3500, 4000, 4500, or more nucleotides in length and hybridizes under stringent conditions to a marker nucleic acid or to a nucleic acid encoding a marker protein. As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in sections 6.3.1-6.3.6 of Current Protocols in Molecular Biology, John Wiley & Sons, N.Y. (1989). A preferred, non-limiting example of stringent hybridization conditions are hybridization in 6× sodium chloride/sodium citrate (SSC) at about 45° C., followed by one or more washes in 0.2× SSC, 0.1% SDS at 50-65° C.

G. Biomarker Applications

The invention provides methods for diagnosing BCR in a subject. The invention further provides methods for prognosing or monitoring progression or monitoring response of BCR to a therapeutic treatment during active treatment or watchful waiting.

In one aspect, the present invention constitutes an application of diagnostic information obtainable by the methods of the invention in connection with analyzing, detecting, and/or measuring the BCR biomarkers of the present invention, i.e., the markers of Tables 1-5, which goes well beyond the discovered correlation between BCR and the biomarkers of the invention.

For example, when executing the methods of the invention for detecting and/or measuring an protein biomarker of the present invention, as described herein, one may contact a biological sample with a detection reagent, e.g., a monoclonal antibody, which selectively binds to the biomarker of interest, forming a protein-protein complex, which is then further detected either directly (if the antibody comprises a label) or indirectly (if a secondary detection reagent is used, e.g., a secondary antibody, which in turn is labeled). Thus, the method of the invention transforms the polypeptide markers of the invention to a protein-protein complex that comprises either a detectable primary antibody or a primary and further secondary antibody. Forming such protein-protein complexes is required in order to identify the presence of the biomarker of interest and necessarily changes the physical characteristics and properties of the biomarker of interest as a result of conducting the methods of the invention.

The same principal applies when conducting the methods of the invention for detecting nucleic acids that correspond to the protein biomarkers of the invention. In particular, when amplification methods are used, the process results in the formation of a new population of amplicons, i.e., molecules that are newly synthesized and which were not present in the original biological sample, thereby physically transforming the biological sample. Similarly, when hybridization probes are used to detect a target biomarker, a physical new species of molecules is in effect created by the hybridization of the probes (optionally comprising a label)

to the target biomarker mRNA (or other nucleic acid), which is then detected. Such polynucleotide products are effectively newly created or formed as a consequence of carrying out the method of the invention.

The invention provides, in one embodiment, methods for diagnosing an oncological disorder, e.g., BCR. The methods of the present invention can be practiced in conjunction with any other method used by the skilled practitioner to prognose the occurrence or recurrence of an oncologic disorder and/or the survival of a subject being treated for an oncologic disorder. The diagnostic and prognostic methods provided herein can be used to determine if additional and/or more invasive tests or monitoring should be performed on a subject. It is understood that a disease as complex as BCR is rarely diagnosed using a single test. Therefore, it is understood that the diagnostic, prognostic, and monitoring methods provided herein are typically used in conjunction with other methods known in the art. For example, the methods of the invention may be performed in conjunction with a morphological or cytological analysis of the sample obtained from the subject, imaging analysis, and/or physical exam. Cytological methods would include immunohistochemical or immunofluorescence detection (and quantitation if appropriate) of any other molecular marker either by itself, in conjunction with other markers. Other methods would include detection of other markers by in situ PCR, or by extracting tissue and quantitating other markers by real time PCR. PCR is defined as polymerase chain reaction.

Methods for assessing BCR progression during watchful waiting or the efficacy of a treatment regimen, e.g., chemotherapy, radiation therapy, surgery, hormone therapy, or any other therapeutic approach useful for treating BCR or prostate cancer in a subject are also provided. In these methods the amount of marker in a pair of samples (a first sample obtained from the subject at an earlier time point or prior to the treatment regimen and a second sample obtained from the subject at a later time point, e.g., at a later time point when the subject has undergone at least a portion of the treatment regimen) is assessed. It is understood that the methods of the invention include obtaining and analyzing more than two samples (e.g., 3, 4, 5, 6, 7, 8, 9, or more samples) at regular or irregular intervals for assessment of marker levels. Pairwise comparisons can be made between consecutive or non-consecutive subject samples. Trends of marker levels and rates of change of marker levels can be analyzed for any two or more consecutive or non-consecutive subject samples.

Using the methods described herein, a variety of molecules, may be screened in order to identify molecules which modulate, e.g., increase or decrease the expression and/or activity of a marker of the invention. Compounds so identified can be provided to a subject in order to inhibit the aggressiveness of an oncologic disorder in the subject, to prevent the recurrence of an oncologic disorder in the subject, or to treat BCR in the subject.

The present invention pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the present invention relates to diagnostic assays for determining the level of expression of one or more marker proteins or nucleic acids, in order to determine whether an individual is at risk of developing a disease or disorder, such as, without limitation, BCR in prostate cancer. Such assays can be used for prognostic or predictive purposes to thereby prophylactically treat an individual prior to the onset of the disorder.

Yet another aspect of the invention pertains to monitoring the influence of agents (e.g., drugs or other therapeutic compounds) on the expression or activity of a biomarker of the invention in clinical trials. These and other applications are described in further detail in the following sections.

1. Diagnostic Assays

An exemplary method for detecting the presence or absence or change of expression level of a marker protein or a corresponding nucleic acid in a biological sample involves obtaining a biological sample (e.g. an oncological disorder-associated body fluid) from a test subject and contacting the biological sample with a compound or an agent capable of detecting the polypeptide or nucleic acid (e.g., mRNA, genomic DNA, or cDNA). The detection methods of the invention can thus be used to detect mRNA, protein, cDNA, or genomic DNA, for example, in a biological sample in vitro as well as in vivo.

Methods provided herein for detecting the presence, absence, change of expression level of a marker protein or corresponding nucleic acid in a biological sample include obtaining a biological sample from a subject that may or may not contain the marker protein or nucleic acid to be detected, contacting the sample with a marker-specific binding agent (i.e., one or more marker-specific binding agents) that is capable of forming a complex with the marker protein or nucleic acid to be detected, and contacting the sample with a detection reagent for detection of the marker— marker-specific binding agent complex, if formed. It is understood that the methods provided herein for detecting an expression level of a marker in a biological sample includes the steps to perform the assay. In certain embodiments of the detection methods, the level of the marker protein or nucleic acid in the sample is none or below the threshold for detection.

The methods include formation of either a transient or stable complex between the marker and the marker-specific binding agent. The methods require that the complex, if formed, be formed for sufficient time to allow a detection reagent to bind the complex and produce a detectable signal (e.g., fluorescent signal, a signal from a product of an enzymatic reaction, e.g., a peroxidase reaction, a phosphatase reaction, a beta-galactosidase reaction, or a polymerase reaction).

In certain embodiments, all markers are detected using the same method. In certain embodiments, all markers are detected using the same biological sample (e.g., same body fluid or tissue). In certain embodiments, different markers are detected using various methods. In certain embodiments, markers are detected in different biological samples.

2. Protein Detection

In certain embodiments of the invention, the marker to be detected is an protein. Proteins are detected using a number of assays in which a complex between the marker protein to be detected and the marker specific binding agent would not occur naturally, for example, because one of the components is not a naturally occurring compound or the marker for detection and the marker specific binding agent are not from the same organism (e.g., human marker proteins detected using marker-specific binding antibodies from mouse, rat, or goat). In a preferred embodiment of the invention, the marker protein for detection is a human marker protein. In certain detection assays, the human markers for detection are bound by marker-specific, non-human antibodies, thus, the complex would not be formed in nature. The complex of the marker protein can be detected directly, e.g., by use of a labeled marker-specific antibody that binds directly to the marker, or by binding a further component to the marker— marker-specific antibody complex. In certain embodiments, the further component is a second marker-specific antibody capable of binding the marker at the same time as the first marker-specific antibody. In certain embodiments, the further component is a secondary antibody that binds to a marker-specific antibody, wherein the secondary antibody preferably linked to a detectable label (e.g., fluorescent label, enzymatic label, biotin). When the secondary antibody is linked to an enzymatic detectable label (e.g., a peroxidase, a phosphatase, a beta-galactosidase), the secondary antibody is detected by contacting the enzymatic detectable label with an appropriate substrate to produce a colorimetric, fluorescent, or other detectable, preferably quantitatively detectable, product. Antibodies for use in the methods of the invention can be polyclonal, however, in a preferred embodiment monoclonal antibodies are used. An intact antibody, or a fragment or derivative thereof (e.g., Fab or F(ab')$_2$) can be used in the methods of the invention. Such strategies of marker protein detection are used, for example, in ELISA, RIA, western blot, and immunofluorescence assay methods.

In certain detection assays, the marker present in the biological sample for detection is an enzyme and the detection reagent is an enzyme substrate. For example, the enzyme can be a protease and the substrate can be any protein that includes an appropriate protease cleavage site. Alternatively, the enzyme can be a kinase and the substrate can be any substrate for the kinase. In preferred embodiments, the substrate which forms a complex with the marker enzyme to be detected is not the substrate for the enzyme in a human subject.

In certain embodiments, the marker—marker-specific binding agent complex is attached to a solid support for detection of the marker. The complex can be formed on the substrate or formed prior to capture on the substrate. For example, in an ELISA, RIA, immunoprecipitation assay, western blot, immunofluorescence assay, in gel enzymatic assay the marker for detection is attached to a solid support, either directly or indirectly. In an ELISA, RIA, or immunofluorescence assay, the marker is typically attached indirectly to a solid support through an antibody or binding protein. In a western blot or immunofluorescence assay, the marker is typically attached directly to the solid support. For in-gel enzyme assays, the marker is resolved in a gel, typically an acrylamide gel, in which a substrate for the enzyme is integrated.

3. Nucleic Acid Detection

In certain embodiments of the invention, the marker is a nucleic acid corresponding to a marker protein. Nucleic acids are detected using a number of assays in which a complex between the marker nucleic acid to be detected and a marker-specific probe would not occur naturally, for example, because one of the components is not a naturally occurring compound. In certain embodiments, the analyte comprises a nucleic acid and the probe comprises one or more synthetic single stranded nucleic acid molecules, e.g., a DNA molecule, a DNA-RNA hybrid, a PNA, or a modified nucleic acid molecule containing one or more artificial bases, sugars, or backbone moieties. In certain embodiments, the synthetic nucleic acid is a single stranded is a DNA molecule that includes a fluorescent label. In certain embodiments, the synthetic nucleic acid is a single stranded oligonucleotide molecule of about 12 to about 50 nucleotides in length. In certain embodiments, the nucleic acid to be detected is an mRNA and the complex formed is an mRNA hybridized to a single stranded DNA molecule that is complementary to the mRNA. In certain embodiments, an RNA is detected by generation of a DNA molecule (i.e., a cDNA molecule) first from the RNA template using the single stranded DNA that hybridizes to the RNA as a primer, e.g., a general poly-T primer to transcribe poly-A RNA. The cDNA can then be used as a template for an amplification reaction, e.g., PCR, primer extension assay, using a marker-specific probe. In certain embodiments, a labeled single stranded DNA can be hybridized to the RNA present in the sample for detection of the RNA by fluorescence in situ hybridization (FISH) or for detection of the RNA by northern blot.

For example, in vitro techniques for detection of mRNA include northern hybridizations, in situ hybridizations, and rtPCR. In vitro techniques for detection of genomic DNA include Southern hybridizations. Techniques for detection of mRNA include PCR, northern hybridizations and in situ hybridizations. Methods include both qualitative and quantitative methods.

A general principle of such diagnostic, prognostic, and monitoring assays involves preparing a sample or reaction mixture that may contain a marker, and a probe, under appropriate conditions and for a time sufficient to allow the marker and probe to interact and bind, thus forming a complex that can be removed and/or detected in the reaction mixture. These assays can be conducted in a variety of ways known in the art, e.g., ELISA assay, PCR, FISH.

4. Detection of Expression Levels

Marker levels can be detected based on the absolute expression level or a normalized or relative expression level. Detection of absolute marker levels may be preferable when monitoring the treatment of a subject or in determining if there is a change in the prostate cancer status of a subject. For example, the expression level of one or more markers can be monitored in a subject undergoing treatment for BCR, e.g., at regular intervals, such a monthly intervals. A modulation in the level of one or more markers can be monitored over time to observe trends in changes in marker levels. Expression levels of the biomarkers of the invention in the subject may be higher than the expression level of those markers in a normal sample, but may be lower than the prior expression level, thus indicating a benefit of the treatment regimen for the subject. Similarly, rates of change of marker levels can be important in a subject who is not subject to active treatment for BCR (e.g., watchful waiting). Changes, or not, in marker levels may be more relevant to treatment decisions for the subject than marker levels present in the population. Rapid changes in marker levels in a subject who otherwise appears to have a normal prostate may be indicative of an abnormal prostate state, even if the markers are within normal ranges for the population.

As an alternative to making determinations based on the absolute expression level of the marker, determinations may be based on the normalized expression level of the marker. Expression levels are normalized by correcting the absolute expression level of a marker by comparing its expression to the expression of a gene that is not a marker, e.g., a housekeeping gene that is constitutively expressed. Suitable genes for normalization include housekeeping genes such as the actin gene, or epithelial cell-specific genes. This normalization allows the comparison of the expression level in one sample, e.g., a patient sample, to another sample, e.g., a non-cancer sample, or between samples from different sources.

Alternatively, the expression level can be provided as a relative expression level as compared to an appropriate control, e.g., population control, adjacent normal tissue control, earlier time point control, etc. Preferably, the samples used in the baseline determination will be from non-cancer cells. The choice of the cell source is dependent on the use of the relative expression level. Using expression found in normal tissues as a mean expression score aids in validating whether the marker assayed is cancer specific (versus normal cells). In addition, as more data is accumulated, the mean expression value can be revised, providing improved relative expression values based on accumulated data. Expression data from cancer cells provides a means for grading the severity of the cancer state.

5. Diagnostic, Prognostic, Monitoring and Treatment Methods

The invention provides methods for diagnosing the presence of BCR in a subject, comprising (a) detecting the level of a BCR marker in a biological sample from the subject, wherein the BCR marker comprises one or more markers selected from Tables 1-5, for example, tenascin C, apolipoprotein A-IV, 1-methyladenosine, PA-18:0/22:0, or any combination thereof; and (b) comparing the level of the BCR marker in the biological sample with a predetermined threshold value; wherein the level of the BCR marker above or below the predetermined threshold value indicates a diagnosis that BCR is present in the subject.

In another aspect, the invention provides methods for diagnosing the presence of BCR in a subject, comprising: (a) contacting a biological sample with one or more reagents that selectively bind to a BCR marker in the biological sample from the subject, wherein the BCR marker comprises one or more markers selected from Tables 1-5, for example, tenascin C, apolipoprotein A-IV, 1-methyladenosine, PA-18:0/22:0, or any combination thereof; (b) allowing a complex to form between the one or more reagents and the BCR marker; (c) detecting the level of the complex; and (d) comparing the level of the complex with a predetermined threshold value; wherein the level of the complex above or below the predetermined threshold value indicates a diagnosis that BCR is present in the subject.

In still another aspect, the invention provides methods for identifying a subject as being at an increased risk for developing BCR, comprising (a) detecting the level of a BCR marker in a biological sample from the subject, wherein the BCR marker comprises one or more markers selected from Tables 1-5, for example, tenascin C, apolipoprotein A-IV, 1-methyladenosine, PA-18:0/22:0, or any combination thereof; and (b) comparing the level of the BCR marker in the biological sample with a predetermined threshold value; wherein the level of the BCR marker above or below the predetermined threshold value indicates that the subject is being at an increased risk for developing BCR.

In still another aspect, the invention provides methods for identifying a subject as being at an increased risk for developing BCR, comprising: (a) contacting a biological sample with one or more reagents that selectively bind to a BCR marker in the biological sample from the subject, wherein the BCR marker comprises one or more markers selected from Tables 1-5, for example, tenascin C, apolipoprotein A-IV, 1-methyladenosine, PA-18:0/22:0, or any combination thereof; (b) allowing a complex to form between the one or more reagents and the BCR marker; (c) detecting the level of the complex; and (d) comparing the level of the complex with a predetermined threshold value; wherein the level of the complex above or below the predetermined threshold value that the subject is being at an increased risk for developing BCR.

The invention provides methods for monitoring BCR in a subject, the method comprising: (1) detecting the level of a BCR marker in a first biological sample obtained at a first time from the subject having BCR, wherein the BCR marker comprises one or more markers selected from Tables 1-5, for example, tenascin C, apolipoprotein A-IV, 1-methyladenosine, PA-18:0/22:0, or any combination thereof; (2) detecting the level of the BCR marker in a second biological sample obtained from the subject at a second time, wherein the second time is later than the first time; and (3) comparing the level of the BCR marker in the second sample with the level of the BCR marker in the first sample; wherein a change in the level of the BCR marker is indicative of a change in BCR status in the subject.

In certain embodiments of the diagnostic methods provided herein, an increase or decrease in the level of one or more BCR markers selected from Tables 1-5, for example, tenascin C, apolipoprotein A-IV, 1-methyladenosine, PA-18:0/22:0, or any combination thereof in the biological sample as compared to the level of the one or more markers in a normal control sample is an indication that the subject is afflicted with BCR. In certain embodiments of the diagnostic methods provided herein, no increase or decrease in the detected expression level of one or more BCR markers selected from Tables 1-5 in the biological sample as compared to the expression level of the one or more markers in a normal control sample is an indication that the subject is not afflicted with BCR in prostate cancer or not predisposed to developing BCR in prostate cancer.

In certain embodiments of the diagnostic methods provided herein, an increase or decrease in the level of one or more BCR markers selected from Tables 1-5, for example, tenascin C, apolipoprotein A-IV, 1-methyladenosine, PA-18:0/22:0, or any combination thereof, in the biological sample as compared to the level of the one or more markers in a normal control sample is an indication that the subject is predisposed to developing BCR.

In certain embodiments of the monitoring methods provided herein, no increase or decrease in the detected level of one or more BCR markers selected from Tables 1-5 in the second sample as compared to the level of the one or more markers in the first sample is an indication that the therapy is efficacious for treating BCR in the subject. In certain embodiments of the monitoring methods provided herein, wherein an increased or decreased expression level of one or more BCR markers selected from Tables 1-5 in the second sample as compared to the expression level in the first sample is an indication that the therapy is not efficacious in the treatment of BCR of prostate cancer.

In certain embodiments the monitoring methods provided herein further comprise comparing the level of the one or more cancer markers selected from Tables 1-5 in the first sample or the level of the one or more BCR markers selected from Tables 1-5 in the second sample with the level of the one or more BCR related markers in a control sample.

In certain embodiments of the monitoring methods provided herein, an increase or decrease in the level of the one or more BCR markers selected from Tables 1-5 in the second sample as compared to the level of the one or more markers in the first sample is an indication for selection of active treatment of BCR in the subject. In certain embodiments of the monitoring methods provided herein, no increase or decrease in the detected level of the one or more BCR markers selected from Tables 1-5 in the second sample as compared to the level of the one or more markers in the first sample is an indication against selection of active treatment of BCR in the subject.

In certain embodiments of the monitoring methods provided herein, modulation of the level of the one or more BCR markers selected from Tables 1-5 in the second sample as compared to the level of the corresponding marker(s) in the first sample is indicative of a change in BCR status in response to treatment of the BCR in the subject. In certain embodiments of the monitoring methods provided herein, the methods further comprise comparing the level of the one or more BCR markers selected from Tables 1-5 in the second sample to the level of the corresponding markers in a normal control sample.

In any of the aforementioned embodiments, the methods may also include a step of determining whether a subject having BCR or who is being treated for BCR is responsive to a particular treatment. Such a step can include, for example, measuring the level of the one or more BCR markers selected from Tables 1-5 prior to administering an anti-BCR treatment, and measuring the level of the one or more BCR markers selected from Tables 1-5 after administering the anti-BCR treatment, and comparing the expression level before and after treatment. Determining that the BCR is responsive to the treatment if the expression level of the one or more markers is higher or lower than before treatment as compared to after treatment. The method may further include the step of adjusting the treatment to a higher dose in order to increase the responsiveness to the treatment, or adjusting the treatment to a lower dose in order to decrease the responsiveness to the treatment.

In any of the aforementioned embodiments, the methods may also include a step of determining whether a subject having BCR or who is being treated for BCR is not responsive to a particular treatment. Such a step can include, for example, measuring the level of the one or more BCR markers selected from Tables 1-5 prior to administering an anti-BCR treatment, and measuring the level of the one or more BCR markers selected from Tables 1-5 after administering the anti-BCR treatment, and comparing the expression level before and after treatment. Determining that the BCR is not responsive to the treatment if the expression level of the one or more markers is higher or lower than before treatment as compared to after treatment. The method may further include the step of adjusting the treatment to a higher dose in order to increase the responsiveness to the treatment.

In certain embodiments, the marker, e.g., a BCR marker, is a protein, for example, a protein listed in Table 1. In some embodiments, the invention also relates to a marker comprising one or more of the proteins listed in Table 1.

In certain embodiments, the marker, e.g., a BCR marker, is a metabolite, for example, a metabolite listed in Table 2. In some embodiments, the invention also relates to a marker set comprising one or more of the metabolites listed in Table 2.

In certain embodiments, the marker, e.g., a BCR marker, is a signaling lipid, for example, a signaling lipid listed in Table 3. In some embodiments, the invention also relates to a marker comprising one or more of the signaling lipids listed in Table 3.

In certain embodiments, the marker, e.g., a BCR marker, is a structural lipid, for example, a structural lipid listed in Table 4. In some embodiments, the invention also relates to a marker set comprising one or more of the structural lipids listed in Table 4.

In certain embodiments, the marker, e.g., a BCR marker, is a protein, metabolite, signaling lipid, and/or a structural lipid listed in Table 5. In some embodiments, the invention also relates to a marker set comprising one or more of markers listed in Table 5.

In some embodiments, the marker, e.g., a BCR marker, comprises at least two or more markers, wherein each of the two of more markers are selected from the proteins set forth in Table 1, the metabolites set forth in Table 2, the signaling lipids set forth in Table 3, the structural lipids set forth in Table 4, and/or the markers listed in Table 5.

In certain embodiments, the level of the marker, e.g., a BCR marker, is increased when compared to the predetermined threshold value in the subject.

In other embodiments, the level of the marker, e.g., a BCR marker, is decreased when compared to the predetermined threshold value in the subject.

In certain embodiments the diagnostic methods provided herein further comprise detecting the level of one or more additional markers of BCR in the biological sample and preferably further comprise comparing the level of prostate specific antigen (PSA) in the biological sample to a PSA expression level in a normal control sample. In certain embodiments, the combination of PSA level with one or more of the prostate-cancer maker levels increases the predictive value of the method.

In certain embodiments the monitoring methods provided herein further comprise detecting the level of prostate specific antigen (PSA) in the first sample and the second sample, and preferably further comprising comparing the level of PSA in the first sample with the level of expression of PSA in the second sample. In certain monitoring methods, the change in PSA level in combination with the change in BCR maker level increases the predictive value of the method.

In certain embodiments the diagnostic and monitoring methods provided herein further comprise comparing the detected level of the one or more BCR markers in the biological samples with one or more control samples wherein the control sample is one or more of a sample from the same subject at an earlier time point than the biological sample, a sample from a subject with benign prostatic hyperplasia (BPH), a sample from a subject with non-metastatic prostate cancer, a sample from a subject with metastatic prostate cancer, a sample from a subject with androgen sensitive prostate cancer, a sample from a subject with androgen insensitive prostate cancer, a sample from a subject with aggressive prostate cancer, and sample obtained from a subject with non-aggressive prostate cancer. Comparison of the marker levels in the biological samples with control samples from subjects with various normal and abnormal prostate states facilitates the differentiation between various prostate states including normal prostate and BCR.

In other embodiments, the present invention also involves the analysis and consideration of any clinical and/or patient-related health data, for example, data obtained from an Electronic Medical Record (e.g., collection of electronic health information about individual patients or populations relating to various types of data, such as, demographics, medical history, medication and allergies, immunization status, laboratory test results, radiology images, vital signs, personal statistics like age and weight, and billing information).

In certain embodiments the diagnostic and monitoring methods provided herein further comprise selecting a subject for having or being suspected of having BCR.

In certain embodiments the diagnostic and monitoring methods provided herein further comprising obtaining a biological sample from a subject suspected of having or being at risk of having BCR.

In certain embodiments the diagnostic and monitoring methods provided herein further comprising selecting a treatment regimen for the subject based on the level of the one or more BCR markers selected from Tables 1-5.

In certain embodiments the diagnostic and monitoring methods provided herein further comprising treating the subject with a regimen including one or more treatments selected from the group consisting of surgery, radiation, hormone therapy, antibody therapy, therapy with growth factors, cytokines, and chemotherapy.

In certain embodiments the diagnostic and monitoring methods provided herein further comprise selecting the one or more specific treatment regimens for the subject based on the results of the diagnostic and monitoring methods provided herein. In one embodiment, a treatment regimen known to be effective against BCR having the biomarker signature detected in the subject/sample is selected for the subject. In certain embodiments, the treatment method is started, change, revised, or maintained based on the results from the diagnostic or prognostic methods of the invention, e.g., when it is determined that the subject is responding to the treatment regimen, or when it is determined that the subject is not responding to the treatment regimen, or when it is determined that the subject is insufficiently responding to the treatment regimen. In certain embodiments, the treatment method is changed based on the results from the diagnostic or prognostic methods.

In certain other embodiments the diagnostic and monitoring methods provided herein further comprise introducing one or more specific treatment regimens for the subject based on the results of the diagnostic and monitoring methods provided herein. In one embodiment, a treatment regimen known to be effective against BCR is selected for the subject. In certain embodiments, the treatment method is started, change, revised, or maintained based on the results from the diagnostic or prognostic methods of the invention, e.g., when it is determined that the subject is responding to the treatment regimen, or when it is determined that the subject is not responding to the treatment regimen, or when it is determined that the subject is insufficiently responding to the treatment regimen. In certain embodiments, the treatment method is changed based on the results from the diagnostic or prognostic methods.

In yet other embodiments the diagnostic and monitoring methods provided herein further comprise the step of administering a therapeutically effective amount of an anti-BCR therapy based on the results of the diagnostic and monitoring methods provided herein. In one embodiment, a treatment regimen known to be effective against BCR is selected for the subject. In certain embodiments, the treatment method is administered based on the results from the diagnostic or prognostic methods of the invention, e.g., when it is determined that the subject expresses one or more biomarkers of the invention (i.e., the one or more BCR markers selected from Tables 1-5) above or below some threshold level that is indicative of BCR.

In certain embodiments, a change in the treatment regimen comprises changing a hormone based therapy treatment. In certain embodiments, treatments for BCR include one or more of surgery, radiation, hormone therapy, antibody therapy, therapy with growth factors, cytokines, or chemotherapy based on the results of a method of the present invention for an interval prior to performing a subsequent diagnostic, prognostic, or monitoring method provided herein.

In certain embodiments of the diagnostic and monitoring methods provided herein, the method further comprises isolating a component of the biological sample.

In certain embodiments of the diagnostic and monitoring methods provided herein, the method further comprises labeling a component of the biological sample.

In certain embodiments of the diagnostic and monitoring methods provided herein, the method further comprises amplifying a component of a biological sample.

In certain embodiments of the diagnostic and monitoring methods provided herein, the method comprises forming a complex with a probe and a component of a biological sample. In certain embodiments, forming a complex with a probe comprises forming a complex with at least one non-naturally occurring reagent. In certain embodiments of the diagnostic and monitoring methods provided herein, the method comprises processing the biological sample. In certain embodiments of the diagnostic and monitoring methods provided herein, the method of detecting a level of at least two markers comprises a panel of markers. In certain embodiments of the diagnostic and monitoring methods provided herein, the method of detecting a level comprises attaching the marker to be detected to a solid surface.

The invention provides methods of selecting for administration of active treatment or against administration of active treatment of BCR in a subject comprising: (1) detecting a level of a BCR marker in a first sample obtained from the subject having BCR at a first time wherein the subject has not been actively treated for BCR, wherein the BCR markers comprises one or more markers selected from Tables 1-5; (2) detecting a level of the BCR marker in a second sample obtained from the subject at a second time, e.g., wherein the subject has not been actively treated; (3) comparing the level of the BCR marker in the first sample with the level of the BCR marker in the second sample; wherein selecting for administration of active treatment or against administration of active treatment of BCR is based on the presence or absence of changes in the level of the BCR marker between the first sample and the second sample.

In certain embodiments, the method further comprising obtaining a third sample obtained from the subject at a third time (e.g., wherein the subject has not been actively treated), detecting a level of a BCR marker in the third sample, wherein the BCR markers comprises one or more markers selected from Tables 1-5, and comparing the level the BCR marker in the third sample with the level of the BCR marker in the first sample and/or the one or more markers in the second sample.

In certain embodiments, an increased or decreased level of the BCR marker in the second sample as compared to the level of the BCR marker in the first sample is an indication that the therapy is not efficacious in the treatment of BCR, wherein the BCR markers comprises one or more markers selected from Tables 1-5.

In certain embodiments, an increased or decreased level the BCR marker in the second sample as compared to the BCR marker in the first sample is an indication for selecting active treatment for BCR, wherein the BCR markers comprises one or more markers selected from Tables 1-5.

In certain embodiments, the methods further comprise detecting the level of prostate specific antigen (PSA) in the first sample and the second sample, and then preferably further comprising comparing the level of PSA in the first sample with the level of PSA in the second sample.

In certain embodiments, a decrease in the level of the BCR marker in the second sample as compared to the level of the BCR marker in the first sample in combination with a decrease in the level of PSA in the second sample as compared to the level of PSA in the first sample has greater predictive value that the therapy is efficacious in treating BCR in the subject than analysis of a single marker alone.

In certain embodiments, a decrease in the level of the BCR marker in the second sample as compared to the level of the BCR marker in the first sample in combination with a decrease in the level of PSA in the second sample as compared to the level of PSA in the first sample has greater predictive value for selecting against active treatment for BCR than analysis of a single marker alone.

6. Monitoring Clinical Trials

Monitoring the influence of agents (e.g., drug compounds) on the level of a marker of the invention can be applied not only in basic drug screening or monitoring the treatment of a single subject, but also in clinical trials. For example, the effectiveness of an agent to affect marker expression can be monitored in clinical trials of subjects receiving treatment for BCR. In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate) comprising the steps of (i) obtaining a pre-administration sample from a subject prior to administration of the agent; (ii) detecting the level of one or more selected markers of the invention in the pre-administration sample; (iii) obtaining one or more post-administration samples from the subject; (iv) detecting the level of the marker(s) in the post-administration samples; (v) comparing the level of the marker(s) in the pre-administration sample with the level of the marker(s) in the post-administration sample or samples; and (vi) altering the administration of the agent to the subject accordingly. For example, increased expression of the lipid marker during the course of treatment may indicate ineffective dosage and the desirability of increasing the dosage. Conversely, decreased expression of the lipid marker may indicate efficacious treatment and no need to change dosage.

H. Treatment/Therapeutics

The present invention provides methods for treating disease states, e.g., BCR in a subject, e.g., a human, using one or more (e.g., 1, 2, 3, 4, 5, 6, 7, 8, 9, 10, 11, 12, 13, 14, 15, 16, 17, 18, 19, 20 or more) markers selected from Tables 1-5, for example, tenascin C, apolipoprotein A-IV, 1-methyladenosine, PA-18:0/22:0, or any combination thereof.

The present invention also provides methods for treating BCR with a therapeutic, e.g., a modulator, that modulates (e.g., reduces, or increases) the level of expression or activity of one or more (e.g., 1, 2, 3, 4, 5, 6, 7, 8, 9, 10, 11, 12, 13, 14, 15, 16, 17, 18, 19, 20 or more) markers selected from Tables 1-5, for example, tenascin C, apolipoprotein A-IV, 1-methyladenosine, PA-18:0/22:0, or any combination thereof.

In certain embodiments, the modulator decreases the level of the marker, e.g., a BCR marker, whose expression level is increased in a subject having BCR.

In other embodiments, the modulator increases the level of the marker, e.g., a BCR marker, whose expression level is decreased in a subject having BCR.

The invention also provides methods for selection and/or administration of known treatment agents, especially hormone based therapies vs. non-hormone based therapies, and aggressive or active treatment vs. "watchful waiting", depending on the detection of a change in the level of one or more (e.g., 1, 2, 3, 4, 5, 6, 7, 8, 9, 10, 11, 12, 13, 14, 15, 16, 17, 18, 19, 20 or more) markers selected from Tables 1-5, as compared to a control. The selection of treatment regimens can further include the detection of PSA to assist in selection of the therapeutic methods. Selection of treatment methods can also include other diagnostic considerations and patient characteristics including results from imaging studies, tumor size or growth rates, risk of poor outcomes, disruption of daily activities, and age, Gleason scores (e.g., grade 1, grade 2, grade 3, grade 4, or grade 5, up to grade 10 prostate cancer), TNM classifications, clinical and/or patient-related health data (e.g., data obtained from an Electronic Medical Record (e.g., collection of electronic health information about individual patients or populations relating to various types of data, such as, demographics, medical history, medication and allergies, immunization status, laboratory test results, radiology images, vital signs, personal statistics like age and weight, and billing information)).

1. Nucleic Acid Therapeutics

Nucleic acid therapeutics are well known in the art. Nucleic acid therapeutics include both single stranded and double stranded (i.e., nucleic acid therapeutics having a complementary region of at least 15 nucleotides in length that may be one or two nucleic acid strands) nucleic acids that are complementary to a target sequence in a cell. Nucleic acid therapeutics can be delivered to a cell in culture, e.g., by adding the nucleic acid to culture media either alone or with an agent to promote uptake of the nucleic acid into the cell. Nucleic acid therapeutics can be delivered to a cell in a subject, i.e., in vivo, by any route of administration. The specific formulation will depend on the route of administration.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

Sequences can be "fully complementary" with respect to each when there is base-pairing of the nucleotides of the first nucleotide sequence with the nucleotides of the second nucleotide sequence over the entire length of the first and second nucleotide sequences. However, where a first sequence is referred to as "substantially complementary" with respect to a second sequence herein, the two sequences can be fully complementary, or they may form one or more, but generally not more than 4, 3 or 2 mismatched base pairs upon hybridization, while retaining the ability to hybridize under the conditions most relevant to their ultimate application. However, where two oligonucleotides are designed to form, upon hybridization, one or more single stranded overhangs as is common in double stranded nucleic acid therapeutics, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes described herein.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled. Such non-Watson-Crick base pairs includes, but not limited to, G:U Wobble or Hoogstein base pairing.

The terms "complementary," "fully complementary", and "substantially complementary" herein may be used with respect to the base matching between the sense strand and the antisense strand of a dsRNA, or between an antisense nucleic acid or the antisense strand of dsRNA and a target sequence, as will be understood from the context of their use.

As used herein, a polynucleotide that is "substantially complementary to at least part of" a messenger RNA (mRNA) refers to a polynucleotide that is substantially complementary to a contiguous portion of the mRNA of interest including a 5' UTR, an open reading frame (ORF), or a 3' UTR. For example, a polynucleotide is complementary to at least a part of the mRNA corresponding to the protein markers of Table 1 or Table 5.

Nucleic acid therapeutics typically include chemical modifications to improve their stability and to modulate their pharmacokinetic and pharmacodynamic properties. For example, the modifications on the nucleotides can include, but are not limited to, LNA, HNA, CeNA, 2'-hydroxyl, and combinations thereof.

Nucleic acid therapeutics may further comprise at least one phosphorothioate or methylphosphonate internucleotide linkage. The phosphorothioate or methylphosphonate internucleotide linkage modification may occur on any nucleotide of the sense strand or antisense strand or both (in nucleic acid therapeutics including a sense strand) in any position of the strand. For instance, the internucleotide linkage modification may occur on every nucleotide on the sense strand or antisense strand; each internucleotide linkage modification may occur in an alternating pattern on the sense strand or antisense strand; or the sense strand or antisense strand may contain both internucleotide linkage modifications in an alternating pattern. The alternating pattern of the internucleotide linkage modification on the sense strand may be the same or different from the antisense strand, and the alternating pattern of the internucleotide linkage modification on the sense strand may have a shift relative to the alternating pattern of the internucleotide linkage modification on the antisense strand.

A. Single Stranded Therapeutics

Antisense nucleic acid therapeutic agent single stranded nucleic acid therapeutics, typically about 16 to 30 nucleotides in length and are complementary to a target nucleic acid sequence in the target cell, either in culture or in an organism.

Patents directed to antisense nucleic acids, chemical modifications, and therapeutic uses are provided, for example, in U.S. Pat. No. 5,898,031 related to chemically modified RNA-containing therapeutic compounds, and U.S. Pat. No. 6,107,094 related methods of using these compounds as therapeutic agent. U.S. Pat. No. 7,432,250 related to methods of treating patients by administering single-stranded chemically modified RNA-like compounds; and U.S. Pat. No. 7,432,249 related to pharmaceutical compositions containing single-stranded chemically modified RNA-like compounds. U.S. Pat. No. 7,629,321 is related to methods of cleaving target mRNA using a single-stranded oligonucleotide having a plurality RNA nucleosides and at least one chemical modification. Each of the patents listed in the paragraph are incorporated herein by reference.

B. Double Stranded Therapeutics

In many embodiments, the duplex region is 15-30 nucleotide pairs in length. In some embodiments, the duplex region is 17-23 nucleotide pairs in length, 17-25 nucleotide pairs in length, 23-27 nucleotide pairs in length, 19-21 nucleotide pairs in length, or 21-23 nucleotide pairs in length.

In certain embodiments, each strand has 15-30 nucleotides.

The RNAi agents that are used in the methods of the invention include agents with chemical modifications as disclosed, for example, in Publications WO 2009/073809 and WO/2012/037254, the entire contents of each of which are incorporated herein by reference.

Nucleic acid therapeutic agents for use in the methods of the invention also include double stranded nucleic acid therapeutics. An "RNAi agent," "double stranded RNAi agent," double-stranded RNA (dsRNA) molecule, also referred to as "dsRNA agent," "dsRNA", "siRNA", "iRNA agent," as used interchangeably herein, refers to a complex of ribonucleic acid molecules, having a duplex structure comprising two anti-parallel and substantially complementary, as defined below, nucleic acid strands. As used herein, an RNAi agent can also include dsiRNA (see, e.g., US Patent publication 20070104688, incorporated herein by reference). In general, the majority of nucleotides of each strand are ribonucleotides, but as described herein, each or both strands can also include one or more non-ribonucleotides, e.g., a deoxyribonucleotide and/or a modified nucleotide. In addition, as used in this specification, an "RNAi agent" may include ribonucleotides with chemical modifications; an RNAi agent may include substantial modifications at multiple nucleotides. Such modifications may include all types of modifications disclosed herein or known in the art. Any such modifications, as used in a siRNA type molecule, are encompassed by "RNAi agent" for the purposes of this specification and claims. The RNAi agents that are used in the methods of the invention include agents with chemical modifications as disclosed, for example, in U.S. Provisional Application No. 61/561,710, filed on Nov. 18, 2011, International Application No. PCT/US2011/051597, filed on Sep. 15, 2010, and PCT Publication WO 2009/073809, the entire contents of each of which are incorporated herein by reference. The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, an RNAi agent may comprise one or more nucleotide overhangs. The term "siRNA" is also used herein to refer to an RNAi agent as described above.

In another aspect, the agent is a single-stranded antisense RNA molecule. An antisense RNA molecule is complementary to a sequence within the target mRNA. Antisense RNA can inhibit translation in a stoichiometric manner by base pairing to the mRNA and physically obstructing the translation machinery, see Dias, N. et al., (2002) Mol Cancer Ther 1:347-355. The antisense RNA molecule may have about 15-30 nucleotides that are complementary to the target mRNA. For example, the antisense RNA molecule may have a sequence of at least 15, 16, 17, 18, 19, 20 or more contiguous nucleotides complementary to the mRNA sequences corresponding to the protein markers of Table 1 or Table 5.

The term "antisense strand" refers to the strand of a double stranded RNAi agent which includes a region that is substantially complementary to a target sequence (e.g., a human TTR mRNA). As used herein, the term "region complementary to part of an mRNA encoding transthyretin" refers to a region on the antisense strand that is substantially complementary to part of a TTR mRNA sequence. Where the region of complementarity is not fully complementary to the target sequence, the mismatches are most tolerated in the terminal regions and, if present, are generally in a terminal region or regions, e.g., within 6, 5, 4, 3, or 2 nucleotides of the 5' and/or 3' terminus.

The term "sense strand," as used herein, refers to the strand of a dsRNA that includes a region that is substantially complementary to a region of the antisense strand.

The invention also includes molecular beacon nucleic acids having at least one region which is complementary to a nucleic acid of the invention, such that the molecular beacon is useful for quantitating the presence of the nucleic acid of the invention in a sample. A "molecular beacon" nucleic acid is a nucleic acid comprising a pair of complementary regions and having a fluorophore and a fluorescent quencher associated therewith. The fluorophore and quencher are associated with different portions of the nucleic acid in such an orientation that when the complementary regions are annealed with one another, fluorescence of the fluorophore is quenched by the quencher. When the complementary regions of the nucleic acid are not annealed with one another, fluorescence of the fluorophore is quenched to a lesser degree. Molecular beacon nucleic acids are described, for example, in U.S. Pat. No. 5,876,930.

I. Drug Screening

As noted above, sets of markers whose expression levels correlate with one or more selected prostate disease characteristics (e.g., BCR or prostate cancer progression) are attractive targets for identification of new therapeutic agents via screens to detect compounds or entities that inhibit or enhance expression of these biomarker genes and/or their products. Accordingly, the present invention provides methods for the identification of compounds potentially useful for modulating BCR or prostate cancer progression. In particular, the present invention provides methods for the identification of agents or compounds potentially useful for modulating BCR or prostate cancer progression wherein the agents or compounds modulate (e.g., increase or decrease) the expression and/or activity of one or more of the markers selected from Tables 1-5, for example, tenascin C, apolipoprotein A-IV, 1-methyladenosine, PA-18:0/22:0, or any combination thereof.

Such assays typically comprise a reaction between a marker of the invention and one or more assay components. The other components may be either the test compound itself, or a combination of test compounds and a natural binding partner of a marker of the invention. Compounds identified via assays such as those described herein may be useful, for example, for modulating, e.g., inhibiting, ameliorating, treating, or preventing the disease. Compounds identified for modulating the expression level of one or more of the markers selected from Tables 1-5 are preferably further tested for activity useful in the treatment of BCR.

The test compounds used in the screening assays of the present invention may be obtained from any available source, including systematic libraries of natural and/or synthetic compounds. Test compounds may also be obtained by any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann et al., 1994, *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, 1997, *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten, 1992, *Biotechniques* 13:412-421), or on beads (Lam, 1991, *Nature* 354:82-84), chips (Fodor, 1993, *Nature* 364:555-556), bacteria and/or spores, (Ladner, USP 5,223,409), plasmids (Cull et al, 1992, *Proc Natl Acad Sci USA* 89:1865-1869) or on phage (Scott and Smith, 1990, *Science* 249:386-390; Devlin, 1990, *Science* 249:404-406; Cwirla et al, 1990, *Proc. Natl. Acad. Sci.* 87:6378-6382; Felici, 1991, *J. Mol. Biol.* 222:301-310; Ladner, supra.).

The screening methods of the invention comprise contacting a cell, e.g., a diseased cell, especially a prostate cancer cell, with a test compound and determining the ability of the test compound to modulate the expression and/or activity of one or more of the markers selected from Tables 1-5, optionally in combination with PSA, in the cell. The screening methods of the invention also comprise contacting a cell, e.g., a diseased cell, with a test compound and determining the ability of the test compound to modulate the expression and/or activity of one or more of the markers selected from Tables 1-5, for example, tenascin C, apolipoprotein A-IV, 1-methyladenosine, PA-18:0/22:0, or any combination thereof, optionally in combination with PSA, in the cell. The expression and/or activity of one or more of the markers selected from Tables 1-5, optionally in combination with PSA, can be determined using any methods known in the art, such as those described herein.

In another embodiment, the invention provides assays for screening candidate or test compounds which are substrates of a marker of the invention or biologically active portions thereof. In yet another embodiment, the invention provides assays for screening candidate or test compounds which bind to a marker of the invention or biologically active portions thereof. Determining the ability of the test compound to directly bind to a marker can be accomplished, for example, by any method known in the art.

This invention further pertains to novel agents identified by the above-described screening assays. Accordingly, it is within the scope of this invention to further use an agent identified as described herein in an appropriate animal model. For example, an agent capable of modulating the expression and/or activity of a marker of the invention identified as described herein can be used in an animal model to determine the efficacy, toxicity, or side effects of treatment (e.g., of BCR) with such an agent. Alternatively, an agent identified as described herein can be used in an animal model to determine the mechanism of action of such an agent. Furthermore, this invention pertains to uses of novel agents identified by the above-described screening assays for treatment as described above.

In certain embodiments, the screening methods are performed using cells contained in a plurality of wells of a multi-well assay plate. Such assay plates are commercially available, for example, from Stratagene Corp. (La Jolla, Calif.) and Corning Inc. (Acton, Mass.) and include, for example, 48-well, 96-well, 384-well and 1536-well plates.

Reproducibility of the results may be tested by performing the analysis more than once with the same concentration of the same candidate compound (for example, by incubating cells in more than one well of an assay plate). Additionally, since candidate compounds may be effective at varying concentrations depending on the nature of the compound and the nature of its mechanism(s) of action, varying concentrations of the candidate compound may be tested. Generally, candidate compound concentrations from 1 fM to about 10 mM are used for screening. Preferred screening concentrations are generally between about 10 pM and about 100 µM.

The screening methods of the invention will provide "hits" or "leads," i.e., compounds that possess a desired but not optimized biological activity. Lead optimization performed on these compounds to fulfill all physicochemical, pharmacokinetic, and toxicologic factors required for clinical usefulness may provide improved drug candidates. The present invention also encompasses these improved drug candidates and their use as therapeutics for modulating BCR progression.

J. Kits/Panels

The invention also provides compositions and kits for diagnosing, prognosing, or monitoring a disease or disorder, recurrence of a disorder, or survival of a subject being treated for a disorder (e.g., BCR). These kits may include one or more of the following: a reagent that specifically binds to a marker of the invention, and a set of instructions for measuring the level of the marker.

The invention also encompasses kits for detecting the presence of a marker protein or nucleic acid in a biological sample. Such kits can be used to determine if a subject has, or is at risk for developing, BCR. For example, the kit can comprise a labeled compound or agent capable of detecting a marker protein or nucleic acid in a biological sample and means for determining the amount of the protein or mRNA in the sample (e.g., an antibody which binds the protein or a fragment thereof, or an oligonucleotide probe which binds to DNA or mRNA encoding the protein). Kits can also include instructions for use of the kit for practicing any of the methods provided herein or interpreting the results obtained using the kit based on the teachings provided herein. The kits can also include reagents for detection of a control protein in the sample not related to the BCR, e.g., actin for tissue samples, albumin in blood or blood derived samples for normalization of the amount of the marker present in the sample. The kit can also include the purified marker for detection for use as a control or for quantitation of the assay performed with the kit.

Kits include a panel of reagents for use in a method to diagnose BCR in a subject (or to identify a subject predisposed to developing prostate cancer, etc.), the panel comprising at least two detection reagents, wherein each detection reagent is specific for one prostate cancer-specific protein, wherein said BCR-specific proteins are selected from the prostate cancer-specific protein sets provided herein.

For antibody-based kits, the kit can comprise, for example: (1) a first antibody (e.g., attached to a solid support) which binds to a first marker protein; and, optionally, (2) a second, different antibody which binds to either the first marker protein or the first antibody and is conjugated to a detectable label. In certain embodiments, the kit includes (1) a second antibody (e.g., attached to a solid support) which binds to a second marker protein; and, optionally, (2) a second, different antibody which binds to either the second marker protein or the second antibody and is conjugated to a detectable label. The first and second marker proteins are different. In an embodiment, the first and second markers are markers of the invention, e.g., one or more of the markers selected from Tables 1-5. In certain embodiments, neither the first marker nor the second marker is PSA. In certain embodiments, the kit comprises a third antibody which binds to a third marker protein which is different from the first and second marker proteins, and a second different antibody that binds to either the third marker protein or the antibody that binds the third marker protein wherein the third marker protein is different from the first and second marker proteins.

For oligonucleotide-based kits, the kit can comprise, for example: (1) an oligonucleotide, e.g., a detectably labeled oligonucleotide, which hybridizes to a nucleic acid sequence encoding a marker protein or (2) a pair of primers useful for amplifying a marker nucleic acid molecule. In certain embodiments, the kit can further include, for example: (1) an oligonucleotide, e.g., a second detectably labeled oligonucleotide, which hybridizes to a nucleic acid sequence encoding a second marker protein or (2) a pair of primers useful for amplifying the second marker nucleic acid molecule. The first and second markers are different. In an embodiment, the first and second markers are markers of the invention, e.g., one or more of the markers selected from Tables 1-5. In certain embodiments, the kit can further include, for example: (1) an oligonucleotide, e.g., a third detectably labeled oligonucleotide, which hybridizes to a nucleic acid sequence encoding a third marker protein or (2) a pair of primers useful for amplifying the third marker nucleic acid molecule wherein the third marker is different from the first and second markers. In certain embodiments, the kit includes a third primer specific for each nucleic acid marker to allow for detection using quantitative PCR methods.

For chromatography methods, the kit can include markers, including labeled markers, to permit detection and identification of one or more markers of the invention, e.g., one or more of the markers selected from Tables 1-5, and optionally PSA, by chromatography. In certain embodiments, kits for chromatography methods include compounds for derivatization of one or more markers of the invention.

In certain embodiments, kits for chromatography methods include columns for resolving the markers of the method.

Reagents specific for detection of a marker of the invention, e.g., one or more of the markers selected from Tables 1-5, allow for detection and quantitation of the marker in a complex mixture, e.g., serum, tissue sample. In certain embodiments, the reagents are species specific. In certain embodiments, the reagents are not species specific. In certain embodiments, the reagents are isoform specific. In certain embodiments, the reagents are not isoform specific.

In certain embodiments, the kits for the diagnosis, monitoring, or characterization of BCR comprise at least one reagent specific for the detection of the level of one or more of the markers selected from Tables 1-5. In certain embodiments, the kits further comprise instructions for the diagnosis, monitoring, or characterization of BCR based on the level of the at least one marker selected from Tables 1-5. In certain embodiments, the kits further comprise instructions to detect the level of PSA in a sample in which the at least one marker selected from Tables 1-5 is detected. In certain embodiments, the kits further comprise at least one reagent for the specific detection of PSA.

The invention provides kits comprising at least one reagent specific for the detection of a level of at least one marker selected from Tables 1-5 and at least one reagent specific for the detection of a level of PSA.

In certain embodiments, the kits can also comprise, e.g., a buffering agents, a preservative, a protein stabilizing agent, reaction buffers. The kit can further comprise components necessary for detecting the detectable label (e.g., an enzyme or a substrate). The kit can also contain a control sample or a series of control samples which can be assayed and compared to the test sample. The controls can be control serum samples or control samples of purified proteins or nucleic acids, as appropriate, with known levels of target markers. Each component of the kit can be enclosed within an individual container and all of the various containers can be within a single package, along with instructions for interpreting the results of the assays performed using the kit.

The kits of the invention may optionally comprise additional components useful for performing the methods of the invention.

The invention further provides panels of reagents for detection of one or more BCR-related marker in a subject sample and at least one control reagent. In certain embodiments, the BCR marker comprises at least two or more markers, wherein each of the two or more markers are selected from the protein markers set forth in Table 1, the metabolite markers set forth in Table 2, the signaling lipid markers set forth in Table 3, and the structural lipid markers set forth in Table 4, or the markers set forth in Table 5.

In certain embodiments, the control reagent is to detect the marker for detection in the biological sample wherein the panel is provided with a control sample containing the marker for use as a positive control and optionally to quantitate the amount of marker present in the biological sample. In certain embodiments, the panel includes a detection reagent for a maker not related to BCR that is known to be present or absent in the biological sample to provide a positive or negative control, respectively. The panel can be provided with reagents for detection of a control protein in the sample not related to BCR, e.g., actin for tissue samples, albumin in blood or blood derived samples for normalization of the amount of the marker present in the sample. The panel can be provided with a purified marker for detection for use as a control or for quantitation of the assay performed with the panel.

In certain embodiments, the level of the BCR marker in the panel is increased when compared to a control or a predetermined threshold value. In certain embodiments, the level of the BCR marker in the panel is decreased when compared to a control or a predetermined threshold value.

In some embodiments, the panel comprises one or more BCR markers with an increased level when compared to a control or a predetermined threshold value, and/or one or more BCR markers with a decreased level when compared to a control or a predetermined threshold value.

In a preferred embodiment, the panel includes reagents for detection of two or more markers of the invention (e.g., 2, 3, 4, 5, 6, 7, 8, 9), preferably in conjunction with a control reagent. In the panel, each marker is detected by a reagent specific for that marker. In certain embodiments, the panel further includes a reagent for the detection of PSA. In certain embodiments, the panel includes replicate wells, spots, or portions to allow for analysis of various dilutions (e.g., serial dilutions) of biological samples and control samples. In a preferred embodiment, the panel allows for quantitative detection of one or more markers of the invention.

In certain embodiments, the panel is a protein chip for detection of one or more markers. In certain embodiments, the panel is an ELISA plate for detection of one or more markers. In certain embodiments, the panel is a plate for quantitative PCR for detection of one or more markers.

In certain embodiments, the panel of detection reagents is provided on a single device including a detection reagent for one or more markers of the invention and at least one control sample. In certain embodiments, the panel of detection reagents is provided on a single device including a detection reagent for two or more markers of the invention and at least one control sample. In certain embodiments, multiple panels for the detection of different markers of the invention are provided with at least one uniform control sample to facilitate comparison of results between panels.

The contents of all documents cited or referenced herein and all documents cited or referenced in the herein cited documents, together with any manufacturer's instructions, descriptions, product specifications, and product sheets for any products mentioned herein or in any document incorporated by reference herein, GenBank Accession and Gene numbers, and published patents and patent applications, are hereby incorporated by reference, and may be employed in the practice of the invention. Those skilled in the art will recognize that the invention may be practiced with variations on the disclosed structures, materials, compositions and methods, and such variations are regarded as within the ambit of the invention.

This invention is further illustrated by the following examples which should not be construed as limiting.

EXAMPLES

Serum Analysis Identification of BCR Markers

The following Examples 1-5 describe a statistical analysis of BCR serum signatures to determine biomarkers for the diagnosis of BCR of prostate cancer.

Biomarkers were obtained using a two-step approach: univariate screening and variable selection or ranking. The first step used permutation testing to assess the significance of the univariate mean difference between groups for each analyte and removes those not differentially expressed. The second step ran through two algorithms on the remaining analytes. One obtained the analytes' rank by the significance from univariate mean difference; the other was based on the variable selection solution path from multivariate regression using an elastic net by tuning parameters. Bootstrapping was implemented in both algorithms to assess the uncertainty and stability of the selected biomarkers. To assess the stability and reproducible rate of selected top analytes, two stability statistics were introduced:

1. The pairwise average percentage of the overlapped analytes given the number of selected analytes;
2. The average selection rate given a ranked analyte list.

Based on the stability statistics, the best approach was chosen and applied to obtain a list of biomarkers. The process comprised the following 5 steps:

1. Scale and center the data by analyte.
2. Remove analytes that have missingness ≥30% within each class.
3. Screen analytes by univariate mean difference.
4. Run two variable selection algorithms: mean difference and regression by elastic net.
5. Compare stability statistics and pick the best approach.

Serum proteomics, structural lipidomics, signaling lipidomics, and metabolomics quantitative profiles were assessed for 75 BCR patients and about 310 non-BCR control subjects. Biomarkers were analyzed using an ensemble of methods for screening and selecting the best discriminators of biochemical recurrence.

An elastic net procedure was performed to identify candidate biomarkers, which yielded candidates with AUCs in the range of 0.55-0.65 alone and 0.55-0.71 when combined. Omics data was analyzed individually and as a whole. Results are set forth below in Examples 1-5.

Example 1: Proteomics Analysis—Identification of Proteins as BCR Markers

Table 1 is a summary table for the top 20 detected proteomics markers. Markers were ranked from high to low difference using a symbol from "A" to "K" correspondingly.

TABLE 1

Protein Markers Indicative of BCR

| Protein | Difference | AUC | Rank |
|---|---|---|---|
| tenascin C | 0.19763 | 0.635 | A |
| apolipoprotein A-IV | 0.20825 | 0.603 | A |
| Poliovirus receptor | 0.13316 | 0.602 | B |
| Coagulation factor XIII A chain | −0.15959 | 0.573 | B |
| apolipoprotein F | −0.26246 | 0.601 | C |
| Thrombospondin-4 | 0.10457 | 0.554 | D |
| Metalloproteinase inhibitor 2 | −0.19821 | 0.608 | E |
| Mimecan | 0.14676 | 0.604 | F |
| Hypoxia up-regulated protein 1 | 0.10338 | 0.583 | F |
| Interleukin-18-binding protein | 0.12678 | 0.584 | G |
| Coagulation factor VII | 0.06142 | 0.583 | G |
| Fibrinogen beta chain | −0.27115 | 0.57 | G |
| SH3 domain-binding glutamic acid-rich-like protein 3 | 0.15857 | 0.554 | H |
| Creatine kinase M-type | −0.15717 | 0.576 | H |
| Follistatin-related protein 1 | 0.06684 | 0.556 | H |
| CD109 antigen | 0.10289 | 0.574 | H |
| Insulin-like growth factor-binding protein 7 | 0.10752 | 0.567 | H |
| Histone H3.3C | −0.14749 | 0.571 | I |
| Complement component C7 | 0.04962 | 0.572 | J |
| 78 kDa glucose-regulated protein | −0.08135 | 0.579 | K |

Receiver operating characteristic (ROC) analysis was also performed for markers identified from Table 1. ROC curve is a graphical plot that illustrates the performance of a binary classifier system as its discrimination threshold is varied. The curve is created by plotting the true positive rate (TPR) against the false positive rate (FPR) at various threshold settings. The true-positive rate is also known as sensitivity. The false-positive rate is also known as the fall-out and can be calculated as (1-specificity). The ROC curve is thus the sensitivity as a function of fall-out. ROC analysis provides tools to select possibly optimal models and to discard suboptimal ones independently from (and prior to specifying) the cost context or the class distribution. ROC analysis is related in a direct and natural way to cost/benefit analysis of diagnostic decision making.

FIG. 1 contains ROC curves for proteomics BCR markers ranked A and B. As shown in FIG. 1, the combination of the four protein markers identified in Table 1 as rank A and B has a predictive diagnostic value of 0.731 for BCR patients. The combination of the two Rank B markers has a predictive diagnostic value of 0.621 for BCR patients. The combination of Rank A markers has a predictive diagnostic value of 0.686 for BCR patients.

Figure 2:
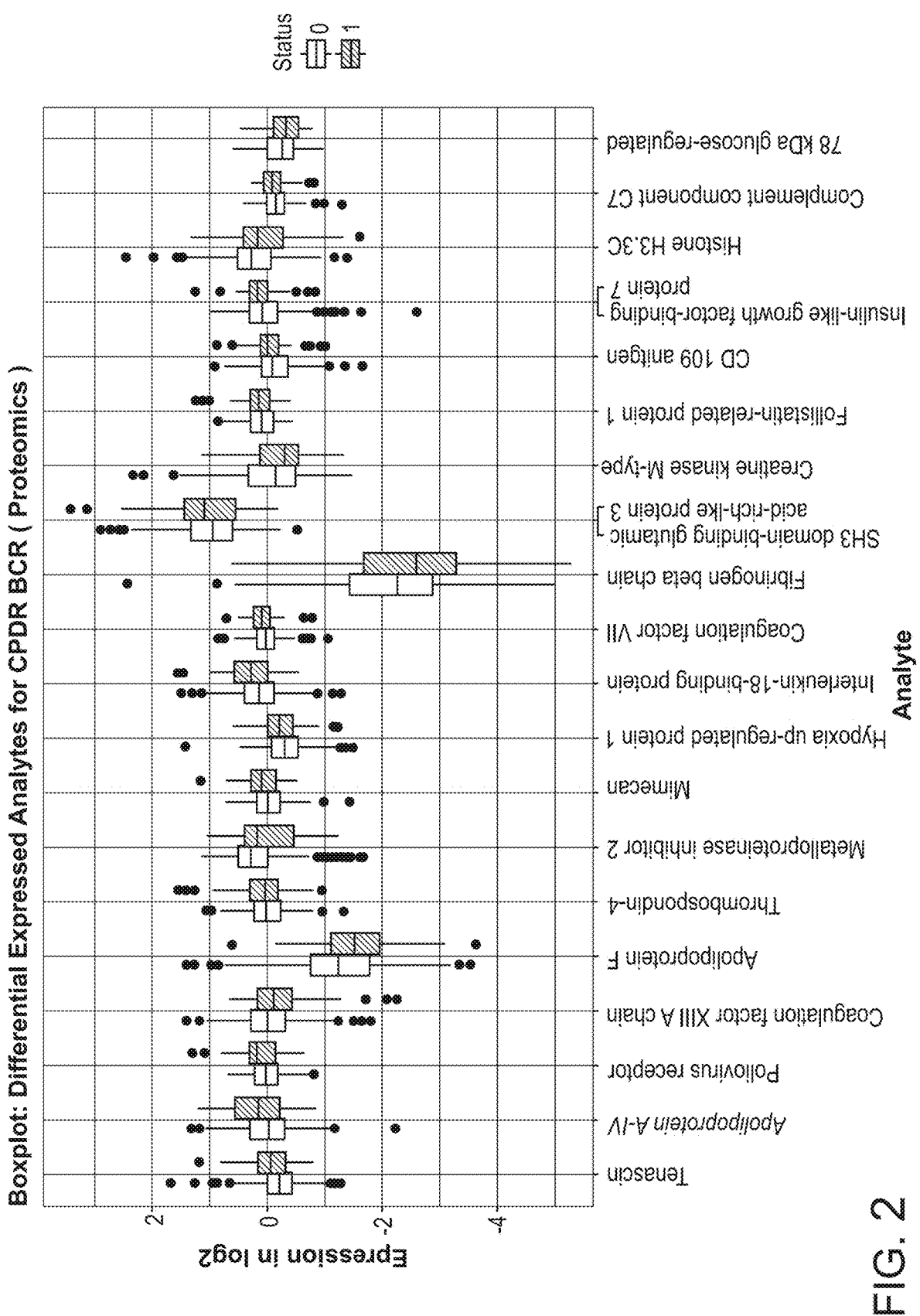
FIG. 2 is a box plot depicting a direct comparison of normalized expression levels of individual protein markers identified in Table 1 between BCR patients and negative controls.

FIG. 2 is a box plot depicting a direct comparison of normalized expression levels of individual protein markers identified in Table 1 between BCR patients and negative controls. As shown in FIG. 2, expression levels of tenascin C, apolipoprotein A-IV, poliovirus receptor, thrombospondin-4, mimecan, hypoxia up-regulated protein 1, interleukin-18-binding protein, coagulation factor VII, SH3 domain-binding glutamic acid-rich-like protein 3, follistatin-related protein 1, CD109 antigen, insulin-like growth factor-binding protein 7, and complement component C7 were increased in BCR patients when compared to a negative control, whereas expression levels of apolipoprotein F, coagulation factor XIII A chain, metalloproteinase inhibitor 2, fibrinogen beta chain, creatine kinase M-type, histone H3.3C, and 78 kDa glucose-regulated protein had a decreased expression level as compared to a negative control.

These data indicate that one or more of the protein markers identified in Table 1 may be used as biomarkers for the diagnosis and prognosis of BCR in prostate cancer, and to improve the accuracy of BCR detection.

Example 2: Metabolomics Analysis—Identification of Metabolites as BCR Markers

Table 2 is a summary table for the top 20 detected metabolomic markers. Markers were ranked from high to low difference using symbol from "A" to "J" correspondingly.

TABLE 2

Metabolite Markers Indicative of BCR

| Metabolite | Difference | AUC | Rank |
|---|---|---|---|
| 1-METHYLADENOSINE | 0.11485 | 0.617 | A |
| DIMETHYLGLYCINE | 0.16405 | 0.59 | A |
| 2-AMINOOCTANOIC ACID | 0.16046 | 0.572 | B |
| ALLANTOATE | 0.13207 | 0.595 | B |
| 1,5-ANHYDROHEXITOL | 0.23902 | 0.596 | B |
| THYMIDINE | −0.37493 | 0.569 | B |
| GLYCEROL | 0.17538 | 0.557 | B |
| GLUCOSE | −0.54122 | 0.529 | C |
| GUANIDINEBUTYRIC ACID | 0.21644 | 0.576 | C |
| THREONINE | 0.10601 | 0.572 | C |
| HYDROXYPROLINE | 0.14359 | 0.554 | C |
| GLUTAMIC ACID | 0.17561 | 0.574 | D |
| OXO-OCTADECANOIC ACID | 0.3 | 0.573 | E |
| PROLINE | 0.13517 | 0.572 | F |
| URIC ACID | 0.12927 | 0.571 | F |
| TARTARIC ACID | −0.31897 | 0.585 | G |
| RIBOSYLIMIDAZOLEACETIC ACID | 0.13408 | 0.568 | H |

TABLE 2-continued

Metabolite Markers Indicative of BCR

| Metabolite | Difference | AUC | Rank |
|---|---|---|---|
| 2-HYDROXYGLUTARATE | 0.12151 | 0.555 | H |
| GUANINE | −0.33995 | 0.593 | I |
| ACETYLLYSINE | 0.15833 | 0.543 | J |

Figure 3:
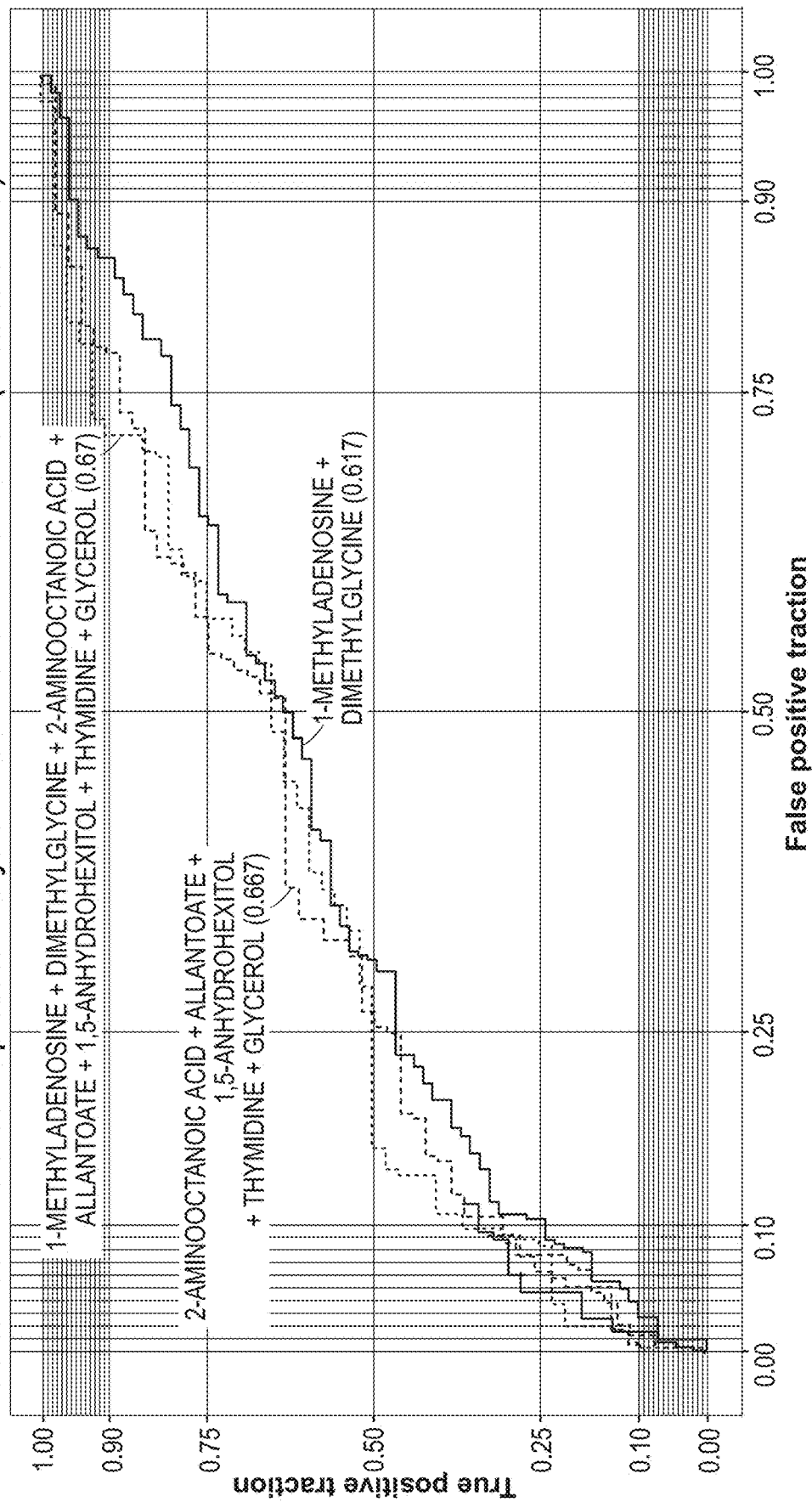
FIG. 3 depicts three ROC curves for three sets of metabolomics markers (Rank A, Rank B, and Rank A+B), identified in Table 2.

FIG. 3 contains ROC curves for metabolite BCR markers ranked A and B. As shown in FIG. 3, the combination of the 7 markers identified in Table 2 as rank A and B has a predictive diagnostic value of 0.67 for BCR patients. The combination of the five Rank B markers have a predictive diagnostic value of 0.667 for BCR patients. The combination of the two Rank A markers have a predictive diagnostic value of 0.617 for BCR patients.

Figure 4:
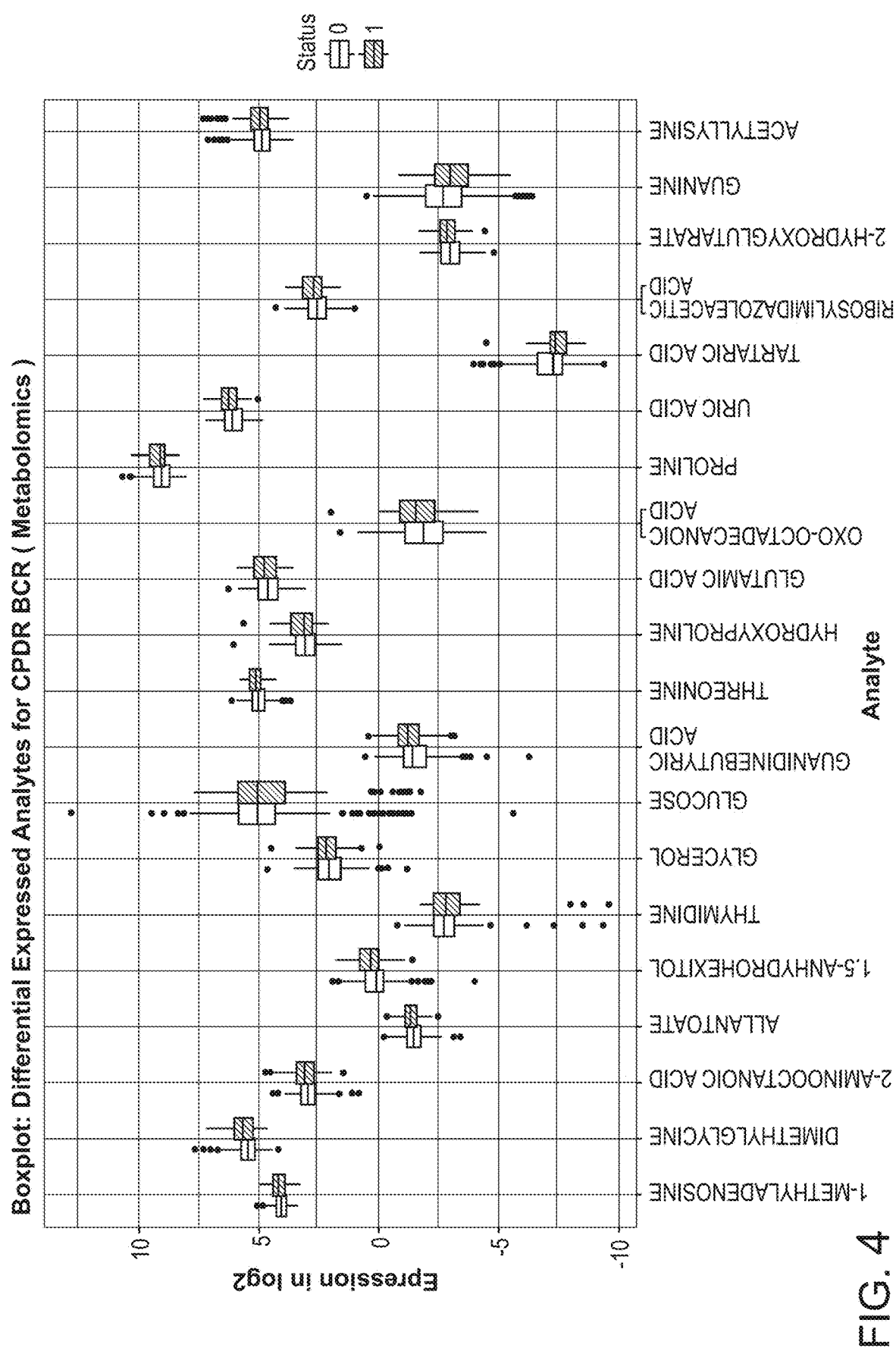
FIG. 4 is a box plot depicting a direct comparison of normalized expression levels of individual metabolite markers identified in Table 2 between BCR patients and negative controls.

FIG. 4 is a box plot depicting a direct comparison of normalized expression levels of individual markers identified in Table 2 between BCR patients and negative controls. As shown in FIG. 4, expression levels of 1-methyladenosine, dimethylglycine, 2-aminooctanoic acid, allantoate, 1,5-anhydrohexitol, glycerol, guanidinebutyric acid, threonine, hydroxyproline, glutamic acid, oxo-octadecanoic acid, proline, uric acid, ribosylimidazoleacetic acid, 2-hydroxyglutarate, and acetyllysine were increased in BCR patients when compared to a negative control, whereas expression levels of thymidine, glucose, tartaric acid, and guanine had a decreased expression level as compared to a negative control.

These data indicate that one or more of the metabolite markers identified in Table 2 may be used as biomarkers for the diagnosis and prognosis of BCR, and to improve the accuracy of BCR detection.

Example 3: Signaling Lipidomics Analysis—Identification of Signaling Lipids as BCR Markers Table 3 is the summary table for the top 8 detected signaling lipid markers. Markers were ranked from high to low difference using symbol from "A" to "C" correspondingly.

TABLE 3

Signaling Lipid Markers Indicative of BCR

| Signaling Lipid | Difference | AUC | Rank |
|---|---|---|---|
| 5-HETrE | 0.163 | 0.538 | A |
| 9-HETE | −0.151 | 0.528 | B |
| 14-HDHA | −0.334 | 0.556 | B |
| TxB3 | 0.152 | 0.515 | B |
| 12-HEPE | −0.063 | 0.518 | C |
| 20-HETE | −0.014 | 0.501 | C |
| LTB4 | 0.165 | 0.535 | C |
| 11-HEPE | 0.007 | 0.519 | C |

Figure 5:
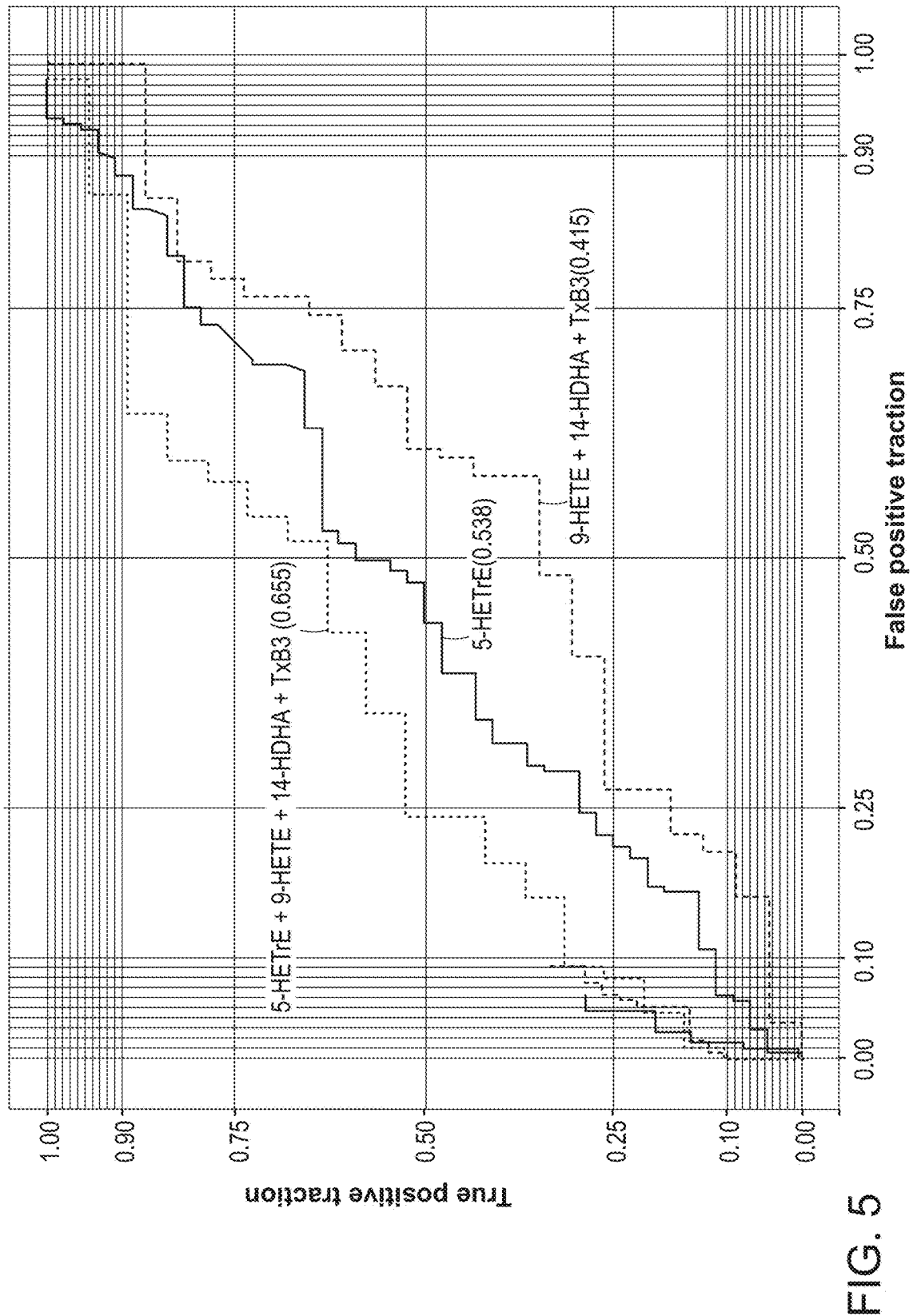
FIG. 5 depicts three ROC curves for three sets of signaling lipidomics markers (Rank A, Rank B, and Rank A+B), identified in Table 3.

FIG. 5 contains ROC curves for signaling lipid markers ranked A and B. As shown in FIG. 5, the combination of the four markers identified in Table 3 as Rank A and B have a predictive diagnostic value of 0.655 for BCR patients. The combination of Rank B markers has a predictive diagnostic value of 0.415 for BCR patients. The Rank A marker has a predictive diagnostic value of 0.538 for BCR patients.

Figure 6:
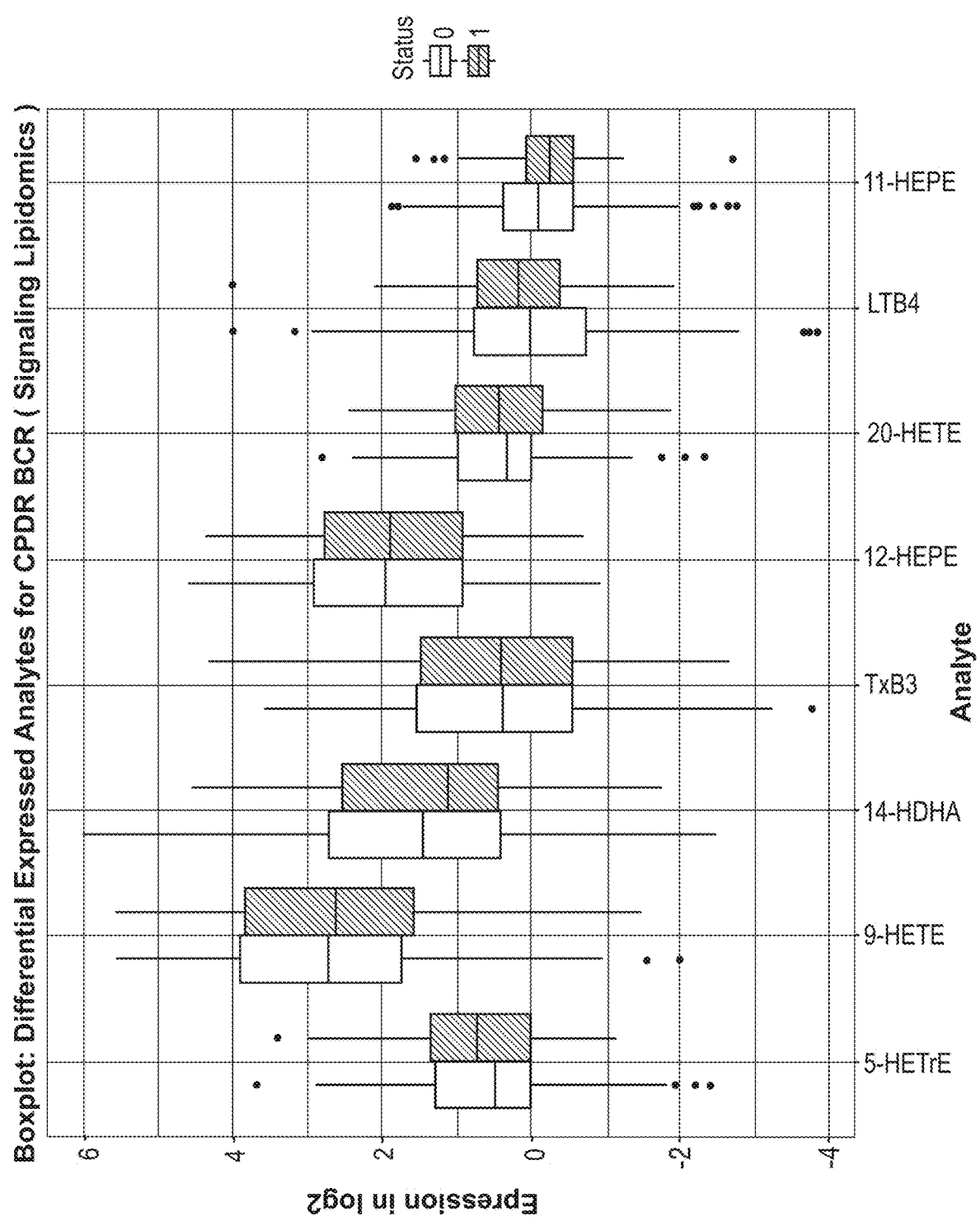
FIG. 6 is a box plot depicting a direct comparison of normalized expression levels of individual signaling lipid markers identified in Table 3 between BCR patients and negative controls.

FIG. 6 is a box plot depicting a direct comparison of normalized expression levels of individual markers identified in Table 3 between BCR patients and negative controls. As shown in FIG. 6, expression levels of 5-HETrE, TxB3, 20-HETE, and LTB4 were increased in BCR patients when compared to a negative control, whereas expression levels of 9-HETE, 14-HDHA, 12-HEPE, and 11-HEPE had a decreased expression level as compared to a negative control.

These data indicate that one or more of the signaling lipid markers identified in Table 3 may be used as biomarkers for the diagnosis and prognosis of BCR, and to improve the accuracy of BCR detection.

Example 4: Structural Lipidomics Analysis—Identification of Structural Lipids as BCR Markers Table 4 is a summary table for the top 20 detected structural lipid markers. Markers were ranked from high to low difference using symbol from "A" to "D" correspondingly.

TABLE 4

Structural Lipid Markers Indicative of BCR

| Structural Lipid | Difference | AUC | Rank |
|---|---|---|---|
| PA-18:0/22:0 | −0.25339 | 0.61705 | A |
| AC-18:2-OH | 0.2454 | 0.63002 | B |
| PS-18:0/22:3 | −0.25584 | 0.60111 | B |
| PA-18:0/22:2 | −0.183 | 0.57061 | C |
| TAG-58:7 + NH4 | −0.18393 | 0.56786 | C |
| AC-16:1-OH | 0.21015 | 0.6066 | C |
| GLYCOLIPID-D18:2/22:0-TRIHEX | 0.26569 | 0.58551 | D |
| PI-18:2/20:0 | −0.19377 | 0.59318 | D |
| GLYCOLIPID-D 18:1/24:0-TRIHEX | 0.22135 | 0.59744 | D |
| PG-18:3/20:1 | 0.22937 | 0.59653 | C |
| CE-22:6 + NH4 | −0.36157 | 0.57565 | D |
| DAG-42:6 + NH4 | −0.46224 | 0.58181 | D |
| PE-40:4 | 0.18858 | 0.56332 | D |
| PG-22:0/22:6 | −0.16070 | 0.54815 | D |
| GLYCOLIPID-D 18:0/22:4-DIHEX | 0.26355 | 0.60465 | D |
| LPC-16:1 | 0.17694 | 0.58351 | D |
| PC-34:4 | 0.12976 | 0.57796 | D |
| FFA-18:3 | 0.16161 | 0.5858 | D |
| SM-D18:2/20:0 | −0.33954 | 0.60759 | D |
| PG-16:1/20:0 | −18665 | 0.56895 | D |

Figure 7:
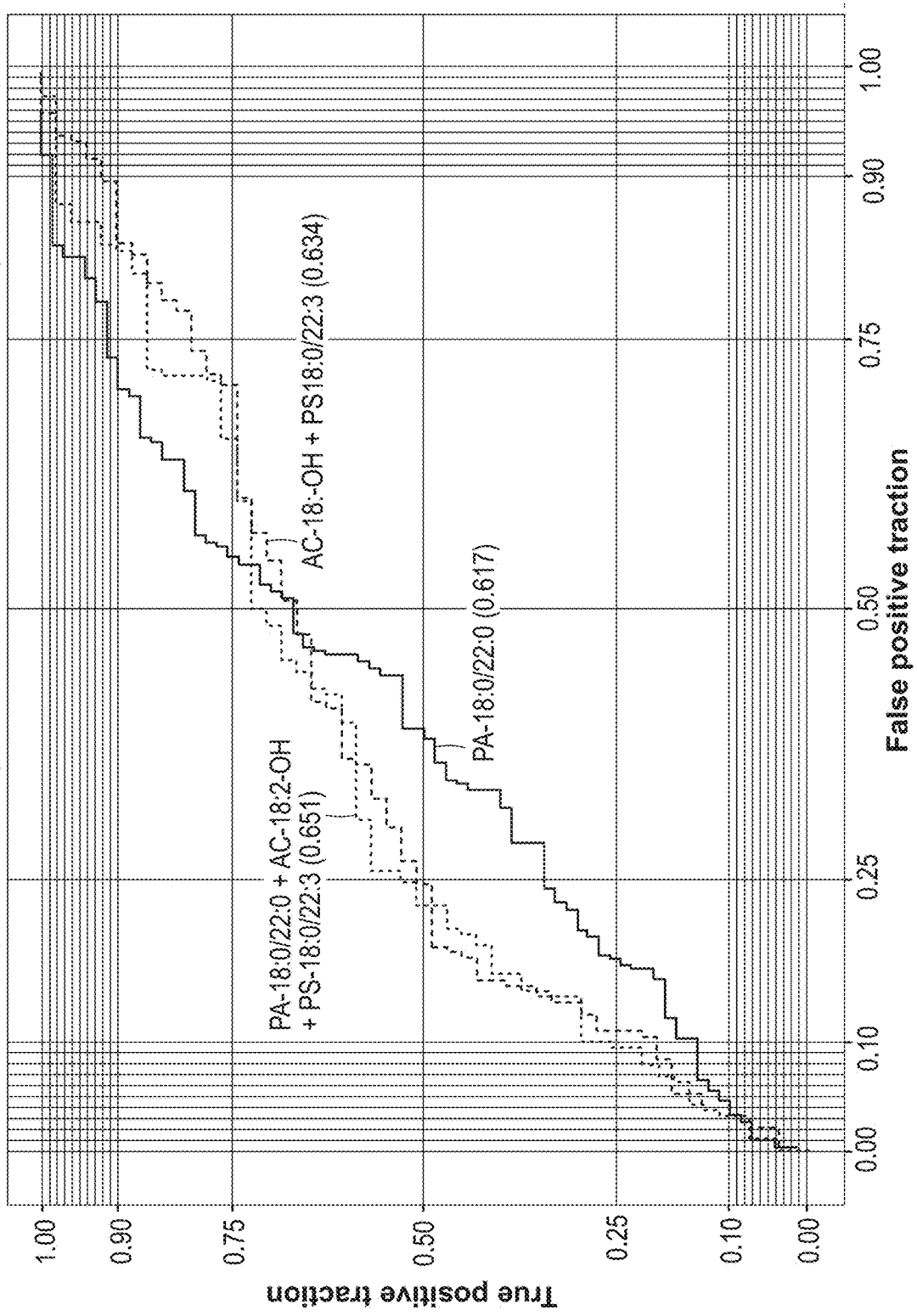
FIG. 7 depicts three ROC curves for three sets of structural lipidomics markers (Rank A, Rank B, and Rank A+B), identified in Table 4.

FIG. 7 contains ROC curves for structural lipidomics markers ranked A and B. As shown in FIG. 7, the combination of the 3 markers identified in Table 4 as rank A and B have a predictive diagnostic value of 0.651 for BCR patients. The combination of Rank B markers has a predictive diagnostic value of 0.634 for BCR patients. The Rank A marker has a predictive diagnostic value of 0.617 for BCR patients.

Figure 8:
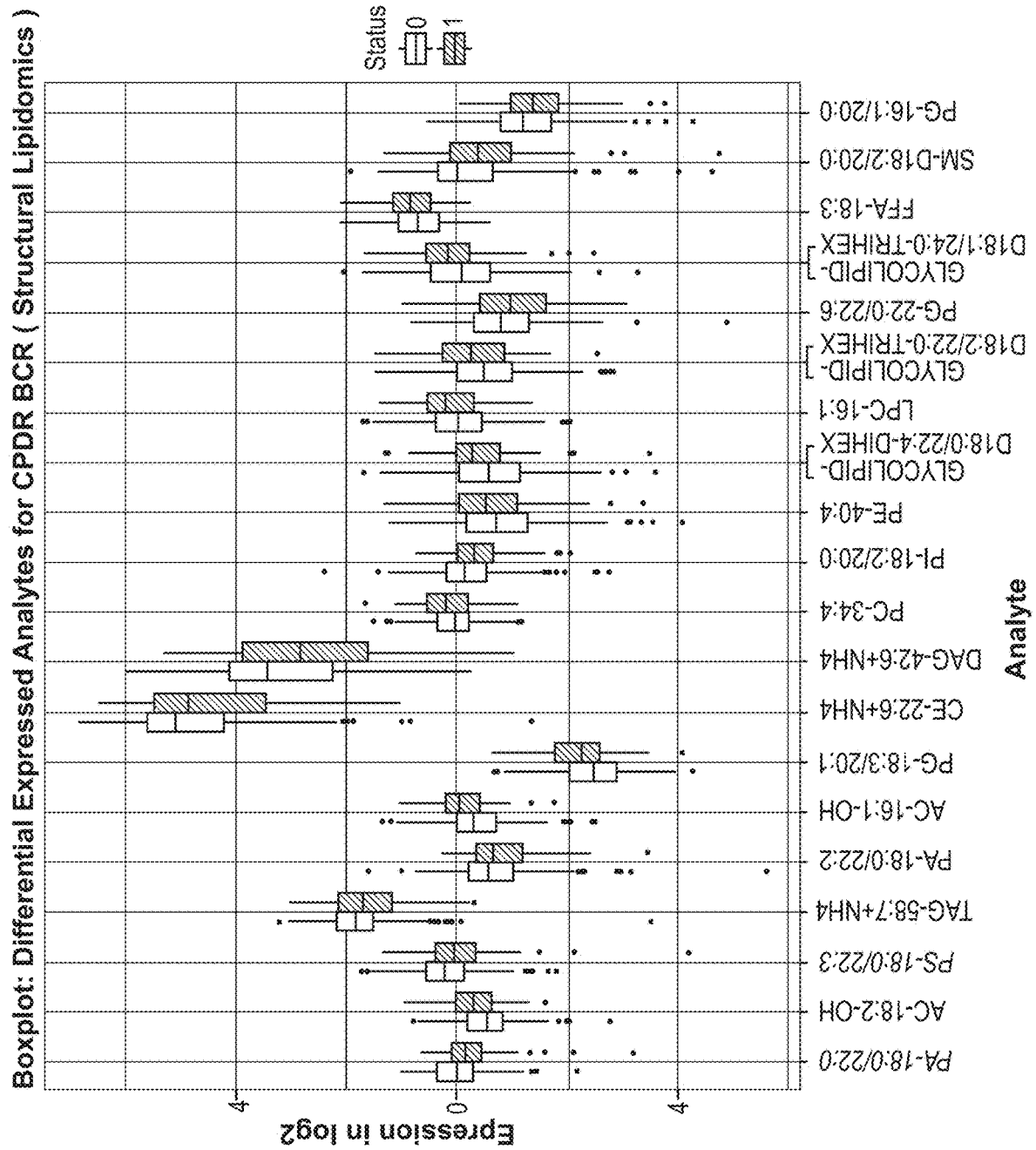
FIG. 8 is a box plot depicting a direct comparison of normalized expression levels of individual structural lipid markers identified in Table 4 between BCR patients and negative controls.

FIG. 8 is a box plot depicting a direct comparison of normalized expression levels of individual markers identified in Table 4 between BCR patients and negative controls. As shown in FIG. 8, expression levels of AC-18:2-OH, AC-16:1-OH, PG-18:3/20:1, PC-34:4, PE-40:4, GLYCOLIPID-D18:0/22:4-DIHEX, GLYCOLIPID-D18:2/22:0-TRIHEX, GLYCOLIPID-D18:1/24:0-TRIHEX, LPC-16:1, PG-22:0/22:6, and FFA-18:3 were increased in BCR patients when compared to a negative control, whereas expression levels of PA-18:0/22:0, PS-18:0/22:3, TAG-58:7+NH4, PA-18:0/22:2, CE-22:6+NH4, DAG-42:6+NH4, PI-18:2/20:0, SM-D18:2/20:0, and PG-16:1/20:0 had a decreased expression level as compared to a negative control.

These data indicate that one or more of the structural lipidomics markers identified in Table 4 may be used as biomarkers for the diagnosis and prognosis of BCR, and to improve the accuracy of BCR detection.

Example 5: Multi-Omics Analysis—Identification BCR Markers

Table 5 is a summary table including "multi-omics" markers, which is a combination of certain proteomics, structural lipidomics, and metabolomics markers described above. Markers were ranked from high to low difference using symbol from "A" to "K" correspondingly.

TABLE 5

Markers Indicative of BCR (All Omics)

| bmk | AUC | Rank |
|---|---|---|
| Tenascin | 0.63339 | A |
| PA.18.0.22.0 | 0.61666 | A |
| 1-METHYLADENOSINE | 0.61638 | B |
| Apolipoprotein A-IV | 0.59983 | B |
| AC.18.2.OH | 0.62963 | G |
| Apolipoprotein F | 0.60207 | C |
| Poliovirus receptor | 0.60166 | G |
| PS.18.0.22.3 | 0.60056 | C |
| DIMETHYGLYCINE | 0.58963 | C |
| AC.16.1.OH | 0.60490 | D |
| PG.18.3.20.1 | 0.59977 | D |
| Coagulation factor XIII A chain | 0.57436 | D |
| 2-AMINOOCTONAIC ACID | 0.57193 | D |
| THYMIDINE | 0.57054 | D |
| SM.D18.2.20.0 | 0.60957 | E |
| Mimecan | 0.60666 | E |
| FFA.18.3 | 0.58670 | E |
| Pl.14.0.22.3 | 0.64878 | F |
| 1,5-anhydrohexitol | 0.59747 | F |
| Pl.18.2.20.0 | 0.59306 | F |
| Interleukin-18-binding protein | 0.58193 | F |
| LPE.18.1 | 0.58158 | F |
| CE.22.6.NH4 | 0.57573 | F |
| TAG.58.7.NH4 | 0.56882 | F |
| GLYCOLIPID.D18.2.18.1.MONOHEX | 0.63656 | G |
| AC.10.0 | 0.59928 | G |
| CE.24.4.NH4 | 0.59613 | G |
| GLYCOLIPID.D18.2.16.1.MONOHEX | 0.58961 | G |
| PS.18.2.18.2 | 0.58824 | G |
| PE.38.7.O.38.0 | 0.58567 | G |
| PI.P20.0.18.3 | 0.57726 | G |
| PROLINE | 0.57207 | G |
| PG.14.0.16.0 | 0.60566 | H |
| LPC.16.1 | 0.58306 | H |
| HISTIDINE | 0.56397 | H |
| PE.42.9.O.42.2 | 0.57670 | I |
| DAG.42.7.NH4 | 0.57584 | I |
| GLYCOLIPID.D18.2.12.0.DIHEX | 0.62364 | J |
| SM.D16.1.16.0 | 0.60511 | J |
| ALLANTOATE | 0.59256 | J |
| AC.14.1.OH | 0.59206 | J |
| PG.P18.0.22.4 | 0.58906 | J |
| TAG.60.8.NH4 | 0.56861 | J |
| PG.20.2.20.5 | 0.56710 | J |
| GLYCOLIPID.D18.1.22.6.MONOHEX | 0.62720 | K |
| PS.18.3.20.1 | 0.60561 | K |
| GLYCOLIPID.D18.1.14.1.MONOHEX | 0.58584 | K |
| PS.20.5.22.3 | 0.58444 | K |
| CE.DES_22.5.NH4 | 0.57478 | K |
| GLUTAMIC ACID | 0.57344 | K |

Figure 9:
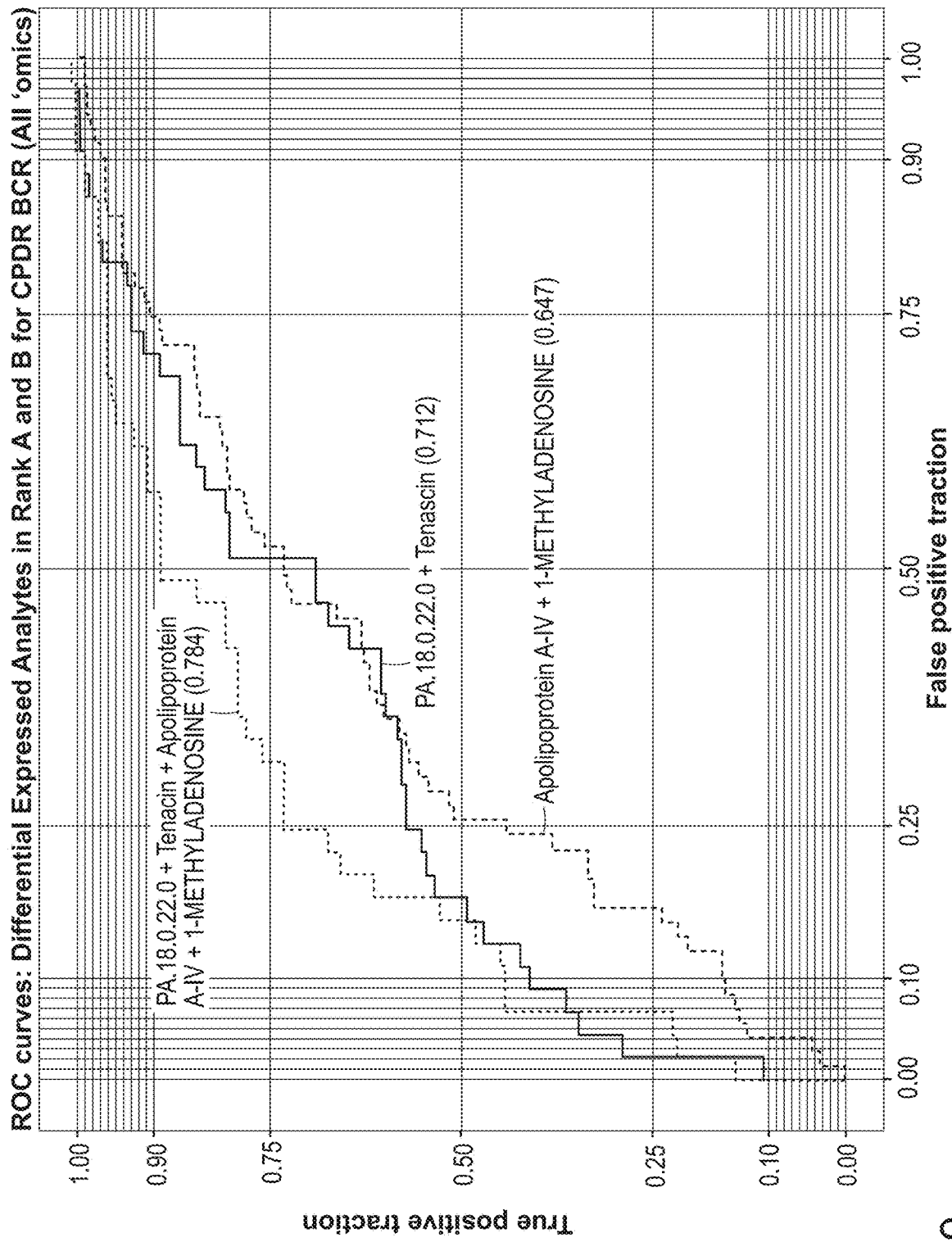
FIG. 9 depicts three ROC curves for three sets of all markers (Rank A, Rank B, and Rank A+B), identified in Table 5.

FIG. 9 contains ROC curves for the markers of Table 5 ranked A and B (tenascin C (TNC) protein, phosphatidic acid (PA) 18:0/22:0 lipid, 1-methyladenosine metabolite, and apolipoprotein A-IV (A-IV) protein). As shown in FIG. 9, the combination of the four markers identified in Table 5 as rank A and B have a predictive diagnostic value of 0.784 for BCR patients. The combination Rank B markers has a predictive diagnostic value of 0.647 for BCR patients. The combination of Rank A markers has a predictive diagnostic value of 0.712 for BCR patients. Thus, overall, a preferred group of analytes as biomarkers is one of more of the Rank A and Rank B proteomics, structural lipidomics, and metabolomics (AUC: 0.64-0.78).

Figure 10:
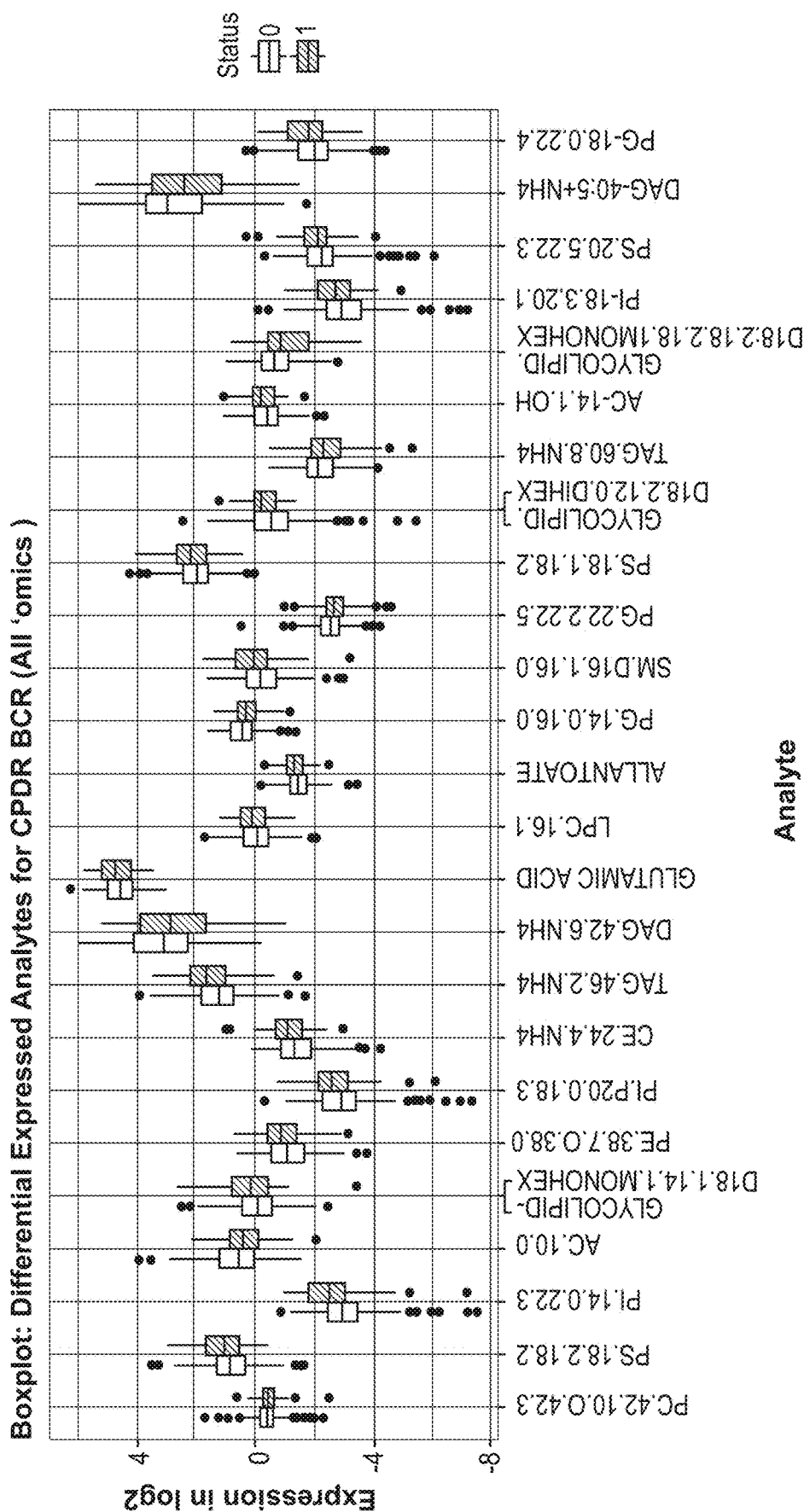
FIG. 10 is a box plot depicting a direct comparison of normalized expression levels of individual markers (protein, metabolite, structural lipid and signaling lipid) identified in Table 5 between prostate cancer patients and negative controls.
Figure 10:
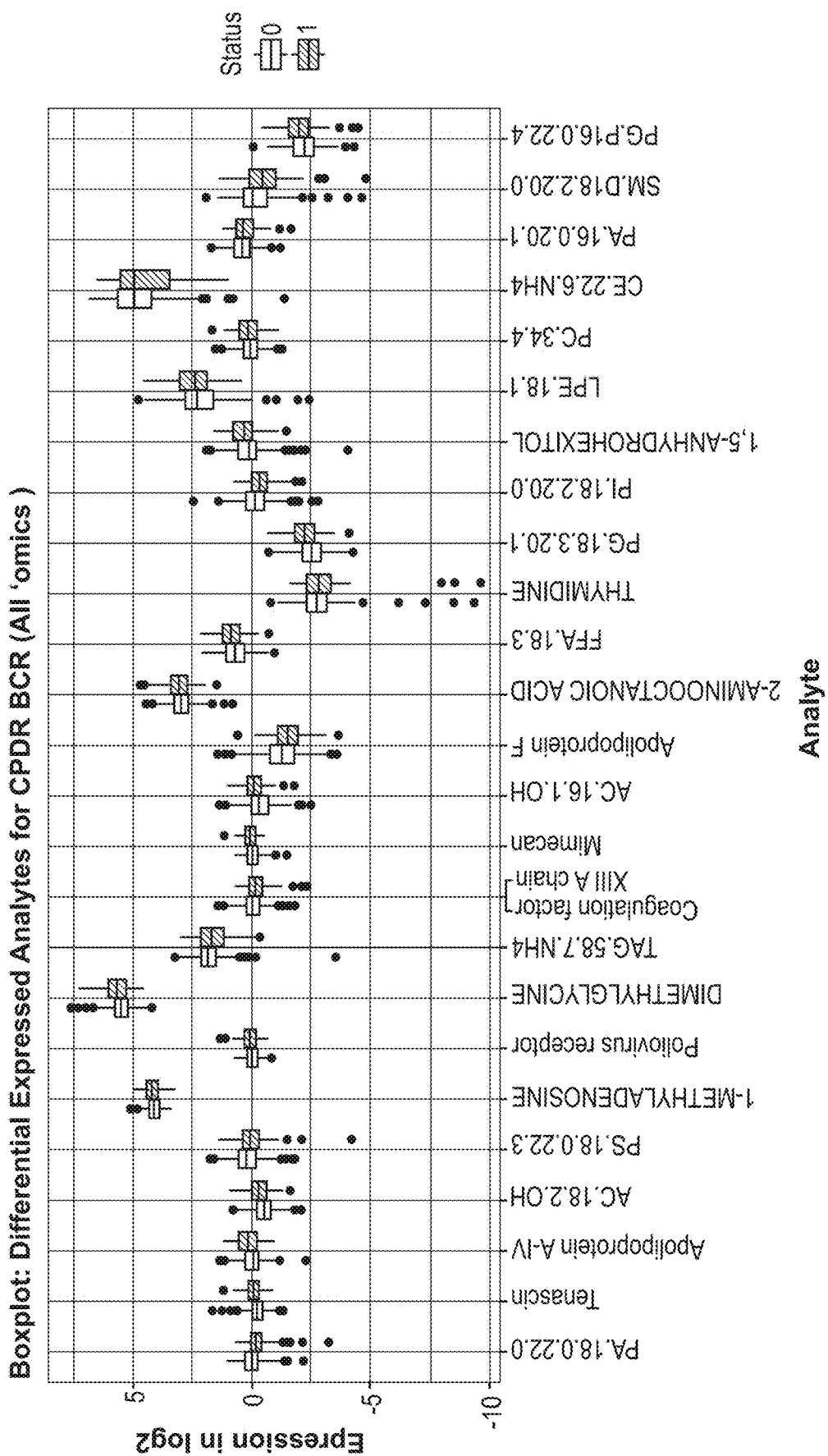

FIG. 10 is a box plot depicting a direct comparison of normalized expression levels of individual markers identified in Table 5 between BCR patients and negative controls.

These data indicate that one or more of the markers identified in Table 5 may be used as biomarkers for the diagnosis and prognosis of BCR, and to improve the accuracy of BCR detection.

Example 6: Identification and Analysis of Serum BCR Markers

This Example summarizes identification of a panel of serum biomarkers including two proteins (tenascin C and apolipoprotein A-IV), one metabolite (1-methyladenosine) and one lipid (PA 18:0/22:0) which are useful for the diagnosis of biochemical recurrence in prostate cancer. Furthermore, the results show that these serum biomarkers synergized with clinical parameters and, thus, can be combined with clinical parameters to generate a combined panel with robust predictive performance in differentiating patients with biochemical recurrence from those with disease-free survival. This prognostic ability allows improved understanding and improvement in the clinical course of disease and also allows more active monitoring in higher risk populations.

Materials and Methods

Study Design and Participants

In this retrospective cohort study, patients who consented to enrollment in the Center for Prostate Disease Research (CPDR) biospecimen databank and a multi-center national clinical database were included. Participants were further restricted to subjects who underwent radical prostatectomy (RP) for treatment of biopsy-confirmed prostate cancer between 1994 through 2014 and donated sera at the time of radical prostatectomy. Detailed information on patient demographic, clinical, pathologic, treatment, and cancer outcomes was obtained as part of routine data abstraction activities for the CPDR multi-center national database.

Demographic, Clinical, Pathologic and Treatment Information

Patient characteristics of interest included: age at RP (years), self-reported race (African American, Caucasian), PSA level (ng/mL) at time of prostate cancer diagnosis, clinical and pathologic T stage (pT2, pT3-4), pathologic Gleason sum (≤6; 3+4; 4+3 and 8-10), NCCN Risk stratum and surgical margin status (positive, negative). Patient follow-up time was calculated as days elapsed between RP date and the last known medical visit and is presented in years. All patients underwent RP without neo-adjuvant therapy. Table 6, below, summarizes characteristics of 360 patients included in the study cohort.

TABLE 6

Study Cohort Characteristics

| Characteristics | n % |
|---|---|
| Age at diagnosis | Continuous |
| Mean (SD) | 57.9 (8.4) |
| Median (min, max) | 58.7 (40.5, 76.5) |
| Follow-up time (years), Median (range) | 7.0 (0.2-18.6) |
| Race/ethnicity | n (%) |
| Caucasian | 169 (46.9%) |

TABLE 6-continued

Study Cohort Characteristics

| | | |
|---|---|---|
| African-American | 181 | (50.3%) |
| Other | 10 | (2.8%) |
| Diagnostic PSA, ng/mL | | n (%) |
| <4 | 87 | (24.2%) |
| 4-9.99 | 228 | (63.5%) |
| ≥10 | 44 | (12.3%) |
| Clinical T stage | | n (%) |
| T1 | 240 | (67%) |
| T2 | 115 | (32.1%) |
| T3-4 | 3 | (0.9%) |
| Biopsy Gleason Sum | | n (%) |
| <=6 | 230 | (68.1%) |
| 7 | 86 | (25.4%) |
| 8-10 | 22 | (5.5%) |
| NCCN Risk Stratum | | n (%) |
| low | 193 | (57.4%) |
| intermediate | 111 | (33.0%) |
| high | 32 | (9.5%) |
| Pathologic T stage | | n (%) |
| T2 | 243 | (67.5%) |
| T3-4 | 96 | (26.7%) |
| Pathologic Gleason Grade (ISUP 2014) | | n (%) |
| <=6 | 98 | (27.2%) |
| 7 | 206 | (57.2%) |
| 8-10 | 43 | (11.9%) |
| Surgical Margins | | n (%) |
| Positive | 68 | (19.0%) |

Study Endpoints

Primary study endpoints included biochemical recurrence (BCR). A BCR event was defined in the following manner: a post-RP PSA level ≥0.2 ng/mL followed by a successive, confirmatory PSA level ≥0.2 or the initiation of salvage radiation or hormonal therapy after a rising PSA level ≥0.1. Any PSA value drawn within eight weeks after RP were not considered due to known fluctuations proximal to RP date. Patients who had salvage therapy without a rising PSA ≥0.1 were classified as a non-BCR event and censored at the date of the initiation of salvage therapy. Patients who had an initial PSA ≥0.2 ng/mL but no confirmatory PSA ≥0.2 and no initiation of salvage therapy, were classified as a non-BCR event and censored at the last known date of PSA of <0.2 ng/mL. Distant metastasis was assessed by a systematic review of the electronic medical record as well as physical copies of physician-ordered scans appropriate for confirming metastasis, including: bone biopsy, bone scan, chest x-ray, computed tomography (CT), MRI, and plain film. Scans were ordered based on clinical judgment and not prescribed at fixed intervals. Patients who were lost to follow-up or who died without any evidence of distant metastasis were censored as non-events at date of last known medical visit or date of death, respectively.

Serum Metabolomics Analysis

Prior to RP, patients completed the informed consent for the Biospecimen Banking and for the CPDR Database. The medical technologist completed the Serum Bank Questionnaire Form and labeled the collection tubes. Blood (12 mL total) was drawn into two Serum Separation (SST) tiger-topped tubes (2×6 mL). The specimens were then allowed to clot for 30 minutes at room temperature. After clotting, the blood was centrifuged for 20 minutes at 1,617 g. Most specimens yielded 7 microtube serum aliquots of at least 1 mL each. The tubes were labeled and stored in −80° C. freezers monitored for temperature and security.

Serum was defrosted at +4° C. and vortexed prior to aliquoting. Serum aliquots (75 µL) were placed in pre-chilled (−80° C.) 1.5 mL Eppendorf tubes. Next, 400 µL of a pre-chilled (−20° C.) mixture of acetonitrile, isopropanol, and deionized water in proportion 3:3:2 (v/v/v) was added. Samples were vortexed for 10 seconds and left in a freezer at −20° C. overnight. Samples were further centrifuged at 4° C. at 12,000 g for 3 minutes. Supernatants were transferred into LC-MS vials or into 0.5 mL Eppendorf tubes. Serum extracts were divided in to three parts: 75 µL for gas chromatography combined with time-of flight mass spectrometry (to be further dried and derivatized with MSTFA and methoxyamine for gas chromatography combined with time-of-flight mass spectrometry) using a time-of-flight Pegasus HT™ mass spectrometer (LECO, St. Josephs, Mich., USA), 200 µL for reversed phase liquid chromatography coupled with high-resolution mass spectrometry using a TripleTOF® 6600™ (SCIEX, Framingham, Mass. USA) (to be further dried and reconstituted with 40 µL mixture of 0.1% formic acid and acetonitrile in proportion 9:1 v.v.), and 100 µL for hydrophilic interaction chromatography with liquid chromatography and tandem mass-spectrometry using a TripleQuad 5500 System™ (SCIEX, Framingham, Mass., USA). A standard quality control sample containing a mixture of amino and organic acids was injected daily to monitor mass spectrometer response. A pooled quality control sample was obtained by taking an aliquot of the same volume of all samples from the study and injected daily with a batch of analyzed samples to determine the optimal dilution of the batch samples and to validate metabolite identification and peak integration.

Structural Lipidomic Profiling

A cocktail of deuterium-labeled and odd chain phospholipid standards from diverse lipid classes was added to 25 µL, serum. Standards were chosen so that they represented each lipid class and were at designated concentrations chosen to provide the most accurate quantitation and dynamic range for each lipid species. 4 mL chloroform: methanol (1:1, v/v) was added to each sample and the lipid extraction was performed as previously described (Catalona W J, et al., *The Journal of urology* 2011, 185(5):1650-1655; Carlsson S, et al., *European urology* 2013, 64(5):693-699). Lipid extraction was automated using a customized sequence on a Hamilton Robotics STARlet™ system (Hamilton, Reno, Nev.) to meet the high-throughput requirements. Lipid extracts were dried under nitrogen and reconstituted in 68 µL, chloroform:methanol (1:1, v/v). Samples were flushed with nitrogen and stored at −20° C. Samples were diluted 50 times in isopropanol:methanol:acetonitrile:water (3:3:3:1, by vol.) with 2 mM ammonium acetate in order to optimize ionization efficiency in positive and negative modes. Electrospray ionization-MS was performed on a TripleTOF® 5600+™ (SCIEX, Framingham, Mass.), coupled to a customized direct injection loop on an Ekspert microLC200™ system (SCIEX). 50 µL, of sample was injected at a flow-rate of 6 µL/min. Lipids were analyzed using a customized data independent analysis strategy on the TripleTOF® 5600+™ allowing for MS/MS$^{ALL}$ high resolution and high mass accuracy analysis. Quantification was performed using an in-house library on MultiQuant™ software (SCIEX).

Mediator Lipidomic Profiling

A mixture of deuterium-labeled internal standards was added to aliquots of 100 µL serum, followed by 3× volume of sample of cold methanol (MeOH). Samples were vortexed for 5 minutes and stored at −20° C. overnight. Cold samples were centrifuged at 14,000 g at 4° C. for 10 minutes, and the supernatant was then transferred to a new tube and 3 mL of acidified $H_2O$ (pH 3.5) was added to each sample prior to C18 SPE and performed as previously described (Lynes Md., et al., *Nat Med* 2017, 23(5):631-637).

The methyl formate fractions were collected, dried under nitrogen, and reconstituted in 50 µL, MeOH:H2O (1:1, by volume). Samples were transferred to 0.5 mL tubes and centrifuged at 20,000 g at 4° C. for 10 minutes. Thirty-five microliters of supernatant was transferred to LC-MS vials for analysis using the BERG LC-MS/MS mediator lipidomics platform. Separation of signaling lipids was performed on an Ekspert MicroLC 200™ system (Eksigent Technologies) with a Synergi™ Fusion-RP capillary C18 column (150×0.5 mm, 4 µm; Phenomenex Inc., Torrance, Calif., USA) heated to 40° C. A sample volume of 11 µL, was injected at a flow rate of 20 µL/min. Lipids were separated using mobile phases A (100% H2O, 0.1% acetic acid) and B (100% MeOH, 0.1% acetic acid) with a gradient starting at 60% B for 0.5 minutes, steadily increasing to 80% B by 5 minutes, reaching 95% B by 9 minutes, holding for 1 minute, and then decreasing to 60% B by 12 minutes. MS analysis was performed on a SCIEX TripleTOF® 5600+ system using the MRMHR strategy consisting of a TOF MS experiment looped with multiple MS/MS experiments. MS spectra were acquired in high-resolution mode (>30,000) using a 100-ms accumulation time per spectrum. Full-scan MS/MS was acquired in high sensitivity mode, with an accumulation time optimized per cycle. Collision energy was set using rolling collision energy with a spread of 15V. The identity of a component was confirmed using PeakView® software (SCIEX), and quantification was performed using MultiQuant™ software (SCIEX).

Serum Proteomic Analysis

Sixty five µL of serum was delipidated using Lipisorb™ and then depleted using a Hu-14, 4.6×50 mm, Multiple Affinity Removal Column™ (Agilent Technologies) on an 1100/1200 Agilent LC system. Low abundant proteins were collected in 100% Agilent Buffer A at 0.125 mL/min from 4.9-7.3 min and high abundant proteins were eluted to waste with 100% Agilent Buffer B at 1 mL/min from 11.51-16 min. Delipidated and depleted serum protein concentration was then determined using a Coomassie Bradford Protein Assay Kit™ (Thermo Pierce). Proteins were reduced with 10 mM Tris(2-carboxyethyl) Phosphine (TCEP) for 30 minutes at 55° C. and alkylated with 18.75 mM iodoacetamide for 30 minutes at room temperature in the dark. Proteins were then precipitated overnight in acetone and pellets were reconstituted in 200 mM Tetraethylammonium bromide (TEAB) at 1 mg/mL and digested with trypsin at 1:40 (trypsin:protein) overnight at 37° C. Tryptic digests were then labeled with Tandem Mass Tag (TMT) 10-plex™ isobaric label reagent set (Thermo Pierce) at 1:1 (peptide:label) ratio for 1 hour at room temperature and quenched with 5% hydroxylamine for 15 minutes before being combined into each respective multi-plex (MP) and dried in a vacuum centrifuge. TMT-labeled MPs were then desalted using C-18 spin columns (Thermo Pierce), dried in a vacuum centrifuge, and stored at −20° C. until LCMS analysis.

LC-MS/MS analysis was performed using a Waters nano-Acquity 2D LC™ system coupled to a Thermo Q Exactive Plus™ MS. TMT-labeled MPs were resolved over 12 fractions, 90 minute gradient per fraction, and fractionated using two-dimensional reversed-phase chromatography prior to MS analysis. The column eluate was directly introduced into the mass spectrometer via a nano-ESI source and candidate ions were selected and fragmented using a data-dependent Top-15 acquisition method. Full MS survey scans were collected at a resolution of 35,000, scan range of 400-1800 Thompsons (Th; Th=Da/z). MS/MS scans were collected at a resolution of 35,000 with a 1.2 Th isolation window. In order for an ion to be considered a candidate for fragmentation it had to be assigned a charge in the range of +2 to +4.

Raw LC-MS/MS data was then processed using Proteome Discoverer v1.4™ (Thermo) by searching a decoy human SwissProt database using the following parameters for both MASCOT™ and Sequest™ search algorithms: tryptic peptides with at least 6 amino acids in length and up to two missed cleavage sites, precursor mass tolerance of 10 ppm, fragment mass tolerance of 0.02 Da, instrument type: ESI-FTICR, static modifications: cysteine carbamidomethylation, N-terminal TMT-10 plex, and dynamic modifications: asparagine and glutamine deamindation, and methionine oxidation, and lysine TMT-10 plex.

Analyte Ranking and Selection

A total of 2,205 analytes (lipids, metabolites and proteins) were analyzed by a differential expression analysis algorithm. Each analyte was standardized before analysis, which refers to the subtraction of each analyte-mean across samples and division by the respective standard deviation. Of the 2,205 analytes, 261 (11.8%) were removed for containing more than 50% of missing data within each experimental group. When applicable, metabolomics and lipidomics missing data was imputed by using a randomization procedure around the lowest detection range, and proteomics by values sampled within 2 standard deviations from the analyte mean. Univariate screening of analytes fold change was conducted on the non-imputed data using non-parametric permutation testing (Dwass M, *The Annals of Mathematical Statistics* 1957, 28(1):181-187). False discovery rate (FDR) (Benjamini Y H, Y., *Journal of the Royal Statistical Society Series B (Methodological)* 1995, 57(1): 289-300) was applied to adjust the analytes' p-values and two analytes passed the univariate screening given the controlled FDR cutoff at 0.05. Permutation based p-values are known for being overly stringent. In order to expand the search space, the top 55 ranked analytes were carried forward to a multivariable analysis on the imputed data, which allowed for the selection of variables that differentiate two groups as well as a stable selection-performance on the data with certain fluctuation. In this regard, linear regression modelling with elastic net (Zou H H, T., *Journal of the Royal Statistical Society Series B (Methodological)* 2005, 67(2): 301-320) and bootstrapping were applied. The implemented elastic net regularization (Friedman J, Hastie T, Tibshirani R, *J Stat Softw* 2010, 33(1):1-22) is composed of two parameters that weight between the LASSO/Ridge penalties and controls the amount of shrinkage. The mixed parameter was determined by a five-fold cross-validation on the error within one standard deviation of the minimum error, and the solution path by tuning the shrinkage parameter from stringent to liberal. Given the solution paths from bootstrapping 200 times, the analytes were ranked by the averaged selection rate at each given size of selected variables, where a single selection rate is calculated as the percentage of selection among the number of bootstrapped sampling (e.g., if one analyte was identified as the top biomarker among half of 200 bootstrapping and ranks the second top for another 50 bootstrapping, its selection rate was 50% and 75% at the size cutoff of one and two respectively, and its averaged selection rate at the size cutoff of two was (50%+75%)/2=62.5%). Therefore, the best analyte had the highest selection rate when one analyte was selected as a biomarker, and the second analyte had the highest averaged selection rate among the remaining analytes given a size of two, and so forth, up to all of the analytes processed in the multivariable analysis. Based on the analytes rank and the selection rate at each size, hierarchical clustering grouped analytes with similar selection performance, and top-ranked clusters were considered for further analysis.

Random Forest Model and ROC Analysis

An ensemble learning method, random forest, was used to predict clinical outcome using the panel of omics features. The number of trees used in ensemble model was tuned. The importance of each feature was assessed by mean decrease accuracy in prediction without the feature. Features were added into the model stepwise based on feature importance and the performance of each model was evaluated by AUC (area under curve) of ROC (Receiver Operating Characteristics) curve. The final model was selected by the best AUC and the least omics feature using an elastic regression approach. Analysis and visualization were done in R using random forest and ROCR libraries (Kuhn M. *Journal of Statistical Software* 2008, 28(5):1-26). Sensitivity was calculated as (Sensitivity=A/(A+C)); Specificity was calculated as Specificity=D/(B+D); Positive predictive value was calculated as PPV=(sensitivity*prevalence)/ ((sensitivity*prevalence)+((1−specificity)*(1−prevalence))); Negative predictive values as calculated as NPV= (specificity*(1−prevalence))/(((1−sensitivityrprevalence)+ ((specificity)*(1−prevalence))) where predicted/reference event=A, predicted event and reference no event=B, predicted no event/reference event=C, predicted no event/ reference no event=D.

Logistic regression (BCR versus no BCR) analysis was used to model each of the four key analytes, as well as patient pathological parameters, individually and then in multivariable binomial logistical regression model which were modeled in a continuous fashion and whose cut-off was defined by the first probable/threshold when sensitivity >0.8.

Odds ratios (OR) are reported for Logistic regression analyses, with corresponding 95% confidence intervals (CI) and p-values (summary alpha error=0.05, two-sided testing). The threshold of p<0.05 was used to define statistical significance. All statistical analyses were conducted using SAS version 9.4 (Cary, N.C.).

Statistical Analysis

Overall frequencies and distributions of demographic, clinical, and pathologic patient features were calculated for the overall study cohort.

Log base 2 fold change values (FIGS. 12A-12D) were created for each of the specific types of markers, for the 50 top analytes, with numerator representing "BCR" and denominator representing "no BCR". Volcano plots were then create to visualize the distribution of the full expression data of each. From the analytes selected from Volcano plot analysis, four metabolites and proteins showed a significant differential abundance for prognosis of prostate cancer (BCR versus no BCR event) (FIGS. 13A-13D). The four analytes chosen were tenascin C, apolipoprotein A-IV, 1-methyladenosine, and PA-18:0/22:0. Box and whisker plots were used to demonstrate the distribution of the four analytes across the patient cohorts, stratified on BCR status. P-values were calculated using LIMMA. The values were log transformed and centered and scaled based on 60% of the least variable analytes.

Results

Study Design for Serum Biomarker Discovery

Serum samples from a retrospective cohort of patients with prostate cancer that were longitudinally monitored were selected for this study. The framework included the following key study elements: (1) pre-surgery clinical context in which the serum markers were intended to be used; (2) specification of outcome (BCR-free survival versus BCR) and its measurement; (3) quantitative identification of multi-omics (proteomic, metabolic, and lipidomic) serum analytes; (4) combinatorial ranking of analytes with coded outcome data by elasticnet regression, as well as Bayesian network analyses to determine the optimal combination of analytes and clinical features.

The Center for Prostate Disease Research (CPDR) prostate cancer bio specimen bank and patient database with longitudinal follow-up data included high representation of African American patients in the equal access military healthcare system. The study cohort with follow-up information included a total of 385 patients. Demographic information were available for 360 patients (see Table 6). Patients' characteristics included PSA levels which were 4-9.9 ng/mL (63.5%) and ≥10 ng/mL (12.3%). Patients diagnosed with Biopsy Gleason Sum 6 (68.1%) and Pathologic Gleason Grade 7 (ISUP 2014), (57.2%), Clinical T Stage T1 (67%) and Pathologic Stage T2 (67.5%) were highly represented in the cohort. National Comprehensive Cancer Network (NCCN) risk stratum low (57.4%) and surgical margin status were positive in 19% of patients. Patient follow-up time was calculated as days elapsed between RP date and the last known medical visit and is presented in years. (see FIG. 11A, Table 6).

Figure 11B:
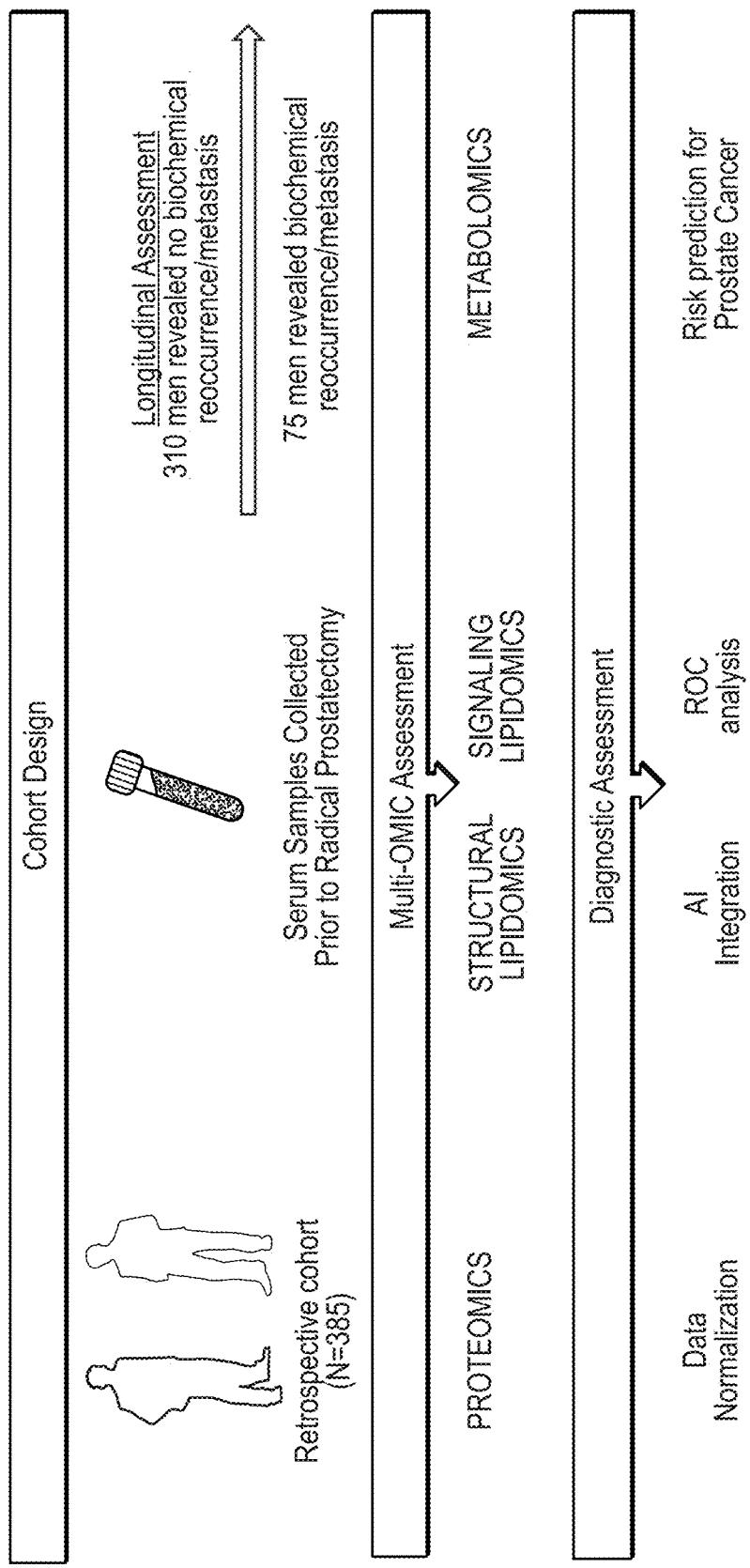
Figure 12A:
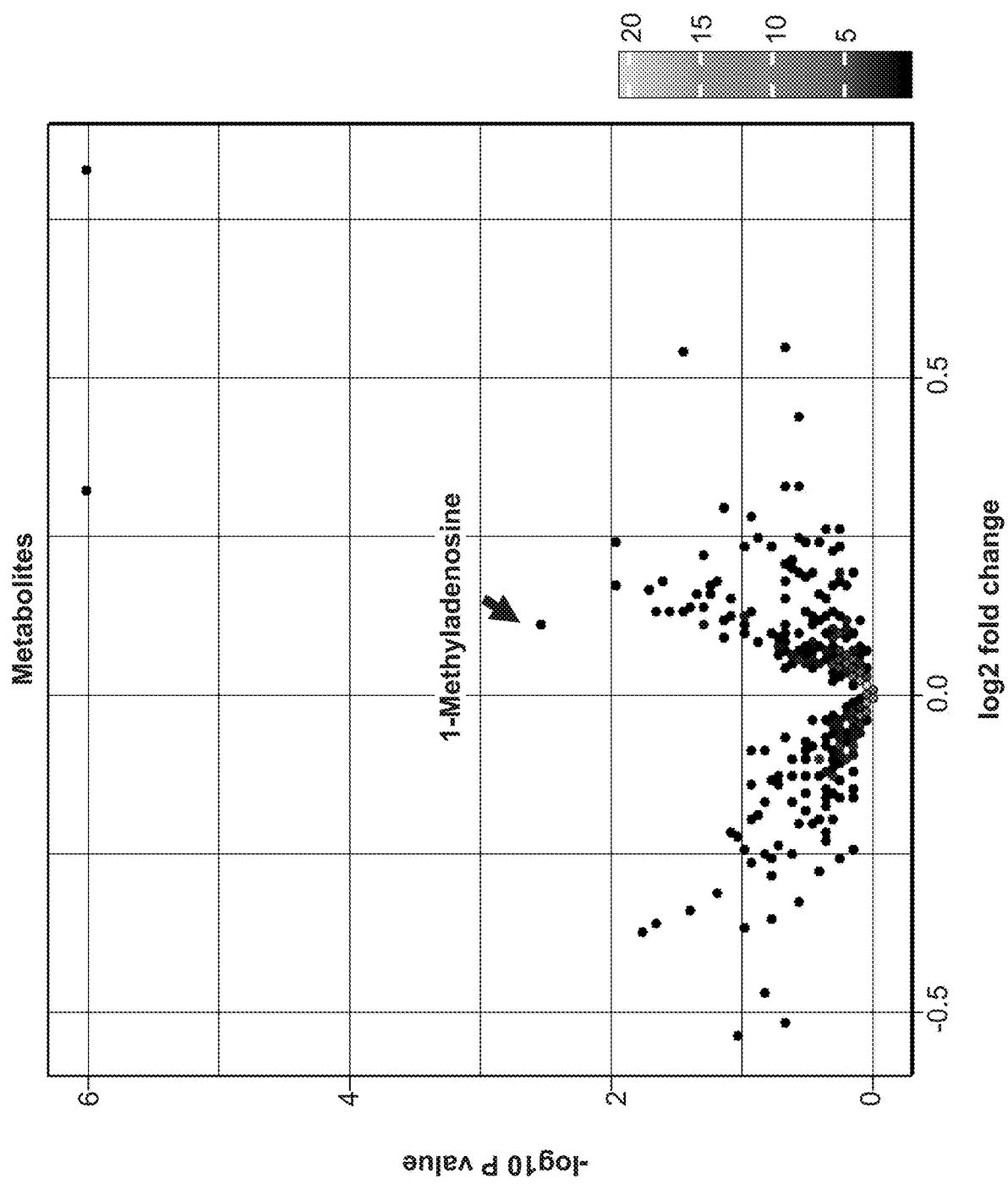
FIGS. 12A-12D are volcano plots representing the top analytes from serum samples of prostate cancer patients with BCR, when run through different platforms of mass spectrometry for metabolites (12A), proteins (12B), structural lipids (12C), and signaling lipids (12D). The X-axis represents the fold change of the analytes in log 2 scale; and the Y-axis represents the P-values in −log 10 scale. The bar to the right of the plots represent the number or analytes that had a fold-change and p-value in that range. For proteins: 13 had an unadjusted pvalue≤0.05. For metabolites: 17 had an unadjusted pvalue≤0.05. For signaling lipids: 2 had an unadjusted pvalue≤0.05. For structural lipids: 56 had an unadjusted pvalue≤0.05. The cut-off value at Y axis is 1.3, for significant analytes in each of the plots.
Figure 12B:
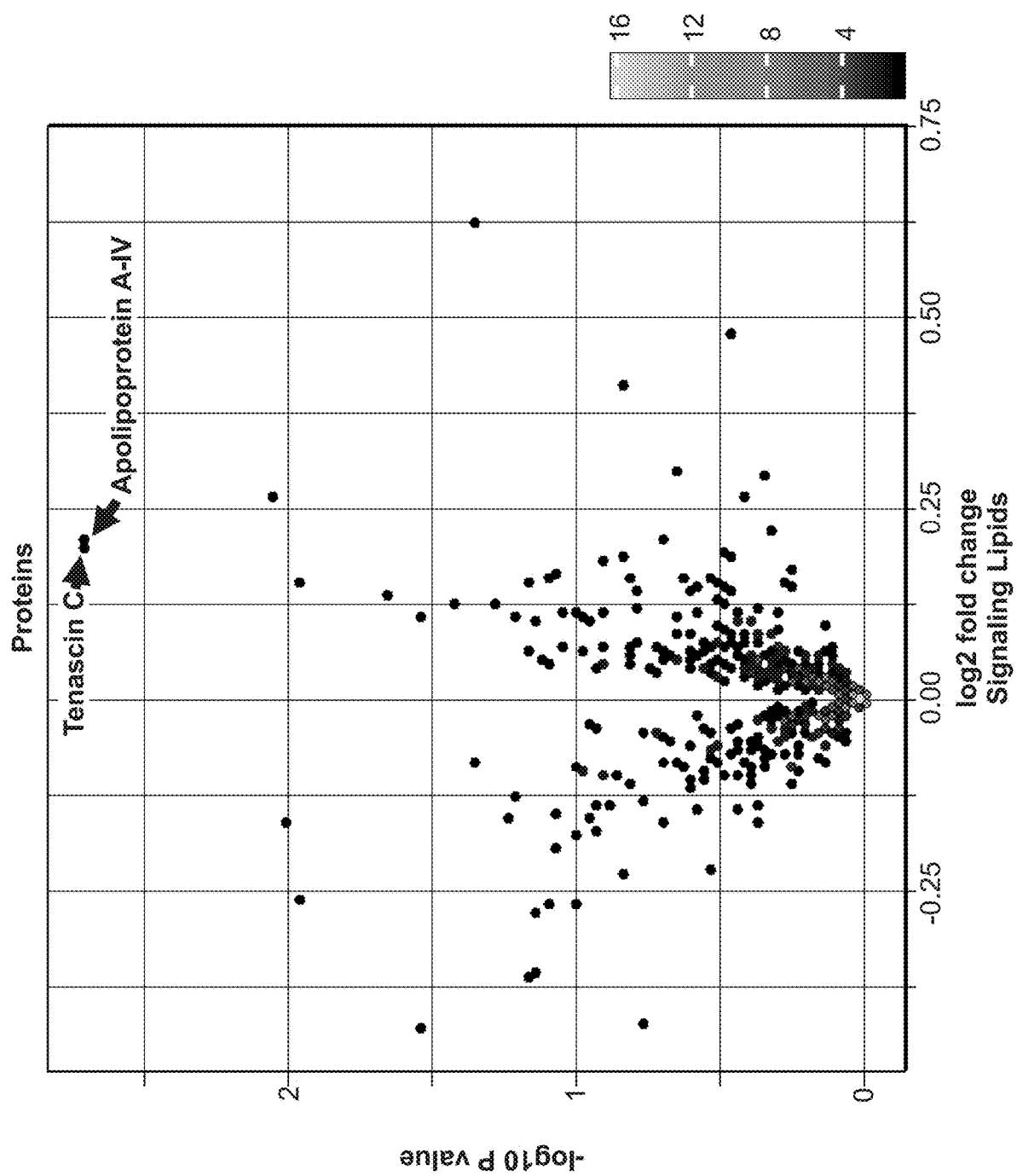
Figure 12C:
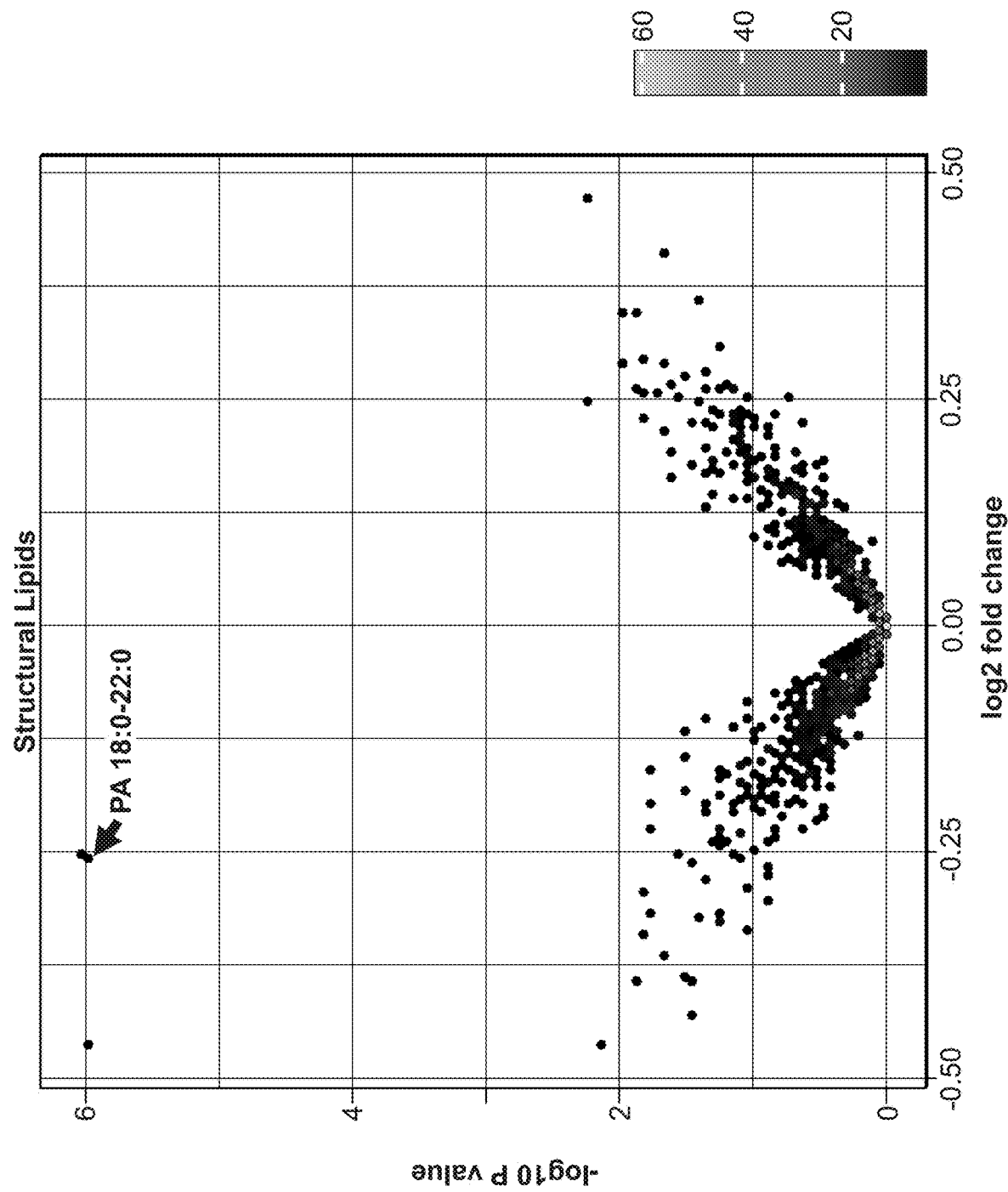
Figure 12D:
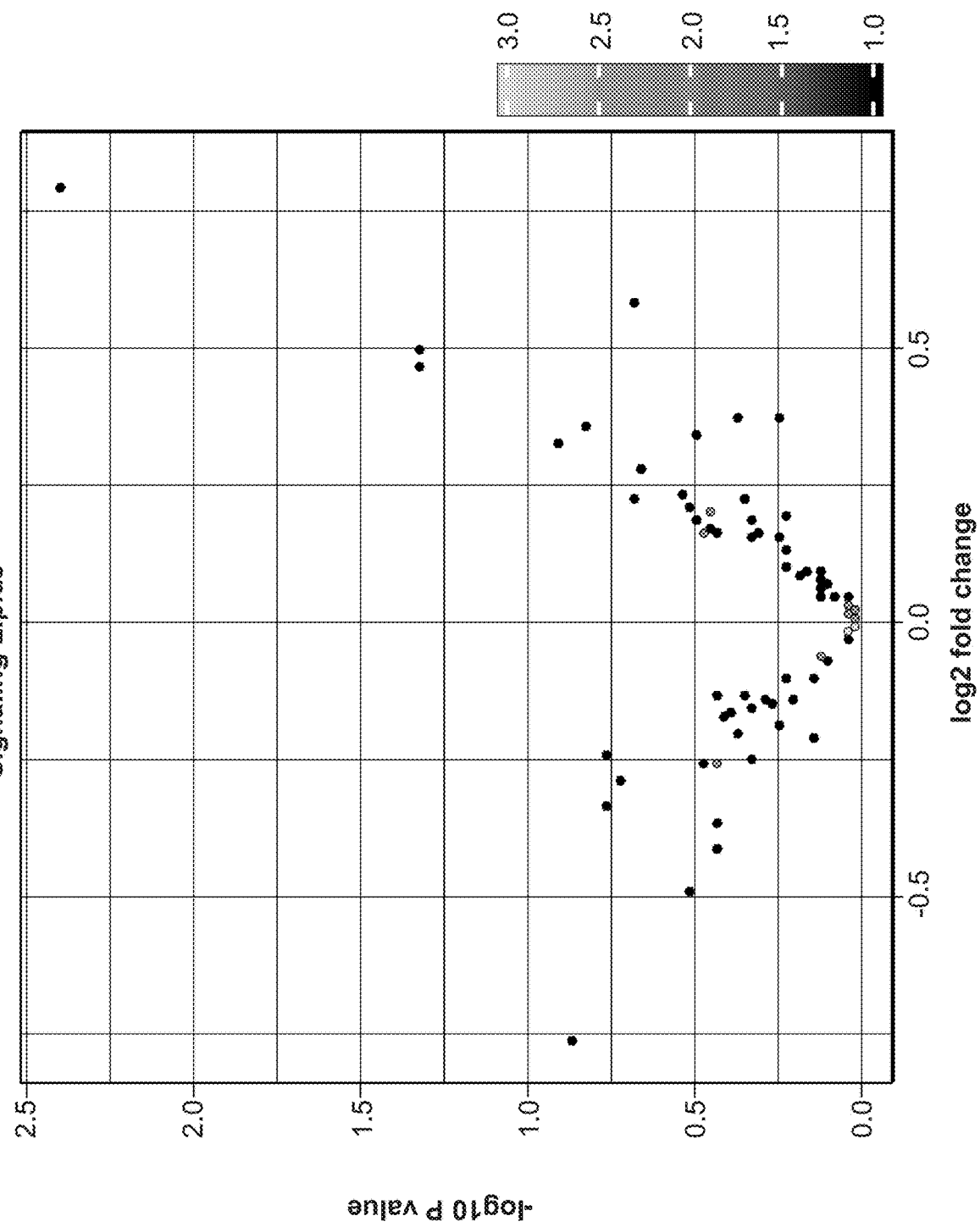

Blood samples were drawn immediately prior to RP, serum samples were processed and stored at −80° C. (FIG. 11B). Serum samples were thawed and analyzed by global proteomics, MS/MS$^{ALL}$ shotgun lipidomic, high resolution targeted MS/MS signaling lipidomics, targeted HILIC-Liquid chromatography mass spectrometry (LC-MS/MS), untargeted metabolomics reverse phase high resolution LC-MS, and volatile metabolite analysis using gas chromatography-time of flight-mass spectrometry (GC-TOF-MS) platforms. Data from individual platforms were streamed into BERG's Interrogative Biology® platform and Bayesian Network Inference (BNI) modules as well as statistical/ regression models and the prognostic risk of biochemical recurrence/metastasis were derived as described in FIG. 11B.

Multi-Omic Profiling of Serum Samples

Prospectively collected pre-surgical serum samples of patients with prostate cancer were assayed by multi-omics platforms for screening and selection of the best discriminators of disease progression vs. progression-free survival (PFS). Global analysis of the serum proteome, structural lipidome, signal lipidome and metabolome, using their respective platforms, identified analytes with differential abundance between PFS and disease progression and were assessed for predictive utility by evaluating those analytes which complemented each other (see FIGS. 12A-12D).

A panel of four analytes emerged based on their ability to discriminate between patients with BCR/non-BCR within longitudinal follow-up. The elastic net regression method was employed to identify the best performing panel that step-wise disqualifies analytes which do not provide any additional discriminatory power.

Figure 13A:
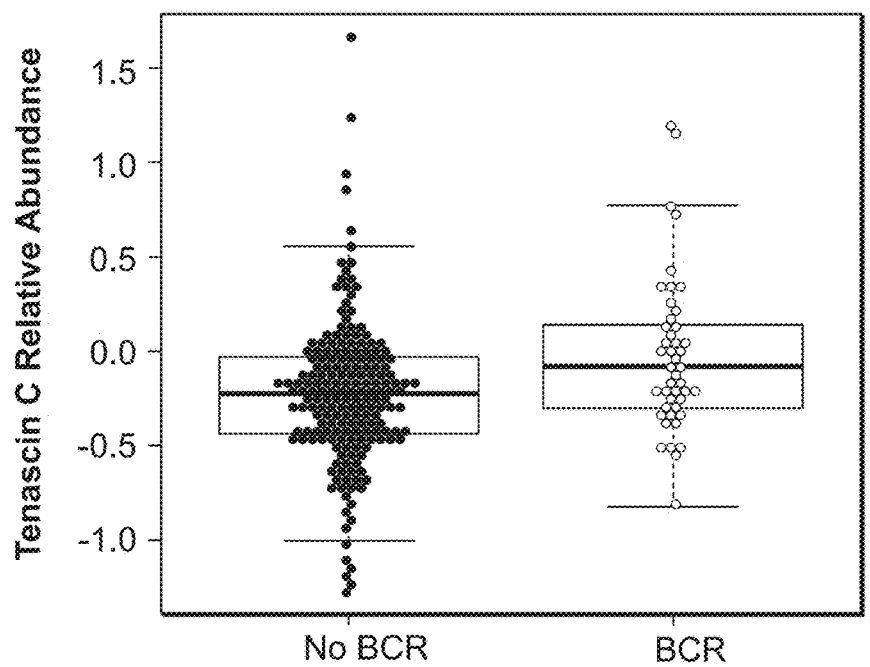
FIGS. 13A-13D are box plots representing specific metabolites and proteins individually with a significant differential abundance selected to form a combinatorial panel for diagnosis or prognosis of prostate cancer, the selected analytes being tenascin C (13A), 1-methyladenosine (13B), apolipoprotein A-IV (13C), and PA-18:0/22:0 (13D). The normalized abundance of the analytes are represented in boxplots. Each dot represents a patient measurement for the stated analyte.
Figure 13B:
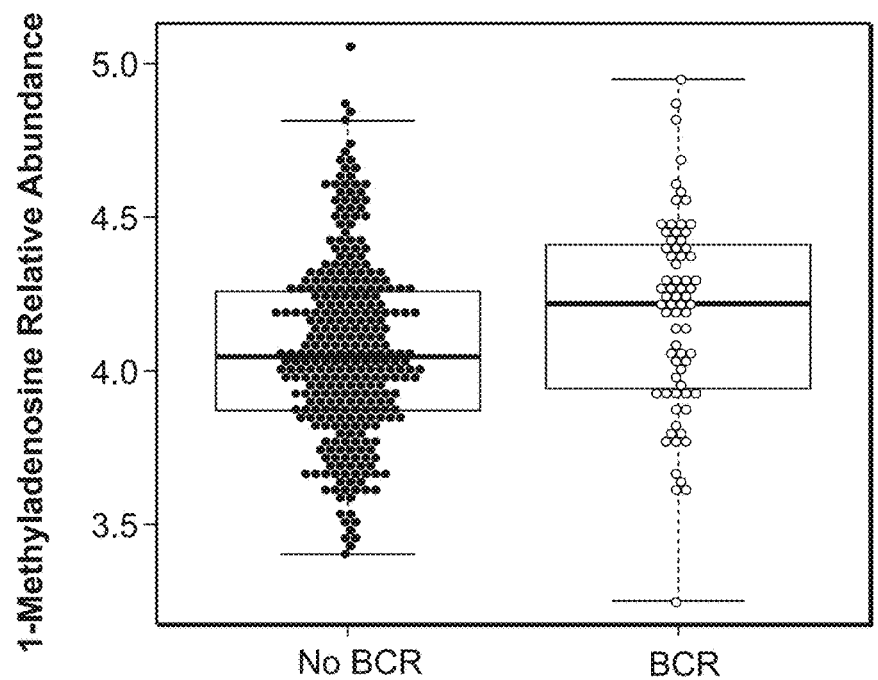
Figure 13C:
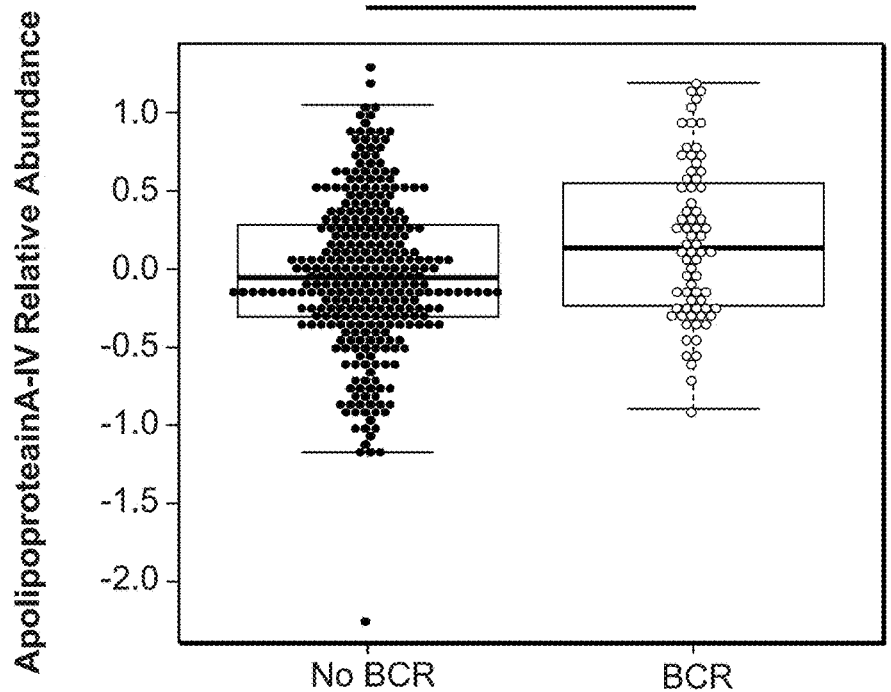
Figure 13D:
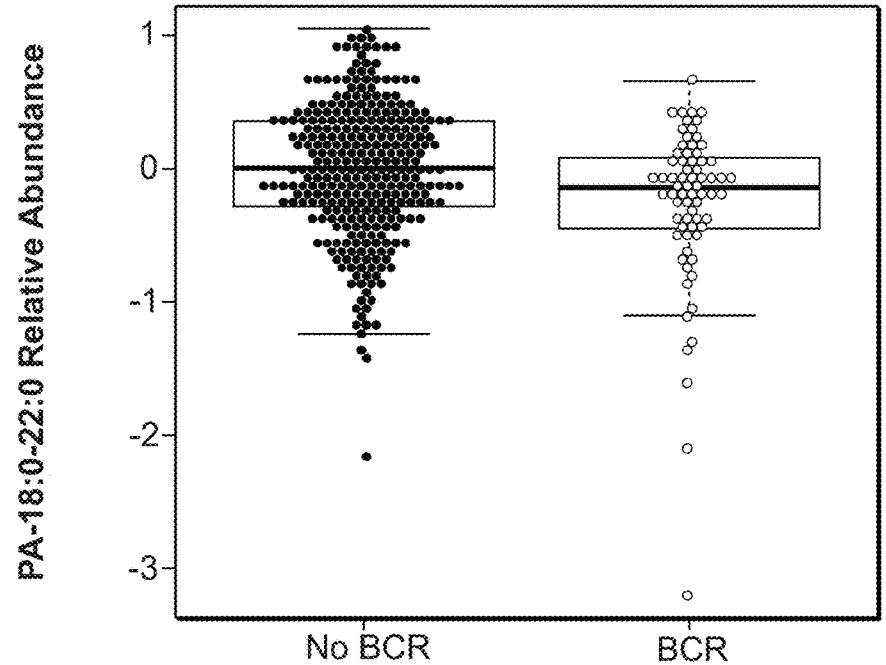

Data for each analyte was recorded as log transformed measurements across OMIC datasets for comparison. The analysis identified four analytes: increases in tenascin C (TNC) protein [AUC=0.60; OR=1.43] (FIG. 13A), 1-methyladenosine metabolite [AUC=0.62; OR=1.82] (FIG. 13B), and apolipoprotein A-IV (A-IV) protein [AUC=0.63; OR=2.58] (FIG. 13C) and a decrease in phosphatidic acid 18:0/22:0 structural lipid [AUC=0.62; OR=2.56] (FIG. 13D).

Table 7, below, summarizes results illustrating the sensitivity and specificity derived from ROC analysis of the four serum analytes, alone and in combination, as well as the combination of the four serum analytes and two clinical parameters.

over, cumulative performance of the panel significantly improved when combined with Gleason score and tumor stage (AUC=0.89).

TABLE 7

Sensitivity and Specificity Derived from ROC Analysis from Combinations of Clinical Parameters and Serum Components

| Model | Cut off | AUC | Sensitivity | Specificity | PPV | NPV | OR (CI) | p-value |
|---|---|---|---|---|---|---|---|---|
| PA-18:0-22:0 | 0.15 | 0.62 | 0.81 | 0.39 | 0.23 | 0.90 | 2.56 (137, 4.80)* | 0.00123 |
| Tenascin C | 0.14 | 0.60 | 0.80 | 0.28 | 0.20 | 0.86 | 1.43 (0.77, 2.66) | 0.2612 |
| Apolipoprotein A-IV | 0.16 | 0.63 | 0.82 | 0.36 | 0.23 | 0.89 | 2.58 (1.14, 5.85) | 0.02047 |
| 1-METHYLADENOSINE | 0.15 | 0.62 | 0.80 | 0.31 | 0.21 | 0.87 | 1.82 (0.97, 3.42) | 0.06153 |
| PA-18:0-22:0 + Apolipoprotein A-IV + Tenascin + 1-METHYLADENOSINE | 0.15 | 0.78 | 0.82 | 0.62 | 0.34 | 0.94 | 6.56 (2.98, 14.40)* | 8.788e-08 |
| PATH_T_STAGE | -inf | 0.67 | 1 | 0 | 0.17 | 0 | 0.21 (0.004, 10.63) | 0.4347 |
| PATH_GLS_SUM | 0.07 | 0.69 | 1 | 0.02 | 0.17 | 1 | 2.68 (0.15, 48.21) | 0.2692 |
| PATH_T_STAGE + PATH_GLS_SUM + PA-18:0-22:0 + Apolipoprotein A-IV + Tenascin C + 1-METHYLADENOSINE | 0.11 | 0.89 | 0.82 | 0.73 | 0.36 | 0.96 | 12.47 (4.85, 32.05)* | 1.003e-09 |

Figure 14A:
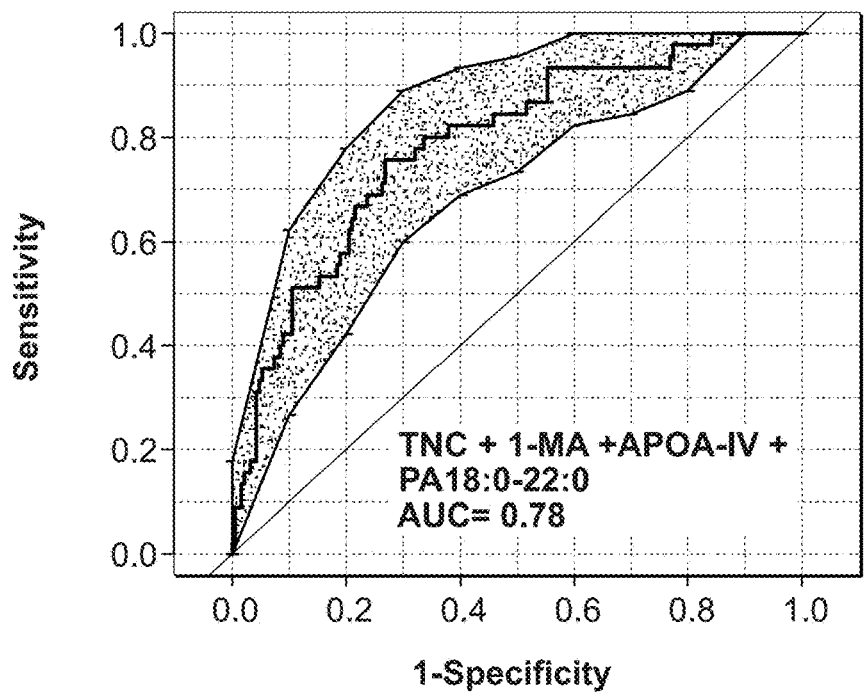
Figure 14B:
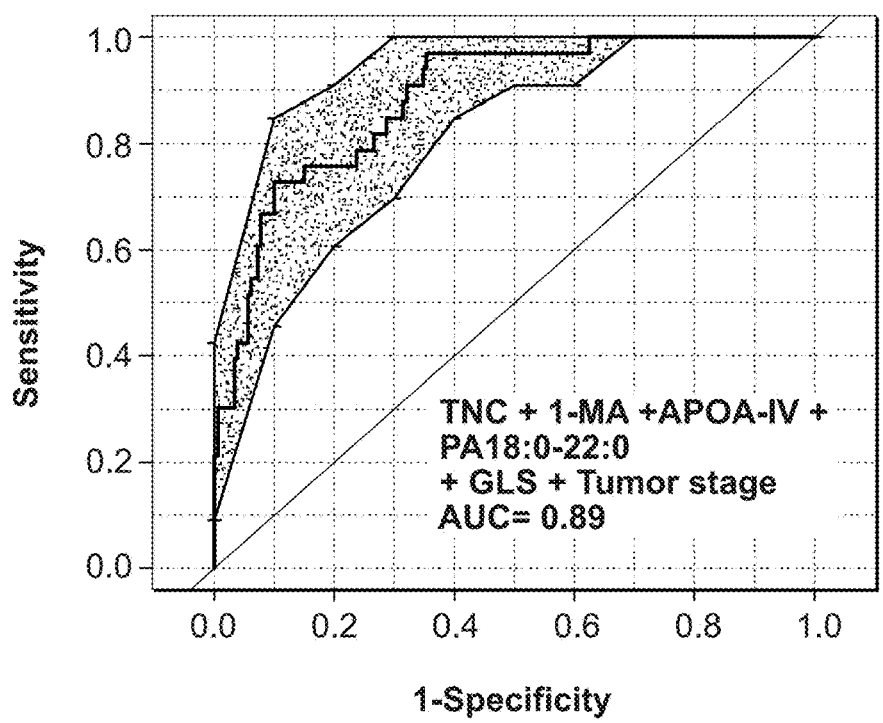

Combined Performance of the Four Analyte Panel is Enhanced by the Addition of Gleason Score and Tumor Stage Analysis of the four molecule panel yielded an AUC of 0.78 and an OR of 6.56 (p=8.7 e-08) in differentiating patients with PFS from those who had BCR (FIG. 14A). Current predictive models include molecular analytes and also, clinical, pathological and demographics features. To evaluate the relationship of clinical features with BCR, a Bayesian causal inference approach was employed to identify drivers of clinical outcome (Vemulapalli V, et al., *Artificial intelligence in medicine* 2016, 74:1-8). Bayesian inference identified two clinical variables, Tumor state (T-stage) and Gleason score, that were causally driving BCR from network analysis. Pathological T-stage alone provided an AUC of 0.67 and an OR of 0.21 (p—0.43) and Gleason score yielded an AUC of 0.69 and OR of 2.68 (p=0.27). Neither were statistically significant (see Table 7). However, combining these two clinical variables with the analyte panel resulted in a combined AUC of 0.89, PPV of 0.3, NPV of 0.96, and an OR of 12.47 (p=1.003 e-09), thus demonstrating a robust performance of the panel in combination with clinical pathological features (FIGS. 14A-14B and Table 7). Indeed, NPV above 0.9 will allow urologists to complement current approaches to identify patients at lower risk of recurrence or metastasis, who would be actively monitored by blood PSA test.

DISCUSSION

The focus of this study was to identify serum analytes and clinical features which can serve as indicators to predict disease progression in patients with prostate cancer prior to RP. Towards this goal, a panel of four serum analytes were identified that, in combination with clinical and pathological features, can serve as early indicators differentiating patients with BCR-free survival from prostate cancer patients with high risk of BCR. The performance of tenascin C, apolipoprotein A-IV, 1-methyladenosine or PA18:0/22:0 individually had AUC range of 0.60-0.63 for differentiating patients with disease progression from those who did not progress. However, it was found that together these analytes in the panel were synergistic in the cumulative performance in predicting cancer progression over time (AUC=0.78). More- To date, there have been numerous biomarker panels that have been identified for early prognosis of prostate cancer. However, all have some limitations to reach extensive use in clinical practices. The serum PSA test still remains as the gold standard for monitoring patients of BCR who have undergone primary treatment. However, there remains a critical unmet need for biomarkers as a tool for early risk stratification of patients undergoing primary treatment. In this regard, a blood-based assay that is more accurate, economical, and can be performed through standard clinical procedures could be a major advance in clinical management. The strength of the four serum analyte panel is the robust performance in predicting BCR-free survival (NPV).

The complementary nature of the analytes when combined in a panel is unanticipated. A unique feature of this study was to engage multiomic discovery in diverse populations encompassing African American and Caucasian American patients. Taken together, the serum-based, four analyte marker panel defined in this study is useful in prognosing PFS and provides new strategies to complement early stages of disease management which represent the majority of prostate cancer patients in the U.S.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

It is understood that the detailed examples and embodiments described herein are given by way of example for illustrative purposes only, and are in no way considered to be limiting to the invention. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present invention will be apparent from the appended claims. Moreover, those skilled in the art will recognize, or be able to ascertain using no more than routine experimentation, many equivalents to the specific embodiments of the invention described herein. Such equivalents are intended to be encompassed by the following claims.

REFERENCES

1. Siegel R L, Miller K D, Jemal A: Cancer Statistics, 2017. *CA: a cancer journal for clinicians* 2017, 67(1):7-30.
2. Cooperberg M R, Davicioni E, Crisan A, Jenkins R B, Ghadessi M, Karnes R J: Combined value of validated clinical and genomic risk stratification tools for predicting prostate cancer mortality in a high-risk prostatectomy cohort. *European urology* 2015, 67(2):326-333.
3. Cooperberg M R, Simko J P, Cowan J E, Reid J E, Djalilvand A, Bhatnagar S, Gutin A, Lanchbury J S, Swanson G P, Stone S et al: Validation of a cell-cycle progression gene panel to improve risk stratification in a contemporary prostatectomy cohort. *Journal of clinical oncology: official journal of the American Society of Clinical Oncology* 2013, 31(11):1428-1434.
4. Cullen J, Rosner I L, Brand T C, Zhang N, Tsiatis A C, Moncur J, Ali A, Chen Y, Knezevic D, Maddala T et al: A Biopsy-based 17-gene Genomic Prostate Score Predicts Recurrence After Radical Prostatectomy and Adverse Surgical Pathology in a Racially Diverse Population of Men with Clinically Low- and Intermediate-risk Prostate Cancer. *European urology* 2015, 68(1):123-131.
5. Klein E A, Cooperberg M R, Magi-Galluzzi C, Simko J P, Falzarano S M, Maddala T, Chan J M, Li J, Cowan J E, Tsiatis A C et al: A 17-gene assay to predict prostate cancer aggressiveness in the context of Gleason grade heterogeneity, tumor multifocality, and biopsy undersampling. *European urology* 2014, 66(3):550-560.
6. Knezevic D, Goddard A D, Natraj N, Cherbavaz D B, Clark-Langone K M, Snable J, Watson D, Falzarano S M, Magi-Galluzzi C, Klein E A et al: Analytical validation of the Oncotype DX prostate cancer assay—a clinical RT-PCR assay optimized for prostate needle biopsies. *BMC genomics* 2013, 14:690.
7. Loeb S, Partin A W: Review of the literature: PCA3 for prostate cancer risk assessment and prognostication. *Reviews in urology* 2011, 13(4):e191-195.
8. Parekh D J, Punnen S, Sjoberg D D, Asroff S W, Bailen J L, Cochran J S, Concepcion R, David R D, Deck K B, Dumbadze I et al: A multi-institutional prospective trial in the USA confirms that the 4Kscore accurately identifies men with high-grade prostate cancer. *European urology* 2015, 68(3):464-470.
9. Tomlins S A, Day J R, Lonigro R J, Hovelson D H, Siddiqui J, Kunju L P, Dunn R L, Meyer S, Hodge P, Groskopf J et al: Urine TMPRSS2:ERG Plus PCA3 for Individualized Prostate Cancer Risk Assessment. *European urology* 2016, 70(1):45-53.
10. Van Neste L, Hendriks R J, Dijkstra S, Trooskens G, Cornel E B, Jannink S A, de Jong H, Hessels D, Smit F P, Melchers W J et al: Detection of High-grade Prostate Cancer Using a Urinary Molecular Biomarker-Based Risk Score. *European urology* 2016, 70(5):740-748.
11. Catalona W J, Smith D S, Ratliff T L, Dodds K M, Coplen D E, Yuan J J, Petros J A, Andriole G L: Measurement of prostate-specific antigen in serum as a screening test for prostate cancer. *The New England journal of medicine* 1991, 324(17):1156-1161.
12. Catalona W J, Partin A W, Sanda M G, Wei J T, Klee G G, Bangma C H, Slawin K M, Marks L S, Loeb S, Broyles D L et al: A multicenter study of [-2]pro-prostate specific antigen combined with prostate specific antigen and free prostate specific antigen for prostate cancer detection in the 2.0 to 10.0 ng/ml prostate specific antigen range. *The Journal of urology* 2011, 185(5):1650-1655.
13. Carlsson S, Maschino A, Schroder F, Bangma C, Steyerberg E W, van der Kwast T, van Leenders G, Vickers A, Lilja H, Roobol M J: Predictive value of four kallikrein markers for pathologically insignificant compared with aggressive prostate cancer in radical prostatectomy specimens: results from the European Randomized Study of Screening for Prostate Cancer section Rotterdam. *European urology* 2013, 64(5):693-699.
14. de Bono J S, Scher H I, Montgomery R B, Parker C, Miller M C, Tissing H, Doyle G V, Terstappen L W, Pienta K J, Raghavan D: Circulating tumor cells predict survival benefit from treatment in metastatic castration-resistant prostate cancer. *Clinical cancer research: an official journal of the American Association for Cancer Research* 2008, 14(19):6302-6309.
15. Cohen J D, Javed A A, Thoburn C, Wong F, Tie J, Gibbs P, Schmidt C M, Yip-Schneider M T, Allen P J, Schattner M et al: Combined circulating tumor DNA and protein biomarker-based liquid biopsy for the earlier detection of pancreatic cancers. *Proc Natl Acad Sci USA* 2017, 114(38):10202-10207.
16. Cohen J D, Li L, Wang Y, Thoburn C, Afsari B, Danilova L, Douville C, Javed A A, Wong F, Mattox A et al: Detection and localization of surgically resectable cancers with a multi-analyte blood test. *Science* 2018, 359(6378): 926-930.
17. Vemulapalli V, Qu J, Garren J M, Rodrigues L O, Kiebish M A, Sarangarajan R, Narain N R, Akmaev V R: Non-obvious correlations to disease management unraveled by Bayesian artificial intelligence analyses of CMS data. *Artificial intelligence in medicine* 2016, 74:1-8.
18. Chang H, Wei J W, Chen K, Zhang S, Han F, Lu L X, Xiao W W, Gao Y H: apolipoprotein A-I Is a Prognosticator of Nasopharyngeal Carcinoma in the Era of Intensity-modulated Radiotherapy. *Journal of Cancer* 2018, 9(4):702-710.
19. Gebauer F, Gelis S, Zander H, Meyer K F, Wolters-Eisfeld G, Izbicki J R, Bockhorn M, Tachezy M: tenascin-C serum levels and its prognostic power in non-small cell lung cancer. *Oncotarget* 2016, 7(15):20945-20952.
20. Kim Y S, Gu B H, Choi B C, Kim M S, Song S, Yun J H, Chung M K, Choi C H, Baek K H: apolipoprotein A-IV as a novel gene associated with polycystic ovary syndrome. *International journal of molecular medicine* 2013, 31(3):707-716.
21. Seidel A, Brunner S, Seidel P, Fritz G I, Herbarth O: Modified nucleosides: an accurate tumour marker for clinical diagnosis of cancer, early detection and therapy control. *British journal of cancer* 2006, 94(11): 1726-1733.
22. Waalkes T P, Abeloff M D, Ettinger D S, Woo K B, Gehrke C W, Kuo K C, Borek E: Biological markers and small cell carcinoma of the lung: a clinical evaluation of urinary ribonucleosides. *Cancer* 1982, 50(11):2457-2464.
23. Yang Z T, Yeo S Y, Yin Y X, Lin Z H, Lee H M, Xuan Y H, Cui Y, Kim S H: tenascin-C, a Prognostic Determinant of Esophageal Squamous Cell Carcinoma. *PLoS One* 2016, 11(1):e0145807.
24. Oskarsson T, Acharyya S, Zhang X H, Vanharanta S, Tavazoie S F, Morris P G, Downey R J, Manova-Todorova K, Brogi E, Massague J: Breast cancer cells produce tenascin C as a metastatic niche component to colonize the lungs. *Nature medicine* 2011, 17(7):867-874.

25. Sung S Y, Hsieh C L, Law A, Zhau H E, Pathak S, Multani A S, Lim S, Coleman I M, Wu L C, Figg W D et al: Coevolution of prostate cancer and bone stroma in three-dimensional coculture: implications for cancer growth and metastasis. *Cancer Res* 2008, 68(23):9996-10003.
26. Miroshnikova Y A, Mouw J K, Barnes J M, Pickup M W, Lakins J N, Kim Y, Lobo K, Persson A I, Reis G F, McKnight T R et al: Tissue mechanics promote IDH1-dependent HIF1alpha-tenascin C feedback to regulate glioblastoma aggression. *Nature cell biology* 2016, 18(12):1336-1345.
27. Catalan V, Gomez-Ambrosi J, Rodriguez A, Ramirez B, Izaguirre M, Hernandez-Lizoain J L, Baixauli J, Marti P, Valenti V, Moncada R et al: Increased Obesity-Associated Circulating Levels of the Extracellular Matrix Proteins Osteopontin, Chitinase-3 Like-1 and tenascin C Are Associated with Colon Cancer. *PLoS One* 2016, 11(9): e0162189.
28. Li M, Peng F, Li G, Fu Y, Huang Y, Chen Z, Chen Y: Proteomic analysis of stromal proteins in different stages of colorectal cancer establishes tenascin-C as a stromal biomarker for colorectal cancer metastasis. *Oncotarget* 2016, 7(24):37226-37237.
29. Ni W D, Yang Z T, Cui C A, Cui Y, Fang L Y, Xuan Y H: tenascin-C is a potential cancer-associated fibroblasts marker and predicts poor prognosis in prostate cancer. *Biochemical and biophysical research communications* 2017, 486(3):607-612.
30. San Martin R, Pathak R, Jain A, Jung S Y, Hilsenbeck S G, Pina-Barba M C, Sikora A G, Pienta K J, Rowley D R: tenascin-C and Integrin alpha9 Mediate Interactions of Prostate Cancer with the Bone Microenvironment. *Cancer Res* 2017, 77(21):5977-5988.
31. Ma M Z, Yuan S Q, Chen Y M, Zhou Z W: Preoperative apolipoprotein B/apolipoprotein A1 ratio: a novel prognostic factor for gastric cancer. *OncoTargets and therapy* 2018, 11:2169-2176.
32. Su W P, Sun L N, Yang S L, Zhao H, Zeng T Y, Wu W Z, Wang D: apolipoprotein C1 promotes prostate cancer cell proliferation in vitro. *Journal of biochemical and molecular toxicology* 2018:e22158.
33. Zheng P, Luo Q, Wang W, Li J, Wang T, Wang P, Chen L, Zhang P, Chen H, Liu Y et al: Tumor-associated macrophages-derived exosomes promote the migration of gastric cancer cells by transfer of functional apolipoprotein E. *Cell death & disease* 2018, 9(4):434.
34. Timms J F, Arslan-Low E, Kabir M, Worthington J, Camuzeaux S, Sinclair J, Szaub J, Afrough B, Podust V N, Fourkala E O et al: Discovery of serum biomarkers of ovarian cancer using complementary proteomic profiling strategies. *Proteomics Clinical applications* 2014, 8(11-12):982-993.
35. Park J Y, Park J H, Jang W, Hwang I K, Kim I J, Kim H J, Cho K H, Lee S T: apolipoprotein A-IV is a novel substrate for matrix metalloproteinases. *Journal of biochemistry* 2012, 151(3):291-298.
36. Abulaizi M, Tomonaga T, Satoh M, Sogawa K, Matsushita K, Kodera Y, Obul J, Takano S, Yoshitomi H, Miyazaki M et al: The application of a three-step proteome analysis for identification of new biomarkers of pancreatic cancer. *International journal of proteomics* 2011, 2011:628787.
37. Jeong D H, Kim H K, Prince A E, Lee D S, Kim Y N, Han J, Kim K T: Plasma proteomic analysis of patients with squamous cell carcinoma of the uterine cervix. *Journal of gynecologic oncology* 2008, 19(3):173-180.
38. Karczmarski J, Rubel T, Mikula M, Wolski J, Rutkowski A, Zagorowicz E, Dadlez M, Ostrowski J: Pre-analytical-related variability influencing serum peptide profiles demonstrated in a mass spectrometry-based search for colorectal and prostate cancer biomarkers. *Acta biochimica Polonica* 2013, 60(3):417-425.
39. Okano T, Seike M, Kuribayashi H, Soeno C, Ishii T, Kida K, Gemma A: Identification of haptoglobin peptide as a novel serum biomarker for lung squamous cell carcinoma by serum proteome and peptidome profiling. *International journal of oncology* 2016, 48(3):945-952.
40. Sasco A J, Rey F, Reynaud C, Bobin J Y, Clavel M, Niveleau A: Breast cancer prognostic significance of some modified urinary nucleosides. *Cancer letters* 1996, 108(2):157-162.
41. Vreken P, Tavenier P: Urinary excretion of six modified nucleosides by patients with breast carcinoma. *Annals of clinical biochemistry* 1987, 24 (Pt 6):598-603.
42. Heldman D A, Greyer M R, Trewyn R W: Differential excretion of modified nucleosides in adult acute leukemia. *Blood* 1983, 61(2):291-296.
43. Itoh K, Konno T, Sasaki T, Ishiwata S, Ishida N, Misugaki M: Relationship of urinary pseudouridine and 1-methyladenosine to activity of leukemia and lymphoma. *Clinica chimica acta; international journal of clinical chemistry* 1992, 206(3):181-189.
44. Koshida K, Harmenberg J, Stendahl U, Wahren B, Borgstrom E, Helstrom L, Andersson L: Urinary modified nucleosides as tumor markers in cancer of the urinary organs or female genital tract. *Urological research* 1985, 13(5):213-218.
45. Hsu W Y, Chen C J, Huang Y C, Tsai F J, Jeng L B, Lai C C: Urinary nucleosides as biomarkers of breast, colon, lung, and gastric cancer in Taiwanese. *PLoS One* 2013, 8(12):e81701.
46. Dominissini D, Nachtergaele S, Moshitch-Moshkovitz S, Peer E, Kol N, Ben-Haim M S, Dai Q, Di Segni A, Salmon-Divon M, Clark W C et al: The dynamic N(1)-methyladenosine methylome in eukaryotic messenger RNA. *Nature* 2016, 530(7591):441-446.
47. Lynes M D, Leiria L O, Lundh M, Bartelt A, Shamsi F, Huang T L, Takahashi H, Hirshman M F, Schlein C, Lee A et al: The cold-induced lipokine 12,13-diHOME promotes fatty acid transport into brown adipose tissue. *Nat Med* 2017, 23(5):631-637.
48. Dwass M: Modified Randomization Tests for Nonparametric Hypotheses *The Annals of Mathematical Statistics* 1957, 28(1):181-187.
49. Benjamini Y H, Y.: Controlling the False Discovery Rate: A Practical and Powerful Approach to Multiple Testing. *Journal of the Royal Statistical Society Series B (Methodological)* 1995, 57(1):289-300.
50. Zou H H, T.: Regularization and Variable Selection via the Elastic *Net Journal of the Royal Statistical Society Series B (Methodological)* 2005, 67(2):301-320.
51. Friedman J, Hastie T, Tibshirani R: Regularization Paths for Generalized Linear Models via Coordinate Descent. *J Stat Softw* 2010, 33(1):1-22.
52. Kuhn M: Building Predictive Models in R Using the caret Package. *Journal of Statistical Software* 2008, 28(5):1-26.

We claim:

1. A method for treating biochemical recurrence (BCR) of prostate cancer in a subject, comprising:
   (a) detecting the level of at least one BCR marker in a biological sample from the subject, wherein the at least one BCR marker comprises phosphatidic acid-18: 0/22:0 and wherein the biological sample is selected from the group consisting of blood, serum and plasma;
   (b) comparing the detected level with a corresponding predetermined threshold value, wherein a lower detected level compared to the corresponding predetermined threshold value indicates a diagnosis that BCR is present in the subject; and
   (c) administering a therapeutic anti-cancer treatment to the subject diagnosed in step (b) as having BCR, wherein the anti-cancer treatment is selected from the group consisting of salvage radiation therapy, salvage prostatectomy, and androgen deprivation therapy.

2. The method of claim 1, further comprising detecting a level of one or more additional markers of BCR.

3. The method of claim 2, wherein the one or more additional markers of BCR comprise prostate specific antigen (PSA), tenascin C, apolipoprotein A-IV, 1-methyladenosine or a combination thereof.

4. The method of claim 1, further comprising before step (a) selecting a subject suspected of having or being at risk of having BCR.

5. The method of claim 1, further comprising before step (a) obtaining a biological sample from a subject suspected of having or being at risk of having BCR.

6. A method for monitoring biochemical recurrence (BCR) of prostate cancer in a subject, the method comprising:
   (a) detecting a first level of at least one BCR marker in a first biological sample obtained from the subject at a first time, wherein the at least one BCR marker comprises phosphatidic acid-18: 0/22:0;
   (b) detecting a second level of the at least one BCR marker in a second biological sample obtained from the subject at a second time, wherein the second time is later than the first time, and wherein the first and second biological sample are selected from the group consisting of blood, serum and plasma;
   (c) comparing the first level and the second level, wherein a lower second level compared to the first level indicates progression of BCR in the subject; and
   (d) administering a therapeutic anti-cancer treatment to the subject indicated in step (c) as having progression of BCR, wherein the anti-cancer treatment is selected from the group consisting of salvage radiation therapy, salvage prostatectomy, and androgen deprivation therapy.

7. The method of claim 6, wherein the subject is actively treated for prostate cancer prior to obtaining the second sample.

* * * * *

SEQUENCE LISTING

<160> NUMBER OF SEQ ID NOS: 23

<210> SEQ ID NO 1
<211> LENGTH: 2201
<212> TYPE: PRT
<213> ORGANISM: Homo sapiens

<400> SEQUENCE: 1

```
Met Gly Ala Met Thr Gln Leu Leu Ala Gly Val Phe Leu Ala Phe Leu
1               5                   10                  15

Ala Leu Ala Thr Glu Gly Gly Val Leu Lys Lys Val Ile Arg His Lys
                20                  25                  30

Arg Gln Ser Gly Val Asn Ala Thr Leu Pro Glu Glu Asn Gln Pro Val
            35                  40                  45

Val Phe Asn His Val Tyr Asn Ile Lys Leu Pro Val Gly Ser Gln Cys
        50                  55                  60

Ser Val Asp Leu Glu Ser Ala Ser Gly Glu Lys Asp Leu Ala Pro Pro
65                  70                  75                  80

Ser Glu Pro Ser Glu Ser Phe Gln Glu His Thr Val Asp Gly Glu Asn
                85                  90                  95

Gln Ile Val Phe Thr His Arg Ile Asn Ile Pro Arg Arg Ala Cys Gly
            100                 105                 110

Cys Ala Ala Ala Pro Asp Val Lys Glu Leu Leu Ser Arg Leu Glu Glu
        115                 120                 125

Leu Glu Asn Leu Val Ser Ser Leu Arg Glu Gln Cys Thr Ala Gly Ala
    130                 135                 140

Gly Cys Cys Leu Gln Pro Ala Thr Gly Arg Leu Asp Thr Arg Pro Phe
145                 150                 155                 160

Cys Ser Gly Arg Gly Asn Phe Ser Thr Glu Gly Cys Gly Cys Val Cys
                165                 170                 175

Glu Pro Gly Trp Lys Gly Pro Asn Cys Ser Glu Pro Ala Cys Pro Gly
            180                 185                 190

Asn Cys His Leu Arg Gly Arg Cys Ile Asp Gly Gln Cys Ile Cys Asp
        195                 200                 205

Asp Gly Phe Thr Gly Glu Asp Cys Ser Gln Leu Ala Cys Pro Ser Asp
    210                 215                 220

Cys Asn Asp Gln Gly Lys Cys Val Asn Gly Val Cys Ile Cys Phe Glu
225                 230                 235                 240

Gly Tyr Ala Gly Ala Asp Cys Ser Arg Glu Ile Cys Pro Val Pro Cys
                245                 250                 255

Ser Glu Glu His Gly Thr Cys Val Asp Gly Leu Cys Val Cys His Asp
            260                 265                 270

Gly Phe Ala Gly Asp Asp Cys Asn Lys Pro Leu Cys Leu Asn Asn Cys
        275                 280                 285

Tyr Asn Arg Gly Arg Cys Val Glu Asn Glu Cys Val Cys Asp Glu Gly
    290                 295                 300

Phe Thr Gly Glu Asp Cys Ser Glu Leu Ile Cys Pro Asn Asp Cys Phe
305                 310                 315                 320

Asp Arg Gly Arg Cys Ile Asn Gly Thr Cys Tyr Cys Glu Glu Gly Phe
                325                 330                 335

Thr Gly Glu Asp Cys Gly Lys Pro Thr Cys Pro His Ala Cys His Thr
            340                 345                 350

Gln Gly Arg Cys Glu Glu Gly Gln Cys Val Cys Asp Glu Gly Phe Ala
        355                 360                 365
```

-continued

```
Gly Val Asp Cys Ser Glu Lys Arg Cys Pro Ala Asp Cys His Asn Arg
    370                 375                 380
Gly Arg Cys Val Asp Gly Arg Cys Glu Cys Asp Asp Gly Phe Thr Gly
385                 390                 395                 400
Ala Asp Cys Gly Glu Leu Lys Cys Pro Asn Gly Cys Ser Gly His Gly
                    405                 410                 415
Arg Cys Val Asn Gly Gln Cys Val Cys Asp Glu Gly Tyr Thr Gly Glu
                420                 425                 430
Asp Cys Ser Gln Leu Arg Cys Pro Asn Asp Cys His Ser Arg Gly Arg
            435                 440                 445
Cys Val Glu Gly Lys Cys Val Cys Glu Gln Gly Phe Lys Gly Tyr Asp
450                 455                 460
Cys Ser Asp Met Ser Cys Pro Asn Asp Cys His Gln His Gly Arg Cys
465                 470                 475                 480
Val Asn Gly Met Cys Val Cys Asp Asp Gly Tyr Thr Gly Glu Asp Cys
                    485                 490                 495
Arg Asp Arg Gln Cys Pro Arg Asp Cys Ser Asn Arg Gly Leu Cys Val
                500                 505                 510
Asp Gly Gln Cys Val Cys Glu Asp Gly Phe Thr Gly Pro Asp Cys Ala
            515                 520                 525
Glu Leu Ser Cys Pro Asn Asp Cys His Gly Gln Gly Arg Cys Val Asn
        530                 535                 540
Gly Gln Cys Val Cys His Glu Gly Phe Met Gly Lys Asp Cys Lys Glu
545                 550                 555                 560
Gln Arg Cys Pro Ser Asp Cys His Gly Gln Gly Arg Cys Val Asp Gly
                    565                 570                 575
Gln Cys Ile Cys His Glu Gly Phe Thr Gly Leu Asp Cys Gly Gln His
                580                 585                 590
Ser Cys Pro Ser Asp Cys Asn Asn Leu Gly Gln Cys Val Ser Gly Arg
            595                 600                 605
Cys Ile Cys Asn Glu Gly Tyr Ser Gly Glu Asp Cys Ser Glu Val Ser
        610                 615                 620
Pro Pro Lys Asp Leu Val Val Thr Glu Val Thr Glu Thr Val Asn
625                 630                 635                 640
Leu Ala Trp Asp Asn Glu Met Arg Val Thr Glu Tyr Leu Val Val Tyr
                    645                 650                 655
Thr Pro Thr His Glu Gly Gly Leu Glu Met Gln Phe Arg Val Pro Gly
                660                 665                 670
Asp Gln Thr Ser Thr Ile Ile Gln Glu Leu Glu Pro Gly Val Glu Tyr
            675                 680                 685
Phe Ile Arg Val Phe Ala Ile Leu Glu Asn Lys Lys Ser Ile Pro Val
        690                 695                 700
Ser Ala Arg Val Ala Thr Tyr Leu Pro Ala Pro Glu Gly Leu Lys Phe
705                 710                 715                 720
Lys Ser Ile Lys Glu Thr Ser Val Glu Val Glu Trp Asp Pro Leu Asp
                    725                 730                 735
Ile Ala Phe Glu Thr Trp Glu Ile Ile Phe Arg Asn Met Asn Lys Glu
                740                 745                 750
Asp Glu Gly Glu Ile Thr Lys Ser Leu Arg Arg Pro Gly Thr Ser Tyr
            755                 760                 765
Arg Gln Thr Gly Leu Ala Pro Gly Gln Glu Tyr Glu Ile Ser Leu His
        770                 775                 780
Ile Val Lys Asn Asn Thr Arg Gly Pro Gly Leu Lys Arg Val Thr Thr
```

-continued

```
            785                 790                 795                 800
        Thr Arg Leu Asp Ala Pro Ser Gln Ile Glu Val Lys Asp Val Thr Asp
                        805                 810                 815
        Thr Thr Ala Leu Ile Thr Trp Phe Lys Pro Leu Ala Glu Ile Asp Gly
                        820                 825                 830
        Ile Glu Leu Thr Tyr Gly Ile Lys Asp Val Pro Gly Asp Arg Thr Thr
                        835                 840                 845
        Ile Asp Leu Thr Glu Asp Glu Asn Gln Tyr Ser Ile Gly Asn Leu Lys
                        850                 855                 860
        Pro Asp Thr Glu Tyr Glu Val Ser Leu Ile Ser Arg Arg Gly Asp Met
        865                 870                 875                 880
        Ser Ser Asn Pro Ala Lys Glu Thr Phe Thr Thr Gly Leu Asp Ala Pro
                        885                 890                 895
        Arg Asn Leu Arg Arg Val Ser Gln Thr Asp Asn Ser Ile Thr Leu Glu
                        900                 905                 910
        Trp Arg Asn Gly Lys Ala Ala Ile Asp Ser Tyr Arg Ile Lys Tyr Ala
                        915                 920                 925
        Pro Ile Ser Gly Gly Asp His Ala Glu Val Asp Val Pro Lys Ser Gln
                        930                 935                 940
        Gln Ala Thr Thr Lys Thr Thr Leu Thr Gly Leu Arg Pro Gly Thr Glu
        945                 950                 955                 960
        Tyr Gly Ile Gly Val Ser Ala Val Lys Glu Asp Lys Glu Ser Asn Pro
                        965                 970                 975
        Ala Thr Ile Asn Ala Ala Thr Glu Leu Asp Thr Pro Lys Asp Leu Gln
                        980                 985                 990
        Val Ser Glu Thr Ala Glu Thr Ser Leu Thr Leu Leu Trp Lys Thr Pro
                        995                 1000                1005
        Leu Ala Lys Phe Asp Arg Tyr Arg Leu Asn Tyr Ser Leu Pro Thr
                        1010                1015                1020
        Gly Gln Trp Val Gly Val Gln Leu Pro Arg Asn Thr Thr Ser Tyr
                        1025                1030                1035
        Val Leu Arg Gly Leu Glu Pro Gly Gln Glu Tyr Asn Val Leu Leu
                        1040                1045                1050
        Thr Ala Glu Lys Gly Arg His Lys Ser Lys Pro Ala Arg Val Lys
                        1055                1060                1065
        Ala Ser Thr Glu Gln Ala Pro Glu Leu Glu Asn Leu Thr Val Thr
                        1070                1075                1080
        Glu Val Gly Trp Asp Gly Leu Arg Leu Asn Trp Thr Ala Ala Asp
                        1085                1090                1095
        Gln Ala Tyr Glu His Phe Ile Ile Gln Val Gln Glu Ala Asn Lys
                        1100                1105                1110
        Val Glu Ala Ala Arg Asn Leu Thr Val Pro Gly Ser Leu Arg Ala
                        1115                1120                1125
        Val Asp Ile Pro Gly Leu Lys Ala Ala Thr Pro Tyr Thr Val Ser
                        1130                1135                1140
        Ile Tyr Gly Val Ile Gln Gly Tyr Arg Thr Pro Val Leu Ser Ala
                        1145                1150                1155
        Glu Ala Ser Thr Gly Glu Thr Pro Asn Leu Gly Glu Val Val Val
                        1160                1165                1170
        Ala Glu Val Gly Trp Asp Ala Leu Lys Leu Asn Trp Thr Ala Pro
                        1175                1180                1185
        Glu Gly Ala Tyr Glu Tyr Phe Phe Ile Gln Val Gln Glu Ala Asp
                        1190                1195                1200
```

```
Thr Val Glu Ala Ala Gln Asn Leu Thr Val Pro Gly Gly Leu Arg
1205                 1210                1215

Ser Thr Asp Leu Pro Gly Leu Lys Ala Ala Thr His Tyr Thr Ile
1220                 1225                1230

Thr Ile Arg Gly Val Thr Gln Asp Phe Ser Thr Thr Pro Leu Ser
1235                 1240                1245

Val Glu Val Leu Thr Glu Glu Val Pro Asp Met Gly Asn Leu Thr
1250                 1255                1260

Val Thr Glu Val Ser Trp Asp Ala Leu Arg Leu Asn Trp Thr Thr
1265                 1270                1275

Pro Asp Gly Thr Tyr Asp Gln Phe Thr Ile Gln Val Gln Glu Ala
1280                 1285                1290

Asp Gln Val Glu Glu Ala His Asn Leu Thr Val Pro Gly Ser Leu
1295                 1300                1305

Arg Ser Met Glu Ile Pro Gly Leu Arg Ala Gly Thr Pro Tyr Thr
1310                 1315                1320

Val Thr Leu His Gly Glu Val Arg Gly His Ser Thr Arg Pro Leu
1325                 1330                1335

Ala Val Glu Val Val Thr Glu Asp Leu Pro Gln Leu Gly Asp Leu
1340                 1345                1350

Ala Val Ser Glu Val Gly Trp Asp Gly Leu Arg Leu Asn Trp Thr
1355                 1360                1365

Ala Ala Asp Asn Ala Tyr Glu His Phe Val Ile Gln Val Gln Glu
1370                 1375                1380

Val Asn Lys Val Glu Ala Ala Gln Asn Leu Thr Leu Pro Gly Ser
1385                 1390                1395

Leu Arg Ala Val Asp Ile Pro Gly Leu Glu Ala Ala Thr Pro Tyr
1400                 1405                1410

Arg Val Ser Ile Tyr Gly Val Ile Arg Gly Tyr Arg Thr Pro Val
1415                 1420                1425

Leu Ser Ala Glu Ala Ser Thr Ala Lys Glu Pro Glu Ile Gly Asn
1430                 1435                1440

Leu Asn Val Ser Asp Ile Thr Pro Glu Ser Phe Asn Leu Ser Trp
1445                 1450                1455

Met Ala Thr Asp Gly Ile Phe Glu Thr Phe Thr Ile Glu Ile Ile
1460                 1465                1470

Asp Ser Asn Arg Leu Leu Glu Thr Val Glu Tyr Asn Ile Ser Gly
1475                 1480                1485

Ala Glu Arg Thr Ala His Ile Ser Gly Leu Pro Pro Ser Thr Asp
1490                 1495                1500

Phe Ile Val Tyr Leu Ser Gly Leu Ala Pro Ser Ile Arg Thr Lys
1505                 1510                1515

Thr Ile Ser Ala Thr Ala Thr Thr Glu Ala Leu Pro Leu Leu Glu
1520                 1525                1530

Asn Leu Thr Ile Ser Asp Ile Asn Pro Tyr Gly Phe Thr Val Ser
1535                 1540                1545

Trp Met Ala Ser Glu Asn Ala Phe Asp Ser Phe Leu Val Thr Val
1550                 1555                1560

Val Asp Ser Gly Lys Leu Leu Asp Pro Gln Glu Phe Thr Leu Ser
1565                 1570                1575

Gly Thr Gln Arg Lys Leu Glu Leu Arg Gly Leu Ile Thr Gly Ile
1580                 1585                1590
```

```
Gly Tyr Glu Val Met Val Ser Gly Phe Thr Gln Gly His Gln Thr
    1595                1600                1605

Lys Pro Leu Arg Ala Glu Ile Val Thr Glu Ala Glu Pro Glu Val
    1610                1615                1620

Asp Asn Leu Leu Val Ser Asp Ala Thr Pro Asp Gly Phe Arg Leu
    1625                1630                1635

Ser Trp Thr Ala Asp Glu Gly Val Phe Asp Asn Phe Val Leu Lys
    1640                1645                1650

Ile Arg Asp Thr Lys Lys Gln Ser Glu Pro Leu Glu Ile Thr Leu
    1655                1660                1665

Leu Ala Pro Glu Arg Thr Arg Asp Ile Thr Gly Leu Arg Glu Ala
    1670                1675                1680

Thr Glu Tyr Glu Ile Glu Leu Tyr Gly Ile Ser Lys Gly Arg Arg
    1685                1690                1695

Ser Gln Thr Val Ser Ala Ile Ala Thr Thr Ala Met Gly Ser Pro
    1700                1705                1710

Lys Glu Val Ile Phe Ser Asp Ile Thr Glu Asn Ser Ala Thr Val
    1715                1720                1725

Ser Trp Arg Ala Pro Thr Ala Gln Val Glu Ser Phe Arg Ile Thr
    1730                1735                1740

Tyr Val Pro Ile Thr Gly Gly Thr Pro Ser Met Val Thr Val Asp
    1745                1750                1755

Gly Thr Lys Thr Gln Thr Arg Leu Val Lys Leu Ile Pro Gly Val
    1760                1765                1770

Glu Tyr Leu Val Ser Ile Ile Ala Met Lys Gly Phe Glu Glu Ser
    1775                1780                1785

Glu Pro Val Ser Gly Ser Phe Thr Thr Ala Leu Asp Gly Pro Ser
    1790                1795                1800

Gly Leu Val Thr Ala Asn Ile Thr Asp Ser Glu Ala Leu Ala Arg
    1805                1810                1815

Trp Gln Pro Ala Ile Ala Thr Val Asp Ser Tyr Val Ile Ser Tyr
    1820                1825                1830

Thr Gly Glu Lys Val Pro Glu Ile Thr Arg Thr Val Ser Gly Asn
    1835                1840                1845

Thr Val Glu Tyr Ala Leu Thr Asp Leu Glu Pro Ala Thr Glu Tyr
    1850                1855                1860

Thr Leu Arg Ile Phe Ala Glu Lys Gly Pro Gln Lys Ser Ser Thr
    1865                1870                1875

Ile Thr Ala Lys Phe Thr Thr Asp Leu Asp Ser Pro Arg Asp Leu
    1880                1885                1890

Thr Ala Thr Glu Val Gln Ser Glu Thr Ala Leu Leu Thr Trp Arg
    1895                1900                1905

Pro Pro Arg Ala Ser Val Thr Gly Tyr Leu Leu Val Tyr Glu Ser
    1910                1915                1920

Val Asp Gly Thr Val Lys Glu Val Ile Val Gly Pro Asp Thr Thr
    1925                1930                1935

Ser Tyr Ser Leu Ala Asp Leu Ser Pro Ser Thr His Tyr Thr Ala
    1940                1945                1950

Lys Ile Gln Ala Leu Asn Gly Pro Leu Arg Ser Asn Met Ile Gln
    1955                1960                1965

Thr Ile Phe Thr Thr Ile Gly Leu Leu Tyr Pro Phe Pro Lys Asp
    1970                1975                1980

Cys Ser Gln Ala Met Leu Asn Gly Asp Thr Thr Ser Gly Leu Tyr
```

Thr Ile Tyr Leu Asn Gly Asp Lys Ala Glu Ala Leu Glu Val Phe
    1985                1990                1995
Cys Asp Met Thr Ser Asp Gly Gly Trp Ile Val Phe Leu Arg
    2000                2005                2010
Arg Lys Asn Gly Arg Glu Asn Phe Tyr Gln Asn Trp Lys Ala Tyr
    2015                2020                2025
Ala Ala Gly Phe Gly Asp Arg Arg Glu Glu Phe Trp Leu Gly Leu
    2030                2035                2040
Asp Asn Leu Asn Lys Ile Thr Ala Gln Gly Gln Tyr Glu Leu Arg
    2045                2050                2055
Val Asp Leu Arg Asp His Gly Glu Thr Ala Phe Ala Val Tyr Asp
    2060                2065                2070
Lys Phe Ser Val Gly Asp Ala Lys Thr Arg Tyr Lys Leu Lys Val
    2075                2080                2085
Glu Gly Tyr Ser Gly Thr Ala Gly Asp Ser Met Ala Tyr His Asn
    2090                2095                2100
Gly Arg Ser Phe Ser Thr Phe Asp Lys Asp Thr Asp Ser Ala Ile
    2105                2110                2115
Thr Asn Cys Ala Leu Ser Tyr Lys Gly Ala Phe Trp Tyr Arg Asn
    2120                2125                2130
Cys His Arg Val Asn Leu Met Gly Arg Tyr Gly Asp Asn Asn His
    2135                2140                2145
Ser Gln Gly Val Asn Trp Phe His Trp Lys Gly His Glu His Ser
    2150                2155                2160
Ile Gln Phe Ala Glu Met Lys Leu Arg Pro Ser Asn Phe Arg Asn
    2165                2170                2175
Leu Glu Gly Arg Arg Lys Arg Ala
    2180                2185                2190

<210> SEQ ID NO 2
<211> LENGTH: 396
<212> TYPE: PRT
<213> ORGANISM: Homo sapiens

<400> SEQUENCE: 2

Met Phe Leu Lys Ala Val Val Leu Thr Leu Ala Leu Val Ala Val Ala
1               5                   10                  15
Gly Ala Arg Ala Glu Val Ser Ala Asp Gln Val Ala Thr Val Met Trp
            20                  25                  30
Asp Tyr Phe Ser Gln Leu Ser Asn Asn Ala Lys Glu Ala Val Glu His
        35                  40                  45
Leu Gln Lys Ser Glu Leu Thr Gln Gln Leu Asn Ala Leu Phe Gln Asp
    50                  55                  60
Lys Leu Gly Glu Val Asn Thr Tyr Ala Gly Asp Leu Gln Lys Lys Leu
65                  70                  75                  80
Val Pro Phe Ala Thr Glu Leu His Glu Arg Leu Ala Lys Asp Ser Glu
                85                  90                  95
Lys Leu Lys Glu Glu Ile Gly Lys Glu Leu Glu Glu Leu Arg Ala Arg
            100                 105                 110
Leu Leu Pro His Ala Asn Glu Val Ser Gln Lys Ile Gly Asp Asn Leu
        115                 120                 125
Arg Glu Leu Gln Gln Arg Leu Glu Pro Tyr Ala Asp Gln Leu Arg Thr
    130                 135                 140

Gln Val Ser Thr Gln Ala Glu Gln Leu Arg Arg Gln Leu Thr Pro Tyr
145                 150                 155                 160

Ala Gln Arg Met Glu Arg Val Leu Arg Glu Asn Ala Asp Ser Leu Gln
            165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
            195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
            245                 250                 255

Ser Ala Ser Ala Glu Glu Leu Arg Gln Arg Leu Ala Pro Leu Ala Glu
            260                 265                 270

Asp Val Arg Gly Asn Leu Arg Gly Asn Thr Glu Gly Leu Gln Lys Ser
            275                 280                 285

Leu Ala Glu Leu Gly Gly His Leu Asp Gln Gln Val Glu Glu Phe Arg
290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
            325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
            355                 360                 365

Ser Leu Pro Glu Leu Glu Gln Gln Gln Glu Gln Gln Gln Glu Gln Gln
370                 375                 380

Gln Glu Gln Val Gln Met Leu Ala Pro Leu Glu Ser
385                 390                 395

<210> SEQ ID NO 3
<211> LENGTH: 372
<212> TYPE: PRT
<213> ORGANISM: Homo sapiens

<400> SEQUENCE: 3

Met Ala Arg Ala Met Ala Ala Trp Pro Leu Leu Leu Val Ala Leu Leu
1               5                   10                  15

Leu Val Leu Ser Trp Pro Pro Gly Thr Gly Asp Val Val Val Gln
                20                  25                  30

Ala Pro Thr Gln Val Pro Gly Phe Leu Gly Asp Ser Val Thr Leu Pro
            35                  40                  45

Cys Tyr Leu Gln Val Pro Asn Met Glu Val Thr His Val Ser Gln Leu
            50                  55                  60

Thr Trp Thr Arg His Gly Glu Ser Gly Ser Met Ala Val Phe His Gln
65                  70                  75                  80

Thr Gln Gly Pro Ser Tyr Ser Glu Ser Lys Arg Leu Glu Phe Val Ala
            85                  90                  95

Ala Arg Leu Gly Ala Glu Leu Arg Asn Ala Ser Leu Arg Met Phe Gly
            100                 105                 110

Leu Arg Val Glu Asp Glu Gly Asn Tyr Thr Cys Leu Phe Val Thr Phe
            115                 120                 125

Pro Gln Gly Ser Arg Ser Val Asp Ile Trp Leu Arg Val Leu Ala Lys
    130                 135                 140

Pro Gln Asn Thr Ala Glu Val Gln Lys Val Gln Leu Thr Gly Glu Pro
145                 150                 155                 160

Val Pro Met Ala Arg Cys Val Ser Thr Gly Arg Pro Pro Ala Gln
                165                 170                 175

Ile Thr Trp His Ser Asp Leu Gly Gly Met Pro Asn Thr Ser Gln Val
                180                 185                 190

Pro Gly Phe Leu Ser Gly Thr Val Thr Val Thr Ser Leu Trp Ile Leu
            195                 200                 205

Val Pro Ser Ser Gln Val Asp Gly Lys Asn Val Thr Cys Lys Val Glu
    210                 215                 220

His Glu Ser Phe Glu Lys Pro Gln Leu Leu Thr Val Asn Leu Thr Val
225                 230                 235                 240

Tyr Tyr Pro Pro Glu Val Ser Ile Ser Gly Tyr Asp Asn Asn Trp Tyr
                245                 250                 255

Leu Gly Gln Asn Glu Ala Thr Leu Thr Cys Asp Ala Arg Ser Asn Pro
            260                 265                 270

Glu Pro Thr Gly Tyr Asn Trp Ser Thr Thr Met Gly Pro Leu Pro Pro
            275                 280                 285

Phe Ala Val Ala Gln Gly Ala Gln Leu Leu Ile Arg Pro Val Asp Lys
    290                 295                 300

Pro Ile Asn Thr Thr Leu Ile Cys Asn Val Thr Asn Ala Leu Gly Ala
305                 310                 315                 320

Arg Gln Ala Glu Leu Thr Val Gln Val Lys Glu Gly Pro Pro Ser Glu
                325                 330                 335

His Ser Gly Thr Glu His Ala Ser Ala Ser Asn Gly His Val Ser
            340                 345                 350

Tyr Ser Ala Val Ser Arg Glu Asn Ser Ser Gln Asp Pro Gln Thr
    355                 360                 365

Glu Gly Thr Arg
    370

<210> SEQ ID NO 4
<211> LENGTH: 732
<212> TYPE: PRT
<213> ORGANISM: Homo sapiens

<400> SEQUENCE: 4

Met Ser Glu Thr Ser Arg Thr Ala Phe Gly Gly Arg Arg Ala Val Pro
1               5                   10                  15

Pro Asn Asn Ser Asn Ala Ala Glu Asp Asp Leu Pro Thr Val Glu Leu
            20                  25                  30

Gln Gly Val Val Pro Arg Gly Val Asn Leu Gln Glu Phe Leu Asn Val
        35                  40                  45

Thr Ser Val His Leu Phe Lys Glu Arg Trp Asp Thr Asn Lys Val Asp
    50                  55                  60

His His Thr Asp Lys Tyr Glu Asn Asn Lys Leu Ile Val Arg Arg Gly
65                  70                  75                  80

Gln Ser Phe Tyr Val Gln Ile Asp Phe Ser Arg Pro Tyr Asp Pro Arg
                85                  90                  95

Arg Asp Leu Phe Arg Val Glu Tyr Val Ile Gly Arg Tyr Pro Gln Glu
            100                 105                 110

Asn Lys Gly Thr Tyr Ile Pro Val Pro Ile Val Ser Glu Leu Gln Ser

```
              115                 120                 125
Gly Lys Trp Gly Ala Lys Ile Val Met Arg Glu Asp Arg Ser Val Arg
        130                 135                 140

Leu Ser Ile Gln Ser Ser Pro Lys Cys Ile Val Gly Lys Phe Arg Met
145                 150                 155                 160

Tyr Val Ala Val Trp Thr Pro Tyr Gly Val Leu Arg Thr Ser Arg Asn
                    165                 170                 175

Pro Glu Thr Asp Thr Tyr Ile Leu Phe Asn Pro Trp Cys Glu Asp Asp
                180                 185                 190

Ala Val Tyr Leu Asp Asn Glu Lys Glu Arg Glu Glu Tyr Val Leu Asn
            195                 200                 205

Asp Ile Gly Val Ile Phe Tyr Gly Glu Val Asn Asp Ile Lys Thr Arg
        210                 215                 220

Ser Trp Ser Tyr Gly Gln Phe Glu Asp Gly Ile Leu Asp Thr Cys Leu
225                 230                 235                 240

Tyr Val Met Asp Arg Ala Gln Met Asp Leu Ser Gly Arg Gly Asn Pro
                    245                 250                 255

Ile Lys Val Ser Arg Val Gly Ser Ala Met Val Asn Ala Lys Asp Asp
                260                 265                 270

Glu Gly Val Leu Val Gly Ser Trp Asp Asn Ile Tyr Ala Tyr Gly Val
            275                 280                 285

Pro Pro Ser Ala Trp Thr Gly Ser Val Asp Ile Leu Leu Glu Tyr Arg
        290                 295                 300

Ser Ser Glu Asn Pro Val Arg Tyr Gly Gln Cys Trp Val Phe Ala Gly
305                 310                 315                 320

Val Phe Asn Thr Phe Leu Arg Cys Leu Gly Ile Pro Ala Arg Ile Val
                    325                 330                 335

Thr Asn Tyr Phe Ser Ala His Asp Asn Asp Ala Asn Leu Gln Met Asp
                340                 345                 350

Ile Phe Leu Glu Glu Asp Gly Asn Val Asn Ser Lys Leu Thr Lys Asp
            355                 360                 365

Ser Val Trp Asn Tyr His Cys Trp Asn Glu Ala Trp Met Thr Arg Pro
        370                 375                 380

Asp Leu Pro Val Gly Phe Gly Gly Trp Gln Ala Val Asp Ser Thr Pro
385                 390                 395                 400

Gln Glu Asn Ser Asp Gly Met Tyr Arg Cys Gly Pro Ala Ser Val Gln
                    405                 410                 415

Ala Ile Lys His Gly His Val Cys Phe Gln Phe Asp Ala Pro Phe Val
                420                 425                 430

Phe Ala Glu Val Asn Ser Asp Leu Ile Tyr Ile Thr Ala Lys Lys Asp
            435                 440                 445

Gly Thr His Val Val Glu Asn Val Asp Ala Thr His Ile Gly Lys Leu
        450                 455                 460

Ile Val Thr Lys Gln Ile Gly Gly Asp Gly Met Met Asp Ile Thr Asp
465                 470                 475                 480

Thr Tyr Lys Phe Gln Glu Gly Gln Glu Glu Arg Leu Ala Leu Glu
                    485                 490                 495

Thr Ala Leu Met Tyr Gly Ala Lys Lys Pro Leu Asn Thr Glu Gly Val
                500                 505                 510

Met Lys Ser Arg Ser Asn Val Asp Met Asp Phe Glu Val Glu Asn Ala
            515                 520                 525

Val Leu Gly Lys Asp Phe Lys Leu Ser Ile Thr Phe Arg Asn Asn Ser
        530                 535                 540
```

```
His Asn Arg Tyr Thr Ile Thr Ala Tyr Leu Ser Ala Asn Ile Thr Phe
545                 550                 555                 560

Tyr Thr Gly Val Pro Lys Ala Glu Phe Lys Lys Glu Thr Phe Asp Val
                565                 570                 575

Thr Leu Glu Pro Leu Ser Phe Lys Lys Glu Ala Val Leu Ile Gln Ala
            580                 585                 590

Gly Glu Tyr Met Gly Gln Leu Leu Glu Gln Ala Ser Leu His Phe Phe
        595                 600                 605

Val Thr Ala Arg Ile Asn Glu Thr Arg Asp Val Leu Ala Lys Gln Lys
    610                 615                 620

Ser Thr Val Leu Thr Ile Pro Glu Ile Ile Lys Val Arg Gly Thr
625                 630                 635                 640

Gln Val Val Gly Ser Asp Met Thr Val Thr Val Glu Phe Thr Asn Pro
                645                 650                 655

Leu Lys Glu Thr Leu Arg Asn Val Trp Val His Leu Asp Gly Pro Gly
            660                 665                 670

Val Thr Arg Pro Met Lys Lys Met Phe Arg Glu Ile Arg Pro Asn Ser
        675                 680                 685

Thr Val Gln Trp Glu Val Cys Arg Pro Trp Val Ser Gly His Arg
    690                 695                 700

Lys Leu Ile Ala Ser Met Ser Ser Asp Ser Leu Arg His Val Tyr Gly
705                 710                 715                 720

Glu Leu Asp Val Gln Ile Gln Arg Arg Pro Ser Met
                725                 730

<210> SEQ ID NO 5
<211> LENGTH: 326
<212> TYPE: PRT
<213> ORGANISM: Homo sapiens

<400> SEQUENCE: 5

Met Thr Gly Leu Cys Gly Tyr Ser Ala Pro Asp Met Arg Gly Leu Arg
1               5                   10                  15

Leu Ile Met Ile Pro Val Glu Leu Leu Leu Cys Tyr Leu Leu Leu His
            20                  25                  30

Pro Val Asp Ala Thr Ser Tyr Gly Lys Gln Thr Asn Val Leu Met His
        35                  40                  45

Phe Pro Leu Ser Leu Glu Ser Gln Thr Pro Ser Ser Asp Pro Leu Ser
    50                  55                  60

Cys Gln Phe Leu His Pro Lys Ser Leu Pro Gly Phe Ser His Met Ala
65                  70                  75                  80

Pro Leu Pro Lys Phe Leu Val Ser Leu Ala Leu Arg Asn Ala Leu Glu
                85                  90                  95

Glu Ala Gly Cys Gln Ala Asp Val Trp Ala Leu Gln Leu Gln Leu Tyr
            100                 105                 110

Arg Gln Gly Gly Val Asn Ala Thr Gln Val Leu Ile Gln His Leu Arg
        115                 120                 125

Gly Leu Gln Lys Gly Arg Ser Thr Glu Arg Asn Val Ser Val Glu Ala
    130                 135                 140

Leu Ala Ser Ala Leu Gln Leu Leu Ala Arg Glu Gln Gln Ser Thr Gly
145                 150                 155                 160

Arg Val Gly Arg Ser Leu Pro Thr Glu Asp Cys Glu Asn Glu Lys Glu
                165                 170                 175

Gln Ala Val His Asn Val Val Gln Leu Leu Pro Gly Val Gly Thr Phe
```

```
                180               185               190
Tyr Asn Leu Gly Thr Ala Leu Tyr Tyr Ala Thr Gln Asn Cys Leu Gly
            195               200               205
Lys Ala Arg Glu Arg Gly Arg Asp Gly Ala Ile Asp Leu Gly Tyr Asp
            210               215               220
Leu Leu Met Thr Met Ala Gly Met Ser Gly Pro Met Gly Leu Ala
225               230               235               240
Ile Ser Ala Ala Leu Lys Pro Ala Leu Arg Ser Gly Val Gln Gln Leu
            245               250               255
Ile Gln Tyr Tyr Gln Asp Gln Lys Asp Ala Asn Ile Ser Gln Pro Glu
            260               265               270
Thr Thr Lys Glu Gly Leu Arg Ala Ile Ser Asp Val Ser Asp Leu Glu
            275               280               285
Glu Thr Thr Thr Leu Ala Ser Phe Ile Ser Glu Val Val Ser Ser Ala
            290               295               300
Pro Tyr Trp Gly Trp Ala Ile Ile Lys Ser Tyr Asp Leu Asp Pro Gly
305               310               315               320
Ala Gly Ser Leu Glu Ile
            325

<210> SEQ ID NO 6
<211> LENGTH: 870
<212> TYPE: PRT
<213> ORGANISM: Homo sapiens

<400> SEQUENCE: 6

Met Gly Arg Leu Asn Lys Ala Ile Leu Arg Tyr Leu Lys Asn Asp Gly
1               5                   10                  15
Lys Val His Leu Val Val Phe Asn Asn Leu Gln Leu Ala Asp Gly Arg
                20                  25                  30
Arg His Arg Ile Leu Leu Arg Leu Ser Asn Leu Gln Arg Gly Ala Gly
            35                  40                  45
Ser Leu Glu Leu Tyr Leu Asp Cys Ile Gln Val Asp Ser Val His Asn
    50                  55                  60
Leu Pro Arg Ala Phe Ala Gly Pro Ser Gln Lys Pro Glu Thr Ile Glu
65                  70                  75                  80
Leu Arg Thr Phe Gln Arg Lys Pro Gln Asp Phe Leu Glu Glu Leu Lys
                85                  90                  95
Leu Val Val Arg Gly Ser Leu Phe Gln Val Ala Ser Leu Gln Asp Cys
                100                 105                 110
Phe Leu Gln Gln Ser Glu Pro Leu Ala Ala Thr Gly Thr Gly Asp Phe
            115                 120                 125
Asn Arg Gln Phe Leu Gly Gln Met Thr Gln Leu Asn Gln Leu Leu Gly
        130                 135                 140
Glu Val Lys Asp Leu Leu Arg Gln Gln Val Lys Glu Thr Ser Phe Leu
145                 150                 155                 160
Arg Asn Thr Ile Ala Glu Cys Gln Ala Cys Gly Pro Leu Lys Phe Gln
                165                 170                 175
Ser Pro Thr Pro Ser Thr Val Val Pro Pro Ala Pro Ala Pro Pro
            180                 185                 190
Thr Arg Pro Pro Arg Arg Cys Asp Ser Asn Pro Cys Phe Arg Gly Val
        195                 200                 205
Gln Cys Thr Asp Ser Arg Asp Gly Phe Gln Cys Gly Pro Cys Pro Glu
    210                 215                 220
```

-continued

Gly Tyr Thr Gly Asn Gly Ile Thr Cys Ile Asp Val Asp Glu Cys Lys
225                 230                 235                 240

Tyr His Pro Cys Tyr Pro Gly Val His Cys Ile Asn Leu Ser Pro Gly
            245                 250                 255

Phe Arg Cys Asp Ala Cys Pro Val Gly Phe Thr Gly Pro Met Val Gln
        260                 265                 270

Gly Val Gly Ile Ser Phe Ala Lys Ser Asn Lys Gln Val Cys Thr Asp
    275                 280                 285

Ile Asp Glu Cys Arg Asn Gly Ala Cys Val Pro Asn Ser Ile Cys Val
290                 295                 300

Asn Thr Leu Gly Ser Tyr Arg Cys Gly Pro Cys Lys Pro Gly Tyr Thr
305                 310                 315                 320

Gly Asp Gln Ile Arg Gly Cys Lys Ala Glu Arg Asn Cys Arg Asn Pro
            325                 330                 335

Glu Leu Asn Pro Cys Ser Val Asn Ala Gln Cys Ile Glu Glu Arg Gln
        340                 345                 350

Gly Asp Val Thr Cys Val Cys Gly Val Gly Trp Ala Gly Asp Gly Tyr
    355                 360                 365

Ile Cys Gly Lys Asp Val Asp Ile Asp Ser Tyr Pro Asp Glu Glu Leu
370                 375                 380

Pro Cys Ser Ala Arg Asn Cys Lys Lys Asp Asn Cys Lys Tyr Val Pro
385                 390                 395                 400

Asn Ser Gly Gln Glu Asp Ala Asp Arg Asp Gly Ile Gly Asp Ala Cys
            405                 410                 415

Asp Glu Asp Ala Asp Gly Asp Gly Ile Leu Asn Glu Gln Asp Asn Cys
        420                 425                 430

Val Leu Ile His Asn Val Asp Gln Arg Asn Ser Asp Lys Asp Ile Phe
    435                 440                 445

Gly Asp Ala Cys Asp Asn Cys Leu Ser Val Leu Asn Asn Asp Gln Lys
450                 455                 460

Asp Thr Asp Gly Asp Gly Arg Gly Asp Ala Cys Asp Asp Asp Met Asp
465                 470                 475                 480

Gly Asp Gly Ile Lys Asn Ile Leu Asp Asn Cys Pro Lys Phe Pro Asn
            485                 490                 495

Arg Asp Gln Arg Asp Lys Asp Gly Asp Gly Val Gly Asp Ala Cys Asp
        500                 505                 510

Ser Cys Pro Asp Val Ser Asn Pro Asn Gln Ser Asp Val Asp Asn Asp
    515                 520                 525

Leu Val Gly Asp Ser Cys Asp Thr Asn Gln Asp Ser Asp Gly Asp Gly
530                 535                 540

His Gln Asp Ser Thr Asp Asn Cys Pro Thr Val Ile Asn Ser Ala Gln
545                 550                 555                 560

Leu Asp Thr Asp Lys Asp Gly Ile Gly Asp Glu Cys Asp Asp Asp Asp
            565                 570                 575

Asp Asn Asp Gly Ile Pro Asp Leu Val Pro Pro Gly Pro Asp Asn Cys
        580                 585                 590

Arg Leu Val Pro Asn Pro Ala Gln Glu Asp Ser Asn Ser Asp Gly Val
    595                 600                 605

Gly Asp Ile Cys Glu Ser Asp Phe Asp Gln Asp Gln Val Ile Asp Arg
610                 615                 620

Ile Asp Val Cys Pro Glu Asn Ala Glu Val Thr Leu Thr Asp Phe Arg
625                 630                 635                 640

Ala Tyr Gln Thr Val Val Leu Asp Pro Glu Gly Asp Ala Gln Ile Asp

```
                645                 650                 655
Pro Asn Trp Val Val Leu Asn Gln Gly Met Glu Ile Val Gln Thr Met
            660                 665                 670

Asn Ser Asp Pro Gly Leu Ala Val Gly Tyr Thr Ala Phe Asn Gly Val
            675                 680             685

Asp Phe Glu Gly Thr Phe His Val Asn Thr Gln Thr Asp Asp Asp Tyr
690                     695                 700

Ala Gly Phe Ile Phe Gly Tyr Gln Asp Ser Ser Ser Phe Tyr Val Val
705                 710                 715                 720

Met Trp Lys Gln Thr Glu Gln Thr Tyr Trp Gln Ala Thr Pro Phe Arg
                725                 730                 735

Ala Val Ala Glu Pro Gly Ile Gln Leu Lys Ala Val Lys Ser Lys Thr
                740                 745                 750

Gly Pro Gly Glu His Leu Arg Asn Ser Leu Trp His Thr Gly Asp Thr
                755                 760                 765

Ser Asp Gln Val Arg Leu Leu Trp Lys Asp Ser Arg Asn Val Gly Trp
770                 775                 780

Lys Asp Lys Val Ser Tyr Arg Trp Phe Leu Gln His Arg Pro Gln Val
785                 790                 795                 800

Gly Tyr Ile Arg Val Arg Phe Tyr Glu Gly Ser Glu Leu Val Ala Asp
                805                 810                 815

Ser Gly Val Thr Ile Asp Thr Thr Met Arg Gly Gly Arg Leu Gly Val
                820                 825                 830

Phe Cys Phe Ser Gln Glu Asn Ile Ile Trp Ser Asn Leu Lys Tyr Arg
                835                 840                 845

Cys Asn Asp Thr Ile Pro Glu Asp Phe Gln Glu Phe Gln Thr Gln Asn
850                 855                 860

Phe Asp Arg Phe Asp Asn
865                 870

<210> SEQ ID NO 7
<211> LENGTH: 220
<212> TYPE: PRT
<213> ORGANISM: Homo sapiens

<400> SEQUENCE: 7

Met Gly Ala Ala Arg Thr Leu Arg Leu Ala Leu Gly Leu Leu Leu Leu
1               5                   10                  15

Leu Ala Thr Leu Leu Arg Pro Ala Asp Ala Cys Ser Cys Ser Pro Val
                20                  25                  30

His Pro Gln Gln Ala Phe Cys Asn Ala Asp Val Val Ile Arg Ala Lys
            35                  40                  45

Ala Val Ser Glu Lys Glu Val Asp Ser Gly Asn Asp Ile Tyr Gly Asn
        50                  55                  60

Pro Ile Lys Arg Ile Gln Tyr Glu Ile Lys Gln Ile Lys Met Phe Lys
65                  70                  75                  80

Gly Pro Glu Lys Asp Ile Glu Phe Ile Tyr Thr Ala Pro Ser Ser Ala
                85                  90                  95

Val Cys Gly Val Ser Leu Asp Val Gly Gly Lys Lys Glu Tyr Leu Ile
            100                 105                 110

Ala Gly Lys Ala Glu Gly Asp Gly Lys Met His Ile Thr Leu Cys Asp
        115                 120                 125

Phe Ile Val Pro Trp Asp Thr Leu Ser Thr Thr Gln Lys Lys Ser Leu
    130                 135                 140
```

```
Asn His Arg Tyr Gln Met Gly Cys Glu Cys Lys Ile Thr Arg Cys Pro
145                 150                 155                 160

Met Ile Pro Cys Tyr Ile Ser Ser Pro Asp Glu Cys Leu Trp Met Asp
                165                 170                 175

Trp Val Thr Glu Lys Asn Ile Asn Gly His Gln Ala Lys Phe Phe Ala
            180                 185                 190

Cys Ile Lys Arg Ser Asp Gly Ser Cys Ala Trp Tyr Arg Gly Ala Ala
        195                 200                 205

Pro Pro Lys Gln Glu Phe Leu Asp Ile Glu Asp Pro
    210                 215                 220

<210> SEQ ID NO 8
<211> LENGTH: 298
<212> TYPE: PRT
<213> ORGANISM: Homo sapiens

<400> SEQUENCE: 8

Met Lys Thr Leu Gln Ser Thr Leu Leu Leu Leu Leu Val Pro Leu
1               5                   10                  15

Ile Lys Pro Ala Pro Pro Thr Gln Gln Asp Ser Arg Ile Ile Tyr Asp
                20                  25                  30

Tyr Gly Thr Asp Asn Phe Glu Glu Ser Ile Phe Ser Gln Asp Tyr Glu
            35                  40                  45

Asp Lys Tyr Leu Asp Gly Lys Asn Ile Lys Lys Glu Thr Val Ile
        50                  55                  60

Ile Pro Asn Glu Lys Ser Leu Gln Leu Gln Lys Asp Glu Ala Ile Thr
65                  70                  75                  80

Pro Leu Pro Pro Lys Lys Glu Asn Asp Glu Met Pro Thr Cys Leu Leu
                85                  90                  95

Cys Val Cys Leu Ser Gly Ser Val Tyr Cys Glu Glu Val Asp Ile Asp
                100                 105                 110

Ala Val Pro Pro Leu Pro Lys Glu Ser Ala Tyr Leu Tyr Ala Arg Phe
            115                 120                 125

Asn Lys Ile Lys Lys Leu Thr Ala Lys Asp Phe Ala Asp Ile Pro Asn
130                 135                 140

Leu Arg Arg Leu Asp Phe Thr Gly Asn Leu Ile Glu Asp Ile Glu Asp
145                 150                 155                 160

Gly Thr Phe Ser Lys Leu Ser Leu Leu Glu Glu Leu Ser Leu Ala Glu
                165                 170                 175

Asn Gln Leu Leu Lys Leu Pro Val Leu Pro Pro Lys Leu Thr Leu Phe
            180                 185                 190

Asn Ala Lys Tyr Asn Lys Ile Lys Ser Arg Gly Ile Lys Ala Asn Ala
        195                 200                 205

Phe Lys Lys Leu Asn Asn Leu Thr Phe Leu Tyr Leu Asp His Asn Ala
    210                 215                 220

Leu Glu Ser Val Pro Leu Asn Leu Pro Glu Ser Leu Arg Val Ile His
225                 230                 235                 240

Leu Gln Phe Asn Asn Ile Ala Ser Ile Thr Asp Asp Thr Phe Cys Lys
                245                 250                 255

Ala Asn Asp Thr Ser Tyr Ile Arg Asp Arg Ile Glu Glu Ile Arg Leu
            260                 265                 270

Glu Gly Asn Pro Ile Val Leu Gly Lys His Pro Asn Ser Phe Ile Cys
        275                 280                 285

Leu Lys Arg Leu Pro Ile Gly Ser Tyr Phe
    290                 295
```

<210> SEQ ID NO 9
<211> LENGTH: 999
<212> TYPE: PRT
<213> ORGANISM: Homo sapiens

<400> SEQUENCE: 9

```
Met Ala Asp Lys Val Arg Arg Gln Arg Pro Arg Arg Val Cys Trp
1               5                   10                  15

Ala Leu Val Ala Val Leu Leu Ala Asp Leu Leu Ala Leu Ser Asp Thr
                20                  25                  30

Leu Ala Val Met Ser Val Asp Leu Gly Ser Glu Ser Met Lys Val Ala
            35                  40                  45

Ile Val Lys Pro Gly Val Pro Met Glu Ile Val Leu Asn Lys Glu Ser
        50                  55                  60

Arg Arg Lys Thr Pro Val Ile Val Thr Leu Lys Glu Asn Glu Arg Phe
65                  70                  75                  80

Phe Gly Asp Ser Ala Ala Ser Met Ala Ile Lys Asn Pro Lys Ala Thr
                85                  90                  95

Leu Arg Tyr Phe Gln His Leu Leu Gly Lys Gln Ala Asp Asn Pro His
            100                 105                 110

Val Ala Leu Tyr Gln Ala Arg Phe Pro Glu His Glu Leu Thr Phe Asp
        115                 120                 125

Pro Gln Arg Gln Thr Val His Phe Gln Ile Ser Ser Gln Leu Gln Phe
    130                 135                 140

Ser Pro Glu Glu Val Leu Gly Met Val Leu Asn Tyr Ser Arg Ser Leu
145                 150                 155                 160

Ala Glu Asp Phe Ala Glu Gln Pro Ile Lys Asp Ala Val Ile Thr Val
                165                 170                 175

Pro Val Phe Phe Asn Gln Ala Glu Arg Arg Ala Val Leu Gln Ala Ala
            180                 185                 190

Arg Met Ala Gly Leu Lys Val Leu Gln Leu Ile Asn Asp Asn Thr Ala
        195                 200                 205

Thr Ala Leu Ser Tyr Gly Val Phe Arg Arg Lys Asp Ile Asn Thr Thr
    210                 215                 220

Ala Gln Asn Ile Met Phe Tyr Asp Met Gly Ser Gly Ser Thr Val Cys
225                 230                 235                 240

Thr Ile Val Thr Tyr Gln Met Val Lys Thr Lys Glu Ala Gly Met Gln
                245                 250                 255

Pro Gln Leu Gln Ile Arg Gly Val Gly Phe Asp Arg Thr Leu Gly Gly
            260                 265                 270

Leu Glu Met Glu Leu Arg Leu Arg Glu Arg Leu Ala Gly Leu Phe Asn
        275                 280                 285

Glu Gln Arg Lys Gly Gln Arg Ala Lys Asp Val Arg Glu Asn Pro Arg
    290                 295                 300

Ala Met Ala Lys Leu Leu Arg Glu Ala Asn Arg Leu Lys Thr Val Leu
305                 310                 315                 320

Ser Ala Asn Ala Asp His Met Ala Gln Ile Glu Gly Leu Met Asp Asp
                325                 330                 335

Val Asp Phe Lys Ala Lys Val Thr Arg Val Glu Phe Glu Glu Leu Cys
            340                 345                 350

Ala Asp Leu Phe Glu Arg Val Pro Gly Pro Val Gln Gln Ala Leu Gln
        355                 360                 365

Ser Ala Glu Met Ser Leu Asp Glu Ile Glu Gln Val Ile Leu Val Gly
```

-continued

```
              370                 375                 380
Gly Ala Thr Arg Val Pro Arg Val Gln Glu Val Leu Lys Ala Val
385                 390                 395                 400

Gly Lys Glu Glu Leu Gly Lys Asn Ile Asn Ala Asp Glu Ala Ala
                405                 410                 415

Met Gly Ala Val Tyr Gln Ala Ala Leu Ser Lys Ala Phe Lys Val
                420                 425                 430

Lys Pro Phe Val Arg Asp Ala Val Val Tyr Pro Ile Leu Val Glu
                435                 440                 445

Phe Thr Arg Glu Val Glu Glu Pro Gly Ile His Ser Leu Lys His
                450                 455                 460

Asn Lys Arg Val Leu Phe Ser Arg Met Gly Pro Tyr Pro Gln Arg Lys
465                 470                 475                 480

Val Ile Thr Phe Asn Arg Tyr Ser His Asp Phe Asn Phe His Ile Asn
                485                 490                 495

Tyr Gly Asp Leu Gly Phe Leu Gly Pro Glu Asp Leu Arg Val Phe Gly
                500                 505                 510

Ser Gln Asn Leu Thr Thr Val Lys Leu Lys Gly Val Gly Asp Ser Phe
                515                 520                 525

Lys Lys Tyr Pro Asp Tyr Glu Ser Lys Gly Ile Lys Ala His Phe Asn
                530                 535                 540

Leu Asp Glu Ser Gly Val Leu Ser Leu Asp Arg Val Glu Ser Val Phe
545                 550                 555                 560

Glu Thr Leu Val Glu Asp Ser Ala Glu Glu Ser Thr Leu Thr Lys
                565                 570                 575

Leu Gly Asn Thr Ile Ser Ser Leu Phe Gly Gly Thr Thr Pro Asp
                580                 585                 590

Ala Lys Glu Asn Gly Thr Asp Thr Val Gln Glu Glu Glu Ser Pro
                595                 600                 605

Ala Glu Gly Ser Lys Asp Glu Pro Gly Glu Gln Val Glu Leu Lys Glu
                610                 615                 620

Glu Ala Glu Ala Pro Val Glu Asp Gly Ser Gln Pro Pro Pro Glu
625                 630                 635                 640

Pro Lys Gly Asp Ala Thr Pro Glu Gly Glu Lys Ala Thr Glu Lys Glu
                645                 650                 655

Asn Gly Asp Lys Ser Glu Ala Gln Lys Pro Ser Glu Lys Ala Glu Ala
                660                 665                 670

Gly Pro Glu Gly Val Ala Pro Glu Gly Glu Lys Lys Gln Lys
                675                 680                 685

Pro Ala Arg Lys Arg Met Val Glu Glu Ile Gly Val Glu Leu Val
                690                 695                 700

Val Leu Asp Leu Pro Asp Leu Pro Glu Asp Lys Leu Ala Gln Ser Val
705                 710                 715                 720

Gln Lys Leu Gln Asp Leu Thr Leu Arg Asp Leu Glu Lys Gln Glu Arg
                725                 730                 735

Glu Lys Ala Ala Asn Ser Leu Glu Ala Phe Ile Phe Glu Thr Gln Asp
                740                 745                 750

Lys Leu Tyr Gln Pro Glu Tyr Gln Glu Val Ser Thr Glu Glu Gln Arg
                755                 760                 765

Glu Glu Ile Ser Gly Lys Leu Ser Ala Ala Ser Thr Trp Leu Glu Asp
                770                 775                 780

Glu Gly Val Gly Ala Thr Thr Val Met Leu Lys Glu Lys Leu Ala Glu
785                 790                 795                 800
```

```
Leu Arg Lys Leu Cys Gln Gly Leu Phe Phe Arg Val Glu Glu Arg Lys
                805                 810                 815

Lys Trp Pro Glu Arg Leu Ser Ala Leu Asp Asn Leu Leu Asn His Ser
            820                 825                 830

Ser Met Phe Leu Lys Gly Ala Arg Leu Ile Pro Glu Met Asp Gln Ile
        835                 840                 845

Phe Thr Glu Val Glu Met Thr Thr Leu Glu Lys Val Ile Asn Glu Thr
    850                 855                 860

Trp Ala Trp Lys Asn Ala Thr Leu Ala Glu Gln Ala Lys Leu Pro Ala
865                 870                 875                 880

Thr Glu Lys Pro Val Leu Leu Ser Lys Asp Ile Glu Ala Lys Met Met
                885                 890                 895

Ala Leu Asp Arg Glu Val Gln Tyr Leu Leu Asn Lys Ala Lys Phe Thr
            900                 905                 910

Lys Pro Arg Pro Arg Pro Lys Asp Lys Asn Gly Thr Arg Ala Glu Pro
        915                 920                 925

Pro Leu Asn Ala Ser Ala Ser Asp Gln Gly Glu Lys Val Ile Pro Pro
    930                 935                 940

Ala Gly Gln Thr Glu Asp Ala Glu Pro Ile Ser Glu Pro Glu Lys Val
945                 950                 955                 960

Glu Thr Gly Ser Glu Pro Gly Asp Thr Glu Pro Leu Glu Leu Gly Gly
                965                 970                 975

Pro Gly Ala Glu Pro Glu Gln Lys Glu Gln Ser Thr Gly Gln Lys Arg
            980                 985                 990

Pro Leu Lys Asn Asp Glu Leu
        995

<210> SEQ ID NO 10
<211> LENGTH: 194
<212> TYPE: PRT
<213> ORGANISM: Homo sapiens

<400> SEQUENCE: 10

Met Thr Met Arg His Asn Trp Thr Pro Asp Leu Ser Pro Leu Trp Val
1               5                   10                  15

Leu Leu Leu Cys Ala His Val Val Thr Leu Leu Val Arg Ala Thr Pro
                20                  25                  30

Val Ser Gln Thr Thr Ala Ala Thr Ala Ser Val Arg Ser Thr Lys
            35                  40                  45

Asp Pro Cys Pro Ser Gln Pro Pro Val Phe Pro Ala Ala Lys Gln Cys
50                  55                  60

Pro Ala Leu Glu Val Thr Trp Pro Glu Val Glu Val Pro Leu Asn Gly
65                  70                  75                  80

Thr Leu Ser Leu Ser Cys Val Ala Cys Ser Arg Phe Pro Asn Phe Ser
                85                  90                  95

Ile Leu Tyr Trp Leu Gly Asn Gly Ser Phe Ile Glu His Leu Pro Gly
            100                 105                 110

Arg Leu Trp Glu Gly Ser Thr Ser Arg Glu Arg Gly Ser Thr Gly Thr
        115                 120                 125

Gln Leu Cys Lys Ala Leu Val Leu Glu Gln Leu Thr Pro Ala Leu His
    130                 135                 140

Ser Thr Asn Phe Ser Cys Val Leu Val Asp Pro Glu Gln Val Val Gln
145                 150                 155                 160

Arg His Val Val Leu Ala Gln Leu Trp Ala Gly Leu Arg Ala Thr Leu
```

-continued

```
                165                 170                 175
Pro Pro Thr Gln Glu Ala Leu Pro Ser Ser His Ser Ser Pro Gln Gln
            180                 185                 190

Gln Gly

<210> SEQ ID NO 11
<211> LENGTH: 466
<212> TYPE: PRT
<213> ORGANISM: Homo sapiens

<400> SEQUENCE: 11

Met Val Ser Gln Ala Leu Arg Leu Leu Cys Leu Leu Leu Gly Leu Gln
1               5                   10                  15

Gly Cys Leu Ala Ala Gly Gly Val Ala Lys Ala Ser Gly Gly Glu Thr
            20                  25                  30

Arg Asp Met Pro Trp Lys Pro Gly Pro His Arg Val Phe Val Thr Gln
        35                  40                  45

Glu Glu Ala His Gly Val Leu His Arg Arg Arg Ala Asn Ala Phe
    50                  55                  60

Leu Glu Glu Leu Arg Pro Gly Ser Leu Glu Arg Glu Cys Lys Glu Glu
65                  70                  75                  80

Gln Cys Ser Phe Glu Glu Ala Arg Glu Ile Phe Lys Asp Ala Glu Arg
                85                  90                  95

Thr Lys Leu Phe Trp Ile Ser Tyr Ser Asp Gly Asp Gln Cys Ala Ser
            100                 105                 110

Ser Pro Cys Gln Asn Gly Gly Ser Cys Lys Asp Gln Leu Gln Ser Tyr
        115                 120                 125

Ile Cys Phe Cys Leu Pro Ala Phe Glu Gly Arg Asn Cys Glu Thr His
    130                 135                 140

Lys Asp Asp Gln Leu Ile Cys Val Asn Glu Asn Gly Gly Cys Glu Gln
145                 150                 155                 160

Tyr Cys Ser Asp His Thr Gly Thr Lys Arg Ser Cys Arg Cys His Glu
                165                 170                 175

Gly Tyr Ser Leu Leu Ala Asp Gly Val Ser Cys Thr Pro Thr Val Glu
            180                 185                 190

Tyr Pro Cys Gly Lys Ile Pro Ile Leu Glu Lys Arg Asn Ala Ser Lys
        195                 200                 205

Pro Gln Gly Arg Ile Val Gly Gly Lys Val Cys Pro Lys Gly Glu Cys
    210                 215                 220

Pro Trp Gln Val Leu Leu Leu Val Asn Gly Ala Gln Leu Cys Gly Gly
225                 230                 235                 240

Thr Leu Ile Asn Thr Ile Trp Val Val Ser Ala Ala His Cys Phe Asp
                245                 250                 255

Lys Ile Lys Asn Trp Arg Asn Leu Ile Ala Val Leu Gly Glu His Asp
            260                 265                 270

Leu Ser Glu His Asp Gly Asp Glu Gln Ser Arg Arg Val Ala Gln Val
        275                 280                 285

Ile Ile Pro Ser Thr Tyr Val Pro Gly Thr Thr Asn His Asp Ile Ala
    290                 295                 300

Leu Leu Arg Leu His Gln Pro Val Val Leu Thr Asp His Val Val Pro
305                 310                 315                 320

Leu Cys Leu Pro Glu Arg Thr Phe Ser Glu Arg Thr Leu Ala Phe Val
                325                 330                 335

Arg Phe Ser Leu Val Ser Gly Trp Gly Gln Leu Leu Asp Arg Gly Ala
```

```
                        340                 345                 350
        Thr Ala Leu Glu Leu Met Val Leu Asn Val Pro Arg Leu Met Thr Gln
                    355                 360                 365

Asp Cys Leu Gln Gln Ser Arg Lys Val Gly Asp Ser Pro Asn Ile Thr
        370                 375                 380

Glu Tyr Met Phe Cys Ala Gly Tyr Ser Asp Gly Ser Lys Asp Ser Cys
        385                 390                 395                 400

Lys Gly Asp Ser Gly Gly Pro His Ala Thr His Tyr Arg Gly Thr Trp
                        405                 410                 415

Tyr Leu Thr Gly Ile Val Ser Trp Gly Gln Gly Cys Ala Thr Val Gly
                    420                 425                 430

His Phe Gly Val Tyr Thr Arg Val Ser Gln Tyr Ile Glu Trp Leu Gln
                    435                 440                 445

Lys Leu Met Arg Ser Glu Pro Arg Pro Gly Val Leu Leu Arg Ala Pro
                    450                 455                 460

Phe Pro
        465

<210> SEQ ID NO 12
<211> LENGTH: 432
<212> TYPE: PRT
<213> ORGANISM: Homo sapiens

<400> SEQUENCE: 12

Met Lys Arg Met Val Ser Trp Ser Phe His Lys Leu Lys Thr Met Lys
        1               5                   10                  15

His Leu Leu Leu Leu Leu Cys Val Phe Leu Val Lys Ser Gln Gly
                    20                  25                  30

Val Asn Asp Asn Glu Glu Gly Phe Phe Ser Ala Arg Gly His Arg Pro
                    35                  40                  45

Leu Asp Lys Lys Arg Glu Glu Ala Leu Leu Gln Gln Glu Arg Pro Ile
        50                  55                  60

Arg Asn Ser Val Asp Glu Leu Asn Asn Asn Val Glu Ala Val Ser Gln
        65                  70                  75                  80

Thr Ser Ser Ser Ser Phe Gln Tyr Met Tyr Leu Leu Lys Asp Leu Trp
                        85                  90                  95

Gln Lys Arg Gln Lys Gln Val Lys Asp Asn Glu Asn Val Val Asn Glu
                    100                 105                 110

Tyr Ser Ser Glu Leu Glu Lys His Gln Leu Tyr Ile Asp Glu Thr Val
                    115                 120                 125

Asn Ser Asn Ile Pro Thr Asn Leu Arg Val Leu Arg Ser Ile Leu Glu
        130                 135                 140

Asn Leu Arg Ser Lys Ile Gln Lys Leu Glu Ser Asp Val Ser Ala Gln
        145                 150                 155                 160

Met Glu Tyr Cys Arg Thr Pro Cys Thr Val Ser Cys Asn Ile Pro Val
                        165                 170                 175

Val Ser Gly Lys Glu Cys Glu Glu Ile Ile Arg Lys Gly Gly Glu Thr
                    180                 185                 190

Ser Glu Met Tyr Leu Ile Gln Pro Asp Ser Ser Val Lys Pro Tyr Arg
                    195                 200                 205

Val Tyr Cys Asp Met Asn Thr Glu Asn Gly Gly Trp Thr Val Ile Gln
        210                 215                 220

Asn Arg Gln Asp Gly Ser Val Asp Phe Gly Arg Lys Trp Asp Pro Tyr
        225                 230                 235                 240
```

```
Lys Gln Gly Phe Gly Asn Val Ala Thr Asn Thr Asp Gly Lys Asn Tyr
                245                 250                 255

Cys Gly Leu Pro Gly Glu Tyr Trp Leu Gly Asn Asp Lys Ile Ser Gln
            260                 265                 270

Leu Thr Arg Met Gly Pro Thr Glu Leu Leu Ile Glu Met Glu Asp Trp
        275                 280                 285

Lys Gly Asp Lys Val Lys Ala His Tyr Gly Gly Phe Thr Val Gln Asn
    290                 295                 300

Glu Ala Asn Lys Tyr Gln Ile Ser Val Asn Lys Tyr Arg Gly Thr Ala
305                 310                 315                 320

Gly Asn Ala Leu Met Asp Gly Ala Ser Gln Leu Met Gly Glu Asn Arg
                325                 330                 335

Thr Met Thr Ile His Asn Gly Met Phe Phe Ser Thr Tyr Asp Arg Asp
            340                 345                 350

Asn Asp Gly Trp Leu Thr Ser Asp Pro Arg Lys Gln Cys Ser Lys Glu
        355                 360                 365

Asp Gly Gly Gly Trp Trp Tyr Asn Arg Cys His Ala Ala Asn Pro Asn
    370                 375                 380

Gly Arg Tyr Tyr Trp Gly Gly Gln Tyr Thr Trp Asp Met Ala Lys His
385                 390                 395                 400

Gly Thr Asp Asp Gly Val Val Trp Met Asn Trp Lys Gly Ser Trp Tyr
                405                 410                 415

Ser Met Arg Lys Met Ser Met Lys Ile Arg Pro Phe Phe Pro Gln Gln
            420                 425                 430

<210> SEQ ID NO 13
<211> LENGTH: 93
<212> TYPE: PRT
<213> ORGANISM: Homo sapiens

<400> SEQUENCE: 13

Met Ser Gly Leu Arg Val Tyr Ser Thr Ser Val Thr Gly Ser Arg Glu
1               5                   10                  15

Ile Lys Ser Gln Gln Ser Glu Val Thr Arg Ile Leu Asp Gly Lys Arg
            20                  25                  30

Ile Gln Tyr Gln Leu Val Asp Ile Ser Gln Asp Asn Ala Leu Arg Asp
        35                  40                  45

Glu Met Arg Ala Leu Ala Gly Asn Pro Lys Ala Thr Pro Pro Gln Ile
    50                  55                  60

Val Asn Gly Asp Gln Tyr Cys Gly Asp Tyr Glu Leu Phe Val Glu Ala
65                  70                  75                  80

Val Glu Gln Asn Thr Leu Gln Glu Phe Leu Lys Leu Ala
                85                  90

<210> SEQ ID NO 14
<211> LENGTH: 381
<212> TYPE: PRT
<213> ORGANISM: Homo sapiens

<400> SEQUENCE: 14

Met Pro Phe Gly Asn Thr His Asn Lys Phe Lys Leu Asn Tyr Lys Pro
1               5                   10                  15

Glu Glu Glu Tyr Pro Asp Leu Ser Lys His Asn Asn His Met Ala Lys
            20                  25                  30

Val Leu Thr Leu Glu Leu Tyr Lys Lys Leu Arg Asp Lys Glu Thr Pro
        35                  40                  45
```

```
Ser Gly Phe Thr Val Asp Asp Val Ile Gln Thr Gly Val Asp Asn Pro
    50                  55                  60
Gly His Pro Phe Ile Met Thr Val Gly Cys Val Ala Gly Asp Glu Glu
 65                  70                  75                  80
Ser Tyr Glu Val Phe Lys Glu Leu Phe Asp Pro Ile Ile Ser Asp Arg
                 85                  90                  95
His Gly Gly Tyr Lys Pro Thr Asp Lys His Lys Thr Asp Leu Asn His
            100                 105                 110
Glu Asn Leu Lys Gly Gly Asp Asp Leu Asp Pro Asn Tyr Val Leu Ser
        115                 120                 125
Ser Arg Val Arg Thr Gly Arg Ser Ile Lys Gly Tyr Thr Leu Pro Pro
    130                 135                 140
His Cys Ser Arg Gly Glu Arg Arg Ala Val Glu Lys Leu Ser Val Glu
145                 150                 155                 160
Ala Leu Asn Ser Leu Thr Gly Glu Phe Lys Gly Lys Tyr Tyr Pro Leu
                165                 170                 175
Lys Ser Met Thr Glu Lys Glu Gln Gln Gln Leu Ile Asp Asp His Phe
            180                 185                 190
Leu Phe Asp Lys Pro Val Ser Pro Leu Leu Leu Ala Ser Gly Met Ala
        195                 200                 205
Arg Asp Trp Pro Asp Ala Arg Gly Ile Trp His Asn Asp Asn Lys Ser
    210                 215                 220
Phe Leu Val Trp Val Asn Glu Glu Asp His Leu Arg Val Ile Ser Met
225                 230                 235                 240
Glu Lys Gly Gly Asn Met Lys Glu Val Phe Arg Arg Phe Cys Val Gly
                245                 250                 255
Leu Gln Lys Ile Glu Glu Ile Phe Lys Lys Ala Gly His Pro Phe Met
            260                 265                 270
Trp Asn Gln His Leu Gly Tyr Val Leu Thr Cys Pro Ser Asn Leu Gly
        275                 280                 285
Thr Gly Leu Arg Gly Gly Val His Val Lys Leu Ala His Leu Ser Lys
    290                 295                 300
His Pro Lys Phe Glu Glu Ile Leu Thr Arg Leu Arg Leu Gln Lys Arg
305                 310                 315                 320
Gly Thr Gly Gly Val Asp Thr Ala Ala Val Gly Ser Val Phe Asp Val
                325                 330                 335
Ser Asn Ala Asp Arg Leu Gly Ser Ser Glu Val Glu Gln Val Gln Leu
            340                 345                 350
Val Val Asp Gly Val Lys Leu Met Val Glu Met Glu Lys Lys Leu Glu
        355                 360                 365
Lys Gly Gln Ser Ile Asp Asp Met Ile Pro Ala Gln Lys
    370                 375                 380

<210> SEQ ID NO 15
<211> LENGTH: 308
<212> TYPE: PRT
<213> ORGANISM: Homo sapiens

<400> SEQUENCE: 15

Met Trp Lys Arg Trp Leu Ala Leu Ala Leu Ala Leu Val Ala Val Ala
  1               5                  10                  15
Trp Val Arg Ala Glu Glu Glu Leu Arg Ser Lys Ser Lys Ile Cys Ala
                 20                  25                  30
Asn Val Phe Cys Gly Ala Gly Arg Glu Cys Ala Val Thr Glu Lys Gly
            35                  40                  45
```

Glu Pro Thr Cys Leu Cys Ile Glu Gln Cys Lys Pro His Lys Arg Pro
50                  55                  60

Val Cys Gly Ser Asn Gly Lys Thr Tyr Leu Asn His Cys Glu Leu His
65                  70                  75                  80

Arg Asp Ala Cys Leu Thr Gly Ser Lys Ile Gln Val Asp Tyr Asp Gly
                85                  90                  95

His Cys Lys Glu Lys Lys Ser Val Ser Pro Ser Ala Ser Pro Val Val
            100                 105                 110

Cys Tyr Gln Ser Asn Arg Asp Glu Leu Arg Arg Ile Ile Gln Trp
        115                 120                 125

Leu Glu Ala Glu Ile Ile Pro Asp Gly Trp Phe Ser Lys Gly Ser Asn
130                 135                 140

Tyr Ser Glu Ile Leu Asp Lys Tyr Phe Lys Asn Phe Asp Asn Gly Asp
145                 150                 155                 160

Ser Arg Leu Asp Ser Ser Glu Phe Leu Lys Phe Val Glu Gln Asn Glu
                165                 170                 175

Thr Ala Ile Asn Ile Thr Thr Tyr Pro Asp Gln Glu Asn Asn Lys Leu
            180                 185                 190

Leu Arg Gly Leu Cys Val Asp Ala Leu Ile Glu Leu Ser Asp Glu Asn
        195                 200                 205

Ala Asp Trp Lys Leu Ser Phe Gln Glu Phe Leu Lys Cys Leu Asn Pro
210                 215                 220

Ser Phe Asn Pro Pro Glu Lys Lys Cys Ala Leu Glu Asp Glu Thr Tyr
225                 230                 235                 240

Ala Asp Gly Ala Glu Thr Glu Val Asp Cys Asn Arg Cys Val Cys Ala
                245                 250                 255

Cys Gly Asn Trp Val Cys Thr Ala Met Thr Cys Asp Gly Lys Asn Gln
            260                 265                 270

Lys Gly Ala Gln Thr Gln Thr Glu Glu Met Thr Arg Tyr Val Gln
        275                 280                 285

Glu Leu Gln Lys His Gln Glu Thr Ala Glu Lys Thr Lys Arg Val Ser
290                 295                 300

Thr Lys Glu Ile
305

<210> SEQ ID NO 16
<211> LENGTH: 1428
<212> TYPE: PRT
<213> ORGANISM: Homo sapiens

<400> SEQUENCE: 16

Met Gln Gly Pro Pro Leu Leu Thr Ala Ala His Leu Leu Cys Val Cys
1               5                   10                  15

Thr Ala Ala Leu Ala Val Ala Pro Gly Pro Arg Phe Leu Val Thr Ala
            20                  25                  30

Pro Gly Ile Ile Arg Pro Gly Gly Asn Val Thr Ile Gly Val Glu Leu
        35                  40                  45

Leu Glu His Cys Pro Ser Gln Val Thr Val Lys Ala Glu Leu Leu Lys
50                  55                  60

Thr Ala Ser Asn Leu Thr Val Ser Val Leu Glu Ala Gly Val Phe
65                  70                  75                  80

Glu Lys Gly Ser Phe Lys Thr Leu Thr Leu Pro Ser Leu Pro Leu Asn
                85                  90                  95

Ser Ala Asp Glu Ile Tyr Glu Leu Arg Val Thr Gly Arg Thr Gln Asp

```
                100                 105                 110
Glu Ile Leu Phe Ser Asn Ser Thr Arg Leu Ser Phe Glu Thr Lys Arg
            115                 120                 125
Ile Ser Val Phe Ile Gln Thr Asp Lys Ala Leu Tyr Lys Pro Lys Gln
            130                 135                 140
Glu Val Lys Phe Arg Ile Val Thr Leu Phe Ser Asp Phe Lys Pro Tyr
145                 150                 155                 160
Lys Thr Ser Leu Asn Ile Leu Ile Lys Asp Pro Lys Ser Asn Leu Ile
                165                 170                 175
Gln Gln Trp Leu Ser Gln Gln Ser Asp Leu Gly Val Ile Ser Lys Thr
            180                 185                 190
Phe Gln Leu Ser Ser His Pro Ile Leu Gly Asp Trp Ser Ile Gln Val
            195                 200                 205
Gln Val Asn Asp Gln Thr Tyr Tyr Gln Ser Phe Gln Val Ser Glu Tyr
            210                 215                 220
Val Leu Pro Lys Phe Glu Val Thr Leu Gln Thr Pro Leu Tyr Cys Ser
225                 230                 235                 240
Met Asn Ser Lys His Leu Asn Gly Thr Ile Thr Ala Lys Tyr Thr Tyr
                245                 250                 255
Gly Lys Pro Val Lys Gly Asp Val Thr Leu Thr Phe Leu Pro Leu Ser
            260                 265                 270
Phe Trp Gly Lys Lys Asn Ile Thr Lys Thr Phe Lys Ile Asn Gly
            275                 280                 285
Ser Ala Asn Phe Ser Phe Asn Asp Glu Glu Met Lys Asn Val Met Asp
            290                 295                 300
Ser Ser Asn Gly Leu Ser Glu Tyr Leu Asp Leu Ser Ser Pro Gly Pro
305                 310                 315                 320
Val Glu Ile Leu Thr Thr Val Thr Glu Ser Val Thr Gly Ile Ser Arg
                325                 330                 335
Asn Val Ser Thr Asn Val Phe Phe Lys Gln His Asp Tyr Ile Ile Glu
                340                 345                 350
Phe Phe Asp Tyr Thr Thr Val Leu Lys Pro Ser Leu Asn Phe Thr Ala
            355                 360                 365
Thr Val Lys Val Thr Arg Ala Asp Gly Asn Gln Leu Thr Leu Glu Glu
            370                 375                 380
Arg Arg Asn Asn Val Val Ile Thr Val Thr Gln Arg Asn Tyr Thr Glu
385                 390                 395                 400
Tyr Trp Ser Gly Ser Asn Ser Gly Asn Gln Lys Met Glu Ala Val Gln
                405                 410                 415
Lys Ile Asn Tyr Thr Val Pro Gln Ser Gly Thr Phe Lys Ile Glu Phe
            420                 425                 430
Pro Ile Leu Glu Asp Ser Ser Glu Leu Gln Leu Lys Ala Tyr Phe Leu
            435                 440                 445
Gly Ser Lys Ser Ser Met Ala Val His Ser Leu Phe Lys Ser Pro Ser
            450                 455                 460
Lys Thr Tyr Ile Gln Leu Lys Thr Arg Asp Glu Asn Ile Lys Val Gly
465                 470                 475                 480
Ser Pro Phe Glu Leu Val Val Ser Gly Asn Lys Arg Leu Lys Glu Leu
                485                 490                 495
Ser Tyr Met Val Val Ser Arg Gly Gln Leu Val Ala Val Gly Lys Gln
                500                 505                 510
Asn Ser Thr Met Phe Ser Leu Thr Pro Glu Asn Ser Trp Thr Pro Lys
            515                 520                 525
```

```
Ala Cys Val Ile Val Tyr Tyr Ile Glu Asp Asp Gly Glu Ile Ile Ser
        530                 535                 540

Asp Val Leu Lys Ile Pro Val Gln Leu Val Phe Lys Asn Lys Ile Lys
545                 550                 555                 560

Leu Tyr Trp Ser Lys Val Lys Ala Glu Pro Ser Glu Lys Val Ser Leu
                565                 570                 575

Arg Ile Ser Val Thr Gln Pro Asp Ser Ile Val Gly Ile Val Ala Val
                580                 585                 590

Asp Lys Ser Val Asn Leu Met Asn Ala Ser Asn Asp Ile Thr Met Glu
                595                 600                 605

Asn Val Val His Glu Leu Glu Leu Tyr Asn Thr Gly Tyr Tyr Leu Gly
610                 615                 620

Met Phe Met Asn Ser Phe Ala Val Phe Gln Glu Cys Gly Leu Trp Val
625                 630                 635                 640

Leu Thr Asp Ala Asn Leu Thr Lys Asp Tyr Ile Asp Gly Val Tyr Asp
                645                 650                 655

Asn Ala Glu Tyr Ala Glu Arg Phe Met Glu Asn Glu Gly His Ile
                660                 665                 670

Val Asp Ile His Asp Phe Ser Leu Gly Ser Pro His Val Arg Lys
                675                 680                 685

His Phe Pro Glu Thr Trp Ile Trp Leu Asp Thr Asn Met Gly Tyr Arg
690                 695                 700

Ile Tyr Gln Glu Phe Glu Val Thr Val Pro Asp Ser Ile Thr Ser Trp
705                 710                 715                 720

Val Ala Thr Gly Phe Val Ile Ser Glu Asp Leu Gly Leu Gly Leu Thr
                725                 730                 735

Thr Thr Pro Val Glu Leu Gln Ala Phe Gln Pro Phe Phe Ile Phe Leu
                740                 745                 750

Asn Leu Pro Tyr Ser Val Ile Arg Gly Glu Glu Phe Ala Leu Glu Ile
                755                 760                 765

Thr Ile Phe Asn Tyr Leu Lys Asp Ala Thr Glu Val Lys Val Ile Ile
                770                 775                 780

Glu Lys Ser Asp Lys Phe Asp Ile Leu Met Thr Ser Asn Glu Ile Asn
785                 790                 795                 800

Ala Thr Gly His Gln Gln Thr Leu Leu Val Pro Ser Glu Asp Gly Ala
                805                 810                 815

Thr Val Leu Phe Pro Ile Arg Pro Thr His Leu Gly Glu Ile Pro Ile
                820                 825                 830

Thr Val Thr Ala Leu Ser Pro Thr Ala Ser Asp Ala Val Thr Gln Met
                835                 840                 845

Ile Leu Val Lys Ala Glu Gly Ile Glu Lys Ser Tyr Ser Gln Ser Ile
850                 855                 860

Leu Leu Asp Leu Thr Asp Asn Arg Leu Gln Ser Thr Leu Lys Thr Leu
865                 870                 875                 880

Ser Phe Ser Phe Pro Pro Asn Thr Val Thr Gly Ser Glu Arg Val Gln
                885                 890                 895

Ile Thr Ala Ile Gly Asp Val Leu Gly Pro Ser Ile Asn Gly Leu Ala
                900                 905                 910

Ser Leu Ile Arg Met Pro Tyr Gly Cys Gly Glu Gln Asn Met Ile Asn
                915                 920                 925

Phe Ala Pro Asn Ile Tyr Ile Leu Asp Tyr Leu Thr Lys Lys Gln
930                 935                 940
```

```
Leu Thr Asp Asn Leu Lys Glu Lys Ala Leu Ser Phe Met Arg Gln Gly
945                 950                 955                 960

Tyr Gln Arg Glu Leu Leu Tyr Gln Arg Glu Asp Gly Ser Phe Ser Ala
            965                 970                 975

Phe Gly Asn Tyr Asp Pro Ser Gly Ser Thr Trp Leu Ser Ala Phe Val
        980                 985                 990

Leu Arg Cys Phe Leu Glu Ala Asp Pro Tyr Ile Asp Ile Asp Gln Asn
    995                 1000                1005

Val Leu His Arg Thr Tyr Thr Trp Leu Lys Gly His Gln Lys Ser
1010                1015                1020

Asn Gly Glu Phe Trp Asp Pro Gly Arg Val Ile His Ser Glu Leu
1025                1030                1035

Gln Gly Gly Asn Lys Ser Pro Val Thr Leu Thr Ala Tyr Ile Val
1040                1045                1050

Thr Ser Leu Leu Gly Tyr Arg Lys Tyr Gln Pro Asn Ile Asp Val
1055                1060                1065

Gln Glu Ser Ile His Phe Leu Glu Ser Glu Phe Ser Arg Gly Ile
1070                1075                1080

Ser Asp Asn Tyr Thr Leu Ala Leu Ile Thr Tyr Ala Leu Ser Ser
1085                1090                1095

Val Gly Ser Pro Lys Ala Lys Glu Ala Leu Asn Met Leu Thr Trp
1100                1105                1110

Arg Ala Glu Gln Glu Gly Gly Met Gln Phe Trp Val Ser Ser Glu
1115                1120                1125

Ser Lys Leu Ser Asp Ser Trp Gln Pro Arg Ser Leu Asp Ile Glu
1130                1135                1140

Val Ala Ala Tyr Ala Leu Leu Ser His Phe Leu Gln Phe Gln Thr
1145                1150                1155

Ser Glu Gly Ile Pro Ile Met Arg Trp Leu Ser Arg Gln Arg Asn
1160                1165                1170

Ser Leu Gly Gly Phe Ala Ser Thr Gln Asp Thr Thr Val Ala Leu
1175                1180                1185

Lys Ala Leu Ser Glu Phe Ala Ala Leu Met Asn Thr Glu Arg Thr
1190                1195                1200

Asn Ile Gln Val Thr Val Thr Gly Pro Ser Ser Pro Ser Pro Leu
1205                1210                1215

Ala Val Val Gln Pro Thr Ala Val Asn Ile Ser Ala Asn Gly Phe
1220                1225                1230

Gly Phe Ala Ile Cys Gln Leu Asn Val Val Tyr Asn Val Lys Ala
1235                1240                1245

Ser Gly Ser Ser Arg Arg Arg Ser Ile Gln Asn Gln Glu Ala
1250                1255                1260

Phe Asp Leu Asp Val Ala Val Lys Glu Asn Lys Asp Asp Leu Asn
1265                1270                1275

His Val Asp Leu Asn Val Cys Thr Ser Phe Ser Gly Pro Gly Arg
1280                1285                1290

Ser Gly Met Ala Leu Met Glu Val Asn Leu Leu Ser Gly Phe Met
1295                1300                1305

Val Pro Ser Glu Ala Ile Ser Leu Ser Glu Thr Val Lys Lys Val
1310                1315                1320

Glu Tyr Asp His Gly Lys Leu Asn Leu Tyr Leu Asp Ser Val Asn
1325                1330                1335

Glu Thr Gln Phe Cys Val Asn Ile Pro Ala Val Arg Asn Phe Lys
```

```
                1340                1345                1350

Val Ser Asn Thr Gln Asp Ala Ser Val Ser Ile Val Asp Tyr Tyr
    1355                1360                1365

Glu Pro Arg Arg Gln Ala Val Arg Ser Tyr Asn Ser Glu Val Lys
    1370                1375                1380

Leu Ser Ser Cys Asp Leu Cys Ser Asp Val Gln Gly Cys Arg Pro
    1385                1390                1395

Cys Glu Asp Gly Ala Ser Gly Ser His His His Ser Ser Val Ile
    1400                1405                1410

Phe Ile Phe Cys Phe Lys Leu Leu Tyr Phe Met Glu Leu Trp Leu
    1415                1420                1425

<210> SEQ ID NO 17
<211> LENGTH: 279
<212> TYPE: PRT
<213> ORGANISM: Homo sapiens

<400> SEQUENCE: 17

Met Glu Arg Pro Ser Leu Arg Ala Leu Leu Leu Gly Ala Ala Gly Leu
1               5                   10                  15

Leu Leu Leu Leu Leu Pro Leu Ser Ser Ser Ser Ser Asp Thr Cys
            20                  25                  30

Gly Pro Cys Glu Pro Ala Ser Cys Pro Pro Leu Pro Pro Leu Gly Cys
                35                  40                  45

Leu Leu Gly Glu Thr Arg Asp Ala Cys Gly Cys Cys Pro Met Cys Ala
    50                  55                  60

Arg Gly Glu Gly Glu Pro Cys Gly Gly Gly Ala Gly Arg Gly Tyr
65                  70                  75              80

Cys Ala Pro Gly Met Glu Cys Val Lys Ser Arg Lys Arg Arg Lys Gly
                85                  90                  95

Lys Ala Gly Ala Ala Ala Gly Gly Pro Gly Val Ser Gly Val Cys Val
            100                 105                 110

Cys Lys Ser Arg Tyr Pro Val Cys Gly Ser Asp Gly Thr Thr Tyr Pro
        115                 120                 125

Ser Gly Cys Gln Leu Arg Ala Ala Ser Gln Arg Ala Glu Ser Arg Gly
    130                 135                 140

Glu Lys Ala Ile Thr Gln Val Ser Lys Gly Thr Cys Glu Gln Gly Pro
145                 150                 155                 160

Ser Ile Val Thr Pro Pro Lys Asp Ile Trp Asn Val Thr Gly Ala Gln
                165                 170                 175

Val Tyr Leu Ser Cys Glu Val Ile Gly Ile Pro Thr Pro Val Leu Ile
            180                 185                 190

Trp Asn Lys Val Lys Arg Gly His Tyr Gly Val Gln Arg Thr Glu Leu
        195                 200                 205

Leu Pro Gly Asp Arg Asp Asn Leu Ala Ile Gln Thr Arg Gly Gly Pro
    210                 215                 220

Glu Lys His Glu Val Thr Gly Trp Val Leu Val Ser Pro Leu Ser Lys
225                 230                 235                 240

Glu Asp Ala Gly Glu Tyr Glu Cys His Ala Ser Asn Ser Gln Gly Gln
                245                 250                 255

Ala Ser Ala Ser Ala Lys Ile Thr Val Val Asp Ala Leu His Glu Ile
            260                 265                 270

Pro Val Lys Lys Gly Thr Gln
        275
```

<210> SEQ ID NO 18
<211> LENGTH: 135
<212> TYPE: PRT
<213> ORGANISM: Homo sapiens

<400> SEQUENCE: 18

Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Thr Pro Ser
            20                  25                  30

Thr Cys Gly Val Lys Pro His Arg Tyr Arg Pro Gly Thr Val Ala Leu
        35                  40                  45

Arg Glu Ile Arg Arg Tyr Gln Lys Ser Thr Glu Leu Leu Ile Arg Lys
50                  55                  60

Leu Pro Phe Gln Arg Leu Val Arg Glu Ile Ala Gln Asp Phe Asn Thr
65                  70                  75                  80

Asp Leu Arg Phe Gln Ser Ala Ala Val Gly Ala Leu Gln Glu Ala Ser
                85                  90                  95

Glu Ala Tyr Leu Val Gly Leu Leu Glu Asp Thr Asn Leu Cys Ala Ile
            100                 105                 110

His Ala Lys Arg Val Thr Ile Met Pro Lys Asp Ile Gln Leu Ala Arg
        115                 120                 125

Arg Ile Arg Gly Glu Arg Ala
    130                 135

<210> SEQ ID NO 19
<211> LENGTH: 843
<212> TYPE: PRT
<213> ORGANISM: Homo sapiens

<400> SEQUENCE: 19

Met Lys Val Ile Ser Leu Phe Ile Leu Val Gly Phe Ile Gly Glu Phe
1               5                   10                  15

Gln Ser Phe Ser Ser Ala Ser Ser Pro Val Asn Cys Gln Trp Asp Phe
            20                  25                  30

Tyr Ala Pro Trp Ser Glu Cys Asn Gly Cys Thr Lys Thr Gln Thr Arg
        35                  40                  45

Arg Arg Ser Val Ala Val Tyr Gly Gln Tyr Gly Gln Pro Cys Val
50                  55                  60

Gly Asn Ala Phe Glu Thr Gln Ser Cys Glu Pro Thr Arg Gly Cys Pro
65                  70                  75                  80

Thr Glu Glu Gly Cys Gly Glu Arg Phe Arg Cys Phe Ser Gly Gln Cys
                85                  90                  95

Ile Ser Lys Ser Leu Val Cys Asn Gly Asp Ser Asp Cys Asp Glu Asp
            100                 105                 110

Ser Ala Asp Glu Asp Arg Cys Glu Asp Ser Glu Arg Arg Pro Ser Cys
        115                 120                 125

Asp Ile Asp Lys Pro Pro Asn Ile Glu Leu Thr Gly Asn Gly Tyr
    130                 135                 140

Asn Glu Leu Thr Gly Gln Phe Arg Asn Arg Val Ile Asn Thr Lys Ser
145                 150                 155                 160

Phe Gly Gly Gln Cys Arg Lys Val Phe Ser Gly Asp Gly Lys Asp Phe
                165                 170                 175

Tyr Arg Leu Ser Gly Asn Val Leu Ser Tyr Thr Phe Gln Val Lys Ile
            180                 185                 190

-continued

```
Asn Asn Asp Phe Asn Tyr Glu Phe Tyr Asn Ser Thr Trp Ser Tyr Val
            195                 200                 205
Lys His Thr Ser Thr Glu His Thr Ser Ser Arg Lys Arg Ser Phe
    210                 215                 220
Phe Arg Ser Ser Ser Ser Ser Arg Ser Tyr Thr Ser His Thr Asn
225                 230                 235                 240
Glu Ile His Lys Gly Lys Ser Tyr Gln Leu Leu Val Val Glu Asn Thr
                245                 250                 255
Val Glu Val Ala Gln Phe Ile Asn Asn Asn Pro Glu Phe Leu Gln Leu
            260                 265                 270
Ala Glu Pro Phe Trp Lys Glu Leu Ser His Leu Pro Ser Leu Tyr Asp
        275                 280                 285
Tyr Ser Ala Tyr Arg Arg Leu Ile Asp Gln Tyr Gly Thr His Tyr Leu
    290                 295                 300
Gln Ser Gly Ser Leu Gly Gly Glu Tyr Arg Val Leu Phe Tyr Val Asp
305                 310                 315                 320
Ser Glu Lys Leu Lys Gln Asn Asp Phe Asn Ser Val Glu Glu Lys Lys
                325                 330                 335
Cys Lys Ser Ser Gly Trp His Phe Val Val Lys Phe Ser Ser His Gly
            340                 345                 350
Cys Lys Glu Leu Glu Asn Ala Leu Lys Ala Ala Ser Gly Thr Gln Asn
        355                 360                 365
Asn Val Leu Arg Gly Glu Pro Phe Ile Arg Gly Gly Ala Gly Phe
    370                 375                 380
Ile Ser Gly Leu Ser Tyr Leu Glu Leu Asp Asn Pro Ala Gly Asn Lys
385                 390                 395                 400
Arg Arg Tyr Ser Ala Trp Ala Glu Ser Val Thr Asn Leu Pro Gln Val
                405                 410                 415
Ile Lys Gln Lys Leu Thr Pro Leu Tyr Glu Leu Val Lys Glu Val Pro
            420                 425                 430
Cys Ala Ser Val Lys Lys Leu Tyr Leu Lys Trp Ala Leu Glu Glu Tyr
        435                 440                 445
Leu Asp Glu Phe Asp Pro Cys His Cys Arg Pro Cys Gln Asn Gly Gly
    450                 455                 460
Leu Ala Thr Val Glu Gly Thr His Cys Leu Cys His Cys Lys Pro Tyr
465                 470                 475                 480
Thr Phe Gly Ala Ala Cys Glu Gln Gly Val Leu Val Gly Asn Gln Ala
                485                 490                 495
Gly Gly Val Asp Gly Gly Trp Ser Cys Trp Ser Ser Trp Ser Pro Cys
            500                 505                 510
Val Gln Gly Lys Lys Thr Arg Ser Arg Glu Cys Asn Asn Pro Pro Pro
        515                 520                 525
Ser Gly Gly Gly Arg Ser Cys Val Gly Glu Thr Thr Glu Ser Thr Gln
    530                 535                 540
Cys Glu Asp Glu Glu Leu Glu His Leu Arg Leu Leu Glu Pro His Cys
545                 550                 555                 560
Phe Pro Leu Ser Leu Val Pro Thr Glu Phe Cys Pro Ser Pro Pro Ala
                565                 570                 575
Leu Lys Asp Gly Phe Val Gln Asp Glu Gly Thr Met Phe Pro Val Gly
            580                 585                 590
Lys Asn Val Val Tyr Thr Cys Asn Glu Gly Tyr Ser Leu Ile Gly Asn
        595                 600                 605
Pro Val Ala Arg Cys Gly Glu Asp Leu Arg Trp Leu Val Gly Glu Met
```

```
                610             615              620
His Cys Gln Lys Ile Ala Cys Val Leu Pro Val Leu Met Asp Gly Ile
625                 630                 635                 640

Gln Ser His Pro Gln Lys Pro Phe Tyr Thr Val Gly Glu Lys Val Thr
                645                 650                 655

Val Ser Cys Ser Gly Gly Met Ser Leu Glu Gly Pro Ser Ala Phe Leu
                660                 665                 670

Cys Gly Ser Ser Leu Lys Trp Ser Pro Glu Met Lys Asn Ala Arg Cys
                675                 680                 685

Val Gln Lys Glu Asn Pro Leu Thr Gln Ala Val Pro Lys Cys Gln Arg
690                 695                 700

Trp Glu Lys Leu Gln Asn Ser Arg Cys Val Cys Lys Met Pro Tyr Glu
705                 710                 715                 720

Cys Gly Pro Ser Leu Asp Val Cys Ala Gln Asp Glu Arg Ser Lys Arg
                725                 730                 735

Ile Leu Pro Leu Thr Val Cys Lys Met His Val Leu His Cys Gln Gly
                740                 745                 750

Arg Asn Tyr Thr Leu Thr Gly Arg Asp Ser Cys Thr Leu Pro Ala Ser
                755                 760                 765

Ala Glu Lys Ala Cys Gly Ala Cys Pro Leu Trp Gly Lys Cys Asp Ala
770                 775                 780

Glu Ser Ser Lys Cys Val Cys Arg Glu Ala Ser Glu Cys Glu Glu
785                 790                 795                 800

Gly Phe Ser Ile Cys Val Glu Val Asn Gly Lys Glu Gln Thr Met Ser
                805                 810                 815

Glu Cys Glu Ala Gly Ala Leu Arg Cys Arg Gly Gln Ser Ile Ser Val
                820                 825                 830

Thr Ser Ile Arg Pro Cys Ala Ala Glu Thr Gln
                835                 840

<210> SEQ ID NO 20
<211> LENGTH: 654
<212> TYPE: PRT
<213> ORGANISM: Homo sapiens

<400> SEQUENCE: 20

Met Lys Leu Ser Leu Val Ala Ala Met Leu Leu Leu Leu Ser Ala Ala
1               5                   10                  15

Arg Ala Glu Glu Glu Asp Lys Lys Glu Asp Val Gly Thr Val Val Gly
                20                  25                  30

Ile Asp Leu Gly Thr Thr Tyr Ser Cys Val Gly Val Phe Lys Asn Gly
            35                  40                  45

Arg Val Glu Ile Ile Ala Asn Asp Gln Gly Asn Arg Ile Thr Pro Ser
50                  55                  60

Tyr Val Ala Phe Thr Pro Glu Gly Glu Arg Leu Ile Gly Asp Ala Ala
65                  70                  75                  80

Lys Asn Gln Leu Thr Ser Asn Pro Glu Asn Thr Val Phe Asp Ala Lys
                85                  90                  95

Arg Leu Ile Gly Arg Thr Trp Asn Asp Pro Ser Val Gln Gln Asp Ile
            100                 105                 110

Lys Phe Leu Pro Phe Lys Val Val Glu Lys Lys Thr Lys Pro Tyr Ile
        115                 120                 125

Gln Val Asp Ile Gly Gly Gly Gln Thr Lys Thr Phe Ala Pro Glu Glu
    130                 135                 140
```

```
Ile Ser Ala Met Val Leu Thr Lys Met Lys Glu Thr Ala Glu Ala Tyr
145                 150                 155                 160

Leu Gly Lys Lys Val Thr His Ala Val Val Thr Val Pro Ala Tyr Phe
            165                 170                 175

Asn Asp Ala Gln Arg Gln Ala Thr Lys Asp Ala Gly Thr Ile Ala Gly
                180                 185                 190

Leu Asn Val Met Arg Ile Ile Asn Glu Pro Thr Ala Ala Ala Ile Ala
    195                 200                 205

Tyr Gly Leu Asp Lys Arg Gly Glu Lys Asn Ile Leu Val Phe Asp
    210                 215                 220

Leu Gly Gly Gly Thr Phe Asp Val Ser Leu Leu Thr Ile Asp Asn Gly
225                 230                 235                 240

Val Phe Glu Val Val Ala Thr Asn Gly Asp Thr His Leu Gly Gly Glu
                245                 250                 255

Asp Phe Asp Gln Arg Val Met Glu His Phe Ile Lys Leu Tyr Lys Lys
                260                 265                 270

Lys Thr Gly Lys Asp Val Arg Lys Asp Asn Arg Ala Val Gln Lys Leu
            275                 280                 285

Arg Arg Glu Val Glu Lys Ala Lys Arg Ala Leu Ser Ser Gln His Gln
290                 295                 300

Ala Arg Ile Glu Ile Glu Ser Phe Tyr Glu Gly Asp Phe Ser Glu
305                 310                 315                 320

Thr Leu Thr Arg Ala Lys Phe Glu Glu Leu Asn Met Asp Leu Phe Arg
                325                 330                 335

Ser Thr Met Lys Pro Val Gln Lys Val Leu Glu Asp Ser Asp Leu Lys
                340                 345                 350

Lys Ser Asp Ile Asp Glu Ile Val Leu Val Gly Gly Ser Thr Arg Ile
                355                 360                 365

Pro Lys Ile Gln Gln Leu Val Lys Glu Phe Phe Asn Gly Lys Glu Pro
    370                 375                 380

Ser Arg Gly Ile Asn Pro Asp Glu Ala Val Ala Tyr Gly Ala Ala Val
385                 390                 395                 400

Gln Ala Gly Val Leu Ser Gly Asp Gln Asp Thr Gly Asp Leu Val Leu
                405                 410                 415

Leu Asp Val Cys Pro Leu Thr Leu Gly Ile Glu Thr Val Gly Gly Val
                420                 425                 430

Met Thr Lys Leu Ile Pro Arg Asn Thr Val Val Pro Thr Lys Lys Ser
            435                 440                 445

Gln Ile Phe Ser Thr Ala Ser Asp Asn Gln Pro Thr Val Thr Ile Lys
    450                 455                 460

Val Tyr Glu Gly Glu Arg Pro Leu Thr Lys Asp Asn His Leu Leu Gly
465                 470                 475                 480

Thr Phe Asp Leu Thr Gly Ile Pro Pro Ala Pro Arg Gly Val Pro Gln
                485                 490                 495

Ile Glu Val Thr Phe Glu Ile Asp Val Asn Gly Ile Leu Arg Val Thr
                500                 505                 510

Ala Glu Asp Lys Gly Thr Gly Asn Lys Asn Lys Ile Thr Ile Thr Asn
                515                 520                 525

Asp Gln Asn Arg Leu Thr Pro Glu Glu Ile Glu Arg Met Val Asn Asp
                530                 535                 540

Ala Glu Lys Phe Ala Glu Glu Asp Lys Lys Leu Lys Glu Arg Ile Asp
545                 550                 555                 560

Thr Arg Asn Glu Leu Glu Ser Tyr Ala Tyr Ser Leu Lys Asn Gln Ile
```

```
                         565                 570                 575
Gly Asp Lys Glu Lys Leu Gly Gly Lys Leu Ser Ser Glu Asp Lys Glu
                580                 585                 590

Thr Met Glu Lys Ala Val Glu Glu Lys Ile Glu Trp Leu Glu Ser His
            595                 600                 605

Gln Asp Ala Asp Ile Glu Asp Phe Lys Ala Lys Lys Lys Glu Leu Glu
        610                 615                 620

Glu Ile Val Gln Pro Ile Ile Ser Lys Leu Tyr Gly Ser Ala Gly Pro
625                 630                 635                 640

Pro Pro Thr Gly Glu Glu Asp Thr Ala Glu Lys Asp Glu Leu
                645                 650

<210> SEQ ID NO 21
<211> LENGTH: 1906
<212> TYPE: DNA
<213> ORGANISM: Homo sapiens

<400> SEQUENCE: 21
agccccaagc ttaccacctg cacccggaga gctgtgtcac catgtgggtc ccggttgtct      60
tcctcaccct gtccgtgacg tggattggtg ctgcacccct catcctgtct cggattgtgg     120
gaggctggga gtgcgagaag cattcccaac cctggcaggt gcttgtggcc tctcgtggca     180
gggcagtctg cggcggtgtt ctggtgcacc ccagtgggt cctcacagct gcccactgca     240
tcaggaacaa agcgtgatc ttgctgggtc ggcacagcct gtttcatcct gaagacacag     300
gccaggtatt tcaggtcagc cacagcttcc cacacccgct ctacgatatg agcctcctga     360
agaatcgatt cctcaggcca ggtgatgact ccagccacga cctcatgctg ctccgcctgt     420
cagagcctgc cgagctcacg gatgctgtga aggtcatgga cctgcccacc caggagccag     480
cactggggac cacctgctac gcctcaggct ggggcagcat tgaaccagag gagttcttga     540
ccccaaagaa acttcagtgt gtggacctcc atgttatttc aatgacgtg tgtgcgcaag     600 ttcaccctca gaaggtgacc aagttcatgc tgtgtgctgg acgctggaca gggggcaaaa     660
gcacctgctc gtgggtcatt ctgatcaccg aactgaccat gccagccctg ccgatggtcc     720
tccatggctc cctagtgccc tggagaggag gtgtctagtc agagagtagt cctggaaggt     780
ggcctctgtg aggagccacg gggacagcat cctgcagatg gtcctggccc ttgtcccacc     840
gacctgtcta caaggactgt cctcgtggac cctcccctct gcacaggagc tggaccctga     900
agtcccttcc ccaccggcca ggactggagc ccctacccct ctgttggaat ccctgcccac     960
cttcttctgg aagtcggctc tggagacatt tctctcttct tccaaagctg ggaactgcta    1020
tctgttatct gcctgtccag gtctgaaaga taggattgcc caggcagaaa ctgggactga    1080
cctatctcac tctctccctg cttttaccct tagggtgatt ctgggggccc acttgtctgt    1140
aatggtgtgc ttcaaggtat cacgtcatgg ggcagtgaac catgtgccct gcccgaaagg    1200
ccttccctgt acaccaaggt ggtgcattac cggaagtgga tcaaggacac catcgtggcc    1260 aaccctgag caccctatc aacccctat tgtagtaaac ttggaacctt ggaaatgacc     1320
aggccaagac tcaagcctcc ccagttctac tgacctttgt ccttaggtgt gaggtccagg    1380
gttgctagga aaagaaatca gcagacacag gtgtagacca gagtgtttct taaatggtgt    1440
aattttgtcc tctctgtgtc ctggggaata ctggccatgc ctggagacat atcactcaat    1500
ttctctgagg acacagatag gatggggtgt ctgtgttatt tgtggggtac agagatgaaa    1560
gaggggtggg atccacactg agagagtgga gagtgacatg tgctggacac tgtccatgaa    1620
```

| | |
|---|---|
| gcactgagca gaaagctggag gcacaacgca ccagacactc acagcaagga tggagctgaa | 1680 |
| aacataaccc actctgtcct ggaggcactg ggaagcctag agaaggctgt gagccaagga | 1740 |
| gggagggtct tcctttggca tgggatgggg atgaagtaag gagagggact ggaccccctg | 1800 |
| gaagctgatt cactatgggg ggaggtgtat tgaagtcctc cagacaaccc tcagatttga | 1860 |
| tgatttccta gtagaactca cagaaataaa gagctgttat actgtg | 1906 |

```
<210> SEQ ID NO 22
<211> LENGTH: 1335
<212> TYPE: DNA
<213> ORGANISM: Homo sapiens

<400> SEQUENCE: 22
```

| | |
|---|---|
| agccccaagc ttaccacctg cacccggaga gctgtgtcac catgtgggtc ccggttgtct | 60 |
| tcctcaccct gtccgtgacg tggattggtg ctgcacccct catcctgtct cggattgtgg | 120 |
| gaggctggga gtgcgagaag cattcccaac cctggcaggt gcttgtggcc tctcgtggca | 180 |
| gggcagtctg cggcggtgtt ctggtgcacc cccagtgggt cctcacagct gcccactgca | 240 |
| tcaggaagcc aggtgatgac tccagccacg acctcatgct gctccgcctg tcagagcctg | 300 |
| ccgagctcac ggatgctgtg aaggtcatgg acctgcccac ccaggagcca gcactgggga | 360 |
| ccacctgcta cgcctcaggc tggggcagca ttgaaccaga ggagttcttg accccaaaga | 420 |
| aacttcagtg tgtggacctc catgttattt ccaatgacgt gtgtgcgcaa gttcaccctc | 480 |
| agaaggtgac caagttcatg ctgtgtgctg gacgctggac aggggggcaaa agcacctgct | 540 |
| cgggtgattc tgggggccca cttgtctgta atggtgtgct tcaaggtatc acgtcatggg | 600 |
| gcagtgaacc atgtgccctg cccgaaaggc cttccctgta caccaaggtg gtgcattacc | 660 |
| ggaagtggat caaggacacc atcgtggcca acccctgagc accccctatca acccctatt | 720 |
| gtagtaaact tggaaccttg gaaatgacca ggccaagact caagcctccc cagttctact | 780 |
| gacctttgtc cttaggtgtg aggtccaggg ttgctaggaa aagaaatcag cagacacagg | 840 |
| tgtagaccag agtgtttctt aaatggtgta attttgtcct ctctgtgtcc tggggaatac | 900 |
| tggccatgcc tggagacata tcactcaatt tctctgagga cacagatagg atggggtgtc | 960 |
| tgtgttattt gtggggtaca gagatgaaag aggggtggga tccacactga gagagtggag | 1020 |
| agtgacatgt gctggacact gtccatgaag cactgagcag aagctggagg cacaacgcac | 1080 |
| cagacactca cagcaaggat ggagctgaaa acataaccca ctctgtcctg gaggcactgg | 1140 |
| gaagcctaga gaaggctgtg agccaaggag ggagggtctt cctttggcat gggatgggga | 1200 |
| tgaagtaagg agagggactg gaccccctgg aagctgattc actatggggg gaggtgtatt | 1260 |
| gaagtcctcc agacaaccct cagatttgat gatttcctag tagaactcac agaaataaag | 1320 |
| agctgttata ctgtg | 1335 |

```
<210> SEQ ID NO 23
<211> LENGTH: 1464
<212> TYPE: DNA
<213> ORGANISM: Homo sapiens

<400> SEQUENCE: 23
```

| | |
|---|---|
| agccccaagc ttaccacctg cacccggaga gctgtgtcac catgtgggtc ccggttgtct | 60 |
| tcctcaccct gtccgtgacg tggattggtg ctgcacccct catcctgtct cggattgtgg | 120 |
| gaggctggga gtgcgagaag cattcccaac cctggcaggt gcttgtggcc tctcgtggca | 180 |
| gggcagtctg cggcggtgtt ctggtgcacc cccagtgggt cctcacagct gcccactgca | 240 |

```
tcaggaacaa aagcgtgatc ttgctgggtc ggcacagcct gtttcatcct gaagacacag      300
gccaggtatt tcaggtcagc cacagcttcc cacaccgct ctacgatatg agcctcctga       360
agaatcgatt cctcaggcca ggtgatgact ccagccacga cctcatgctg ctccgcctgt     420
cagagcctgc cgagctcacg gatgctgtga aggtcatgga cctgcccacc caggagccag     480
cactggggac cacctgctac gcctcaggct ggggcagcat tgaaccagag gagttcttga     540
ccccaaagaa acttcagtgt gtggacctcc atgttatttc caatgacgtg tgtgcgcaag     600
ttcaccctca gaaggtgacc aagttcatgc tgtgtgctgg acgctggaca gggggcaaaa    660
gcacctgctc gggtgattct gggggcccac ttgtctgtaa tggtgtgctt caaggtatca    720
cgtcatgggg cagtgaacca tgtgccctgc ccgaaaggcc ttccctgtac accaaggtgg    780
tgcattaccg gaagtggatc aaggacacca tcgtggccaa cccctgagca ccctatcaa    840 cccctattg tagtaaactt ggaaccttgg aaatgaccag gccaagactc aagcctcccc    900
agttctactg acctttgtcc ttaggtgtga ggtccagggt tgctaggaaa agaaatcagc    960
agacacaggt gtagaccaga gtgtttctta aatggtgtaa ttttgtcctc tctgtgtcct   1020
ggggaatact ggccatgcct ggagacatat cactcaattt ctctgaggac acagatagga   1080
tggggtgtct gtgttatttg tggggtacag agatgaaaga ggggtgggat ccacactgag   1140
agagtggaga gtgacatgtg ctggacactg tccatgaagc actgagcaga agctggaggc   1200
acaacgcacc agacactcac agcaaggatg gagctgaaaa cataacccac tctgtcctgg   1260
aggcactggg aagcctagag aaggctgtga gccaaggagg gagggtcttc ctttggcatg   1320
ggatggggat gaagtaagga gagggactgg acccctgga agctgattca ctatgggggg    1380
aggtgtattg aagtcctcca gacaaccctc agatttgatg atttcctagt agaactcaca   1440
gaaataaaga gctgttatac tgtg                                            1464
```